US011066709B2

(12) United States Patent
Klijn et al.

(10) Patent No.: US 11,066,709 B2
(45) Date of Patent: Jul. 20, 2021

(54) METHODS FOR DIAGNOSING AND TREATING CANCER BY MEANS OF THE EXPRESSION STATUS AND MUTATIONAL STATUS OF NRF2 AND DOWNSTREAM TARGET GENES OF SAID GENE

(71) Applicants: Genentech, Inc., South San Francisco, CA (US); Foundation Medicine, Inc., Cambridge, MA (US)

(72) Inventors: Christiaan Nicolaas Klijn, San Francisco, CA (US); James Lee, San Bruno, CA (US); David Hugh Stokoe, San Francisco, CA (US); Robert Gentleman, San Mateo, CA (US); Florian Gnad, Boston, MA (US); Leonard David Goldstein, Burlingame, CA (US); Juliann Chmielecki, Medford, MA (US); Ryan J. Hartmaier, Cambridge, MA (US)

(73) Assignees: Genentech, Inc., South San Francisco, CA (US); Foundation Medicine, Inc., Cambridge, MA (US)

( * ) Notice: Subject to any disclaimer, the term of this patent is extended or adjusted under 35 U.S.C. 154(b) by 0 days.

(21) Appl. No.: 16/230,223

(22) Filed: Dec. 21, 2018

(65) Prior Publication Data

US 2019/0218618 A1 Jul. 18, 2019

Related U.S. Application Data

(63) Continuation of application No. PCT/US2017/041398, filed on Jul. 10, 2017.

(60) Provisional application No. 62/360,294, filed on Jul. 8, 2016.

(51) Int. Cl.

| | |
|---|---|
| ***C12Q 1/68*** | (2018.01) |
| ***C07H 21/04*** | (2006.01) |
| ***C12Q 1/6886*** | (2018.01) |
| ***A61P 35/00*** | (2006.01) |
| ***A61K 31/337*** | (2006.01) |
| ***C12Q 1/6806*** | (2018.01) |
| ***C12Q 1/686*** | (2018.01) |
| ***C12Q 1/6872*** | (2018.01) |
| *A61K 45/06* | (2006.01) |

(52) U.S. Cl.

CPC .......... *C12Q 1/6886* (2013.01); *A61K 31/337* (2013.01); *A61P 35/00* (2018.01); *C12Q 1/6806* (2013.01); *C12Q 1/686* (2013.01); *C12Q 1/6872* (2013.01); *A61K 45/06* (2013.01)

(58) Field of Classification Search

None

See application file for complete search history.

(56) References Cited

FOREIGN PATENT DOCUMENTS

WO WO-2015/178508 A1 11/2015

OTHER PUBLICATIONS

Arisawa et al., "Nrf2 gene promoter polymorphism and gastric carcinogenesis," Hepatogastroenterology. 55(82-83):750-4 (2008) (5 pages).

Hu et al., "Mutation of the Nrf2 gene in non-small cell lung cancer," Mol Biol Rep. 39(4):4743-7 (2012) (5 pages).

Mine et al., "Activation of Nrf2 pathways correlates with resistance of NSCLC cell lines to CBP501 in vitro," Mol Cancer Ther. 13(9):2215-25 (2014) (12 pages).

Nishinaka et al., "Regulation of aldo-keto reductase AKR1B10 gene expression: involvement of transcription factor Nrf2," Chem Biol Interact. 191(1-3):185-91 (2011) (7 pages).

Sasaki et al., "Genotype analysis of the NRF2 gene mutation in lung cancer," Int J Mol Med. 31(5):1135-8 (2013) (4 pages).

Sasaki et al., "Increased NRF2 gene (NFE2L2) copy number correlates with mutations in lung squamous cell carcinomas," Mol Med Rep. 6(2):391-4 (2012) (4 pages).

Sasaki et al., "RagD gene expression and NRF2 mutations in lung squamous cell carcinomas," Oncol Lett. 4(6):1167-70 (2012) (4 pages).

Shibata et al., "NRF2 mutation confers malignant potential and resistance to chemoradiation therapy in advanced esophageal squamous cancer," Neoplasia. 13(9):864-73 (2011) (13 pages).

International Preliminary Report on Patentability for International Patent Application No. PCT/US2017/041398, dated Jan. 8, 2019 (12 pages).

International Search Report and Written Opinion for International Patent Application No. PCT/US2017/041398, dated Nov. 30, 2017 (24 pages).

Invitation to Pay Additional Fees for International Patent Application No. PCT/US2017/041398, dated Oct. 9, 2017 (21 pages).

Invitation to Pay Additional Fees for European Patent Application No. 17743124.4, dated Oct. 2, 2020 (8 pages).

*Primary Examiner* — Jeanine A Goldberg

(74) *Attorney, Agent, or Firm* — Clark & Elbing LLP; Karen E. Elbing

(57) ABSTRACT

The invention provides methods of identifying a subject having cancer, such as lung cancer, by analyzing expression levels of one or more NRF2 splice variants or NRF2 target genes. The invention also provides methods of treating cancer in a subject with a NRF2 pathway antagonist, wherein the subject expresses one or more NRF2 splice variants or overexpresses one or more NRF2 target genes.

20 Claims, 67 Drawing Sheets

Specification includes a Sequence Listing.

Exon 3

Exon 1

FIG. 12B

Nrf2 Exon 2 deletion : 516 a.a. MW 57,193

FIG. 12C

Nrf2 wild type : 605 a.a. MW 67,808

Exon 2 sequences

FIG. 20
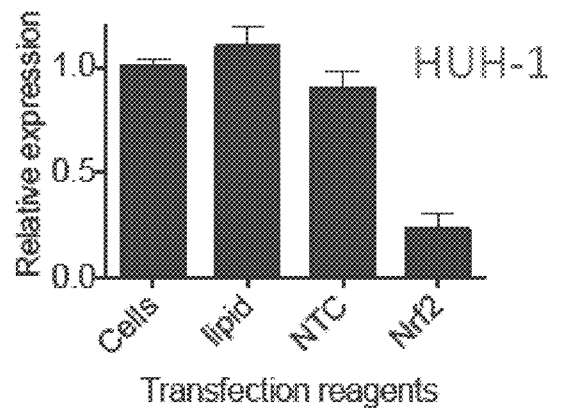
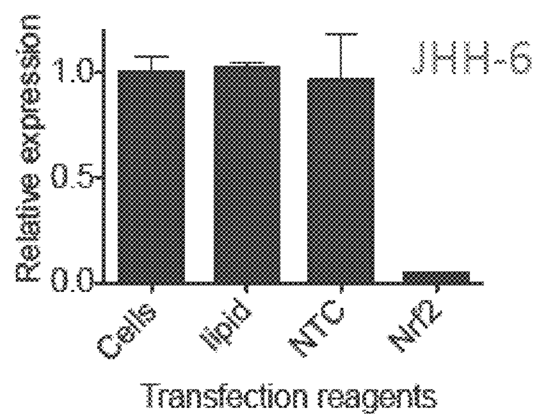
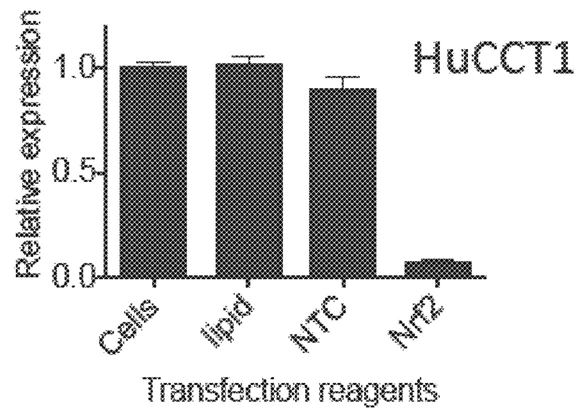

SLC7A11
GCLC
NR0B1
SRGN
Relative expression
2.0
1.5
1.0
0.5
0.0
cells
lipid
NTC
NRF2
Transfection reagents
HUH-1
JHH-6
HuCCT1

SLC7A11
GCLC
NR0B1
SRGN
GPX2
Relative expression
transfection condition
lipid
WT
Δe2
Δe2,3
KEAP1
WT+KEAP1
Δe2+KEAP1
Δe2,3+KEAP1

Exon 2 Deletion

Exon 2 & Exon 3 Deletion

FIG. 34

JHH-6 (chr2:178,098,731~178,103,415 deleted)

3'end AAACCTGCCATAACTTTCCCAAGAACTGAGTACTCTGTACCTGGGAGTAGTTGGCAGATCCACTGGTTTTCTGACTGGA SEQ ID NO:61

5'end TGTGGACCTAACTAGGGGGAGCCTAAAATAATGTTGGGACTACCTAGATGGTCAGAAAGAATGAGCCAATTAACTTCT SEQ ID NO:62

Junction read AAACCTGCCATAACTTTCCCAAGAACTGAGTACTCTGTACTACCTAGATGGTCAGAAAGAATGAGCCAATTAACTTCT SEQ ID NO:63

KMS-27 (chr2:178,098,602~178,101,582 deleted)

3'end AGGTTAGGTACTGAACTCATCAGGAGGCTGAGGTTGGAAAGTAGATTTGACAAGGTTAAGTAAAAGAAAGGCAAAGCTG SEQ ID NO:64

5'end ATTTTTTCGGGTTTTTTTTCCACTTTTTTTCCTTTTGAAATTTTATTATTTATTTACTCATTTTGAGATAGGGTCTCACT SEQ ID NO:65

Junction read AGGTTGGGTACTGAACTCATCAGGAGGCTGAGTTTGAAATTTTATTATTTATTTACTCATTTTGAGATAGGGTCTCACT SEQ ID NO:66

Primary tumor 041078 (chr2:178,098,465~178,103,697 deleted)

3'end CTTGGTTCTCCTGCTACTACTTCTGTTGCTGCCTACTTGATCCTTACAGGATGTTTCTATACTTTACAAAACTCTTTGGT SEQ ID NO:67

5'end GTGATGGCAGTGGGCACGCCCATATACATTTGCATACACTCTAATATAAATGTTTACAAACATACACACACACACATTC SEQ ID NO:68

Junction read CTTGGTTCTCCTGCTACTACTTCTGTTGCTGCCTACTTGATCTAATATAAATGTTTACAAACATACACACACACACATTC SEQ ID NO:69 dox
Nrf2 sh1
Nrf2 sh3
Nrf2 sh10
- +
- +
- +
Nrf2
A549
H460
H1437
H1355
H2122
KEAP1 mut
H2228
EBC1
Nrf2 mut
Calu6
H441
Calu1
H1048
H1838
KEAP1 WT
BEAS2B

SEQUENCE LISTING

```
<160> NUMBER OF SEQ ID NOS: 74

<210> SEQ ID NO 1
<211> LENGTH: 5446
<212> TYPE: RNA
<213> ORGANISM: Homo sapiens

<400> SEQUENCE: 1

uacuuuggga acuggugagu cucccugucc cuagggcuuu uuagucacau guccauccac     60

uguuucaaug uaacaugcau cuaggcaagg uuaacgauua aaugguuggg augaaagguc    120

auccuuuacg gagaacauca gaaugguaga uaauuccugu uccacuuucu uugaugaaac    180

aaguaaagaa gaaacaacac aaucauauua auagaagagu cuucguucca gacgcagucc    240

aggaaucaug cuggagaagu ucugcaacuc uacuuuuugg aauuccucau uccuggacag    300
```

```
uccggaggca gaccugccac uuuguuuuga gcaaacuguu cuggugugga uucccuuggg    360
cuuccuaugg cuccuggccc ccuggcagcu ucuccacgug uauaaaucca ggaccaagag    420
auccucuacc accaaacucu aucuugcuaa gcagguauuc guugguuuuc uucuuauucu    480
agcagccaua gagcuggccc uuguacucac agaagacucu ggacaagcca caguccccugc   540
uguucgauau accaauccaa gccucuaccu aggcacaugg cuccugguuu ugcugaucca    600
auacagcaga caauggugug uacagaaaaa cuccugguuc cugucccuau ucuggauucu    660
cucgauacuc uguggcacuu uccaauuuca gacucugauc cggacacucu uacagggguga   720
caauucuaau cuagccuacu ccugccuguu cuucaucucc uacggauucc agauccugau    780
ccugaucuuu ucagcauuuu cagaaaauaa ugagucauca aauaauccau cauccauagc    840
uucauuccug aguagcauua ccuacagcug guaugacagc aucauucuga aaggcuacaa    900
gcguccucug acacucgagg augucuggga aguugaugaa gagaugaaaa ccaagacauu    960
agugagcaag uuugaaacgc acaugaagag agagcugcag aaagccaggc gggcacucca   1020
gagacggcag gagaagagcu cccagcagaa cucuggagcc aggcugccug gcuugaacaa   1080
gaaucagagu caaagccaag augcccuugu ccuggaagau guugaaaaga aaaaaaagaa   1140
gucugggacc aaaaaagaug uuccaaaauc cugguugaug aaggcucugu ucaaaacuuu   1200
cuacauggug cuccugaaau cauuccuacu gaagcuagug aaugacaucu ucacguuugu   1260
gaguccucag cugcugaaau ugcugaucuc cuuugcaagu gaccgugaca cauauuugug   1320
gauuggauau cucugugcaa uccucuuauu cacugcggcu cucauucagu cuuucugccu   1380
ucaguguuau uuccaacugu gcuucaagcu ggguguaaaa guacggacag cuaucauggc   1440
uucuguauau aagaaggcau ugacccuauc caacuuggcc aggaaggagu acaccguugg   1500
agaaacagug aaccugaugu cuguggaugc ccagaagcuc auggauguga ccaacuucau   1560
gcacaugcug uggucaagug uucuacagau ugucuuaucu aucuucuucc uauggagaga   1620
guugggaccc ucagucuuag cagguguugg ggugauggug cuuguaaucc caauuaaugc   1680
gauacugucc accaagagua agaccauuca ggucaaaaau augaagaaua aagacaaacg   1740
uuuaaagauc augaaugaga uucuuagugg aaucaagauc cugaaauauu uugccuggga   1800
accuucauuc agagaccaag uacaaaaccu ccggaagaaa gagcucaaga accugcuggc   1860
cuuuagucaa cuacagugug uaguaauauu cgucuuccag uuaacuccag uccugguauc   1920
ugugguucaca uuuucuguuu auguccuggu ggauagcaac aauauuuugg augcacaaaa  1980
ggccuucacc uccauuaccc ucuucaauau ccugcgcuuu ccccugagca ugcuucccau   2040
gaugaucucc uccaugcucc aggccagugu uuccacagag cggcuagaga aguacuuggg   2100
aggggaugac uuggacacau cugccauucg acaugacugc aauuuugaca aagccaugca   2160
guuuucugag gccuccuuua ccugggaaca ugauucggaa gccacagucc gagaugugaa   2220
ccuggacauu auggcaggcc aacuuguggc ugugauaggc ccugucggcu cugggaaauc   2280
cuccuugaua ucagccaugc ugggagaaau ggaaaauguc cacgggcaca ucaccaucaa   2340
gggcaccacu gccuaugucc cacagcaguc cuggauucag aauggcacca uaaaggacaa   2400
cauccuuuuu ggaacagagu uuaaugaaaa gagguaccag caaguacugg aggccugugc   2460
ucuccuccca gacuuggaaa ugcugccugg aggagauuug gcugagauug gagagaaggg   2520
uauaaaucuu aguggggguc agaagcagcg gaucagccug gccagagcua ccuaccaaaa   2580
uuuagacauc uaucuucuag augacccccu gucugcagug gaugcucaug uaggaaaaca   2640
```

-continued

```
uauuuuuaau aaggucuugg gccccaaugg ccuguugaaa ggcaagacuc gacucuuggu   2700
uacacauagc augcacuuuc uuccucaagu ggaugagauu guaguucugg ggaauggaac   2760
aauuguagag aaaggauccu acagugcucu ccuggccaaa aaggagagu uugcuaagaa   2820
ucugaagaca uuucuaagac auacaggccc ugaagaggaa gccacagucc augauggcag   2880
ugaagaagaa gacgaugacu augggcugau auccagugug gaagagaucc ccgaagaugc   2940
agccuccaua accaugagaa gagagaacag cuuucgucga acacuuagcc gcaguucuag   3000
guccaauggc aggcaucuga agucccugag aaacuccuug aaaacucgga augugaauag   3060
ccugaaggaa gacgaagaac uagugaaagg acaaaaacua auuaagaagg aauucauaga   3120
aacuggaaag gugaaguucu ccaucuaccu ggaguaccua caagcaauag gauuguuuuc   3180
gauauucuuc aucauccuug cguuugugau gaauucugug gcuuuuauug gauccaaccu   3240
cuggcucagu gcuuggacca gugacucuaa aaucuucaau agcaccgacu auccagcauc   3300
ucagagggac augagaguug gagucuacgg agcucuggga uuagcccaag guauauuugu   3360
guucauagca cauuucugga gugccuuugg uuucguccau gcaucaaaua ucuugcacaa   3420
gcaacugcug aacaauaucc uucgagcacc uaugagauuu uuugacacaa cacccacagg   3480
ccggauugug aacagguuug ccggcgauau uuccacagug gaugacaccc ugccucaguc   3540
cuugcgcagc uggauuacau gcuuccuggg gauaaucagc acccuuguca ugaucugcau   3600
ggccacuccu gucuucacca ucaucgucau uccucuuggc auuauuuaug uaucuguuca   3660
gauguuuuau gugucuaccu cccgccagcu gaggcgucug gacucuguca ccaggucccc   3720
aaucuacucu cacuucagcg agaccguauc agguuugcca guuauccgug ccuuugagca   3780
ccagcagcga uuucugaaac acaaugaggu gaggauugac accaaccaga aaugugucuu   3840
uuccuggauc accuccaaca gguggcuugc aauucgccug gagcugguug ggaaccugac   3900
ugucuucuuu ucagccuuga ugaugguuau uuauagagau acccuaagug gggacacugu   3960
uggcuuuguu cuguccaaug cacucaauau cacacaaacc cugaacuggc uggugaggau   4020
gacaucagaa auagagacca acauuguggc uguugagcga auaacugagu acacaaaagu   4080
ggaaaaugag gcacccuggg ugacugauaa gaggccuccg ccagauuggc ccagcaaagg   4140
caagauccag uuuaacaacu accaagugcg guaccgaccu gagcuggauc ugguccucag   4200
agggaucacu ugugacaucg guagcaugga gaagauuggu gugguggca ggacaggagc   4260
uggaaaguca ucccucacaa acugccucuu cagaaucuua gaggcugccg guggucagau   4320
uaucauugau ggaguagaua uugcuuccau ugggcuccac gaccuccgag agaagcugac   4380
caucaucccc caggacccca uccuguucuc uggaagccug aggaugaauc ucgacccuuu   4440
caacaacuac ucagaugagg agauuuggaa ggccuuggag cuggcucacc ucaagucuuu   4500
uguggccagc cugcaacuug gguuauccca cgaagugaca gaggcuggug gcaaccugag   4560
cauaggccag aggcagcugc ugugccuggg cagggcucug cuucggaaau ccaagauccu   4620
gguccuggau gaggccacug cugcggugga ucuagagaca gacaaccuca uucagacgac   4680
cauccaaaac gaguucgccc acugcacagu gaucaccauc gcccacaggc ugcacaccau   4740
cauggacagu gacaagguaa ugguccuaga caacgggaag auuauagagu gcggcagccc   4800
ugaagaacug cuacaaaucc cuggacccuu uuacuuuaug gcuaaggaag cuggcauuga   4860
gaaugugaac agcacaaaau ucuagcagaa ggccccaugg guuagaaaag gacuauaaga   4920
auaauuucuu auuuaauuuu auuuuuuaua aaauacagaa uacauacaaa agugguauaa   4980
aaauguacgu uuuaaaaaag gauaagugaa cacccaugaa ccuacuaccc agguuaagaa   5040
```

```
aauaaauguc accagguacu ugagaaaccc cucgauuguc uaccucgauc guacuuccuu   5100

gcuacccacc ccucccaggg acaaccacug uccugaauuu cacgauaauu auuccuuugc   5160

cuuucauuuc uguuuuauca ccuuuguaug uaucuuuaaa caacauauac ccuuuuuuac   5220

uuauguaaau ggacugacuc auacugcaua caucuucuau gacuugauuc uuuuguucaa   5280

uauuauaucu gagauucauc cauggugaug caaauaggug cauuauuuuu uuucacugcu   5340

cuguagucug gcauuguaug aauacagcac aauguaucag uuuuaauauu ggggaucauu   5400

agcauuauuc ucagguuuuu aaaaauuaua agcaguacua cuaugg                  5446
```

<210> SEQ ID NO 2
<211> LENGTH: 1610
<212> TYPE: RNA
<213> ORGANISM: Homo sapiens

<400> SEQUENCE: 2

```
acaguagcuc acaccuguaa ucccagcacu uuggaaggcc gaggugggcg gaucaccuga     60

gcucaggagu uugagaccag ccugucucua cuaacaauau aaaaauuagc ugggagucac    120

ggugggcgcc uguaauccca gcuacucggg aggcugaggc aggagaauug cuugaaccca    180

ggagacagag guuguaguga gcugagaucg caccacugca cucuagccuu ggcaacagug    240

caagacuguc ucaaaaacag caacagagag caggacguga gacuucuacc ugcucacuca    300

gaaucauuuc ugcaccaacc auggccacgu uuguggagcu caguaccaaa gccaagaugc    360

ccauuguggg ccugggcacu uggaagucuc cucuuggcaa agugaaagaa gcagugaagg    420

uggccauuga ugcaggauau cggcacauug acugugccua ugucuaucag aaugaacaug    480

aaguggggga agccauccaa gagaagaucc aagagaaggc ugugaagcgg gaggaccugu    540

ucaucgucag caaguugugg cccacuuucu uugagagacc ccuugugagg aaagccuuug    600

agaagacccu caaggaccug aagcugagcu aucuggacgu cuaucuuauu cacuggccac    660

agggauucaa gucuggggau gaccuuuucc ccaaagauga uaaagguaau gccaucggug    720

gaaaagcaac guucuuggau gccugggagg ccauggagga gcugguggau gaggggcugg    780

ugaaagcccu uggggucucc aauuucagcc acuuccagau cgagaagcuc uugaacaaac    840

cuggacugaa auauaaacca gugacuaacc agguugagug ucacccauac cucacacagg    900

agaaacugau ccaguacugc cacuccaagg gcaucaccgu uacggccuac agcccccugg    960

gcucuccgga uagaccuugg gccaagccag aagacccuuc ccugcuggag gaucccaaga   1020

uuaaggagau ugcugcaaag cacaaaaaaa ccgcagccca gguucugauc cguuuccaua   1080

uccagaggaa ugugauuguc auccccaagu cugugacacc agcacgcauu guugagaaca   1140

uucaggucuu ugacuuuaaa uugagugaug aggagauggc aaccauacuc agcuucaaca   1200

gaaacuggag ggccuguaac guguugcaau ccucucauuu ggaagacuau cccuucaaug   1260

cagaauauug agguugaauc uccuggugag auuauacagg agauucucuu ucuucgcuga   1320

agugugacua ccuccacuca ugucccauuu uagccaagcu uauuuaagau cacagugaac   1380

uuaguccugu uauagacgag aaucgaggug cuguuuuaga cauuuauuuc uguauguuca   1440

acuaggauca gaauaucaca gaaaagcaug gcuugaauaa ggaaaugaca auuuuuucca   1500

cuuaucugau cagaacaaau guuuauuaag caucagaaac ucugccaaca cugaggaugu   1560

aaagaucaau aaaaaaaaua auaaucauaa ccaacaaaaa aaaaaaaaaa              1610
```

<210> SEQ ID NO 3

<211> LENGTH: 1625
<212> TYPE: RNA
<213> ORGANISM: Homo sapiens

<400> SEQUENCE: 3

```
uccgggcuuc cccagacaga cagcuggcuu acagggccac cugaagacgu uccagggcuc     60

cacaggccac ugucuucugg aggggaacgg aucgacugcc ggugcgccca gccaaauuca    120

acuccugagu ccucagucuc uagucccggg aagguuucac cgagcugccc uacuccuugu    180

accccuucua gcuggccuua gcauagcuac gucagcagcu auuggcacga cugcccugau    240

ucaaggagaa acuggacuaa uaucacuauc ucaacaggau cgaggccauc aagcuacaga    300

uggucuuaca aauggaaccc caagugaacu caacuaacaa cuuccaccaa ggaccccugg    360

accaacccgu uggcccuuug acuggccuaa agaguucccu ucugaaggac acuacaagug    420

cagggccccu ucuucgcccc uauccagcau cucuucucgg caaagugaaa gaagcgguga    480

agguggccau ugaugcagaa uaucgccaca uugacugugc cuauuucuau gagaaucaac    540

augaggyggg agaagccauc caagagaaga uccaagagaa ggcugugaug cgggaggacc    600

uguucaucgu cagcaaggug uggcccacuu ucuuugagag accccuugug aggaaagccu    660

uugagaagac ccucaaggac cugaagcuga gcuaucugga cgucuaucuu auucacuggc    720

cacagggauu caagacuggg gaugacuuuu uccccaaaga ugauaaaggu aauaugauca    780

guggaaaagg aacguucuug gaugccuggg aggccaugga ggagcuggug gacgaggggc    840

uggugaaagc ccuugggguc ucaaauuuca accacuucca gaucgagagg cucuugaaca    900

aaccuggacu gaaauauaaa ccagugacua accagguuga gugucaccca uaccucacgc    960

aggagaaacu gauccaguac ugccacucca agggcaucac cguuacggcc uacagccccc   1020

ugggcucucc ggauagaccu ugggccaaac cugaggaccc uucccugcug gaggauccca   1080

agauuaagga gauugcugca aagcacaaaa aaaccacagc ccagguucug auccguuucc   1140

auauccagag gaaugugaca gugaucccca agucuaugac accagcacac auuguugaga   1200

acauucaggu cuuugacuuu aaauugagug augaggagau ggcaaccaua cucagcuuca   1260

acagaaacug gagggccuuu gacuucaagg aauucucuca uuuggaggac uuucccuucg   1320

augcagaaua uugagguuga aucuccuggu gagauuacac aggggauucu cuuucuucgc   1380

ugaaguguga cugucuccac ucaagaacua uuuuagccaa gcuuaucuga gaucacagug   1440

aacuuugucc uguuguagac cagaauggag gugcuguuuu agacauguau uucuguaugu   1500

ucaacuagga uaagaauauc acagaaaagc auggccugaa uaagcaaaug acaauuuuuu   1560

ccacuuaucu gaucugauca aaugucuguu aagcaccaga aacucugcca acacugagga   1620

uguaa                                                               1625
```

<210> SEQ ID NO 4
<211> LENGTH: 1098
<212> TYPE: RNA
<213> ORGANISM: Homo sapiens

<400> SEQUENCE: 4

```
guaagaaacg guugaacugg augcaauuuu uaucacagcu uguguaagac ugccucuguc     60

ccuccucuca caugccauug guuaaccagc agacagugug cucaggggcg uugccagcuc    120

auugcucuua uagccuguga gggaggaaga aacauuugcu aaccaggcca gugacagaaa    180

uggauucgaa auaccagugu gugaagcuga augaugguca cuucaugccu guccugggau    240

uuggcaccua ugcgccugca gagguuccua aaaguaaagc ucuagaggcc gucaaauugg    300
```

```
caauagaagc cggguuccac cauauugauu cugcacaugu uuacaauaau gaggagcagg    360
uuggacuggc cauccgaagc aagauugcag auggcagugu gaagagagaa gacauauucu    420
acacuucaaa gcuuuggagc aauucccauc gaccagaguu gguccgacca gccuuggaaa    480
ggucacugaa aaaucuucaa uuggacuaug uugaccucua ucuuauucau uuuccagugu    540
cuguaaagga ggacauaggg auuuuaacau ggaagaagag cccuaaacau aacuccuaau    600
uccuuucuau ggaacagaaa gcaauuuuga auccauacuu ccgugauugc augucuacaa    660
gaaaagagag ugcagaaucc ucaaagccuc ugccucaaaa acuugaggaa augacaauca    720
ucuccuugaa ggcacaaggu cuuauuuaug auuccugauu ucaccucuug ggauguucac    780
agacacagag uuucaugaag cuguggugc cagaaaaccu gcugcacaua gggugcacaa    840
ugaguuucca ucuucuugcc ucuuuucaag gggcaagaac ucaguccggg aaugucuuaa    900
acuacaaacc uucaugggaa accuuguugc uucugcuucc ucucuuuuca cacuggaggu    960
uuuauuuuug cuuagccaug aauucuugug ucauucauaa cuuuugucuu aagguacuga   1020
aaacuaguca ggcuaguuaa ugcaaaaggg uauauuagau augauaaugg gaaaucaaag   1080
ccagggcuac auuaagaa                                                 1098
```

<210> SEQ ID NO 5
<211> LENGTH: 1064
<212> TYPE: RNA
<213> ORGANISM: Homo sapiens

<400> SEQUENCE: 5

```
gcccauuguu uuuguaaucu cugaggagaa gcagcagcaa acauuugcua gucagacaag     60
ugacagggaa uggauuccaa acaccagugu guaaagcuaa augauggcca cuucaugccu    120
guauugggau uuggcaccua ugcaccucca gagguuccga gaaguaaagc uuuggagguc    180
acaaaauuag caauagaagc uggguuccgc cauauagauu cugcucauuu auacaauaau    240
gaggagcagg uuggacuggc cauccgaagc aagauugcag auggcagugu gaagagagaa    300
gacauauucu acacuucaaa gcuuuggucc acuuuucauc gaccagaguu gguccgacca    360
gccuuggaaa acucacugaa gaaagcucaa uuggacuaug uugaccucua ucuuauucau    420
ucuccaaugu cucuaaaggu augcaguuug uaugagcaua aaauugcgcu ucugcuguca    480
uuauaaacau uguuuaucug gauaguugaa cagagcuuuu uauuaggagg auguagggau    540
uaucacacag aagaagaacc guaaguggaa caccuaauuu ccuuucuuuc gaguaaauuu    600
ugaauccuac uucucuaaug cacaccuaca agagaagaga guacagcaac cucaaagccu    660
cuuccucaaa aacuugaaau uacaauaguc ucuuucaagg cacugucuua guuguggcuu    720
uugaguccau cucuugggau guucccagac acagaguuuc augcaguugu ggugcccaau    780
aaaacugcug cacaugugau gcacaaugag uuuccaccau cucuccccau uucaagcuga    840
agcagauuug guggaagcca cuaugcaugg uucuuaaauu agaaacccuu aauguggacu    900
ugcaaagcuu uauuauucug cugccucuuc uuucacaaua gaguuugaag cuguauuuag    960
ccaggaauua cuguguagug uauaacuuuu gauuuaaagu uacagaaaac uacucaggcu   1020
aguuaaugca aaagaguuua cugaguuaug uaaaauggga aguc                    1064
```

<210> SEQ ID NO 6
<211> LENGTH: 1192
<212> TYPE: RNA
<213> ORGANISM: Homo sapiens

<400> SEQUENCE: 6

```
acaggaucug cuuagugaaa gaaguggcaa gcaauggauc ccaaauauca gcguguagag     60
cuaaaugaug gucacuucau gcccguauug ggauuuggca ccuaugcacc uccagagguu    120
ccgaggaaca gagcuguaga ggucaccaaa uuagcaauag aagcuggcuu ccgccauauu    180
gauucugcuu auuuauacaa uaaugaggag cagguuggac uggccauccg aagcaagauu    240
gcagauggca gugugaagag agaagacaua uucuacacuu caaagcuuug gugcacuuuc    300
uuucaaccac agauggucca accagccuug gaaagcucac ugaaaaaacu ucaacuggac    360
uauguugacc ucuaucuucu ucauuuccca auggcucuca agccagguga gacgccacua    420
ccaaaagaug aaaauggaaa aguaauauuc gacacagugg aucucucugc cacaugggag    480
gucauggaga aguguaagga ugcaggauug gccaagucca ucgggggugu aaacuucaac    540
ugcaggcagc uggagaugau ccucaacaag ccaggacuca aguacaagcc ugucugcaac    600
cagguagaau gucauccuua ccucaaccag agcaaacugc uggauuucug caagucaaaa    660
gacauuguuc ugguugccca cagugcucug ggaacccaac gacauaaacu auggguggac    720
ccaaacuccc caguucuuuu ggaggaccca guucuuugug ccuuagcaaa gaaacacaaa    780
cgaaccccag cccugauugc ccugcgcuac cagcugcagc gugggguugu gguccuggcc    840
aagagcuaca augagcagcg gaucagagag aacauccagg uuuuugaauu ccaguugaca    900
ucagaggaua ugaaaguucu agauggucua aacagaaauu aucgauaugu ugucauggau    960
uuucuuaugg accauccuga uuauccauuu ucagaugaau auuagcauag agggguguugc   1020
acgacaucua gcagaaggcc cuguguguggg auggugaugc agaggauguc ucuaugcugg   1080
ugacuggaca cacggccucu gguuaaaucc cuccccuccu gcuuggcaac uucagcuagc   1140
uagauauauc cauggucag aaagcaaaca uaauaaauuu uuaucuugaa gu             1192
```

<210> SEQ ID NO 7
<211> LENGTH: 1425
<212> TYPE: RNA
<213> ORGANISM: Homo sapiens

<400> SEQUENCE: 7

```
ggccccgccu ccuugagugg ugcggagcuu ugugaugcgg agcuucguga ugcacgcccc     60
gaugccugcg gggcuauaaa aacgcucgca agcgccaagu cuccucagga gccgccggca    120
agggggcaac gaggaagcuc uuaagagcgc ggccggaaag caguugaguu acagacaucc    180
ugccaaaaug auuucuucaa agcccagacu ugucguaccc uauggccuca agacucugcu    240
cgagggaauu agcagagcug uucucaaaac caacccauca aacaucaacc aguuugcagc    300
agcuuauuuu caagaacuua cuauguauag agggaauacu acuauggaua uaaaagaucu    360
gguuaaacaa uuucaucaga uuaaaguaga gaaaugguca gaaggaacga caccacagaa    420
gaaauuagaa uguuuaaaag aaccaggaaa aacaucugua gaaucuaaag uaccuaccca    480
gauggaaaaa ucuacagaca cagacgagga caauguaacc agaacagaau auagugacaa    540
aaccacccag uuuccaucag uuuaugcugu gccaggcacu gagcaaacgg aagcaguugg    600
uggucuuucu uccaaaccag ccaccccuaa gacuacuacc ccacccucau caccaccucc    660
aacagcuguc ucaccagagu uugccuacgu cccagcugac ccagcucagc uugcugcuca    720
gauguuagca auggcaacaa gugaacgagg acaaccacca ccauguucua acauguggac    780
ccuuuauugu cuaacugaua agaaucaaca aggucaccca ucaccgccac cugcaccugg    840
gccuuuuccc caagcaaccc ucuauuuacc uaauccuaag gauccacagu uucagcagca    900
```

```
uccaccaaaa gucacuuuuc caacuuaugu gaugggcgac accaagaaga ccagugcccc    960

accuuuuauc uuaguaggcu caaauguuca ggaagcacag ggauggaaac cucuuccugg   1020

acaugcuguc guuucacagu cagaugucuu gagauauguu gcaaugcaag ugcccauugc   1080

uguuccugca gaugagaaau accagaaaca uacccuaagu ccccagaaug cuaauccucc   1140

aaguggacaa gaugucccca ggccaaaaag cccuguuuuc cuuucuguug cuuucccagu   1200

agaagaugua gcuaaaaaaa guucaggauc uggugacaaa ugugcucccu uuggaaguua   1260

cgguauugcu ggggagguaa ccgugacuac ugcucacaaa cgucgcaaag cagaaacuga   1320

aaacugaucc agaaaugacg cugucugggu caacauuuca gggaggaguc ugccaccagu   1380

guaauguauc aauaaacuuc augcaagcau aaaaaaaaaa aaaaa                   1425
```

<210> SEQ ID NO 8
<211> LENGTH: 1765
<212> TYPE: RNA
<213> ORGANISM: Homo sapiens

<400> SEQUENCE: 8

```
aucugccucc agcacugccc auccuugccc cuuuccacug uccuuggagc uuccugggcc     60

cuucccuggg ccucaggauc ccacccucca ucccgucugc ccugcaggau gccgcagcug    120

agccuguccu ggcugggccu cgggcccgug gcagcauccc cguggcugcu ucugcugcug    180

guuggggggcu ccuggcuccu ggcccgcguc cuggccugga ccuacaccuu cuaugacaac    240

ugccgccguc uccaguguuu uccucaaccc ccgaaacaga acugguuuug gggacaccag    300

ggccugguca cucccacgga agagggcaug aagacauuga cccagcuggu gaccacauau    360

ccccagggcu uuaaguugug gcugggucccu accuuccccc uccucauuuu augccacccu    420

gacaucaucc ggccuaucac cagugccuca gcugcugucg cacccaagga uaugauuuuc    480

uauggcuucc ugaagcccug gcugggggau gggcuccugc ugaguggugg ugacaagugg    540

agccgccacc gucggauguu gacgccugcc uuccauuuca acaucuugaa gccuuauaug    600

aagauuuuca acaagagugu gaacaucaug cacgacaagu ggcagcgccu ggccucagag    660

ggcagcgcca gacuggacau guuugaacac aucagccuca ugaccuugga cagucugcag    720

aaaugugucu ucagcuuuga aagcaauugu caggagaagc ccagugaaua uauugccgcc    780

aucuuggagc ucagugccuu uguagaaaag agaaaccagc agauucucuu gcacacggac    840

uuccuguauu aucucacucc ugaugggcag cgcuuccgca gggccugcca ccuggugcac    900

gacuucacag augccgucau ccaggagcgg cgccgcaccc uccccacuca ggguauugau    960

gauuuccuca agaacaaggc aaaguccaag acuuuagacu ucauugaugu gcuucugcug   1020

agcaaggaug aagaugggaa ggaauugucu gaugaggaca uaagagcaga agcugacacc   1080

uucauguuug agggccauga cacuacagcc aguggucucu ccugggucccu auaccaccuu   1140

gcaaagcacc cagaauacca ggaacagugc cggcaagaag ugcaagagcu ucugaaggac   1200

cgugaaccua uagagauuga augggacgac cuggcccagc ugcccuuccu gaccaugugc   1260

auuaaggaga gccugcgguu gcaucccccca gucccgguca ucucccgaug uugcacgcag   1320

gacuuugugc ucccagacgg ccgcgucauc cccaaaggca uugucugccu uaucaauauu   1380

aucgggaucc auuacaaccc aacuguguggg ccagacccug aggucuacga ccccuuccgu   1440

uucaaccaag agaacaucaa ggagagguca ccucuggcuu uuauucccuu cucggcaggg   1500

cccagaaacu gcaucgggca ggcguucgcc auggcugaga ugaagguggu ccuggcgcuc   1560
```

```
acguugcugc acuuccgcau ccugccgacc cacauugaac cccgcaggaa acccgagcug   1620

auauugcgcg cagagggugg acuuuggcug cgggguggagc cccugggugc gaacucacag   1680

ugacugcccu acccacccac ccaccuuugu agagucccag aaacaaaacu augcugacaa   1740

aaaaaaaaaa aaaaaaaaaa aaaaa                                         1765
```

<210> SEQ ID NO 9
<211> LENGTH: 7277
<212> TYPE: RNA
<213> ORGANISM: Homo sapiens

<400> SEQUENCE: 9

```
aggucagggg gcuggggacg cgcgugggga ucgcuacccg gcucggccac ugcugggcgg     60

acaccugggc gcgccgccgc gggaggagcc cggacucggg ccgaggcugc ccaggcaaug    120

cguucacucg gcgcaaacau ggcugcggcc cugcgcgccg cgggcguccu gcuccgcgau    180

ccgcuggcau ccagcagcug gagggucugu cagccaugga gguggaaguc aggugcagcu    240

gcagcggccg ucaccacaga aacagcccag caugcccagg gugcaaaacc ucaaguucaa    300

ccgcagaaga ggaagccgaa aacuggaaua uuaaugcuaa acaugggagg cccugaaacu    360

cuuggagaug uucacgacuu ccuucugaga cucuucuugg accgagaccu caugacacuu    420

ccuauucaga auaagcuggc accauucauc gccaaacgcc gaacccccaa gauucaagag    480

caguaccgca ggauuggagg cggauccccc aucaagauau ggacuuccaa gcagggagag    540

ggcaugguga agcugcugga ugaauugucc cccaacacag ccccucacaa auacuauauu    600

ggauuucggu acguccaucc uuuaacagaa gaagcaauug aagagaugga gagagauggc    660

cuagaaaggg cuauugcuuu cacacaguau ccacaguaca gcugcuccac cacaggcagc    720

agcuuaaaug ccauuuacag auacuauaau caagugggac ggaagcccac gaugaagugg    780

agcacuauug acagguggcc cacacaucac cuccucaucc agugcuuugc agaucauauu    840

cuaaaggaac uggaccauuu uccacuugag aagagaagcg agguggucau ucuguuuucu    900

gcucacucac ugcccauguc uguggucaac agaggcgacc cauauccuca ggagguaagc    960

gccacugucc aaaaagucau ggaaaggcug gaguacugca accccuaccg acuggugugg   1020

caauccaagg uugguccaau gcccugguug gguccucaaa cagacgaauc uaucaaaggg   1080

cuuugugaga gggggaggaa gaauauccuc uugguuccga uagcauuuac cagugaccau   1140

auugaaacgc uguaugagcu ggacaucgag uacucucaag uuuuagccaa ggagugugga   1200

guugaaaaca ucagaagagc ugagucucuu aauggaaauc cauuguucuc uaaggcccug   1260

gccgacuugg ugcauucaca cauccaguca aacgagcugu guuccaagca gcugacccug   1320

agcuguccgc ucugugucaa uccugucugc agggagacua aauccuucuu caccagccag   1380

cagcugugac ccccgccggu ggaccccgug gcguuaggca aaugcccaac cuccagauac   1440

cuccgaugug gagagggugu uauuuagaga ucaaggaagg aagucauccu uccuugauau   1500

auauacagcc uuuggguaca aauugugugg uuucuugagg auuggacucu ugauggauuu   1560

cuauuuuuau auaacuauac aguaagcauu uguauuuucu cucucuaggu auaaguuacu   1620

aguuuggaau guccaucagg accuuuaaua aaugaguuaa aaauuugucu uaugagacac   1680

accuauuuaa guacagauuu uggcuuuauu gcccaaaacc cuccugaaag gguacggaga   1740

guccccucug ugggcuggca gugugaauga gaucuguuua gucucgugca uauaguugcu   1800

guuuuuuaaa ugaacacagu ugaguauuug aagugaauuu gaaaaagaaa uguuacuuaa   1860

ucuuucccua agcccauggg uuacagaaug cuagggaggc aauuugguua ccugcaaugg   1920
```

```
cugcuuuugc cagcgaggcc accauucauu ggucaucuug guauuugugu gugaaucuca   1980
cuuuccucaa uguaaaaagg aaucaaguau ggauuucaga ggugcucuua gauuccccau   2040
acacccaagg guaauaaacg uguacaagua caguguucau gauacgugcc uuggugggag   2100
uccguggugc cacagggaag ggcucccac ugcuucuggu cuccagggac agugcugcug   2160
gaaaggcuag ugaugagcuu cacccuggag cuccucccgg gaccuugcaa gccucuccau   2220
ccagcaucuu cucuaucuua guugaaugcc uucuuucuga acauuuguuu uaagaauuau   2280
uuuauaaagu caacaauacu uugcuugaau ucuuucuuaa uuuacgauuu uuuauuauaa   2340
aaauguauag ugauacaaug ggacauguga agaauacaga aaaguaacca cuuuaaugca   2400
auaacuguua ucauaauauu guauuucgug guaguccuuu ccuguagaua uuuuuaaugc   2460
cauuuaaugc cauugucacc uuggauuuau gagugaaaag uguuucuaaa aauauagaaa   2520
uaaugucaga ucagagucug aucuucuaug uuuguauuua aauggauuaa aagaucccg    2580
gugguuccau gaagaauuug uaaagaucac uuucucuuuc cuccaagccc ugaaacuuug   2640
uucuucaaaa gagcguuucu uuuuuuuuuu uuuuuuagcc aguuuauaaa guggaaguau   2700
uaggagauuc auaaaucuuc uauauugaga auuggcuaug uuaauaaaua uuacaacauc   2760
auuaagguuu uagcuaaguu ugauucaugc ugucuguuaa aucaaaacug aucuaaauca   2820
gaauuauuaa augugaggag cuuuuuuaau acaggaaaag aaacauguca uccacuugag   2880
uuaauaguuu uccuacguug augacagccc ucaugaguag cauccacauu uuuaaaauuu   2940
caaauugguu uuucuacuag uagauugugu uucuagagaa agauacaagg cauaggugau   3000
uguuuaggau uuuccucuag ccuuugccau uaccuuuuug gggaugaggu ucacaguaga   3060
cuuugaguga ccgucccacc gugaagugaa uucucugagc ugguggugug gugcuggaag   3120
gaagguuauu uuuggagcca cucucucccc uuaaggauau uucccaaggg ccugcuucaa   3180
uucuuugaug acuuuagagg ugaaaaaaua uuuuuaugga gaugaugcag aaaacuccaa   3240
uucaggagcc cuugcgagua uaucugaagc acuuauuugc uaaggaaacc ugaauugaua   3300
gcaguacugu gcugucugga auaaugucuu ugauacugag uugggaccag acuggcuuuu   3360
auagugacag gcaaagagga auuuauugag aucacugcuc auggcauuug uugcuguaag   3420
aaguguugcc uuugauuguu acuaaccacg gaugguaac ggucauacau uaggcuagug    3480
uuugguagga caaaaucuuu uuagagcuuu gagaauuguc auccuguugg ucaacuuuga   3540
aauacaaaug uuugcccugg uaauuagcaa ugaacugcug gcaguuucuu cagcugugua   3600
uauacggauc uggcuuuuaa uugaugaauc aacuucuaca gaaacuuuug cagggacagu   3660
guugaugagg caguuuagcu ugccagggug augauaaagc ccaggucccu gcauguauag   3720
ugcucuucua aagaauaugc auucuugaac uacuuaacuu uuuaaaaauc acaauaaauu   3780
uuugcacuca aaauuugcuu cguaucagga gaaaugaacu cauuguuuug uuuuguuuuu   3840
uuuuuuuuuu aagauggagu cuugcuaugu cacccaggcu ggagggcagu ggugcgaucu   3900
cggcucacug cuacuuccac cuccugggcu caagugaucc ucccaccuca gccuccaagu   3960
agcugggacu acaggagugc uucaccacgc ugggcuacuu uuuuauauuu uuuguagaga   4020
uggggguuug ccauguuguc caggcugguc uugaacuccu gggcucaagg gauucuccug   4080
ccucagucuc ccaaagugcu gggauuacaa ggaugagccu cugcaccugg cccugaacuc   4140
auuauuaaaa gcccuuuaaa ugugaggcug ggugccgugc cuuacaugug uaauuccaau   4200
acuuuggaag gccaagguug gaggauugcu ugaucccaag aguucaagac cagccugggc   4260
```

-continued

```
aacauaggga gacccugacu cuacaaaaaa uaaaguaaaa auuaacuggg uguaguguca   4320
caugccugua guuccagcua cuuaggaggc ugagguggua ggauugcuug agcccagcag   4380
uuugagguug cagugaggug ugauugcacc acugcacucc agccugggug acagaggaag   4440
acccuguccc aaaaccaaaa aaaagaaaag aaauacagag acugggucau uuacaaagga   4500
aagagguuua auugacucgg uucggcuuuc ugaggaagcc uuaggaaauu gacaaucaug   4560
gcagaagggg aagcagaugu cuuacauggc agugagugag agcaagcaaa ggggaagagc   4620
ccccuuauaa aaccaucaga ucucgugaga acuggcuguc acaagaacag caugggggaa   4680
cugucuccau guuccaaucu ccuuccacca ggucccuccc ucaacacgug gggauuaugg   4740
ggauuacaau uugaaaugag auuugggugg ggaacagagc caaaucauau cauuccaccc   4800
uggccccucc caaaucacau guccuuuuua cauuucaaaa ccaaucaugc cuucacaaca   4860
guccuccaga gucuuaacuc auuccagcau uaacccaaaa guccaaguuc aaagucucau   4920
ccaagacaag gcaagucccu ucugccugug agccuguaac auuaaaagca aguuagugac   4980
uuccaagaua caaugggagu acagacauug guaaauguuc ccauuccaaa ugggagaaau   5040
uggccaaaac acaggggcua caggccccau gcaccacugc acuccacugu gcaagucuga   5100
aacccggcag ggcacuccuu aaauuuuuuu uuuuuuuuuu ugagauggag ucucgcucug   5160
uugcccaagc uggaguacag uggcacgauc ucggcucacu gcaaccuccg ccucuugggu   5220
ucaaaggauc auccugccuc agccuccgga guagcugggc uacucaggcg ugugccacca   5280
ugcccggcua auuuuuguau uuuuaguaga gauggggccu gaccauguug gucaggcugg   5340
ucucuaauuc cugaccucgu gauccacccg ccucagccuc ugaaaguguu gggauuacag   5400
gcgugagcca ccauccccgg ccuacucaau aaaucuuaaa guuccggaau aaucuccuuu   5460
gacuccaugu cucaccucca ggucacgcug augcaagagg ugggcuaauc uuucuaguaa   5520
auuccauauu uaauucaaga aaccauaacu uaaggcaugu aaaagagauc cuuugcucaa   5580
ugugaugcca uugugcuuau ccaaaguaua uuauuauuac ccacaaaggg ugagagauua   5640
ggcugcagcc auaccccaag uggagugagc agcaagaccu gcccccugcu cagaguguag   5700
augacugggg gcaccugcau uccuaggggc ucugccguau gagcuccugu cgaugcggca   5760
aaggaccacc uugcccaacg acagcgggaa ggcagaauuu aaagcuggca gcuguaagcg   5820
aacgucuaug ugugcgcacg gggcacgug aaggcacagg ugcaucagcc aagaaccucc   5880
aauucaccuc uuaaccuucu caccucaccu gaaaccccuu cugccagaau ccugaaggug   5940
gcccaggaac agggcuccua acguuaggug gaaaugggaa auucauugag augucacaag   6000
cuggaauaag aaaauucuga gcucacccgg aaacuaaugc ccuaaauuaa gauuauucag   6060
cuucucaauu uuuaauagca aaauggagac cugagugugg auaacuuuua guaucugugg   6120
gggauccugg aaccaauucc cugccaauau agaaggacaa cugucuacag uacuugaagu   6180
auuauuaacu acauucgcca ugcuguaugu uagaucccca gaacauauuu auccugcaua   6240
ucuaaaauuu ugaucauuuu acaaacuuuc uauuuuuuuu gucaauuuuc uccagcuaga   6300
cacuugugca auacggcuau uaucugaucu uugccuuaaa uguugugcuu cuuuuccaua   6360
ugcacguauu uugcaaaaua uaaagugugu agagcuauau agcacucagc caaguggugg   6420
guaccugcag gugcuucaga gaaguaaauu gaugcugcua auauuuguug aauggcacga   6480
auaugaugag caauagcagg uggugcccuu cagccagacc aucgcuccgu gcgucugaug   6540
caucuugcca aagaguaguu cugggaggug guugccucua gagaacacau uccuccuauu   6600
cuggggaccc gugagagaaa gaaaugcuuu ugcuuuugau gugggacucu uacuaagccu   6660
```

```
uucuucagag aaaaggaagu gaaaaaugca ccccaugaua aucaguuucu uacaacauac   6720

ugugauagua ccggcuucgu uguuuuuagc uggaaucauu agcuuccauu uuuagaauaa   6780

cagcuauugg cuaaauuagg cuacaguagg ccauuaagau ggauguugga auuaaaaaca   6840

uuuuuggaaa aaagccugcu uugagccuuu guuauaagcc cuuggguaga gaucuggguc   6900

cuguuucuga uuucuuguga gccuucacuc ugacaguuuu guuuccagaa acacacucuu   6960

agccugcucc ugaaauggga acagacaggc caacuucccc ucuccagucu ccccugcggg   7020

ucaaagcuuu acuuuccugu cauguuaaga aagaauagau uuaaccuuga uaauccaugu   7080

aguauucugu auuuuuaccu uuuccuuauc ugaaaaaaag uguauauaug gcauggaauu   7140

gauugcacag gcacauggca uguuggcuug ugaaccaauu guuaaaauuu caaguuaaauc  7200

auuaaaauaa uaucuuucaa auuaaguuau auuaaaaaca aagguaacau ucuaaauuca   7260

aaaaaaaaaa aaaaaaa                                                  7277
```

<210> SEQ ID NO 10
<211> LENGTH: 889
<212> TYPE: RNA
<213> ORGANISM: Homo sapiens

<400> SEQUENCE: 10

```
gcaguucggc ggucccgcgg gucugucucu ugcuucaaca guguuuggac ggaacagauc     60

cggggacucu cuuccagccu ccgaccgccc uccgauuucc ucuccgcuug caaccuccgg    120

gaccaucuuc ucggccaucu ccugcuucug ggaccugcca gcaccguuuu ugugguuagc    180

uccuucuugc caaccaacca ugagcuccca gauucgucag aauuauucca ccgacgugga    240

ggcagccguc aacagccugg ucaauuugua ccugcaggcc uccuacaccu accucucucu    300

gggcuucuau uucgaccgcg augauguggc ucuggaaggc gugagccacu ucuuccgcga    360

auuggccgag gagaagcgcg agggcuacga gcgucuccug aagaugcaaa accagcgugg    420

cggccgcgcu cucuuccagg acaucaagaa gccagcugaa gaugaguggg guaaaacccc    480

agacgccaug aaagcugcca uggcccugga gaaaaagcug aaccaggccc uuuuggaucu    540

ucaugcccug gguucugccc gcacggaccc ccaucucugu gacuuccugg agacucacuu    600

ccuagaugag gaagugaagc uuaucaagaa gaugggugac caccugacca accuccacag    660

gcuggguggc ccggaggcug ggcugggcga guaucucuuc gaaaggcuca cucucaagca    720

cgacuaagag ccuucugagc ccagcgacuu cugaagggcc ccuugcaaag uaauagggcu    780

ucugccuaag ccucucccuc cagccaauag gcagcuuucu uaacuauccu aacaagccuu    840

ggaccaaaug gaaauaaagc uuuuugaugc aaaaaaaaaa aaaaaaaaa                889
```

<210> SEQ ID NO 11
<211> LENGTH: 5000
<212> TYPE: RNA
<213> ORGANISM: Homo sapiens

<400> SEQUENCE: 11

```
acccgucgcc acgcccgccg caggccaagg gccagucacu ugcgggccgg cgucccgcag     60

cccauucgcg ccccgccccu gccccgccgc gggaugagua acgguuacga agcacuuucu    120

cggcuacgau uucugcuuag ucauugucuu ccaggaaaca gcucccucag uuuggaauca    180

gcucucccgc ugcggccgca guagccggag ccggagccgc agccaccggu gccuuccuuu    240

cccgccgccg cccagccgcc guccggccuc ccucgggccc gagcgcagac caggcuccag    300
```

-continued

```
ccgcgcggcg ccggcagccu cgcgcucccu cucgggucuc ucucgggccu cgggcaccgc    360
guccuguggg gcggccgccu gccugcccgc ccgcccgcag ccccuucgcu gcgcggcccc    420
ugggcggccg cugccauggg caccgacagc cgcgcggcca aggcgcuccu ggcgcgggcc    480
cgcacccugc accugcagac ggggaaccug cugaacuggg gccgccugcg gaagaagugc    540
ccguccacgc acagcgagga ggaguuucca gaugucuugg aaugcacugu aucucaugca    600
guagaaaaga uaaauccuga ugaaagagaa gaaaugaaag uuucugcaaa acuguucauu    660
guagaaucaa acucuucauc aucaacuaga agugcaguug acauggccug uucaguccuu    720
ggaguugcac agcuggauuc ugugaucauu gcuucaccuc cuauugaaga uggaguuaau    780
cuuuccuugg agcauuuaca gccuuacugg gaggaauuag aaaacuuagu ucagagcaaa    840
aagauuguug ccauagguac cucugaucua gacaaaacac aguuggaaca gcuguaucag    900
ugggcacagg uaaaaccaaa uaguaaccaa guuaaucuug ccuccugcug ugugaugcca    960
ccagauuuga cugcauuugc uaaacaauuu gacauacagc uguugacuca caaugaucca   1020
aaagaacugc uuucugaagc aaguuuccaa gaagcucuuc aggaaagcau uccugacauu   1080
caagcgcacg agugggugcc gcuguggcua cugcgguauu cggucauugu gaaaaguaga   1140
ggaauuauca aaucaaaagg cuacauuuua caagcuaaaa gaagggguuc uuaacugacu   1200
uaggagcaua acuuaccugu aauuuccuuc aauaugagag aaaauugaga uguguaaaaa   1260
ucuaguuacu gccuguaaau ggugucauug aggcagauau ucuuucguca uauuugacag   1320
uauguugucu gucaaguuuu aaauacuuau cuugccucca uaucaaucca uucucaugaa   1380
ccucuguauu gcuuuccuua aacuauuguu uucuaauuga aauugucuau aaagaaaaua   1440
cuugcaauau auuuuuccuu uauuuuuaug acuaauauaa aucaagaaaa uuuguuguua   1500
gauauauuuu ggccuaggua ucaggguaau guauauacau auuuuuuauu uccaaaaaaa   1560
auucauuaau ugcuucuuaa cucuuauuau aaccaagcaa uuuaauuaca auuguuaaaa   1620
cugaaauacu ggaagaagau auuuuuccug ucauugauga gauauaucag aguaacugga   1680
guagcuggga uuuacuagua guguaaauaa aauucacucu ucaauacaug aauggaaacu   1740
uaaauuuuuu uuuauguguc cuugcuuaua guuuagcugu aauaauuuaa ccuuguauuc   1800
uugugccaua uucugucuuu uuauuacuua uaaagacaaa ccaaaguaaa ucugaaagga   1860
gacuagaagc uuugaaauua uuguuugggg guuuuauaaa agcaacuacu gucaccucca   1920
uccagauucu uuuaaauuau ugauccaucc auaguauaua uugcuacuca uucaagaauc   1980
cucaauaagu auugaguauu uaccauaugu ugggauacug ugggcucugg agagaggagg   2040
gggcaauaga gcuaggaauu aagaaucagu ugaguaaaau guguaauauu uauuccccau   2100
uaauaacuga cuaggaagga cuaaaagcca gaaaggggau gaaaaaaaaa uccuuaauuc   2160
agggccgaca uuaucuacuu aaacaacuuu gagauauggu cuuaauuauu uuaaagcaga   2220
auaauauaau ugaaaguuua uagcuaaaag agacuauaua ggucauuuag uauaauucuu   2280
cauuaguuua cgaaccacaa aauugcaaau aaauaagcua ugaacuuuga uguacacuau   2340
aaaucuccuu aauucuauaa auuugugucu guaaccugaa uaguuugaaa acuucuuuaa   2400
aaaucucuug uauuucaucc gggcgcagug gcucacaccu guaaucccag cacuuuggga   2460
ggccgaggug ggcagaucac gaggucagga guuugagacc agccugacca acaugguaaa   2520
accccaucuc uacuaaaaua caaaaauugg cugggcgugg uggcacucgc cuguaaucuc   2580
agcuacuugg gaggcugagg caggagaauc gcuugaaccc gggaggcgga gguuacagug   2640
agccgagauc acaucacugc acuccagccu gggcgacaga gcgagacucc aucucaaaaa   2700
```

-continued

```
aaaaaaaaaa cucuuguauc ucaauauuuu uaaaccacag gccuaaauaa aacuaauuuu   2760
gcucaaguuu ucucaaccua gggaaaaaga acuaugguuc cauauucaaa auaaauauua   2820
uagacccuuu uccuaaguag gauuuugugg uuuacugauu ggguaauuug aucauuaaaa   2880
uuaugugaaa ucugcccggg cacaccucau gccuguaauc ccagcacucu gggaggccaa   2940
ggcagaugau caccugaggu caggaguucu agaccagccu ggcuaacaug gugaaacccu   3000
guaucugcua aaaauacaaa aauuagccag gcgugguggc gggcuccugu aaucccagcu   3060
acuuuggagg cgaggcacga gaaucgcuug aaccugggag gcggaguuug cagugagccg   3120
agaucacgcc auugcacucc agccugggcg acagagcgag acugcgucuc aaaaaaaaaa   3180
aaaaaagaaa aauuauguga aaucauguga uuugccuggg aaaacuuguu uagauauuga   3240
gcuacuuaug ccuucuagcc uuuauauuaa uuguauguaa uguuauuaaa uauauauaua   3300
guucaucuuu acauuuggaa augcccaaca uuuuuuucau auaaguccuu aaacaagcgu   3360
ucauuuuauu uuaaaucuau acagugaacu ggccaagaua uuuuaagagg gaacuuuaau   3420
aucccauuua uuguuuuuau aacccuggac uuauaaaaau ggguuguuug aaggguuauu   3480
uugaaagugg gggaaaaaaa aacuuaguug cuaauguauc uaaacuucag cagagcuuuu   3540
uggugaucuc cuaccugcac ccucaacucu ugacaaagaa gcaagacuau agauucauuu   3600
ucugaagggg aucauguaug gaauuuuuug augaguuuuu acuuuuaccu cucuacucuu   3660
gauuuucuau uauugaauac ucuuuuaaaa cacugauuuu uaaggcuuua uauauguuuu   3720
ccaggcugau guucacaucu uuuuuucaug aacuaucaga auauagugaa cacuuuucaa   3780
auauuuaagg acuuaauguu uaaaaagcca uaaaauagag agugguaaua cuaccaaaua   3840
auuacuuaaa acugaaagcu aaguuaucaa uaguuuauau aagagauguu uucugaggag   3900
augugcaucc agugagacca agguagaaag uuuauauaau uguuuuuuuu ccaguaaaua   3960
ugaaaaaaaa agcuguagcu uguuuauuac auguccaaaa uacaguggag ccuuacuuua   4020
acacaaugua cuguaacuug gaauuuguuc uguuaugagu cuaucuugaa uucccaucca   4080
ugaaacugua gucaccaaaa gcaacaagua uuuucacaug auguaaaaga ccauacuaug   4140
auggccauug cuagaaauug aaucacaaau aauagcuaau aauuuuucau uuuucaaaaa   4200
agaucauuug gauagcagcu auguauaaaa uggaaaauaa aaaauuauuc uauuuugcau   4260
gaauaguuca gacuuuccca uaccacagcc aagcaguaac uaaaauuagg aucuuaauuu   4320
ucaaugauaa aaggucuaag guucauuuaa uuaugcuccu uuaacacugu cuuucuagau   4380
uuuucaccca guauuuucaa aauuugggaa uguaaacaau ugauauauuu auuguauguu   4440
ggcuagcagu ucauccuucu gcaaaauaug cauucagaga aaugugaagc uuguuuuaau   4500
gaagacuuaa accauuugug ucauuugugu uuucauauuc aaauacacca aauuaaaauu   4560
cugaaccuau auuuuucauc auuaacuucc uaauauacca gaacauauac cuuuuucaug   4620
uaaaguuggc aaugggauau ggcaguuuua uuuuugaaaa auauguaaca ugacuuuaau   4680
auuuuuauag uuuucagaau uagaaacaua ggaagggaaa auguuuuaau uagauaaguc   4740
aacuuuuuau gugucuguag ugguguacua uaauagcaaa uuauaaagca uuauuaaaug   4800
uuuauaauaa uuuuuaauau uaccuacauu augaauuuaa cuaaaauaaa gugugaguug   4860
uauauuuuuu aauuggguug uuucaauagc uggaagcauc cugaagcauu auauugauuu   4920
uugaacuauu ugaacucaaa cugaguauga uuugaaaaua aauuaauaau uuaaaaacau   4980
ccaaaaaaaa aaaaaaaaaa                                               5000
```

<210> SEQ ID NO 12
<211> LENGTH: 2928
<212> TYPE: RNA
<213> ORGANISM: Homo sapiens

<400> SEQUENCE: 12

```
uccuccuggg ucuugccuag cggcgggcgc augcuuaguc accgugaggc ugcgcuugcc     60
cggggcccgc gcccccccuac cccggggacc gcccccgggc cgcccgcccc acuuggcgcg    120
ccacuuccgc gugcauggcc cugcugcccc gagcccugag cgccggcgcg ggaccgagcu    180
ggcggcgggc ggcgcgcgcc uuccgaggcu uccugcugcu ucugcccgag cccgcggccc    240
ucacgcgcgc ccucucccgu gccauggccu gcaggcagga gccgcagccg cagggcccgc    300
cgcccgcugc uggcgccgug gccuccuaug acuaccuggu gaucgggggc ggcucgggcg    360
ggcuggccag cgcgcgcagg gcggccgagc ugggugccag ggccgccgug guggagagcc    420
acaagcuggg uggcacuugc gugaauguug gauguguacc caaaaaggua auguggaaca    480
cagcugucca cucugaauuc augcaugauc augcugauua uggcuuucca aguugugagg    540
guaaauucaa uuggcguguu auuaaggaaa agcgggaugc cuaugugagc cgccugaaug    600
ccaucuauca aaacaaucuc accaaguccc auauagaaau cauccguggc caugcagccu    660
ucacgaguga ucccaagccc acaauagagg ucagugggaa aaaguacacc gccccacaca    720
uccugaucgc cacagguggu augcccucca ccccucauga gagccagauc cccggugcca    780
gcuuaggaau aaccagcgau ggauuuuuuc agcuggaaga auugcccggc cgcagcguca    840
uuguuggugc agguuacauu gcuguggaga uggcagggau ccugucagcc cuggguucua    900
agacaucacu gaugauacgg caugauaagg ggauucaaac cgaugacaag ggucauauca    960
ucguagacga auuccagaau accaacguca aaggcaucua ugcaguuggg gauguaugug   1020
gaaaagcucu ucuuacucca guugcaauag cugcuggccg aaaacuugcc caucgacuuu   1080
uugaauauaa ggaagauucc aaauuagauu auaacaacau cccaacugug gucuucagcc   1140
acccccccuau ugggacagug ggacucacgg aagaugaagc cauucauaaa uauggaauag   1200
aaaaugugaa gaccuauuca acgagcuuua ccccgaugua ucacgcaguu accaaaagga   1260
aaacaaaaug ugugaugaaa auggucugug cuaacaagga agaaaaggug guugggaucc   1320
auaugcaggg acuugggugu gaugaaaugc ugcaggguuu ugcuguugca gugaagaugg   1380
gagcaacgaa ggcagacuuu gacaacacag ucgccauuca cccuaccucu ucagaagagc   1440
uggucacacu ucguugagaa ccaggagaca cguguggcgg gcagugggac ccauagaucu   1500
ucugaaauga aacaaauaau cacauugacu uacuguuuga guuuuaugua uuucuuuauu   1560
uuaaucagga ucuucugaua guggaaauuu uuaguacaua auagaacuua uuuauggagu   1620
uagaaauuug uaguguuauc caggauugau uuucauuuga ucacaucuca caguaauuaa   1680
uauuuucaag uuuuuuuuuu auuaacagcu cugugcuagu uuuuuuuuuc uguuuuagcc   1740
ucaucccaaa uauaaagcuu ugugaaguac aauuaacuua auguacuuga augaauagaa   1800
cuugcuacuu uuuuuuuuuu uuuuuuugag acagaguuuu gcucucauug cccaggcugg   1860
agugcggugg ugcuauuuca gcucaccaca accucugccu ccuggguuca agugauucuc   1920
cugccuuagc cucccgaaua gcuggaauua caggcacgca ccaccaugcc ugacuaauuu   1980
uguauuuuua guagacaugg gguuucucca uguuggucag gcuggucuca aacucccacc   2040
uucaggugau ccgcccaccu cggccuccug aggugcugag auuacaggcg ugagccacug   2100
ugccagcuug cuaauuuuca cagaaguuga uggcaauucu ucacauguaa acagugccag   2160
```

```
ugcacagaac cuuuauauau uuuuugaagc caguacugug cucugcauau aacaaagcug   2220

cuucaaggau gagaccuuuu ucuaaaagca uguaauguga gaagccggcc ugccuuauuu   2280

ucuuuuuucu uuuuuaauga uuaaaaaauag uuuguggcaa ggcacggugg cucaggccug   2340

uaauucuagc acuuugggag gccgaggcag gaggauuacu ugagccuaca aguuugaggc   2400

cagcaugcac agcauagcaa gacugcaucu cuacagagag uaaaaaaaau uacccgagug   2460

uggugaugug caucuguaau cucagcuacu ugggaggcug aggugagagg aucacuugag   2520

cuugggugag gugaggcugc agugaguccu gaucaugcug cugcacucaa ucuuggacaa   2580

cagagcaaga cccugucuca aaaaaaaaaa aaaaaaauau auauauauau auauauuauu   2640

uuuaugaggu gaagugcauc aaacuuggga aagauuugag gaggcuggga accuccugga   2700

aaaccacucc uugaagaaag auaugagaga cauuuagaag ugauuccugc uuucagaagg   2760

agguggauuc aaauacauca aaagucccuu ccucugcuaa guguuuauag uucaaugaau   2820

aauuucaaua uuuguaugug uucuugucau uuuauuuuuu ucugaaaaac uuccaaaaau   2880

uugaaaauaa aauuacagcc uuuucuucuu auaaaaaaaa aaaaaaaa               2928
```

<210> SEQ ID NO 13
<211> LENGTH: 1774
<212> TYPE: RNA
<213> ORGANISM: Homo sapiens

<400> SEQUENCE: 13

```
gcaguucuuu gaauuucuca cccuaagauc uggccuguac auuuucaagg aauucuugag     60

agguucuugg agagauucug ggagccaaac acuccauugg gauccuagcu ggaauauaaa    120

gaauggcuua ucaguggaga ccaucgacag uugagaaaag aagaagccca aaaaguacaa    180

gaaugaaaau cgagaguuuu uagagaacaa cuuguaaugg agccuucauc ucuugagcug    240

ccggcugaca cagugcagcg cauugcggcu gaacucaaau gccacccaac ggaugagagg    300

guggcucucc accuagauga ggaagauaag cugaggcacu ucagggagug cuuuuauauu    360

cccaaaauac aggaucugcc uccaguugau uuaucauuag ugaauaaaga ugaaaaugcc    420

aucuauuucu ugggaaauuc ucuuggccuu caaccaaaaa ugguuaaaac auaucuugaa    480

gaagaacuag auaagugggc caaaauagca gccuaugguc augaaguggg gaagcguccu    540

uggauuacag gagaugagag uauuguaggc cuuaugaagg acauuguagg agccaaugag    600

aaagaaauag cccuaaugaa ugcuuugacu guaaauuuac aucuucuaau guuaucauuu    660

uuuaagccua cgccaaaacg auauaaaauu cuucuagaag ccaaagccuu cccuucugau    720

cauuaugcua uugagucaca acuacaacuu cacggacuua acauugaaga aaguaugcgg    780

augauaaagc caagagaggg ggaagaaacc uuaagaauag aggauauccu ugaaguaauu    840

gagaaggaag gagacucaau ugcagugauc cuguucagug ggguccauuu uuacacugga    900

cagcacuuua auauuccugc caucacaaaa gcuggacaag cgaaggguug uuauguuggc    960

uuugaucuag cacaugcagu uggaaauguu gaacucuacu uacaugacug gggaguugau   1020

uuugccugcu gguguuccua caaguauuua aaugcaggag caggaggaau ugcuggugcc   1080

uucauucaug aaaagcaugc ccauacgauu aaaccugcau uagugggaug guuuggccau   1140

gaacucagca ccagauuuaa gauggauaac aaacugcagu uaaucccugg ggucugugga   1200

uuccgaauuu caaauccucc cauuuuguug gucuguuccu ugcaugcuag uuuagagauc   1260

uuuaagcaag cgacaaugaa ggcauugcgg aaaaaaucug uuuugcuaac uggcuaucug   1320
```

```
gaauaccuga ucaagcauaa cuauggcaaa gauaaagcag caaccaagaa accaguugug   1380

aacauaauua cuccgucuca uguagaggag cgggggugcc agcuaacaau aacauuuucu   1440

guuccaaaca aagauguuuu ccaagaacua gaaaaaagag gagugguuug ugacaagcgg   1500

aauccaaaug gcauucgagu ggcuccaguu ccucucuaua auucuuucca ugauguuuau   1560

aaauuuacca aucugcucac uucuauacuu gacucugcag aaacaaaaaa uuagcagugu   1620

uuucuagaac aacuuaagca aauuauacug aaagcugcug ugguuauuuc aguauuauuc   1680

gauuuuuaau uauugaaagu augucaccau ugaccacaug uaacuaacaa uaaauaauau   1740

accuuacaga aaaucugaaa aaaaaaaaaa aaaa                                1774
```

<210> SEQ ID NO 14
<211> LENGTH: 3519
<212> TYPE: RNA
<213> ORGANISM: Homo sapiens

<400> SEQUENCE: 14

```
cucacacgcc ggcucggaug aucuccugcc augacucagc gcuucucgca ggcugcccug     60

cuggggacac cggcuucgcu cgggccccuc ccgacgcguc cacccccucu cgccacccac    120

gcccgccccc agccgcuggg ccuuucccag ugcggccgcc gccgccacag cugcagucag    180

caccgucacc ccagcagcau ccgccgccug caccgcgcgu gcggcccgcc ccggccugac    240

cccgccgccg aacccggcgc cagccaugga gcccgaagcc ccccgucgcc gccacaccca    300

ucagcgcggc uaccugcuga cacggaaccc ucaccucaac aaggacuugg ccuuuacccu    360

ggaagagaga cagcaauuga acauucaugg auuguugcca ccuuccuuca acagucagga    420

gauccagguu cuuagaguag uaaaaaauuu cgagcaucug aacucugacu uugacaggua    480

ucuucucuua auggaucucc aagauagaaa ugaaaaacuc uuuuauagag ugcugacauc    540

ugacauugag aaauucaugc cuauuguuua uacucccacu gugggucugg cuugccaaca    600

auauaguuug guguuucgga agccaagagg ucucuuuauu acuauccacg aucgagggca    660

uauugcuuca guucucaaug cauggccaga agaugucauc aaggccauug uggugacuga    720

uggagagcgu auucuuggcu ugggagaccu uggcuguaau ggaaugggca ucccuguggg    780

uaaauuggcu cuauauacag cuugcggagg gaugaauccu caagaauguc ugccugucau    840

ucuggaugug ggaaccgaaa augaggaguu acuuaaagau ccacucuaca uuggacuacg    900

gcagagaaga guaagagguu cugaauauga ugauuuuuug gacgaauuca uggaggcagu    960

uucuuccaag uauggcauga auugccuuau ucaguuugaa gauuuugcca augugaaugc   1020

auuucgucuc cugaacaagu aucgaaacca guauugcaca uucaaugaug auauucaagg   1080

aacagcaucu guugcaguug caggucuccu ugcagcucuu cgaauaacca agaacaaacu   1140

gucugaucaa acaauacuau uccaaggagc uggagaggcu gcccuaggga uugcacaccu   1200

gauugugaug gccuuggaaa aagaagguuu accaaaagag aaagccauca aaaagauaug   1260

gcugguugau ucaaaaggau uaauaguuaa gggacgugcu uccuuaacac aagagaaaga   1320

gaaguuugcc caugaacaug aagaaaugaa gaaccuagaa gccauuguuc aagaaauaaa   1380

accaacugcc cucauaggag uugcugcaau ugguggugca uucucagaac aaauucucaa   1440

agauauggcu gccuucaaug aacggccuau uauuuuugcu uugaguaauc caacuagcaa   1500

agcagaaugu ucugcagagc agugcuacaa aauaaccaag ggacgugcaa uuuuugccag   1560

uggcaguccu uuugauccag ucacucuucc aaauggacag acccuauauc cuggccaagg   1620

caacaauucc uauguguucc cuggaguugc ucuuggugu uguggcgugug gauugaggca   1680
```

```
gaucacagau aauauuuucc ucacuacugc ugagguuaua gcucagcaag ugucagauaa   1740

acacuuggaa gagggucggc uuuauccucc uuugaauacc auuagagaug uuucucugaa   1800

aauugcagaa aagauuguga aagaugcaua ccaagaaaag acagccacag uuuauccuga   1860

accgcaaaac aaagaagcau uuguccgcuc ccagauguau aguacugauu augaccagau   1920

ucuaccugau uguuauucuu ggccugaaga ggugcagaaa auacagacca aaguugacca   1980

guaggauaau agcaaacauu ucuaacucua uuaaugaggu cuuuaaaccu uucauaauuu   2040

uuaaagguug gaaucuuuua uaaugauuca uaagacacuu agauuaagau uuuacuuuaa   2100

cagucuaaaa auugauagaa gaauaucgau auaaaauugg auaaacauca caugagacaa   2160

uuuugcuuca cuuugccuuc ugguuauuua ugguuucugu cugaauuauu cugccuacgu   2220

ucucuuuaaa agcuguugua cguacuacgg agaaacucau cauuuuuaua caggacacua   2280

augggaagac caaaauuacu aauaaauuga cauaaccaac auuaaaacuc auaauuauuu   2340

uguugaccau uuuguuaaaa ucuacuuuuc aaaaaaaaaa agcuagaaau gaaucuaggc   2400

guaggugaac uuuugcuaag cagaaauaac acuacuuugu ugccuagaga aagauaacuu   2460

cucaaguauu uuuauuccag uccuagauca uauauguucu uuugugcaac ggaauucuaa   2520

caguucuaag agaaagauca cugcuguuua cagcgccuug ugcagccuua gauuuuaaua   2580

uucuuuuguc auuguuacau cucauagagu aaagcucuua uuaccuugau ccugagucag   2640

aaaucccacc ugaaaucacc uuuuuucccc cuugaucaaa caucccaucc uucagcuacc   2700

auacuguugc uacagggauu uuguggacug uggccccugu cccgagguug gcaccuucag   2760

uucagcacag ccugagcagu gagaaggucu gaaaggagag uauauaguua agauccuuga   2820

gaaagggcug ccugaggaac ugaccucuua aagaucucag gaucuuuaag acaacaaguu   2880

agguuccuac uggaguuacc ugccagaaug gccucuuaau uaacucaggu aaugaagagc   2940

uaacuguguu auaaucaucu ugcuuuugcc ugaauuugga gaaaguauua uaauuaaguu   3000

cccaguauca gaaauguccu uacauaagau uaaaaauaucu ugaugacuaa uaccauucua   3060

ugagaaagag uaguuauaug cccagacugu auuaauuuac uuuagaaacu aauguuugaa   3120

guaauggaaa aaauuuuaaa uuauaaagcu aaggugcaau aacauuugcu acuuauuuau   3180

agaauuauuu gaagaauuuu guuuuugaag uaaugcuuua aggaguauaa gauauucaag   3240

auaaauuaua cuauaaaaug auuuuauuga aaguugaagg uuacacaaau uguuuuaggu   3300

augagcagaa gagguuaagg uauuucuaaa gguaacauau agucaagagu uuccucaaaa   3360

uaguuauuug gagaagaauc agaaugucug uguauuucuu gucuguuucu auguugucuu   3420

auagcucuga cuaaaugugu uuaccuaugc aaaagauuua uuaaagcaua gaaaagguga   3480

augaauaaaa auauaaaaua auuguccuuu uucuuaaaa                          3519
```

<210> SEQ ID NO 15
<211> LENGTH: 2917
<212> TYPE: RNA
<213> ORGANISM: Homo sapiens

<400> SEQUENCE: 15

```
ggcccuuccg gggcugcgcg gcuccccccgc cucggugccg gcaaaaaugu gccuagucac     60

ggggccgcuc ucgggggaac ugaggucgcc uucgggcugg gacccggagc cccuucgccg    120

cgccccaaga ccuccuugag ugcgggcugc gacgcgcuca ccccgcuggg ccgucugugg    180

gcgcggcuuu gcgaagucau ccaucucucg gaucacucuc uggcagccuu gagcucucuu    240
```

```
gaaagcccag ccccgggacg agggaggagc gccuuaagug cccagcgggc ucagaagccc    300
cgacgugugg cggcugagcc gggccccgcg cacuuucucg gccggggagg gguucgggcu    360
cgggcacccg gaguuggccc cucguaacgc cgcgggaaag ugcgggcgag ggcaguggac    420
ucugaggccg gagucggcgg cacccggggc uucuaguucg gacgcggugc cccuggugg     480
cgcucaccgc gcgcguggcc uuggcuuccg ugacagcgcu cgguuggccg ucacagcagc    540
ccucgguugg cccuuuccug cuuuauagcg ugcaaaccuc gccgcgccag ggccaaggga    600
cagguuggag cuguugaucu guugcgcaau ugcuauuuuc cccagagcgg cuuugucuuu    660
ggauuuagcg uuucagaauu gcaauuccaa aauguguaag acgggauauu cucuucugug    720
cugucaaggg acauggauuu gauugacaua cuuuggaggc aagauauaga ucuuggagua    780
agucgagaag uauuugacuu cagucagcga cggaaagagu augagcugga aaaacagaaa    840
aaacuugaaa aggaaagaca agaacaacuc caaaaggagc aagagaaagc cuuuuucgcu    900
caguuacaac uagaugaaga gacagguugc ccacauuccc aaaucagaug cuuuguacuu    960
ugaugacugc augcagcuuu uggcgcagac auucccguuu guagaugaca augagguuuc   1020
uucggcuacg uuucagucac uuguuccuga uauucccggu cacaucgaga gcccagucuu   1080
cauugcuacu aaucaggcuc agucaccuga aacuucuguu gcucagguag ccccuguuga   1140
uuuagacggu augcaacagg acauugagca aguuugggag gagcuauuau ccauuccuga   1200
guuacagugu cuuaauauug aaaaugacaa gcugguugag acuaccaugg uuccaagucc   1260
agaagccaaa cugacagaag uugacaauua ucauuuuuac ucaucuauac ccucaaugga   1320
aaaagaagua gguaacugua guccacauuu ucuuaaugcu uuugaggauu ccuucagcag   1380
cauccucucc acagaagacc ccaaccaguu gacagugaac ucauuaaauu cagaugccac   1440
agucaacaca gauuuuggug augaauuuua uucugcuuuc auagcugagc ccaguaucag   1500
caacagcaug cccucaccug cuacuuuaag ccauucacuc ucugaacuuc uaaaugggcc   1560
cauugauguu ucugaucuau cacuuugcaa agcuuucaac caaaaccacc cugaaagcac   1620
agcagaauuc aaugauucug acuccggcau uucacuaaac acaaguccca guguggcauc   1680
accagaacac ucaguggaau cuuccagcua uggagacaca cuacuuggcc ucagugauuc   1740
ugaaguggaa gagcuagaua gugccccugg aagugucaaa cagaaugguc cuaaaacacc   1800
aguacauucu ucuggggaua ugguacaacc cuugucacca ucucaggggc agagcacuca   1860
cgugcaugau gcccaaugug agaacacacc agagaaagaa uugccuguaa guccuggguca   1920
ucggaaaacc ccauucacaa aagacaaaca uucaagccgc uuggaggcuc aucucacaag   1980
agaugaacuu agggcaaaag cucuccauau cccauucccu guagaaaaaa ucauuaaccu   2040
cccuguuguu gacuucaacg aaaugauguc caaagagcag uucaaugaag cucaacuugc   2100
auuaauucgg gauauacgua ggaggguaa gaauaaagug gcugcucaga auugcagaaa    2160
aagaaaacug gaaaauauag uagaacuaga gcaagauuua gaucauuuga aagaugaaaa   2220
agaaaaauug cucaaagaaa aaggagaaaa ugacaaaagc cuucaccuac ugaaaaaaca   2280
acucagcacc uuauaucucg aaguuuucag caugcuacgu gaugaagaug gaaaaccuua   2340
uucuccuagu gaauacuccc ugcagcaaac aagagauggc aauguuuucc uuguucccaa   2400
aaguaagaag ccagauguua agaaaaacua gauuuaggag gauuugaccu uuucugagcu   2460
aguuuuuuug uacuauuaua cuaaaagcuc cuacugugau gugaaaugcu cauacuuuau   2520
aaguaauucu augcaaaauc auagccaaaa cuaguauaga aaauaauacg aaacuuuaaa   2580
aagcauugga gugucaguau guugaaucag uaguuucacu uuaacuguaa acaauuucuu   2640
```

```
aggacaccau uugggcuagu uucuguguaa guguaaauac uacaaaaacu uauuuauacu   2700
guucuuaugu cauuuguuau auucauagau uuauaugaug auaugacauc uggcuaaaaa   2760
gaaauuauug caaaacuaac cacuauguac uuuuuuauaa auacuguaug gacaaaaaau   2820
ggcauuuuuu auauuaaauu guuuagcucu ggcaaaaaaa aaaaauuuua agagcuggua   2880
cuaauaaagg auuauuauga cuguuaaauu auuaaaa                            2917

<210> SEQ ID NO 16
<211> LENGTH: 2423
<212> TYPE: RNA
<213> ORGANISM: Homo sapiens

<400> SEQUENCE: 16

auccuccgcc cagcacccca ggauucaggc guugggaccc gcccuuguag gcuguccacc     60
ucaaacgggc cggacaggau auauaagaga gaaugcaccg ugcacuacac acgcgacucc    120
cacaagguug cagccggagc cgcccagcuc accgagagcc uaguuccggc cagggucgcc    180
ccggcaacca cgagcccagc caaucagcgc cccggacugc accagagcca uggucggcag    240
aagagcacug aucguacugg cucacucaga gaggacgucc uucaacuaug ccaugaagga    300
ggcugcugca gcggcuuuga agaagaaagg augggaggug guggagucgg accucuaugc    360
caugaacuuc aaucccauca uuuccagaaa ggacaucaca gguaaacuga aggacccugc    420
gaacuuucag uauccugccg agucuguucu ggcuuauaaa gaaggccauc ugagcccaga    480
uauuguggcu gaacaaaaga agcuggaagc cgcagaccuu gugauauucc agaguggcau    540
ucugcauuuc uguggcuucc aagucuuaga accucaacug acauauagca uugggcacac    600
uccagcagac gcccgaauuc aaauccugga aggauggaag aaacgccugg agaauauuug    660
ggaugagaca ccacuguauu uugcuccaag cagccucuuu gaccuaaacu uccaggcagg    720
auucuuaaug aaaaaagagg uacaggauga ggagaaaaac aagaaauuug gccuuucugu    780
gggccaucac uugggcaagu ccaucccaac ugacaaccag aucaaagcua gaaaaugaga    840
uuccuuagcc uggauuuccu ucuaacaugu uaucaaaucu ggguaucuuu ccaggcuucc    900
cugacuugcu uuaguuuuua agauuugugu uuuucuuuuu ccacaaggaa uaaaugagag    960
ggaaucgacu guauucgugc auuuuuggau cauuuuuaac ugauucuuau gauuacuauc   1020
auggcauaua accaaaaucc gacugggcuc aagaggccac uuagggaaag auguagaaag   1080
augcuagaaa aauguucuuu aaaggcaucu acacaauuua auuccucuuu uuagggcuaa   1140
aguuuuaggg uacaguuugg cuagguauca uucaacucuc caauguucua uuaaucaccu   1200
cucuguaguu uauggcagaa gggaauugcu cagagaagga aaagacugaa ucuaccugcc   1260
cuaagggacu uaacuuguuu gguaguuagc caucuaaugc uuguuuauga uauuucuugc   1320
uuucaauuac aaagcaguua cuaauaugcc uagcacaagu accacucuug gucagcuuuu   1380
guuguuuaua uacaguacac agauaccuug aaaggaagag cuaauaaauc ucuucuuugc   1440
ugcagucauc uacuuuuuuu uuaauuaaaa aaaauuuuuu uuugaagcag ucuugcucug   1500
uuacccaggc uggagugcag uggugugauc ucggcucacu gcaaccucug ccucccaggu   1560
uccagcaauu cuccugccuc agccucccua guagcuggga ugacaggcgc cugccaucau   1620
gccugacuaa uuuuuguauu uuuaguagag acggcguuuc accauguugg ccaggcuggu   1680
cucaaacucc ugaccucagg ugauccgccu accucagccu cccaaagugc ugggauuaca   1740
ggcgugaucc accacaccug gcccuugcaa ucuucuacuu uaagguuugc agagauaaac   1800
```

```
caauaaaucc acaccguaca ucugcaauau gaauucaaga aaggaaauag uaccuucaau   1860

acuuaaaaau agucuuccac aaaaaauacu uuauuucuga ucuauacaaa uuuucagaag   1920

guuauuuucu uuaucauugc uaaacugaug acuuacuaug ggaugggguc cagucccaug   1980

accuuggggu acaauuguaa accuagaguu uuaucaacuu uggugaacag uuuuggcaua   2040

auagucaauu ucuacuucug gaagucaucu cauuccacug uugguauuau auaauucaag   2100

gagaauauga uaaaacacug cccucuugug gugcauugaa agaagagaug agaaaugaug   2160

aaaagguugc cugaaaaaug ggagacagcc ucuuacuugc caagaaaaug aagggauugg   2220

accgagcugg aaaaccuccu uuaccagaug cugacuggca cuggugguuu uugcucucga   2280

caguauccac aauagcugac ggcugggugu uucaguuuga aaauauuuug uugccuucau   2340

cuucacugca auuuugugua aauuucucaa agaucugaau uaaauaaaua aaauucauuu   2400

cuacagaccc acaaaaaaaa aaa                                           2423
```

<210> SEQ ID NO 17
<211> LENGTH: 1591
<212> TYPE: RNA
<213> ORGANISM: Homo sapiens

<400> SEQUENCE: 17

```
cgggcgccgc gggccauggc gggcgagaac caccaguggc agggcagcau ccucuacaac     60

augcuuauga gcgcgaagca aacgcgcgcg gcuccugagg cuccagagac gcggcuggug    120

gaucagugcu ggggcuguuc gugcggcgau gagcccgggg ugggcagaga ggggcugcug    180

ggcgggcgga acguggcgcu ccuguaccgc ugcugcuuuu gcgguaaaga ccacccacgg    240

cagggcagca uccucuacag caugcugacg agcgcaaagc aaacguacgc ggcaccgaag    300

gcgcccgagg cgacgcuggg uccgugcugg ggcuguucgu gcggcucuga ucccggggug    360

ggcagagcgg ggcuuccggg ugggcggccc guggcacucc uguaccgcug cugcuuuugu    420

ggugaagacc acccgcggca gggcagcauc cucuacagcu ugcucacuag cucaaagcaa    480

acgcacgugg cuccggcagc gcccgaggca cggccagggg gcgcguggug ggaccgcucc    540

uacuucgcgc agaggccagg ggguaaagag gcgcuaccag gcgggcgggc cacggcgcuu    600

cuguaccgcu gcugcuuuug cggugaagac cacccgcagc agggcagcac ccucuacugc    660

gugcccacga gcacaaauca agcgcaggcg gcuccggagg agcggccgag ggcccccugg    720

ugggacaccu ccucuggugc gcugcggccg guggcgcuca agaguccaca gguggucugc    780

gaggcagccu cagcgggccu guugaagacg cugcgcuucg ucaaguacuu gcccugcuuc    840

caggugcugc cccuggacca gcagcuggug cuggugcgca acugcugggc gucccugcuc    900

augcuugagc uggcccagga ccgcuugcag uucgagacug uggaagucuc ggagcccagc    960

augcugcaga agauccucac caccaggcgg cgggagaccg ggggcaacga gccacugccc   1020

gugcccacgc ugcagcacca uuuggcaccg ccggcggagg ccaggaaggu gcccuccgcc   1080

ucccaggucc aagccaucaa gugcuuucuu uccaaaugcu ggagucugaa caucaguacc   1140

aaggaguacg ccuaccucaa ggggaccgug cucuuuaacc cggacgugcc gggccugcag   1200

ugcgugaagu acauucaggg acuccagugg ggaacucagc aaauacucag ugaacacacc   1260

aggaugacgc accaagggcc ccaugacaga uucaucgaac uuaauaguac ccuuuuccug   1320

cugagauuca ucaaugccaa ugucauugcu gaacuguucu ucaggcccau caucggcaca   1380

gucagcaugg augauaugau gcuggaaaug cucuguacaa agauauaaag ucaugugggc   1440

cacacaagug caguagugca guucaccaug agggaagaau aaagagcugu gggcaaaaga   1500
```

```
guguaaaaua uuuuaaaaua aacuuucuua auauuuuuac augcagagua uuuuuguauu   1560

caauuaaaga aauaauuuua uuccaaaaaa a                                  1591
```

<210> SEQ ID NO 18
<211> LENGTH: 1958
<212> TYPE: RNA
<213> ORGANISM: Homo sapiens

<400> SEQUENCE: 18

```
acuucccucu ggccucucag agccucuugg auccccacag gguaaugggu gucccgaucu     60

cgcgggggac ucugugaucc guguuccccu gacccuccua gugcacaacu uggccgggcu    120

cacugggcuc cugcaccacu gccugucagg uccgcugcca gccccaagcc ccccaccagc    180

caugagcucc uccagaaagg accaccucgg cgccagcagc ucagagcccc ucccggucau    240

cauugugggu aacggccccu cugguaucug ccuguccuac cugcucuccg gcuacacacc    300

cuacacgaag ccagaugcca uccacccaca cccccugcug cagaggaagc ucaccgaggc    360

cccgggggguc uccauccugg accaggaccu ggacuaccug uccgaaggcc ucgaaggccg    420

aucccaaagc cccguggccc ugcucuuuga ugcccuucua cgcccagaca cagacuuugg    480

gggaaacaug aagucggucc ucaccuggaa gcaccggaag gagcacgcca ucccccacgu    540

gguucugggc cggaaccucc ccgggggagc cuggcacucc aucgaaggcu ccauggugau    600

ccugagccaa ggccagugga uggggcuccc ggaccuggag gucaaggacu ggaugcagaa    660

gaagcgaaga ggucuucgca acagccgggc cacugccggg gacaucgccc acuacuacag    720

ggacuacgug gucaagaagg gucuggggca uaacuuugug uccggugcug uagucacagc    780

cguggagugg gggacccccg aucccagcag cugugggggcc caggacucca gcccccucuu    840

ccaggugagc ggcuuccuga ccaggaacca ggcccagcag cccuucucgc ugugggcccg    900

caacgugguc cucgccacag gcacguucga cagcccggcc cggcugggca uccccgggga    960

ggcccugccc uucauccacc augagcuguc ugcccuggag gccgccacaa gggugggugc   1020

ggugaccccg gccucagacc cuguccucau cauuggcgcg gggcugucag cggccgacgc   1080

gguccucuac gcccgccacu acaacauccc ggugauccau gccuuccgcc gggccgugga   1140

cgacccuggc cugguguuca accagcugcc caagaugcug uaccccgagu accacaaggu   1200

gcaccagaug augcgggagc aguccauccu gucgcccagc cccuaugagg guuaccgcag   1260

ccuccccagg caccagcugc ugugcuucaa ggaagacugc caggccgugu uccaggaccu   1320

cgagggguguc gagaaggugu uuggggucuc ccuggugcug guccucaucg gcucccaccc   1380

cgaccucucc uuccugccug gggcaggggc ugacuuugca guggauccug accagccgcu   1440

gagcgccaag aggaacccca uugacgugga ccccuucacc uaccagagca cccgccagga   1500

gggccuguac gccauggggc cgcuggccgg ggacaacuuc gugagguuug ugcagggggg   1560

cgccuuggcu guggccagcu cccugcuaag gaaggagacc aggaagccac ccuaacacuc   1620

ggccagaccc gcuggcuccc aggcccugag aggacagaga ugaccacauc ccugcuggau   1680

gcaggacccg uccaaagaug ccccggggag gggugucagc ccacguugcu ggccuuuggg   1740

gucaagagga guagggaucc caggcugccc uggacuuaga ccagugucug aggugguaac   1800

agcggccgca ggccaggguu ggccuagacc ugggauuugu ggggaaagcu gcuggugugua   1860

ccagcugagc acccagccag gagaccugca gcccugcgcc uuccagaagc agguccccaaa   1920

uaaagccagu gcccaccugc aaaaaaaaaa aaaaaaaa                           1958
```

<210> SEQ ID NO 19
<211> LENGTH: 2432
<212> TYPE: RNA
<213> ORGANISM: Homo sapiens

<400> SEQUENCE: 19

```
auggcccagu gagugacucg ccaggggcag cccggcucgg ccucagcggg cggggaacuc     60
uuugggggguc gagaucuccc ucguucucuc cgacgccucc cacccugggg gucgccugag    120
cucacuuggg gcucugugac ccuggcccua cggcgucucg ggcccagagc uccuucccug    180
cgggcccggc ccccugcccu cucggccgcg cagagcugac aucgcgcuga ucggauuggc    240
cgucaugggc cagaacuuaa uucugaacau gaaugaccac ggcuuugugg ucugugcuuu    300
uaauaggacu gucuccaaag uugaugauuu cuuggccaau gaggcaaagg gaaccaaagu    360
ggugggugcc caguccccuga aagagauggu cuccaagcug aagaagcccc ggcggaucau    420
ccuccuggug aaggcugggc aagcugugga ugauuucauc gagaaauugg uaccauuguu    480
ggauacuggu gacaucauca uugacggagg aaauucugaa uauagggaca ccacaagacg    540
gugccgagac cucaaggcca agggaauuuu auuugugggg agcggaguca gugguggaga    600
ggaaggggcc cgguauggcc caucgcucau gccaggaggg aacaaagaag cguggcccca    660
caucaagacc aucuuccaag gcauugcugc aaaaguggga acuggagaac ccugcuguga    720
cugggugggga gaugagggag caggccacuu cgugaagaug gugcacaacg ggauagagua    780
uggggacaug cagcugaucu gugaggcaua ccaccugaug aaagacgugc ugggcauggc    840
gcaggacgag auggcccagg ccuuugagga uuggaauaag acagagcuag acucauuccu    900
gauugaaauc acagccaaua uucucaaguu ccaagacacc gauggcaaac accugcugcc    960
aaagaucagg gacagcgcgg ggcagaaggg cacagggaag uggaccgcca ucuccgcccu   1020
ggaauacggc guacccguca cccucauugg agaagcuguc uuugcucggu gcuuaucauc   1080
ucugaaggau gagagaauuc aagcuagcaa aaagcugaag gguccccaga aguuccaguu   1140
ugauggugau aagaaaucau uccuggagga cauucggaag gcacucuacg cuuccaagau   1200
caucucuuac gcucaaggcu uuaugcugcu aaggcaggca gccaccgagu uuggcuggac   1260
ucucaauuau gguggcaucg cccugaugug gagagggggc ugcaucauua gaaguguauu   1320
ccuaggaaag auaaaggaug cauuugaucg aaacccggaa cuucagaacc uccuacugga   1380
cgacuucuuu aagucagcug uugaaaacug ccaggacucc uggcggcggg cagucagcac   1440
uggggucccag gcuggcauuc ccaugcccug uuuuaccacu gcccucuccu ucuaugacgg   1500
guacagacau gagaugcuuc cagccagccu cauccaggcu cagcgggauu acuucggggc   1560
ucacaccuau gaacucuugg ccaaaccagg gcaguuuauc cacaccaacu ggacaggcca   1620
ugguggcacc gugucauccu cgucauacaa ugccugauca ugcugcuccu gucacccucc   1680
acgauuccac agaccaggac auuccaugug ccucauggca cugccaccug gcccuuugcc   1740
cuauuuucug uucaguuuuu uaaaagaguu guaagagacu ccugaggaag acacacaguu   1800
uauuuguaaa guagcucugu gagagccacc augcccucug cccuugccuc uugggacuga   1860
ccaggagcug cucaugugcg ugagaguggg aaccaucucc uugcggcagu ggcuuccgcg   1920
ugccccgugu gcuggugcgg uucccaucac gcagacagga agggguguuug cgcacucuga   1980
ucaacuggaa ccucuguauc augcggcuga auucccuuuu uccuuuacuc aauaaaagcu   2040
acaucagacu gaugcucuuu cuccagauuc uuagucucac cucggccaca uggagccauu   2100
auccccauug gcagaaagau uuuucuuuaa aaaaaaagac uagaauaaca caagaaacca   2160
```

```
cauuuaggau uaugcuucac ucagaggagg caggcaggga ggacacacca ggggcuuuaa   2220

uacacugggc auguuuucuu ucuccaauug ggcaaugggu acauggacgu ucacuguaac   2280

gugcuuuuuc uuucgucuuu uuuuuuuuuu uuuuuuuuuu ugcuccuggc aagcugugcg   2340

ugacauucuu uauggcuuuu uguaugucaa auacuucaua cuaaacuuuc uagagaauua   2400

aacuuuaaug augggcucaa aaaaaaaaaa aa                                 2432
```

<210> SEQ ID NO 20
<211> LENGTH: 4583
<212> TYPE: RNA
<213> ORGANISM: Homo sapiens

<400> SEQUENCE: 20

```
gcggccgccc cggcggcucc uggaaccccg guucgcggcg augccagcca ccccagcgaa     60

gccgccgcag uucagugcuu ggauaauuug aaaguacaau aguugguuuc ccuguccacc    120

cgccccacuu cgcuugccau cacagcacgc cuaucggaug ugagaggaga agucccgcug    180

cucgggcacu gucuauauac gccuaacacc uacauauauu uuaaaaacau uaaauauaau    240

uaacaaucaa aagaaagagg agaaaggaag ggaagcauua cuggguuacu augcacuugc    300

gacugauuuc uuggcuuuuu aucauuuuga acuuuaugga auacaucggc agccaaaacg    360

ccucccgggg aaggcgccag cgaagaaugc auccuaacgu uagucaaggc ugccaaggag    420

gcugugcaac augcucagau uacaauggau guuugucaug uaagcccaga cuauuuuuug    480

cucuggaaag aauuggcaug aagcagauug gaguaugucu cucuucaugu ccaaguggau    540

auuauggaac ucgauaucca gauauaaaua aguguacaaa augcaaagcu gacugugaua    600

ccuguuucaa caaaaauuuc ugcacaaaau guaaaagugg auuuuacuua caccuuggaa    660

agugccuuga caauugccca gaaggguugg aagccaacaa ccauacuaug gaguguguca    720

guauugugca cugugagguc agugaaugga auccuuggag uccaugcacg aagaagggaa    780

aaacaugugg cuucaaaaga gggacugaaa cacggguccg agaaauaaua cagcauccuu    840

cagcaaaggg uaaccugugu cccccaacaa augagacaag aaaguguaca gugcaaagga    900

agaaguguca gaagggagaa cgaggaaaaa aaggaaggga gaggaaaaga aaaaaaccua    960

auaaaggaga aaguaaagaa gcaauaccug acagcaaaag ucuggaaucc agcaaagaaa   1020

ucccagagca acgagaaaac aaacagcagc agaagaagcg aaaaguccaa gauaaacaga   1080

aaucgguauc agucagcacu guacacuaga ggguuccaug agauuauugu agacucauga   1140

ugcugcuauc ucaaccagau gcccaggaca ggugcucuag ccauuaggac cacaaaugga   1200

caugucaguu auugcucugu cuaaacaaca uucccaguag uugcuauauu cuucauacaa   1260

gcauaguuaa caacaaagag ccaaaagauc aaagaaggga uacuuucaga ugguugucuu   1320

gugugcuucu cugcauuuuu aaaagacaag acauucuugu acauauuauc aauaggcuau   1380

aagauguaac aacgaaauga ugacaucugg agaagaaaca ucuuuuccuu auaaaaaugu   1440

guuuucaagc uguuguuuua agaagcaaaa gauaguucug caaauucaaa gauacaguau   1500

cccuucaaaa caaauaggag uucagggaag agaaacaucc uucaaaggac aguguuguuu   1560

ugaccgggag aucuagagag ugcucagaau uagggccugg cauuuggaau cacaggauuu   1620

aucaucacag aaacaacugu uuuaagauua guuccaucac ucucauccug uauuuuuaua   1680

agaaacacaa gagugcauac cagaauugaa uauaccauau gggauuggag aaagacaaau   1740

guggaagaaa ucauagagcu ggagacuacu uuugugcuuu acaaaacugu gaaggauugu   1800
```

-continued

```
ggucaccugg aacaggucuc caaucuaugu uagcacuaug uggcucagcc ucuguuaccc   1860
cuuggauuau auaucaaccu guaaacaugu gccuguaacu uacuuccaaa aacaaaauca   1920
uacuuauuag aagaaaauuc ugauuuuaua gaaaaaaaau agagcaagga gaauauaaca   1980
uguuugcaaa gucauguguu uucuuucuca augagggaaa aacaauuuua uuaccugcuu   2040
aaugguccac cuggaacuaa aagggauacu auuuucuaac aagguauauc uaguaggga    2100
gaaagccacc acaauaaaua uauuuguuaa uaguuuuuca aguuuuguuc acucuguuuu   2160
auuguuuguu uuauugagaa auucuuacuc uuagagacuc augaauuaag aaagagaauu   2220
cugcuaacuc agagaaccug guuccuaugu aauucagaau auauuacauu ucucaguaau   2280
auuuguuuuu ugaauccacc uuuaucugag ccaauggaga uuuacuuaua gcguauuagg   2340
agauauuuau uccauuuucu uauuuuaauc aacauucuaa uuauagacac augggccucc   2400
cuagcugauu ucacugcucc cccuucauug cuuagaaaug ggcaucauuu cuuguauguc   2460
agaucccccu gcaucuucaa cauuuagucu uuucuucucc auauuuucua ucuguggauc   2520
ucuuuagggg auugaaguca cccuagcuga aggccucacc aguguuucac agaggacaca   2580
gcccaccccu ugcaggagga gguaucucug agugugcagc acagaaucgc augacccacc   2640
uuaaccuucc uguugucaug gaaggaugca cggcugcucu guccacugug auuccuagcc   2700
cucucaagau cacugcuuuc ugaagaauuu gcaaugacuc uggcuucugg cugcuuaucu   2760
cuggacaccc guucuccacc aguuguacag uucauguaau cuacuuggcu uaauugauuu   2820
uccacuucuc ucuuccucuu cuaagauaua aacauuuuaa augauuuauu ccuguuucuu   2880
auucuggugu uucuuuccuu gucccuauga gauaaguguc ucaacucacu aaaucuauuc   2940
ccaauguaua aaauaauucu aauuccauuu ucagcuaaaa cauauauuac caagaagaaa   3000
caaacuuuau ccuacagaau gauguuaggu agaaauaugu ccccagguuu gagaccuuuc   3060
ggaugauuuc auauaccauc uuucuucuga guguuaccca gucaaguaua aguagccaaa   3120
uuauuuuugc acaucuuucu guuucucaug ucuucauuua uucaacaagc acuuacuggg   3180
aaggucuaca ccugcauagg caaugcugga aaaaggguua aguaaaccag gacaugacaa   3240
ugguggcaaa ugacuaucag gucuucccau guguuugacu caaacuuauu acccuauggu   3300
ccuucugaca auggcagaag gucugaaucc uugaugcuaa acuuauauaa aaguagaauu   3360
auuacaaagg aaaaagaaau aaaaacuaac auucauuuuc auauguugga ugaaauauaa   3420
augaagaaaa agauaacauc aauuuuaacu guaauucucc auccaccagu aacagauccu   3480
uaagacaaua gaaucauaca guauucaaac cagcagccuu cucaaauuug agcaaaaacu   3540
cuaucaaccu cugguaaagu uccuacacua gucacagaag guguuaacuu ucuacucuga   3600
uucugucucc auaauggggu aaacuguuga uaguuuaccc caucaacaga uggucgguaa   3660
auuauugauu cgaagaaucg agagagugca gcaacauaaa ucuguuaaug ucugaucaag   3720
cuccugcccu guucuccgaa uucagcuuca uaauuaaggg aaggccuguu uucuauccuc   3780
agauuuaggu ucuaguagca guuguguaac cacuagugag ucacuuaacu ccucuggguc   3840
cccauuucuc augugcaaca agaaagaggg gaacuggaga ugaucacucu aguuccagac   3900
aagggaacau uucacacuuu guuuacuuca gggugauguc ccugaguccu cauuagugac   3960
ugcguccuuu ggaaguuauc ccaacccugc uuuucucaaa agugaaaaug uauaggcucu   4020
cagaggagac agauuuaacu cugcuucucu aauguuauug aauuaaaagc uguucacauu   4080
agugguuauu aaauauugaa auaacacugg gaagaaaaag cauauauaaa uacagcuaaa   4140
aacaagaaua gauauucauu cucacaaagg gagacagcaa agaaaaugga aagugcacug   4200
```

```
gugcuagcgu uagacagcuu guguuaaugu cucaauucug cuacuaacug guugcagcuu   4260

gugugaccuu gggcacauug uaugaucucg cagaauauca ucccaaaucu gcaaaaugga   4320

auuggcauca ucucuuuugc aagauuguua ugagaauuaa aagguucuuc auucaauaua   4380

auaauaaaua uuuuguauau aaaugaauau caauuaaaag uuaugacuaa uuccacaagu   4440

caaacauaua aauuuuauuu cuugauucau gauaugugau aguauucaua aaaauguaca   4500

ugcaugauaa uuucaaggaa uaaguauaua ugugagaauc auggaaauga aauuaauaau   4560

auuaacuagu aauuaaauug uaa                                           4583
```

```
<210> SEQ ID NO 21
<211> LENGTH: 9648
<212> TYPE: RNA
<213> ORGANISM: Homo sapiens

<400> SEQUENCE: 21

gguuuguaau gauagggcgg cagcagcagc agcagcagca gugguggaac gaggaggugg     60

agaauugaga gcacgaugca uacacaggug uuucugagua guaauuagau cgcugugaag    120

gaaaaagcac accuuugagu uuucaccugu gaacacuaua gcgcugagag agacagucug    180

aaagcagagg aagacaucga ucaguaacac caagagacac caaaguugaa aguuuuguuu    240

ucuuucccuc uguuuuauuu uucccccgug ugucccuacu auggucagaa agccuguugu    300

guccaccauc uccaaaggag guuaccugca gggaaauguu aacgggaggc ugccuucccu    360

gggcaacaag gagccaccug ggcaggagaa agugcagcug aagaggaaag ucacuuuacu    420

gaggggaguc uccauuauca uuggcaccau cauuggagca ggaaucuuca ucucuccuaa    480

gggcgugcuc cagaacacgg gcagcguggg caugucucug accaucugga cggugugugg    540

gguccuguca cuauuuggag cuuugucuua ugcugaauug ggaacaacua uaaagaaauc    600

uggaggucau uacacauaua uuuuggaagu cuuuggucca uuaccagcuu uuguacgagu    660

cuggguggaa cuccucauaa uacgcccugc agcuacugcu gugauauccc uggcauuugg    720

acgcuacauu cuggaaccau uuuuuauuca augugaaauc ccugaacuug cgaucaagcu    780

cauuacagcu guggggcauaa cuguagugau gguccuaaau agcaugagug ucagcuggag    840

cgcccggauc cagauuuucu uaaccuuuug caagcucaca gcaauucuga uaauuauagu    900

cccuggaguu augcagcuaa uuaaagguca aacgcagaac uuuaaagacg ccuuuucagg    960

aagagauuca aguauuacgc gguugccacu ggcuuuuuau uauggaaugu augcauaugc   1020

uggcugguuu uaccucaacu uuguuacuga agaaguagaa aacccugaaa aaaccauucc   1080

ccuugcaaua uguauaucca uggccauugu caccauuggc uaugugcuga caaauguggc   1140

cuacuuuacg accauuaaug cugaggagcu gcugcuuuca aaugcagugg cagugaccuu   1200

uucugagcgg cuacugggaa auuucucauu agcaguuccg aucuuuguug cccucuccug   1260

cuuuggcucc augaacggug guguguuugc ugucuccagg uuauucuaug uugcgucucg   1320

agagggucac cuuccagaaa uccucuccau gauucauguc cgcaagcaca cuccucuacc   1380

agcuguuauu guuuugcacc cuuugacaau gauaaugcuc uucucuggag accucgacag   1440

ucuuuugaau uuccucaguu uugccaggug gcuuuuuauu gggcuggcag uugcugggcu   1500

gauuuaucuu cgauacaaau gcccagauau gcaucguccu uucaaggugc cacuguucau   1560

cccagcuuug uuuuccuuca caugccucuu caugguugcc cuuucccucu auucggaccc   1620

auuuaguaca gggauuggcu ucgucaucac ucugacugga gucccugcgu auuaucucuu   1680
```

```
uauuauaugg gacaagaaac ccaggugguu uagaauaaug ucagagaaaa uaaccagaac   1740
auuacaaaua auacuggaag uuguaccaga agaagauaag uuaugaacua auggacuuga   1800
gaucuuggca aucugcccaa ggggagacac aaaauaggga uuuuuacuuc auuuucugaa   1860
agucuagaga auuacaacuu uggugauaaa caaaaggagu caguuauuuu uauucauaua   1920
uuuuagcaua uucgaacuaa uuucuaagaa auuuaguuau aacucuaugu aguuauagaa   1980
agugaauaug caguuauucu augagucgca caauucuuga gucucugaua ccuaccuauu   2040
gggguuagga gaaaagacua gacaauuacu auguggucau ucucuacaac auauguuagc   2100
acggcaaaga accuucaaau ugaagacuga gauuuuucug uauauauggg uuuuguaaag   2160
augguuuuac acacuauaga ugucuauacu gugaaaagug uuuucaauuc ugaaaaaaag   2220
cauacaucau gauuauggca aagaggagag aaagaaauuu auuuuacauu gacauugcau   2280
ugcuuccccu uagauaccaa uuuagauaac aaacacucau gcuuuaaugg auuauaccca   2340
gagcacuuug aacaaagguc aguggggauu guugaauaca uuaaagaaga guuucuaggg   2400
gcuacuguuu augagacaca uccaggaguu auguuuaagu aaaaauccuu gagaauuuau   2460
uaugucagau guuuuuucau ucauuaucag gaaguuuuag uuaucuguca uuuuuuuuuu   2520
ucacaucagu uugaucagga aaguguauaa cacaucuuag agcaagaguu aguuugguau   2580
uaaauccuca uuagaacaac caccuguuuc acuaauaacu uaccccugau gagucuaucu   2640
aaacauaugc auuuuaagcc uucaaauuac auuaucaaca ugagagaaau caccaacaaa   2700
gaagauguuc aaaauaauag ucccauaucu guaaucauau cuacaugcaa uguuaguaau   2760
ucugaaguuu uuuaaauuua uggcuauuuu uacacgauga ugaauuuuga caguuugugc   2820
auuuucuuua uacauuuuau auucuucugu uaaaauaucu cuucagauga aacuguccag   2880
auuaauuagg aaaaggcaua uauuaacaua aaaauugcaa aagaaauguc gcuguaaaua   2940
agauuuacaa cugauguuuc uagaaaauuu ccacuucuau aucuaggcuu ugucaguaau   3000
uuccacaccu uaauuaucau ucaacuugca aaagagacaa cugauaagaa gaaaauugaa   3060
augagaaucu guggauaagu guuuguguuc agaagauguu guuuugccag uauuagaaaa   3120
uacugugagc cgggcauggu ggcuuacauc uguaauccca gcacuuuggg aggcugaggg   3180
gguggaucac cugaggucgg gaguucuaga ccagccugac caacauggag aaaccccauc   3240
ucuacuaaaa auacaaaauu agcugggcau gguggcacau gcugguaauc ucagcuauug   3300
aggaggcuga ggcaggagaa uugcuugaac ccgggaggcg gagguugcag ugagccaaga   3360
uugcaccacu guacuccagc cugggugaca aagucagacu ccaucuccaa aaaaaaaaga   3420
uuauauauau auauauaugu guguguaugu gugugugugu gugugugugu auauauauau   3480
auauauauau acacacacac acacacacuu uuuauauaua uauauauaua uauauagugg   3540
aacuuacaaa ugagaguaau auaaugauga aauuuugaac uguuauuuau aaacaucuaa   3600
gguaaaaugg uuagucaugg ccagaguaug uuucauccuu uaauuuuugu ccauuugaaa   3660
auaaggauuu uugaaagaau uauaccaauu aaaauuauua aaggcaaaca uagaauucau   3720
aaaaaauugu ccaaaguaga aaugaugacc uauaauuugg agcauuucca auucaguaau   3780
uucaauuuug cucuugaaaa cauuuaauau auauccaaga cugacauuuc uuuagcugaa   3840
ccuaacguuu gggucucuga gugaauuuau aauaacuccu uccuuccuua gcauaggguu   3900
uucaaaauuu gauuuauaau uccuauuucc aguaaauauu guucauuugu ccacaucucu   3960
cccuaugaua uguugcugga gguaagaauu ucuuucauau uccuauuuuu uuuuuuccca   4020
uagacuaggc ucauagaauu uaaacaagca aauuuuccug agcuuuuucu ugccaaauga   4080
```

```
aagaagacug guaaauucuc auagagaggu uuguguaguu cuuggcucuu ccugggguua   4140
augugcuuau auucacagug gcaaauuggu cucagacuuu aauuuauuua uuuuugauuu   4200
gaauuucucu uuaaaaguau caauuuaaaa gguaacuaga auuauucuuu cucauuuuca   4260
aaagugauuu uugcauuauu aaauuucccu gccauuguaa ugccauuuca cgcagaaaaa   4320
aagucagcca guaauuaaga aaaaaaguga uggagauuaa guaguauuuu ggcuuauuuu   4380
uaggacucau caugagaaga cacaguuccu uuaaucagga aauuaauauc cauaauuuuc   4440
acucaaaauu gcaguaugua aagcagauuc ucaaaaacuc uccugaacac uuauuuauau   4500
auauguuuuu auauaaguaa aauuuuucuc auauuuuuau acgauaugca cacacacaca   4560
uacaugcaca uacuacuuac uacauguucu guacuuguac uuuguaccau gcauauucaa   4620
auguuuauau acauaaguuu auuauaacau aaacaguaaa aguaaugaau acuguuuaaa   4680
auaacuaaua uaguauuuuu uaauuuuugu ggggauggau ucucaaauac uugugauuuu   4740
aaaagauucu aaagcuaaaa cacaacuuga uuuuaaaaag aaugauucuc cuuacacaau   4800
uauaaauauu ugcaguaaau auuuuccuua uaauacuguu uugaccccau uuaaaaagua   4860
uuagauuaua uuccuuugau ccaaugaaaa cugaaccuua uaaauggaua gcugaaagua   4920
gaccuuauuc uuguccuucu uuagaagagu aaagauuugu ccuagggaag auggcugacu   4980
ucgguuccca acaugcguau gcauuuagac uguagcuccu cagcccugug gacacaaaau   5040
uuggacagcu uauuagguua cguuagcaau gcaugacggu uucuccaaca cuaagauauu   5100
cacguugaaa cagauuuccu guucgucuua ugugucuggu aaaauuguuu ccccaauuac   5160
aauuugacau aucaauagag gguuaacaag aguauaauua cauaacagaa uuccucauga   5220
acuguaauca gucuacagga aaaucauuau uuuaucuuga uuugcagaug aauauacugc   5280
uaagaaaggg agcaacucug accuuuguua aaguugaucu uuuguaauug agguauaagg   5340
uaugaaaaga uaaaaaaccg aaggccagag aaucaggaaa ugaaagauag uauggacuga   5400
agguaacaau auuuuaaugu uaugcaauau agucagagaa auauuaaaaa uuaguuguuu   5460
gcugugcaua gguggaucuc gcaggaagcu aaugaaaccu aagcuucagu gccucucacu   5520
uagacauguu ccauucgagg uccugaaccu aacuuuguau uaggaauucu guacuaauuu   5580
uguugaagaa gaccagcaaa guuguguaca cuucuacccc cacaaaaucu gcauugucca   5640
ugugaguaaa guaaaauaau uccuguuauu uuuuucuguu agaaauaagu auggaggaua   5700
uguuuuuaaa aauuuaugag uuaaauugaaa uauccauaua uaacaaguga cuuucucaca   5760
auauauauga ugugauauau agggagauag uuucacuuuc aucauauuuu auacguugau   5820
ucugaacuau agaaaaauaa uaaaugggau uuuaauuaua gcucuuaguu gggaaagaaa   5880
uauagagaga ugugggauuu gaaugcccau gaaagacauu uuauuuuacu ugaauauauu   5940
cuugcuucac uuuacccucc auaauauguu guacauuagu gcugaucaag uuuacagagu   6000
uacauuuugc uuuccuaacc auucagucag gaauuaaaau auggcauugu auaacaacug   6060
ggaagaagcu cauaguggau auaaauuaga guagauaaug ggucaccuug auagccucug   6120
uuuacauuac uuguauaugg gcaaaauaau uauuaccuau acguguauuu aagcuuaauu   6180
uucauauaaa caguauuuuu aaucuauguu aaaauagaua auaucuaaaa gugugaucuc   6240
uagguagucc uuaguuuauu aguacuguac uucaaaaaga uuuuuaaaua gguccggcac   6300
gguggcucau gccuguaauc ccagcacuuu gggaggcuga ggcgggcgaa ucaccugagg   6360
ucaggaguuc gagaucagcc uggccaacau ggugaaaccc ugucucaacu aaaaauauaa   6420
```

```
aaauuagccg ggcguggugg caggcgccug uaaucccagc uacucgggag gcugaggcag   6480
gagaaucacu ugaacccaag ggcagaagc ugcaguuagc caagaucgca ucauugcacu   6540
ccagccuagg ggacaagagc gcgagacuuc aucucaaaaa aaaaaaaaaa aaaaaaaaaa   6600
gauuuuuaaa uaauagcuaa agguaugcuc ucuaggucau ccuuaguuua uuaguacugu   6660
acuuaaaaau uauuuuuuaa uagucaauuu ugggagauaa uuauuucuuu ccuuauauuu   6720
uccaauuagu ugguguuaa aaauaaaugu uuugucuaau uuuagaucag guauacauuc   6780
acaaaagcau aaaucauagu cucacaggaa auucaccaau uuuccauaug ucgugagaua   6840
acuguccuuu cuacaaccuc auaacaauga auuuauauaa uuaccuagau uuucuuagug   6900
ugaaucuacc cauuaguuuu auuuucuugg uaguuauuuu uuucccuccu cucuguuacu   6960
auuggccuua aaauacacag aggacgguua caguguccua auagcuguua caugugugug   7020
uuucagcgua cuugaaucaa guguacauuu auaguaccaa uaaccgccuu uacagcuuua   7080
caguuaacaa uucucucaca aaacuguaga gcauuaggca ucugagagcc auagagggcc   7140
aacuuuguuc cagagugaac augcuuuuuu uccucaacau auacacuacu gauuuuuuuu   7200
aaaaguauga cuuucaagug aauuaaugua uugguuagga gaacugcuug cuaaguccuu   7260
auuaccucuu guuaaagccu cagaaggccg ugcugaaagc cagaggggaa aaaaagagua   7320
augcacaggu aucucuuuug caguggugac uguauuuuga guaccuugug ugacagggua   7380
uuauuacagc aucuuguggg aaaaccuauu aggccuuugc auguuaaagc uguauaauuu   7440
guuggguugu gaguggucug acuuaaaugu guauuauaaa auuuagacau caaauuuucc   7500
uacuaacuaa cuuuauuaga ugcauacuug gaagcacagu cauaucacac ugggaggcaa   7560
ugcaaugugg uuaccugguc cuagguuuga acugucuuau uucaaaagau uucugaauua   7620
auuuuucccu agaauuucuc cuucauucca aaguacaaac auacuuugaa gaaugaaaca   7680
gauuguuccc augaauguau gcucauacuc gacuagaaac gaucuauguu aaaugacugu   7740
guauaugaau uauuucaagu acuaccccaa auaacuuucu uauugcucug aaagaagaaa   7800
agcaauguaa aucacuauga uuauugcaca aacaaccaga auucuccaac aauuuuaagu   7860
aaucugaucc ucuucuugga gaaaauuguu accuaauagu uuuuccuuau gaauguuauu   7920
acuacuggua uaaaucaaau uucuauaaau uuccuacuua agucuuaaga acuggguucu   7980
uccuuugaug uuauucaugu ucagaaagga aacaacacuu uacucuuuua ggacaauucc   8040
uagaaucuau aguaguauca ggauauauuu ugcuuuaaaa uauauuuugg uuauuuugaa   8100
uacagacauu ggcuccaaau uuucaucuuu gcacaauagu augacuuuuc acuagaacuu   8160
cucaacauuu gggaacuuug caaauaugag caucauaugu guuaaggcug uaucauuuaa   8220
ugcuaugaga uacauuguuu ucucccuaug ccaaacaggu gaacaaacgu aguuguuuuu   8280
uacugauacu aaauguuggc uaccugugau uuuauaguau gcacauguca gaaaaaggca   8340
agacaaaugg ccucuuguac ugaauacuuc ggcaaacuua uugggucuuc auuuucugac   8400
agacaggauu ugacucaaua uuuguagagc uugcguagaa uggauuacau gguagugaug   8460
cacugguaga aaugguuuuu aguuauugac ucagaauuca ucucaggaug aaucuuuuau   8520
gucuuuuuau uguaagcaua ucugaauuua cuuuauaaag augguuuuag aaagcuuugu   8580
cuaaaaauuu ggccuaggaa ugguaacuuc auuuucaguu gccaaggggu agaaaaauaa   8640
uaugugguu guuauguuua uguuaacaua uuauuaggua cuaucuauga auguauuuaa   8700
auauuuuuca uauucuguga caagcauuua uaauuugcaa caaguggagu ccauuuagcc   8760
cagugggaaa gucuuggaac ucagguuacc cuugaaggau augcuggcag ccaucucuuu   8820
```

gaucugugcu uaaacuguaa uuuauagacc agcuaaaucc cuaacuugga ucuggaaugc 8880
auuaguuaug accuuguacc auucccagaa uuucaggggc aucgugggguu uggucuagug 8940 auugaaaaca caagaacaga gagauccagc ugaaaaagag ugauccucaa uauccuaacu 9000
aacugguccu caacucaagc agaguuucuu cacucuggca cugugaucau gaaacuuagu 9060
agaggggauu guguguauuu uauacaaauu uaauacaaug ucuuacauug auaaaaauucu 9120 uaaagagcaa aacugcauuu uauuucugca uccacauucc aaucauauua gaacuaagau 9180
auuuaucuau gaagauauaa auggugcaga gagacuuuca ucuguggauu gcguuguuuc 9240
uuaggguucc uagcacugau gccugcacaa gcaugugaua ugugaaauaa aauggauucu 9300
ucuauagcua aaugaguucc cucuggggag aguucuggua cugcaaucac aaugccagau 9360
gguguuuaug ggcuauuugu guaaguaagu gguaagaugc uaugaaguaa guguguuugu 9420
uuucaucuua uggaaacucu ugaugcaugu gcuuuuguau ggaauaaauu uuggugcaau 9480
augaugucau ucaacuuugc auugaauuga auuuugguug uauuuauaug uauuauaccu 9540
gucacgcuuc uaguugcuuc aaccauuuua uaaccauuuu uguacauauu uuacuugaaa 9600
auauuuuaaa uggaaauuua aauaaacauu ugauaguuua cauaauaa 9648

<210> SEQ ID NO 22
<211> LENGTH: 2704
<212> TYPE: RNA
<213> ORGANISM: Homo sapiens

<400> SEQUENCE: 22
cggcaccugg cgagcggagc cggagucggg cuggggaccg cggggucgag gccggaccgc 60
ggcggggucg ggggagaaac gcgcgcugcc cuggcacggg cccccccccc cggccgcgcg 120
gaaugguaug gcccggccgg aguuaaggcc ggggggaggc ggcgagaccc gcggcggcgg 180
cgacgauggg gcugcgugca ggaggaacgc ugggcagggc cggcgcgggu cggggggcgc 240
ccgaggggcc cgggccgagc ggcggcgcgc agggcggcag cauccacucg ggccgcaucg 300
ccgcggugca caacgugccg cugagcgugc ucauccggcc gcugccgucc guguuggacc 360
ccgccaaggu gcagagccuc guggacacga uccgggagga cccagacagc gugcccccca 420
ucgauguccu cuggaucaaa ggggcccagg gaggugacua cuucuacucc uuugggggcu 480
gccaccgcua cgcggccuac cagcaacugc agcgagagac cauccccgcc aagcuugucc 540
aguccacucu cucagaccua aggguguacc ugggagcauc cacaccagac uugcaguagc 600
agccuccuug gcaccugcug ccaccuucaa gagcccagaa gacacaccug gccuccagca 660
ggcugggcca ugcagaaggg auagcagggg ugcauucucu uugcaccugg cgagaggguc 720
ugacucuggg caccccucuc accagcuaca aggccuugga cucacuguac agugugggag 780
ccccaguucc caccucugug acaauaggau cauggccuua cccuugaagc auuaccgaga 840
aggagaacag agaugggcuu gaagagccac gugcugccgg cuccaaauuc ccaaggacaa 900
ggaucccucu gcauuuuugu cuauguaacc ucuuauaugg acuacauuca gcugcaagga 960
aaggaaaacc uugauugcag ugguuuaaac aaacagaaga uuguuuuucc acauagcaug 1020
gauucuggag augggguggcu aaugguauug guucaacaac uccacgaagg uaggggucac 1080
gucuuggauc cuuuugccuu aaucucagug cucguuacuu cauggucccca agauggcugc 1140 uguaucccca agaaucaugu cugcguucaa ggaaggaggg guggaggaag aggaagggcc 1200
aaacuagcug gacccgucac cuucuaucag aaaguaaaac cucgucagaa gucuguuucc 1260

```
ugcucucucc cucugcauau cuucacuuag augcccuugg cccgagccag cuaccauugc   1320

accucuagcu gcaaacaaag cuaagacagc agggaacaga auugucaugg cugaauagac   1380

caaucguguu ccaucuacug agacuggcac acugccuccu gcaauaaaac ugggauccca   1440

uuaccaagag agaaaugcag aauuguguac caguuagcuu uugcugugua acaaaccauc   1500

cccaaacuug gcagcuagaa acaaacccug uauuuuccca caauccuaug gguuggcaau   1560

uugggcuggg cucaacaggg caguucugcu gcucacaccu gggaucccuc auggagcuaa   1620

ggucagcugu uaccucagcu gggccuggau ggucuaggau agccuuacuc acuugccugg   1680

caggugacag gcuguuggcu ggaauugcuu gguucuccuc cauguggccu cuccagcagg   1740

cuagcucagg cuuauucaca ugauggcuuc aggauuccaa agagagugag aguagaagcu   1800

gaaagacuuc uugaguucuu ggccuggaac ugggacuagg acagugucac uucugcuaag   1860

uucuuuuggu cagagcaaau cacaaggcuu uacccagauu caagggauga gaaacagacu   1920

acaugucuug augaggggaa ccacaaagag cuuguggcca uuuuucaccu aucacaaaua   1980

auuuuggaug gguauuuauu uggauaaagg uauuucccuc uucccccuuu cucucugucu   2040

cauggggccu cacucugcca aguuggaagg cacuaagaca uuguccuggc ccucaggguc   2100

uaggggaaga gguguugggg caggaaguga gucucuccau gggcuggacc cacuguagua   2160

ggagugccuc cuugucugca cugcugguau gggguuaggc cagguaggac auuccagagg   2220

ggcuucugaa aaccaagagu cccuggggaa agggaacaga guaaggcagg ccuuguucuc   2280

acugcccucu aagggaacuu ggucacucgg cacuuuuaag ccucaguuuc uccaguucaa   2340

uaauaaggac aagagcuuuu cccaugcauu cucuuucccc gggaaaguug acugagguga   2400

ccaguaauag aauugaaaag ggagaguguc uucagugcaa uguggcaucc uggauugggu   2460

cuuggaacaa aaacaggaca uuagugggaa aauuggaaau cugaaaaaag ucugaauuuu   2520

aguuaauaua ccaauuucag ucucuugguu uugacagaug uaccauggug auguaagaug   2580

uugaccuugg gguaggcugg gugaagggua uacaggaacu cuuuguacua ucucugcaac   2640

uucucuguaa aucuaguauc auuccaaaau aaaaguuuau uuaauuuaaa aaaaaaaaaa   2700

aaaa                                                                2704
```

<210> SEQ ID NO 23
<211> LENGTH: 1319
<212> TYPE: RNA
<213> ORGANISM: Homo sapiens

<400> SEQUENCE: 23

```
cgcgcccguc ccgucgccgc cgccgccgcc gcagaccccu cggucuugcu augucgagcu     60

cacccgugaa gcgucagagg auggaguccg cgcuggacca gcucaagcag uucaccaccg    120

ugguggccga cacgggcgac uuccacgcca ucgacgagua caagccccag gaugcuacca    180

ccaacccguc ccugauccug gccgcagcac agaugcccgc uuaccaggag cugguggagg    240

aggcgauugc cuauggccgg aagcugggcg ggucacaaga ggaccagauu aaaaaugcua    300

uugauaaacu uuuuguguug uuuggagcag aaauacuaaa gaagauuccg ggccgaguau    360

ccacagaagu agacgcaagg cucuccuuug auaaagaugc gaugguggcc agagccaggc    420

ggcucaucga gcucuacaag gaagcuggga ucagcaagga ccgaauucuu auaaagcugu    480

caucaaccug ggaaggaauu caggcuggaa aggagcucga ggagcagcac ggcauccacu    540

gcaacaugac guuacucuuc uccuucgccc aggcuguggc cugugccgag gcggguguga    600

cccucaucuc cccauuuguu gggcgcaucc uugauuggca uguggcaaac accgacaaga    660
```

```
aauccuauga gccccuggaa gacccugggg uaaagagugu cacuaaaauc uacaacuacu    720

acaagaaguu uagcuacaaa accauuguca ugggcgccuc cuuccgcaac acgggcgaga    780

ucaaagcacu ggccggcugu gacuucccuca ccaucucacc caagcuccug ggagagcugc    840

ugcaggacaa cgccaagcug gugccugugc ucucagccaa ggcggcccaa gccagugacc    900

uggaaaaaau ccaccuggau gagaagucuu uccguugguu gcacaacgag gaccagaugg    960

cuguggagaa gcucucugac gggauccgca aguuugccgc ugaugcagug aagcuggagc   1020

ggaugcugac agaacgaaug uucaaugcag agaauggaaa guagcgcauc ccugaggcug   1080

gacuccagau cugcaccgcc ggccagcugg gaucugacug cacguggcuu cugaugaauc   1140

uugcguuuuu uacaaauugg agcagggaca gaucauagau uucugauuuu auguaaaauu   1200

uugccuaaua cauuaaagca gucacuuuuc cugugcuguu ucaaaaaaaa aaaaaaaaaa   1260

aaaaaaaaaa aaaaaaaaaa aaaaaaaaaa aaaaaaaaaa aaaaaaaaaa aaaaaaaaa    1319
```

<210> SEQ ID NO 24
<211> LENGTH: 2920
<212> TYPE: RNA
<213> ORGANISM: Homo sapiens

<400> SEQUENCE: 24

```
gauuuaugga aagcaccugg ugcguguucu gcccucugag gacccugccc uuucccaaaa     60

gggguaucuu aagaaggaaa auauggcugc ucuuugccgg acagcagagu cccaguagga    120

uuuccauuuu ccaaaccugg uaucaucucc uaguuggaag aagugguaag cccacgaaca    180

caaaugcagg agggagaggu gccaagaagc agcgguacac agcaggcaca gagacacgug    240

gucuucagca gagccuaugg gguucagaug auucacauaa gaauagaagu uucagggcug    300

gaccugggga ggcagccuga gccugagccg gcuguccuga gccugaguac ucuagcugcc    360

uugucgucau cgcaucuggc ugccauccag cgccagcaca caguaaugag uggccgagcu    420

ucccucuggga gggaggaaac aguuaaaauc uugcagcagc ugcaaucauc uaggcguggu    480

ucucuugucu gacuugggcu gcacagaucc ugggccaagg gacagaagaa agacagccua    540

ggagcagagc cucccagaug gcugaguugg aucuaauggc uccagggcca cugcccaggg    600

ccacugcuca gcccccagcc ccucucagcc cagacucugg gucacccagc ccagauucug    660

ggucagccag cccaguggaa gaagaggacg ugggcuccuc ggagaagcuu ggcagggaga    720

cggaggaaca ggacagcgac ucugcagagc agggggaucc ugcugguga gggaaagagg    780

uccuguguga cuucugccuu gaugacacca gaagagugaa ggcagugaag uccugucuaa    840

ccugcauggu gaauuacugu gaagagcacu ugcagccgca ucaggugaac aucaaacugc    900

aaagccaccu gcugaccgag ccagugaagg accacaacug gcgauacugc ccugcccacc    960

acagcccacu gucugccuuc ugcugcccug aucagcagug caucugccag gacuguugcc   1020

aggagcacag uggccacacc auagucuccc uggaugcagc ccgcagggac aaggaggcug   1080

aacuccagug cacccaguua gacuuggagc ggaaacucaa guugaaugaa aaugccaucu   1140

ccaggcucca ggcuaaccaa aagucuguuc uggugucggu gucagagguc aaagcggugg   1200

cugaaaugca guuuggggaa cuccuugcug cugugaggaa ggcccaggcc aaugugaugc   1260

ucuucuuaga ggagaaggag caagcugcgc ugagccaggc caacgguauc aaggcccacc   1320

uggaguacag gagugccgag auggagaaga gcaagcagga gcuggagagg auggcggcca   1380

ucagcaacac uguccaguuc uuggaggagu acugcaaguu uaagaacacu gaagacauca   1440
```

```
ccuucccuag uguuuacgua gggcugaagg auaaacucuc gggcauccgc aaaguuauca   1500

cggaauccac uguacacuua auccaguugc uggagaacua uaagaaaaag cuccaggagu   1560

uuuccaagga agaggaguau gacaucagaa cucaagugc ugccguuguu cagcgcaaau   1620

auuggacuuc caaaccugag cccagcacca gggaacaguu ccuccaauau gcguaugaca   1680

ucacguuuga cccggacaca gcacacaagu aucuccggcu gcaggaggag aaccgcaagg   1740

ucaccaacac cacgcccugg gagcaucccu acccggaccu ccccagcagg uuccugcacu   1800

ggcggcaggu gcugucccag cagagucugu accugcacag guacuauuuu gagguggaga   1860

ucuucggggc aggcaccuau guuggccuga ccugcaaagg caucgaccgg aaaggggagg   1920

agcgcaacag uugcauuucc ggaaacaacu ucuccuggag ccuccaaugg aacgggaagg   1980

aguucacggc cugguacagu gacauggaga ccccacucaa agcuggcccu uuccggaggc   2040

ucgggggucua uaucgacuuc ccgggaggga uccuuuccuu cuauggcgua gaguaugaua   2100

ccaugacucu gguucacaag uuugccugca aauuuucaga accagucuau gcugccuucu   2160

ggcuuuccaa gaaggaaaac gccauccgga uuguagaucu gggagaggaa cccgagaagc   2220

cagcaccguc cuuggugggg acugcucccu agacuccagg agccauaucc cagaccuuug   2280

ccagcuacag ugaugggauu ugcauuuuag ggugauuugg gggcagaaau aacugcugau   2340

gguagcuggc uuuugaaauc cuaugggguc ucugaaugaa aacauucucc agcugcucuc   2400

uuuugcucca uaugguguug uucucuaugu guuugcagua auucuuuuuu uuuuuuuuga   2460

gacggagucu cgcacuguug cccaggcugg agagcagugg cgcgaucuug gcucacugca   2520

agcuccgccu cccgaguuca agcaauucuc cugccucagc cucccgagua gcugggauua   2580

caggugccug ccaccacacc cagcuaaugu uuuguauuuu uaguagagau gggguuucac   2640

cauguuggcc aggcagaucu caaacuccug accucgugau gcacccaccu cggccuccca   2700

aagugcuggg auuacaugcg ugagccacug cgcccugccu guuuguagua auuuuuaggc   2760

accaaaucuc ccucaucuuc uagugccauu cuccucucug uucagguaaa ugucacacug   2820

ugcccagaau ggaugaccag gaaccuuaaa gaguggcuga aaagauugca gaguuaucau   2880

aauaaauugc uaacuugcgu aaaaaaaaaa aaaaaaaaaa                         2920
```

```
<210> SEQ ID NO 25
<211> LENGTH: 1982
<212> TYPE: RNA
<213> ORGANISM: Homo sapiens

<400> SEQUENCE: 25

gugccucccg gcugguuucu gagaucagcc acagaaguua aacuucuuuc cagggaagaa     60

gggcggggau gucagggcug gagagugccc guguccuucu gugugcauug ggcuccuucc    120

uccuuaauuc ucugcuuucc acuuuuaggc ugaacuccag ugcacccagu uagacuugga    180

gcggaaacuc aaguugaaug aaaaugccau cuccaggcuc caggcuaacc aaaagucugu    240

ucuggugucg gugucagagg ucaaagcagu ggcugaaaug caguuugggg aacuccuugc    300

ugcugugagg aaggcccagg ccaaugugau gcucuucuua gaggagaagg agcaagcugc    360

gcugagccag gccaacggua ucaaggccca ccuggaguac aggagugccg agauggagaa    420

gaguaagcag gagcuggaga cgauggcggc caucagcaac acuguccagu ucuuggagga    480

guacugcaag uuuaagaaca cugaagacau caccuucccu aguguuuaca uagggcugaa    540

ggauaaacuc ucgggcaucc gcaaaguuau cacggaaucc acuguacacu uaauccaguu    600

gcuggagaac uauaagaaaa agcuccagga guuuuccaag gaagaggagu augacaucag    660
```

```
aacucaagug ucugccauug uucagcgcaa auauuggacu uccaaaccug agcccagcac    720

cagggaacag uuccuccaau augugcauga caucacguuc gacccggaca cagcacacaa    780

guaucuccgg cugcaggagg agaaccgcaa ggucaccaac accacgcccu gggagcaucc    840

cuacccggac cuccccagca gguuccugca cuggcggcag gugcuguccc agcagagucu    900

guaccugcac agguacuauu uugaggugga gaucuucggg gcaggcaccu auguuggccu    960

gaccugcaaa ggcaucgacc agaaagggga ggagcgcagc aguugcauuu ccggaaacaa   1020

cuucuccugg agccuccaau ggaacgggaa ggaguucacg gccugguaca gugacaugga   1080

gaccccacuc aaagcuggcc cuuucuggag gcucggggcuc uauauugacu ucccaggagg   1140

gauccuuucc uucuauggcg uagaguauga uuccaugacu cugguucaca aguuugccug   1200

caaguuuuca gaaccagucu augcugccuu cuggcuuucc aagaaggaaa acgccauccg   1260

gauuguagau cugggagagg aacccgagaa gccagcaccg uccuuggugg ggacugcucc   1320

cuagacucca ggagccauau cccagaccuu ugccagcuac agugauggga uuugcauuuu   1380

agggugauuu gggggcaaaa auaacugcug augguagcug gcuuuugaaa uccuaugggg   1440

ucucugaaug aaaacauucu ccagcugcuc ucuuuugcuc cauauggugc uguucucuau   1500

guguuugcag uaauucuuuu uuuuuuuuuu uuugagacgg agucucgcac uguugcccag   1560

gcuggagugc aguggcguga ucuuggcuca cugcaagcuc cgccuccega guucaagcaa   1620

uucuccugcc ucagccuccc gaguagcugg gauuacaggu gccugccacc acacccagcu   1680

aacguuuugu auuuuuagua gagauggggu uucaccaugu uggccaggca gaucucaaac   1740

uucugaccuc gugaugcacu caccucggcc ucccaaagug cugggauuac aggcgugagc   1800

cacugcgccc ugccuguuug uaguaauuuu uaggcaccaa aucucccuca ucuucuagug   1860

ccauucuccu cucuguucag guaaauguca cacugugccc agaauggaug accaggaacc   1920

uucaagagug gcugaaaaga uugcagaguu aucauaauaa auugcuaacu ugcguauuuc   1980

cu                                                                  1982
```

<210> SEQ ID NO 26
<211> LENGTH: 826
<212> TYPE: RNA
<213> ORGANISM: Homo sapiens

<400> SEQUENCE: 26

```
cucgcaggcu ccaggggcgg ggcguggccg gggcgcagcg acgggcgcgg agguccggcc     60

gggcgcgcgc gcccccgcca cacgcacgcc gggcgugcca guuuauaaag ggagagagca    120

agcagcgagu cuugaagcuc uguuuggugc uuuggaucca uuuccaucgg uccuuacagc    180

cgcucgucag acuccagcag ccaagauggu gaagcagauc gagagcaaga cugcuuuuca    240

ggaagccuug gacgcugcag gugauaaacu uguaguaguu gacuucucag ccacguggug    300

ugggccuugc aaaaugauca agccuuucuu ucaugauguu gcuucagagu gugaagucaa    360

augcaugcca acauuccagu uuuuuaagaa gggacaaaag gugggugaau uuucuggagc    420

caauaaggaa aagcuugaag ccaccauuaa ugaauuaguc uaaucauguu uucugaaaau    480

auaaccagcc auuggcuauu uaaaacuugu aauuuuuuua auuuacaaaa auauaaaaua    540

ugaagacaua aacccaguug ccaucugcgu gacaauaaaa cauuaaugcu aacacuuuuu    600

aaaaccgucu caugucugaa uagcuuucaa aauaaaugug aaauggucau uuaauguauu    660

uuccuauauu cucaaucacu uuuuaguaac cuuguaggcc acugauuauu uuaagauuuu    720
```

```
aaaaauuauu auugcuaccu uaauguauug cuacaaaaau cucuuguugg gggcaaugca    780

gguaauaaag uaguauguug uuauuuguaa aaaaaaaaaa aaaaaa                  826


<210> SEQ ID NO 27
<211> LENGTH: 3846
<212> TYPE: RNA
<213> ORGANISM: Homo sapiens

<400> SEQUENCE: 27

agacccucac gugaugacaa cagcuagcaa aguucuguag cuacugccuu agggcauagu     60

cuaauuucuu caguaaaaac acacuuauuc caaauuuggu uccagaauug ccuuaaauug    120

uuuuugcucu guucuuaggu ugggggcggc uaugagcagg cagaggaugu ggugucaccc    180

aauuaggagc ucucagcuua cgaggcaauu agcauagguu gccagggcug cacgaggagu    240

ggauuucugc uuugucauuc ugacucuggc aguuagcccg cccgcucggc gcagggcgug    300

gcuucucgua gccauuagga aacagcaacc cuuucaccuc aguuuucuuc acuccggcau    360

uugcagcaga gcgaaaggug gucgaguccu gaaggagggc cugaugucuu caucauucuc    420

aaauucuuag gacggucggg cccuggaagg aacgcucucg gaauuggccg cggaaaccga    480

ucugcccguu guguuuguga aacagagaaa gauaggcggc cauggucaa ccuugaagga     540

ggcagcccaa uauggcaaga aggugauggu ccuggacuuu gucacuccca ccccucuugg    600

aacuagaugg ggucucggag gaacaugugu gaaugugggu ugcauaccua aaaaacugau    660

gcaucaagca gcuuuguuag gacaagcccu gcaagacucu cgaaauuaug gauggaaagu    720

cgaggagaca guuaagcaug auugggacag aaugauagaa gcuguacaga aucacauugg    780

cucuuugaau uggggcuacc gaguagcucu gcgggagaaa aaagucgucu augagaaugc    840

uuaugggcaa uuuauugguc cucacaggau uaaggcaaca aauaauaaag gcaaagaaaa    900

aauuuauuca gcagagagau uucucauugc cacuggugaa agaccacguu acuugggcau    960

cccuggugac aaagaauacu gcaucagcag ugaugaucuu uucuccuugc cuuacugccc   1020

ggguaagacc cugguuguug gagcauccua ugucgcuuug gagugcgcug gauuucuugc   1080

ugguauuggu uuagacguca cuguuauggu uagguccauu cuucuuagag gauuugacca   1140

ggacauggcc aacaaaauug gugaacacau ggaagaacau ggcaucaagu uuauaagaca   1200

guucguacca auuaaaguug aacaaauuga agcagggaca ccaggccgac ucagaguagu   1260

agcucagucc accaauagug aggaaaucau ugaaggagaa uauaauacgg ugaugcuggc   1320

aauaggaaga gaugcuugca caagaaaaau uggcuuagaa accguagggg ugaagauaaa   1380

ugaaaagacu ggaaaaauac cugucacaga ugaagaacag accaaugugc cuuacaucua   1440

ugccauuggc gauauauugg aggauaaggu ggagcucacc ccaguugcaa uccaggcagg   1500

aagauugcug gcucagaggc ucuaugcagg uuccacuguc aagugugacu augaaaaugu   1560

uccaaccacu guauuuacuc cuuuggaaua uggugcuugu ggccuuucug aggagaaagc   1620

uguggagaag uuuggggaag aaaauauuga gguuuaccau aguuacuuuu ggccauugga   1680

auggacgauu ccgucaagag auaacaacaa auguuaugca aaaauaaucu guaauacuaa   1740

agacaaugaa cguguugugg gcuuucacgu acugggucca aaugcuggag aaguuacaca   1800

aggcuuugca gcugcgcuca aauguggacu gaccaaaaag cagcuggaca gcacaauugg   1860

aauccacccu gucugugcag agguauucac aacauugucu gugaccaagc gcucuggggc   1920

aagcauccuc caggcuggcu gcugagguua agccccagug uggaugcugu ugccaagacu   1980

gcaaaccacu ggcucguuuc cgugcccaaa uccaaggcga aguuuucuag aggguucuug   2040
```

```
ggcucuuggc accugcgugu ccugugcuua ccaccgccca aggcccccuu ggaucucuug   2100

gauaggaguu ggugaauaga aggcaggcag caucacacug ggguacacuga cagacuugaa   2160

gcugacauuu ggcagggcau cgaagggaug cauccaugaa gucaccaguc ucaagcccau   2220

gugguaggcg gugauggaac aacugucaaa ucaguuuuag caugaccuuu ccuuguggau   2280

uuucuuauuc ucguugucaa guuuucuagg guugaauuuu uuucuuuuuu cuccauggug   2340

uuaaugauau uagagaugaa aaacguuagc aguugauuuu uguccaaaag caagucaugg   2400

cuagaguauc caugcaaggu gucuuguugc auggaaggga uaguuuggcu cccuuggagg   2460

cuauguaggc uugucccggg aaagagaacu guccugcagc ugaaauggac uguucuuuac   2520

ugaccugcuc agcaguuucu ucucucauau auucccaaaa caaguacauc ugcgaucaac   2580

ucuagccaaa uuugccccug ugugcuacau gauggaugau uauuauuuua aggucuguuu   2640

aggaagggaa auggcuacuu ggccagccau ugccuggcau uugguaguau aguaugauuc   2700

ucaccauuau uugucaugga ggcagacaua caccagaaau gggggagaaa caguacauau   2760

cuuucugucu uuaguuuauu gugugcuggu cuaagcaagc ugagaucauu ugcaauggaa   2820

aacacguaac uuguuuaaaa guuuuucugg uagcuuuagc uuuaugcuaa aaaaaauaau   2880

gacauugggu aucuauuucu uucuaagacu acauuaguag gaaaauaagu cuuuucaugc   2940

uuaugauuua gcuguuuugu gguaauugcu uuuuaaagga aguuauuaau aucauaaguu   3000

auuauuaaua uuuugaacac agguggaugu gaaggauuuu cauuuaaaaa ccaagugguu   3060

uugacuuuuu cuguugaaug aacaacugug ccuuguggaa uuuuugcaga aguguuuaug   3120

cuuuguuagc auuucaacuu gcauuauuau aaagagguau uaaugccuca guuauguguu   3180

ugucaaugua cuggcugagg auucuaucuc agcugucuuu ucuaacugug uagguugagu   3240

uuugaacacg ugcuugugga caucaggccu ccugccagca guucuugaag cuucuuuuuc   3300

auuccugcua cucuaccugu auuucucagu ugcagcacug aguggucaaa auacauuucu   3360

gggccaccuc agggaaccca ugcaucugcc uggcauuuag gcagcagagc cccugaccgu   3420

cccccacagg gcucugccuc acguccucau cucauuuggc uguguaaaga aaugggaaaa   3480

gggaaaagga gagagcaauu gaggcaguug accauauuca guuuuauuua uuuauuuuua   3540

auuuguuuuu uucuccaagu ccaccagucu cugaaauuag aacaguaggc gguaugagau   3600

aaucaggccu aaucauguug ugauucucuu uucuuagugg aguggaaugu ucuaucccca   3660

caagaaggau uauaucuuau agacuugucu uguucagauu cuguauuuac ccauuuuauu   3720

gaaacauaua cuaaguucca uguauuuuug uuacaaaucu ucugaaaaaa aacaaaacaa   3780

ugugaaacau uaaaauuaaa aggcauuaau aauauccacg ugugccuucu uacugaaaaa   3840

aaaaaa                                                              3846
```

<210> SEQ ID NO 28
<211> LENGTH: 3013
<212> TYPE: RNA
<213> ORGANISM: Homo sapiens

<400> SEQUENCE: 28

```
gugaaggaaa uagggaccug gcccugggcc uuguguagcg ggagggggag cuaggaagca     60

gcugagggca gaauccagga gggccuggcu gcgggggaau gaagccuccg ccuucgcagg    120

caaaagccuu uaaaauacggg cucaggcccg ggacucagag uguaacgcgu ggcagccuga    180

gggaggggcg ugcgccgaga gggagcucag aucgagcggg gcgcgggugg agaagcugcg    240
```

-continued

```
gcggcgcggc ccguaggaag gugcuguccg aacgaucggg auaggagcgg ucccugcgcu    300
ugcugcuggg aagugguaca aucauguuug aaauuaagaa gaucuguugc aucggugcag    360
gcuauguugg aggacccaca uguaguguca uugcucauau guguccugaa aucaggguaa    420
cgguuguuga ugucaaugaa ucaagaauca augcguggaa uucuccuaca cuuccuauuu    480
augagccagg acuaaaagaa gugguagaau ccugucgagg aaaaaaucuu uuuuuuucua    540
ccaauauuga ugaugccauc aaagaagcug aucuuguauu uauuucugug cuguccaacc    600
cugaguuucu ggcagaggga acagccauca aggaccuaaa gaacccagac agaguacuga    660
uuggagggga ugaaacucca gagggccaga gagcugugca ggcccugugu gcuguauaug    720
agcacugggu ucccagagaa aagauccuca ccacuaauac uuggucuuca gagcuuucca    780
aacuggcagc aaaugcuuuu cuugcccaga gaauaagcag cauuaacucc auaagugcuc    840
ugugugaagc aacaggagcu gauguagaag agguagcaac agcgauugga auggaccaga    900
gaauuggaaa caaguuucua aaagccagug uuggguuugg ugggagcugu uuccaaaagg    960
auguucugaa uuugguuuau cucugugagg cucugaauuu gccagaagua gcucguuauu   1020
ggcagcaggu cauagacaug aaugacuacc agaggaggag guuugcuucc cggaucauag   1080
auagucuguu uaauacagua acugauaaga agauagcuau uuugggauuu gcauucaaaa   1140
aggacacugg ugauacaaga gaaucuucua guauauauau uagcaaauau uugauggaug   1200
aaggugcaca ucuacauaua uaugauccaa aaguaccuag ggaacaaaua guuguggauc   1260
uuucucaucc agguguuuca gaggaugacc aagugucccg gcucgugacc auuuccaagg   1320
auccauauga agcaugugau ggugcccaug cuguuguuau uugcacugag ugggacaugu   1380
uuaaggaauu ggauuaugaa cgcauucaua aaaaaaugcu aaagccagcc uuuaucuucg   1440
auggacggcg uguccuggau gggcuccaca augaacuaca aaccauuggc uuccagauug   1500
aaacaauugg caaaaaggug ucuucaaaga gaauuccaua ugcuccuucu ggugaaauuc   1560
cgaaguuuag ucuucaagau ccaccuaaca agaaaccuaa aguguagaga uugccauuuu   1620
uauuugugau uuuuuuuuuu uuuuuuuggu acuucaggau agcaaauauc uaucugcuau   1680
uaaaugguaa augaaccaag uguuuuuuuu uguuuuuuuu uugagacaga gucucacugu   1740
ugcccaggcu ggagugcagu ggugcaaucu cggcucacug caagcucugc uucccagguu   1800
cacgccauuc uccuggcuca gccucccaag uagcugggac uacaggcacc cgccacagug   1860
ccuggcuaau uuuuuguauu uuuaguagag acaggguuuc accaugugag ccaggauggu   1920
cucaaucucc ugaccuugug aaccacccgu cucggccucc caaagugcug ggauuacagg   1980
ugugagccac cacgccuggc ccaugaacca aguguuuuua aggaaacaaa acuauuuuuu   2040
uaaucaucag auuuauacua gcuauaugga uauuagcaua ucugguaauu augaaucuag   2100
aauuuuuuua cauauuuuua uaauacuguu agcucaguua uuggaugagu gaaagauaau   2160
cauguugguu uuaauagugu caauuuuugu aaaauaaaaa uuaaacuuca aacucuuuac   2220
uuuauaaauu guccauaggc cacacuuuaa uaucacauua uaaagggaag gacagucuuc   2280
auuccuccug guuauugguu uguuugucau uaaagauaua uuuugaaucc augaaauugc   2340
uaugcuaaac agccuuuaca uguauggucu gguuaaaguu ccuuuguucc uuuuguuuua   2400
auaaaaaugug ucacugauuu uuuagcucaa aaucaucacu guuaauuucc agucacccca   2460
aauaugguua aaagauuuuu uuuuuaauca ugaagagaaa auuaguagca uuucuuucuc   2520
uccccauuau uuauugguuu uccucacuaa ucuuuuuuuu uuuaguccaa aagccaaaaa   2580
uauuuaucuu gguuuuacau uuuaauuucc auucuuaauu guaauuuuuu ucuuuaaaua   2640
```

aggaaaccaa uauaaucuca uguauaaaaa cuuaaauauu uuacaaguua cauauagcau 2700
cauucuaaaa uaagaauuuu uuuuguuuuc ugucugcuuu uuucuuaugu cucuuguuga 2760
guuuuauauu uucagugguu auuuuugcuu guguuagauc auuauuaaaa uauauccaau 2820
gucccuuuga uacuugugcu cugcugagaa uguacaguuu gcauuaaaca ucccaggucu 2880
cauccuucag gaauuuugca guucaaugag aagagggaga caaauauaaa gaugaggaca 2940
gaagcaucuc uacagaugaa aauuacauaa auaaaacauu cuccaucaac aacuaaaaaa 3000
aaaaaaaaaa aaa 3013

<210> SEQ ID NO 29
<211> LENGTH: 19
<212> TYPE: RNA
<213> ORGANISM: Homo sapiens

<400> SEQUENCE: 29
uggaguaagu cgagaagua 19

<210> SEQ ID NO 30
<211> LENGTH: 19
<212> TYPE: RNA
<213> ORGANISM: Homo sapiens

<400> SEQUENCE: 30
acaacuagau gaagagaca 19

<210> SEQ ID NO 31
<211> LENGTH: 19
<212> TYPE: RNA
<213> ORGANISM: Homo sapiens

<400> SEQUENCE: 31
ugacagaagu ugacaauua 19

<210> SEQ ID NO 32
<211> LENGTH: 19
<212> TYPE: RNA
<213> ORGANISM: Homo sapiens

<400> SEQUENCE: 32
guaagaagcc agauguuaa 19

<210> SEQ ID NO 33
<211> LENGTH: 1545
<212> TYPE: PRT
<213> ORGANISM: Homo sapiens

<400> SEQUENCE: 33

```
Met Leu Glu Lys Phe Cys Asn Ser Thr Phe Trp Asn Ser Ser Phe Leu
1               5                   10                  15

Asp Ser Pro Glu Ala Asp Leu Pro Leu Cys Phe Glu Gln Thr Val Leu
            20                  25                  30

Val Trp Ile Pro Leu Gly Tyr Leu Trp Leu Leu Ala Pro Trp Gln Leu
        35                  40                  45

Leu His Val Tyr Lys Ser Arg Thr Lys Arg Ser Ser Thr Thr Lys Leu
    50                  55                  60

Tyr Leu Ala Lys Gln Val Phe Val Gly Phe Leu Leu Ile Leu Ala Ala
65                  70                  75                  80

Ile Glu Leu Ala Leu Val Leu Thr Glu Asp Ser Gly Gln Ala Thr Val
```

```
                85                  90                  95

Pro Ala Val Arg Tyr Thr Asn Pro Ser Leu Tyr Leu Gly Thr Trp Leu
            100                 105                 110

Leu Val Leu Leu Ile Gln Tyr Ser Arg Gln Trp Cys Val Gln Lys Asn
        115                 120                 125

Ser Trp Phe Leu Ser Leu Phe Trp Ile Leu Ser Ile Leu Cys Gly Thr
    130                 135                 140

Phe Gln Phe Gln Thr Leu Ile Arg Thr Leu Leu Gln Gly Asp Asn Ser
145                 150                 155                 160

Asn Leu Ala Tyr Ser Cys Leu Phe Phe Ile Ser Tyr Gly Phe Gln Ile
                165                 170                 175

Leu Ile Leu Ile Phe Ser Ala Phe Ser Glu Asn Asn Glu Ser Ser Asn
            180                 185                 190

Asn Pro Ser Ser Ile Ala Ser Phe Leu Ser Ser Ile Thr Tyr Ser Trp
        195                 200                 205

Tyr Asp Ser Ile Ile Leu Lys Gly Tyr Lys Arg Pro Leu Thr Leu Glu
    210                 215                 220

Asp Val Trp Glu Val Asp Glu Glu Met Lys Thr Lys Thr Leu Val Ser
225                 230                 235                 240

Lys Phe Glu Thr His Met Lys Arg Glu Leu Gln Lys Ala Arg Arg Ala
                245                 250                 255

Leu Gln Arg Arg Gln Glu Lys Ser Ser Gln Gln Asn Ser Gly Ala Arg
            260                 265                 270

Leu Pro Gly Leu Asn Lys Asn Gln Ser Gln Ser Gln Asp Ala Leu Val
        275                 280                 285

Leu Glu Asp Val Glu Lys Lys Lys Lys Lys Ser Gly Thr Lys Lys Asp
    290                 295                 300

Val Pro Lys Ser Trp Leu Met Lys Ala Leu Phe Lys Thr Phe Tyr Met
305                 310                 315                 320

Val Leu Leu Lys Ser Phe Leu Leu Lys Leu Val Asn Asp Ile Phe Thr
                325                 330                 335

Phe Val Ser Pro Gln Leu Leu Lys Leu Leu Ile Ser Phe Ala Ser Asp
            340                 345                 350

Arg Asp Thr Tyr Leu Trp Ile Gly Tyr Leu Cys Ala Ile Leu Leu Phe
        355                 360                 365

Thr Ala Ala Leu Ile Gln Ser Phe Cys Leu Gln Cys Tyr Phe Gln Leu
    370                 375                 380

Cys Phe Lys Leu Gly Val Lys Val Arg Thr Ala Ile Met Ala Ser Val
385                 390                 395                 400

Tyr Lys Lys Ala Leu Thr Leu Ser Asn Leu Ala Arg Lys Glu Tyr Thr
                405                 410                 415

Val Gly Glu Thr Val Asn Leu Met Ser Val Asp Ala Gln Lys Leu Met
            420                 425                 430

Asp Val Thr Asn Phe Met His Met Leu Trp Ser Ser Val Leu Gln Ile
        435                 440                 445

Val Leu Ser Ile Phe Phe Leu Trp Arg Glu Leu Gly Pro Ser Val Leu
    450                 455                 460

Ala Gly Val Gly Val Met Val Leu Val Ile Pro Ile Asn Ala Ile Leu
465                 470                 475                 480

Ser Thr Lys Ser Lys Thr Ile Gln Val Lys Asn Met Lys Asn Lys Asp
                485                 490                 495

Lys Arg Leu Lys Ile Met Asn Glu Ile Leu Ser Gly Ile Lys Ile Leu
            500                 505                 510
```

```
Lys Tyr Phe Ala Trp Glu Pro Ser Phe Arg Asp Gln Val Gln Asn Leu
        515                 520                 525

Arg Lys Lys Glu Leu Lys Asn Leu Leu Ala Phe Ser Gln Leu Gln Cys
    530                 535                 540

Val Val Ile Phe Val Phe Gln Leu Thr Pro Val Leu Val Ser Val Val
545                 550                 555                 560

Thr Phe Ser Val Tyr Val Leu Val Asp Ser Asn Asn Ile Leu Asp Ala
                565                 570                 575

Gln Lys Ala Phe Thr Ser Ile Thr Leu Phe Asn Ile Leu Arg Phe Pro
            580                 585                 590

Leu Ser Met Leu Pro Met Met Ile Ser Ser Met Leu Gln Ala Ser Val
        595                 600                 605

Ser Thr Glu Arg Leu Glu Lys Tyr Leu Gly Gly Asp Asp Leu Asp Thr
    610                 615                 620

Ser Ala Ile Arg His Asp Cys Asn Phe Asp Lys Ala Met Gln Phe Ser
625                 630                 635                 640

Glu Ala Ser Phe Thr Trp Glu His Asp Ser Glu Ala Thr Val Arg Asp
                645                 650                 655

Val Asn Leu Asp Ile Met Ala Gly Gln Leu Val Ala Val Ile Gly Pro
            660                 665                 670

Val Gly Ser Gly Lys Ser Ser Leu Ile Ser Ala Met Leu Gly Glu Met
        675                 680                 685

Glu Asn Val His Gly His Ile Thr Ile Lys Gly Thr Thr Ala Tyr Val
    690                 695                 700

Pro Gln Gln Ser Trp Ile Gln Asn Gly Thr Ile Lys Asp Asn Ile Leu
705                 710                 715                 720

Phe Gly Thr Glu Phe Asn Glu Lys Arg Tyr Gln Gln Val Leu Glu Ala
                725                 730                 735

Cys Ala Leu Leu Pro Asp Leu Glu Met Leu Pro Gly Gly Asp Leu Ala
            740                 745                 750

Glu Ile Gly Glu Lys Gly Ile Asn Leu Ser Gly Gly Gln Lys Gln Arg
        755                 760                 765

Ile Ser Leu Ala Arg Ala Thr Tyr Gln Asn Leu Asp Ile Tyr Leu Leu
    770                 775                 780

Asp Asp Pro Leu Ser Ala Val Asp Ala His Val Gly Lys His Ile Phe
785                 790                 795                 800

Asn Lys Val Leu Gly Pro Asn Gly Leu Leu Lys Gly Lys Thr Arg Leu
                805                 810                 815

Leu Val Thr His Ser Met His Phe Leu Pro Gln Val Asp Glu Ile Val
            820                 825                 830

Val Leu Gly Asn Gly Thr Ile Val Glu Lys Gly Ser Tyr Ser Ala Leu
        835                 840                 845

Leu Ala Lys Lys Gly Glu Phe Ala Lys Asn Leu Lys Thr Phe Leu Arg
    850                 855                 860

His Thr Gly Pro Glu Glu Glu Ala Thr Val His Asp Gly Ser Glu Glu
865                 870                 875                 880

Glu Asp Asp Asp Tyr Gly Leu Ile Ser Ser Val Glu Glu Ile Pro Glu
                885                 890                 895

Asp Ala Ala Ser Ile Thr Met Arg Arg Glu Asn Ser Phe Arg Arg Thr
            900                 905                 910

Leu Ser Arg Ser Ser Arg Ser Asn Gly Arg His Leu Lys Ser Leu Arg
        915                 920                 925
```

```
Asn Ser Leu Lys Thr Arg Asn Val Asn Ser Leu Lys Glu Asp Glu Glu
    930                 935                 940

Leu Val Lys Gly Gln Lys Leu Ile Lys Lys Glu Phe Ile Glu Thr Gly
945                 950                 955                 960

Lys Val Lys Phe Ser Ile Tyr Leu Glu Tyr Leu Gln Ala Ile Gly Leu
                965                 970                 975

Phe Ser Ile Phe Phe Ile Ile Leu Ala Phe Val Met Asn Ser Val Ala
            980                 985                 990

Phe Ile Gly Ser Asn Leu Trp Leu  Ser Ala Trp Thr Ser  Asp Ser Lys
        995                 1000                1005

Ile Phe  Asn Ser Thr Asp Tyr  Pro Ala Ser Gln Arg  Asp Met Arg
    1010                1015                1020

Val Gly  Val Tyr Gly Ala Leu  Gly Leu Ala Gln Gly  Ile Phe Val
    1025                1030                1035

Phe Ile  Ala His Phe Trp Ser  Ala Phe Gly Phe Val  His Ala Ser
    1040                1045                1050

Asn Ile  Leu His Lys Gln Leu  Leu Asn Asn Ile Leu  Arg Ala Pro
    1055                1060                1065

Met Arg  Phe Phe Asp Thr Thr  Pro Thr Gly Arg Ile  Val Asn Arg
    1070                1075                1080

Phe Ala  Gly Asp Ile Ser Thr  Val Asp Asp Thr Leu  Pro Gln Ser
    1085                1090                1095

Leu Arg  Ser Trp Ile Thr Cys  Phe Leu Gly Ile Ile  Ser Thr Leu
    1100                1105                1110

Val Met  Ile Cys Met Ala Thr  Pro Val Phe Thr Ile  Ile Val Ile
    1115                1120                1125

Pro Leu  Gly Ile Ile Tyr Val  Ser Val Gln Met Phe  Tyr Val Ser
    1130                1135                1140

Thr Ser  Arg Gln Leu Arg Arg  Leu Asp Ser Val Thr  Arg Ser Pro
    1145                1150                1155

Ile Tyr  Ser His Phe Ser Glu  Thr Val Ser Gly Leu  Pro Val Ile
    1160                1165                1170

Arg Ala  Phe Glu His Gln Gln  Arg Phe Leu Lys His  Asn Glu Val
    1175                1180                1185

Arg Ile  Asp Thr Asn Gln Lys  Cys Val Phe Ser Trp  Ile Thr Ser
    1190                1195                1200

Asn Arg  Trp Leu Ala Ile Arg  Leu Glu Leu Val Gly  Asn Leu Thr
    1205                1210                1215

Val Phe  Phe Ser Ala Leu Met  Met Val Ile Tyr Arg  Asp Thr Leu
    1220                1225                1230

Ser Gly  Asp Thr Val Gly Phe  Val Leu Ser Asn Ala  Leu Asn Ile
    1235                1240                1245

Thr Gln  Thr Leu Asn Trp Leu  Val Arg Met Thr Ser  Glu Ile Glu
    1250                1255                1260

Thr Asn  Ile Val Ala Val Glu  Arg Ile Thr Glu Tyr  Thr Lys Val
    1265                1270                1275

Glu Asn  Glu Ala Pro Trp Val  Thr Asp Lys Arg Pro  Pro Pro Asp
    1280                1285                1290

Trp Pro  Ser Lys Gly Lys Ile  Gln Phe Asn Asn Tyr  Gln Val Arg
    1295                1300                1305

Tyr Arg  Pro Glu Leu Asp Leu  Val Leu Arg Gly Ile  Thr Cys Asp
    1310                1315                1320

Ile Gly  Ser Met Glu Lys Ile  Gly Val Val Gly Arg  Thr Gly Ala
```

```
    1325                1330                1335

Gly Lys  Ser Ser Leu Thr Asn  Cys Leu Phe Arg Ile  Leu Glu Ala
    1340                1345                1350

Ala Gly  Gly Gln Ile Ile Ile  Asp Gly Val Asp Ile  Ala Ser Ile
    1355                1360                1365

Gly Leu  His Asp Leu Arg Glu  Lys Leu Thr Ile Ile  Pro Gln Asp
    1370                1375                1380

Pro Ile  Leu Phe Ser Gly Ser  Leu Arg Met Asn Leu  Asp Pro Phe
    1385                1390                1395

Asn Asn  Tyr Ser Asp Glu Glu  Ile Trp Lys Ala Leu  Glu Leu Ala
    1400                1405                1410

His Leu  Lys Ser Phe Val Ala  Ser Leu Gln Leu Gly  Leu Ser His
    1415                1420                1425

Glu Val  Thr Glu Ala Gly Gly  Asn Leu Ser Ile Gly  Gln Arg Gln
    1430                1435                1440

Leu Leu  Cys Leu Gly Arg Ala  Leu Leu Arg Lys Ser  Lys Ile Leu
    1445                1450                1455

Val Leu  Asp Glu Ala Thr Ala  Ala Val Asp Leu Glu  Thr Asp Asn
    1460                1465                1470

Leu Ile  Gln Thr Thr Ile Gln  Asn Glu Phe Ala His  Cys Thr Val
    1475                1480                1485

Ile Thr  Ile Ala His Arg Leu  His Thr Ile Met Asp  Ser Asp Lys
    1490                1495                1500

Val Met  Val Leu Asp Asn Gly  Lys Ile Ile Glu Cys  Gly Ser Pro
    1505                1510                1515

Glu Glu  Leu Leu Gln Ile Pro  Gly Pro Phe Tyr Phe  Met Ala Lys
    1520                1525                1530

Glu Ala  Gly Ile Glu Asn Val  Asn Ser Thr Lys Phe
    1535                1540                1545
```

<210> SEQ ID NO 34
<211> LENGTH: 316
<212> TYPE: PRT
<213> ORGANISM: Homo sapiens

<400> SEQUENCE: 34

```
Met Ala Thr Phe Val Glu Leu Ser Thr Lys Ala Lys Met Pro Ile Val
1               5                   10                  15

Gly Leu Gly Thr Trp Lys Ser Pro Leu Gly Lys Val Lys Glu Ala Val
            20                  25                  30

Lys Val Ala Ile Asp Ala Gly Tyr Arg His Ile Asp Cys Ala Tyr Val
        35                  40                  45

Tyr Gln Asn Glu His Glu Val Gly Glu Ala Ile Gln Glu Lys Ile Gln
    50                  55                  60

Glu Lys Ala Val Lys Arg Glu Asp Leu Phe Ile Val Ser Lys Leu Trp
65                  70                  75                  80

Pro Thr Phe Phe Glu Arg Pro Leu Val Arg Lys Ala Phe Glu Lys Thr
                85                  90                  95

Leu Lys Asp Leu Lys Leu Ser Tyr Leu Asp Val Tyr Leu Ile His Trp
            100                 105                 110

Pro Gln Gly Phe Lys Ser Gly Asp Asp Leu Phe Pro Lys Asp Asp Lys
        115                 120                 125

Gly Asn Ala Ile Gly Gly Lys Ala Thr Phe Leu Asp Ala Trp Glu Ala
    130                 135                 140
```

```
Met Glu Glu Leu Val Asp Glu Gly Leu Val Lys Ala Leu Gly Val Ser
145                 150                 155                 160

Asn Phe Ser His Phe Gln Ile Glu Lys Leu Leu Asn Lys Pro Gly Leu
                165                 170                 175

Lys Tyr Lys Pro Val Thr Asn Gln Val Glu Cys His Pro Tyr Leu Thr
            180                 185                 190

Gln Glu Lys Leu Ile Gln Tyr Cys His Ser Lys Gly Ile Thr Val Thr
        195                 200                 205

Ala Tyr Ser Pro Leu Gly Ser Pro Asp Arg Pro Trp Ala Lys Pro Glu
    210                 215                 220

Asp Pro Ser Leu Leu Glu Asp Pro Lys Ile Lys Glu Ile Ala Ala Lys
225                 230                 235                 240

His Lys Lys Thr Ala Ala Gln Val Leu Ile Arg Phe His Ile Gln Arg
                245                 250                 255

Asn Val Ile Val Ile Pro Lys Ser Val Thr Pro Ala Arg Ile Val Glu
            260                 265                 270

Asn Ile Gln Val Phe Asp Phe Lys Leu Ser Asp Glu Glu Met Ala Thr
        275                 280                 285

Ile Leu Ser Phe Asn Arg Asn Trp Arg Ala Cys Asn Val Leu Gln Ser
    290                 295                 300

Ser His Leu Glu Asp Tyr Pro Phe Asn Ala Glu Tyr
305                 310                 315


<210> SEQ ID NO 35
<211> LENGTH: 316
<212> TYPE: PRT
<213> ORGANISM: Homo sapiens

<400> SEQUENCE: 35

Met Ala Thr Phe Val Glu Leu Ser Thr Lys Ala Lys Met Pro Ile Val
1               5                   10                  15

Gly Leu Gly Thr Trp Arg Ser Leu Leu Gly Lys Val Lys Glu Ala Val
            20                  25                  30

Lys Val Ala Ile Asp Ala Glu Tyr Arg His Ile Asp Cys Ala Tyr Phe
        35                  40                  45

Tyr Glu Asn Gln His Glu Val Gly Glu Ala Ile Gln Glu Lys Ile Gln
    50                  55                  60

Glu Lys Ala Val Met Arg Glu Asp Leu Phe Ile Val Ser Lys Val Trp
65                  70                  75                  80

Pro Thr Phe Phe Glu Arg Pro Leu Val Arg Lys Ala Phe Glu Lys Thr
                85                  90                  95

Leu Lys Asp Leu Lys Leu Ser Tyr Leu Asp Val Tyr Leu Ile His Trp
            100                 105                 110

Pro Gln Gly Phe Lys Thr Gly Asp Asp Phe Phe Pro Lys Asp Asp Lys
        115                 120                 125

Gly Asn Met Ile Ser Gly Lys Gly Thr Phe Leu Asp Ala Trp Glu Ala
    130                 135                 140

Met Glu Glu Leu Val Asp Glu Gly Leu Val Lys Ala Leu Gly Val Ser
145                 150                 155                 160

Asn Phe Asn His Phe Gln Ile Glu Arg Leu Leu Asn Lys Pro Gly Leu
                165                 170                 175

Lys Tyr Lys Pro Val Thr Asn Gln Val Glu Cys His Pro Tyr Leu Thr
            180                 185                 190

Gln Glu Lys Leu Ile Gln Tyr Cys His Ser Lys Gly Ile Thr Val Thr
        195                 200                 205
```

```
Ala Tyr Ser Pro Leu Gly Ser Pro Asp Arg Pro Trp Ala Lys Pro Glu
    210                 215                 220

Asp Pro Ser Leu Leu Glu Asp Pro Lys Ile Lys Glu Ile Ala Ala Lys
225                 230                 235                 240

His Lys Lys Thr Thr Ala Gln Val Leu Ile Arg Phe His Ile Gln Arg
                245                 250                 255

Asn Val Thr Val Ile Pro Lys Ser Met Thr Pro Ala His Ile Val Glu
            260                 265                 270

Asn Ile Gln Val Phe Asp Phe Lys Leu Ser Asp Glu Glu Met Ala Thr
        275                 280                 285

Ile Leu Ser Phe Asn Arg Asn Trp Arg Ala Phe Asp Phe Lys Glu Phe
    290                 295                 300

Ser His Leu Glu Asp Phe Pro Phe Asp Ala Glu Tyr
305                 310                 315


<210> SEQ ID NO 36
<211> LENGTH: 323
<212> TYPE: PRT
<213> ORGANISM: Homo sapiens

<400> SEQUENCE: 36

Met Asp Ser Lys Tyr Gln Cys Val Lys Leu Asn Asp Gly His Phe Met
1               5                   10                  15

Pro Val Leu Gly Phe Gly Thr Tyr Ala Pro Ala Glu Val Pro Lys Ser
            20                  25                  30

Lys Ala Leu Glu Ala Val Lys Leu Ala Ile Glu Ala Gly Phe His His
        35                  40                  45

Ile Asp Ser Ala His Val Tyr Asn Asn Glu Glu Gln Val Gly Leu Ala
    50                  55                  60

Ile Arg Ser Lys Ile Ala Asp Gly Ser Val Lys Arg Glu Asp Ile Phe
65                  70                  75                  80

Tyr Thr Ser Lys Leu Trp Ser Asn Ser His Arg Pro Glu Leu Val Arg
                85                  90                  95

Pro Ala Leu Glu Arg Ser Leu Lys Asn Leu Gln Leu Asp Tyr Val Asp
            100                 105                 110

Leu Tyr Leu Ile His Phe Pro Val Ser Val Lys Pro Gly Glu Glu Val
        115                 120                 125

Ile Pro Lys Asp Glu Asn Gly Lys Ile Leu Phe Asp Thr Val Asp Leu
    130                 135                 140

Cys Ala Thr Trp Glu Ala Met Glu Lys Cys Lys Asp Ala Gly Leu Ala
145                 150                 155                 160

Lys Ser Ile Gly Val Ser Asn Phe Asn His Arg Leu Leu Glu Met Ile
                165                 170                 175

Leu Asn Lys Pro Gly Leu Lys Tyr Lys Pro Val Cys Asn Gln Val Glu
            180                 185                 190

Cys His Pro Tyr Phe Asn Gln Arg Lys Leu Leu Asp Phe Cys Lys Ser
        195                 200                 205

Lys Asp Ile Val Leu Val Ala Tyr Ser Ala Leu Gly Ser His Arg Glu
    210                 215                 220

Glu Pro Trp Val Asp Pro Asn Ser Pro Val Leu Leu Glu Asp Pro Val
225                 230                 235                 240

Leu Cys Ala Leu Ala Lys Lys His Lys Arg Thr Pro Ala Leu Ile Ala
                245                 250                 255

Leu Arg Tyr Gln Leu Gln Arg Gly Val Val Val Leu Ala Lys Ser Tyr
```

```
            260                 265                 270

Asn Glu Gln Arg Ile Arg Gln Asn Val Gln Val Phe Glu Phe Gln Leu
        275                 280                 285

Thr Ser Glu Glu Met Lys Ala Ile Asp Gly Leu Asn Arg Asn Val Arg
    290                 295                 300

Tyr Leu Thr Leu Asp Ile Phe Ala Gly Pro Pro Asn Tyr Pro Phe Ser
305                 310                 315                 320

Asp Glu Tyr


<210> SEQ ID NO 37
<211> LENGTH: 323
<212> TYPE: PRT
<213> ORGANISM: Homo sapiens

<400> SEQUENCE: 37

Met Asp Ser Lys His Gln Cys Val Lys Leu Asn Asp Gly His Phe Met
1               5                   10                  15

Pro Val Leu Gly Phe Gly Thr Tyr Ala Pro Pro Glu Val Pro Arg Ser
            20                  25                  30

Lys Ala Leu Glu Val Thr Lys Leu Ala Ile Glu Ala Gly Phe Arg His
        35                  40                  45

Ile Asp Ser Ala His Leu Tyr Asn Asn Glu Glu Gln Val Gly Leu Ala
    50                  55                  60

Ile Arg Ser Lys Ile Ala Asp Gly Ser Val Lys Arg Glu Asp Ile Phe
65                  70                  75                  80

Tyr Thr Ser Lys Leu Trp Ser Thr Phe His Arg Pro Glu Leu Val Arg
                85                  90                  95

Pro Ala Leu Glu Asn Ser Leu Lys Lys Ala Gln Leu Asp Tyr Val Asp
            100                 105                 110

Leu Tyr Leu Ile His Ser Pro Met Ser Leu Lys Pro Gly Glu Glu Leu
        115                 120                 125

Ser Pro Thr Asp Glu Asn Gly Lys Val Ile Phe Asp Ile Val Asp Leu
    130                 135                 140

Cys Thr Thr Trp Glu Ala Met Glu Lys Cys Lys Asp Ala Gly Leu Ala
145                 150                 155                 160

Lys Ser Ile Gly Val Ser Asn Phe Asn Arg Arg Gln Leu Glu Met Ile
                165                 170                 175

Leu Asn Lys Pro Gly Leu Lys Tyr Lys Pro Val Cys Asn Gln Val Glu
            180                 185                 190

Cys His Pro Tyr Phe Asn Arg Ser Lys Leu Leu Asp Phe Cys Lys Ser
        195                 200                 205

Lys Asp Ile Val Leu Val Ala Tyr Ser Ala Leu Gly Ser Gln Arg Asp
    210                 215                 220

Lys Arg Trp Val Asp Pro Asn Ser Pro Val Leu Leu Glu Asp Pro Val
225                 230                 235                 240

Leu Cys Ala Leu Ala Lys Lys His Lys Arg Thr Pro Ala Leu Ile Ala
                245                 250                 255

Leu Arg Tyr Gln Leu Gln Arg Gly Val Val Val Leu Ala Lys Ser Tyr
            260                 265                 270

Asn Glu Gln Arg Ile Arg Gln Asn Val Gln Val Phe Glu Phe Gln Leu
        275                 280                 285

Thr Ala Glu Asp Met Lys Ala Ile Asp Gly Leu Asp Arg Asn Leu His
    290                 295                 300

Tyr Phe Asn Ser Asp Ser Phe Ala Ser His Pro Asn Tyr Pro Tyr Ser
```

305 310 315 320

Asp Glu Tyr

<210> SEQ ID NO 38
<211> LENGTH: 323
<212> TYPE: PRT
<213> ORGANISM: Homo sapiens

<400> SEQUENCE: 38

Met Asp Pro Lys Tyr Gln Arg Val Glu Leu Asn Asp Gly His Phe Met
1 5 10 15

Pro Val Leu Gly Phe Gly Thr Tyr Ala Pro Pro Glu Val Pro Arg Asn
20 25 30

Arg Ala Val Glu Val Thr Lys Leu Ala Ile Glu Ala Gly Phe Arg His
35 40 45

Ile Asp Ser Ala Tyr Leu Tyr Asn Asn Glu Glu Gln Val Gly Leu Ala
50 55 60

Ile Arg Ser Lys Ile Ala Asp Gly Ser Val Lys Arg Glu Asp Ile Phe
65 70 75 80

Tyr Thr Ser Lys Leu Trp Cys Thr Phe Phe Gln Pro Gln Met Val Gln
85 90 95

Pro Ala Leu Glu Ser Ser Leu Lys Lys Leu Gln Leu Asp Tyr Val Asp
100 105 110

Leu Tyr Leu Leu His Phe Pro Met Ala Leu Lys Pro Gly Glu Thr Pro
115 120 125

Leu Pro Lys Asp Glu Asn Gly Lys Val Ile Phe Asp Thr Val Asp Leu
130 135 140

Ser Ala Thr Trp Glu Val Met Glu Lys Cys Lys Asp Ala Gly Leu Ala
145 150 155 160

Lys Ser Ile Gly Val Ser Asn Phe Asn Cys Arg Gln Leu Glu Met Ile
165 170 175

Leu Asn Lys Pro Gly Leu Lys Tyr Lys Pro Val Cys Asn Gln Val Glu
180 185 190

Cys His Pro Tyr Leu Asn Gln Ser Lys Leu Leu Asp Phe Cys Lys Ser
195 200 205

Lys Asp Ile Val Leu Val Ala His Ser Ala Leu Gly Thr Gln Arg His
210 215 220

Lys Leu Trp Val Asp Pro Asn Ser Pro Val Leu Leu Glu Asp Pro Val
225 230 235 240

Leu Cys Ala Leu Ala Lys Lys His Lys Gln Thr Pro Ala Leu Ile Ala
245 250 255

Leu Arg Tyr Gln Leu Gln Arg Gly Val Val Val Leu Ala Lys Ser Tyr
260 265 270

Asn Glu Gln Arg Ile Arg Glu Asn Ile Gln Val Phe Glu Phe Gln Leu
275 280 285

Thr Ser Glu Asp Met Lys Val Leu Asp Gly Leu Asn Arg Asn Tyr Arg
290 295 300

Tyr Val Val Met Asp Phe Leu Met Asp His Pro Asp Tyr Pro Phe Ser
305 310 315 320

Asp Glu Tyr

<210> SEQ ID NO 39
<211> LENGTH: 493
<212> TYPE: PRT
<213> ORGANISM: Homo sapiens

<400> SEQUENCE: 39

```
Met Ile Ser Ser Lys Pro Arg Leu Val Val Pro Tyr Gly Leu Lys Thr
1               5                   10                  15

Leu Leu Glu Gly Ile Ser Arg Ala Val Leu Lys Thr Asn Pro Ser Asn
            20                  25                  30

Ile Asn Gln Phe Ala Ala Ala Tyr Phe Gln Glu Leu Thr Met Tyr Arg
        35                  40                  45

Gly Asn Thr Thr Met Asp Ile Lys Asp Leu Val Lys Gln Phe His Gln
    50                  55                  60

Ile Lys Val Glu Lys Trp Ser Glu Gly Thr Thr Pro Gln Lys Lys Leu
65                  70                  75                  80

Glu Cys Leu Lys Glu Pro Gly Lys Thr Ser Val Glu Ser Lys Val Pro
                85                  90                  95

Thr Gln Met Glu Lys Ser Thr Asp Thr Asp Glu Asp Asn Val Thr Arg
            100                 105                 110

Thr Glu Tyr Ser Asp Lys Thr Thr Gln Phe Pro Ser Val Tyr Ala Val
        115                 120                 125

Pro Gly Thr Glu Gln Thr Glu Ala Val Gly Gly Leu Ser Ser Lys Pro
    130                 135                 140

Ala Thr Pro Lys Thr Thr Thr Pro Pro Ser Ser Pro Pro Pro Thr Ala
145                 150                 155                 160

Val Ser Pro Glu Phe Ala Tyr Val Pro Ala Asp Pro Ala Gln Leu Ala
                165                 170                 175

Ala Gln Met Leu Gly Lys Val Ser Ser Ile His Ser Asp Gln Ser Asp
            180                 185                 190

Val Leu Met Val Asp Val Ala Thr Ser Met Pro Val Val Ile Lys Glu
        195                 200                 205

Val Pro Ser Ser Glu Ala Ala Glu Asp Val Met Val Ala Ala Pro Leu
    210                 215                 220

Val Cys Ser Gly Lys Val Leu Glu Val Gln Val Val Asn Gln Thr Ser
225                 230                 235                 240

Val His Val Asp Leu Gly Ser Gln Pro Lys Glu Asn Glu Ala Glu Pro
                245                 250                 255

Ser Thr Ala Ser Ser Val Pro Leu Gln Asp Glu Gln Glu Pro Pro Ala
            260                 265                 270

Tyr Asp Gln Ala Pro Glu Val Thr Leu Gln Ala Asp Ile Glu Val Met
        275                 280                 285

Ser Thr Val His Ile Ser Ser Val Tyr Asn Asp Val Pro Val Thr Glu
    290                 295                 300

Gly Val Val Tyr Ile Glu Gln Leu Pro Glu Gln Ile Val Ile Pro Phe
305                 310                 315                 320

Thr Asp Gln Val Ala Cys Leu Lys Glu Asn Glu Gln Ser Lys Glu Asn
                325                 330                 335

Glu Gln Ser Pro Arg Val Ser Pro Lys Ser Val Val Glu Lys Thr Thr
            340                 345                 350

Ser Gly Met Ser Lys Lys Ser Val Glu Ser Val Lys Leu Ala Gln Leu
        355                 360                 365

Glu Glu Asn Ala Lys Tyr Ser Ser Val Tyr Met Glu Ala Glu Ala Thr
    370                 375                 380

Ala Leu Leu Ser Asp Thr Ser Leu Lys Gly Gln Pro Glu Val Pro Ala
385                 390                 395                 400

Gln Leu Leu Asp Ala Glu Gly Ala Ile Lys Ile Gly Ser Glu Lys Ser
```

```
                405                 410                 415

Leu His Leu Glu Val Glu Ile Thr Ser Ile Val Ser Asp Asn Thr Gly
            420                 425                 430

Gln Glu Glu Ser Gly Glu Asn Ser Val Pro Gln Glu Met Glu Gly Lys
        435                 440                 445

Pro Val Leu Ser Gly Glu Ala Ala Glu Ala Val His Ser Gly Thr Ser
    450                 455                 460

Val Lys Ser Ser Ser Gly Pro Phe Pro Pro Ala Pro Glu Gly Leu Thr
465                 470                 475                 480

Ala Pro Glu Ile Glu Pro Glu Gly Glu Ser Thr Ala Glu
                485                 490


<210> SEQ ID NO 40
<211> LENGTH: 524
<212> TYPE: PRT
<213> ORGANISM: Homo sapiens

<400> SEQUENCE: 40

Met Pro Gln Leu Ser Leu Ser Trp Leu Gly Leu Gly Pro Val Ala Ala
1               5                   10                  15

Ser Pro Trp Leu Leu Leu Leu Leu Val Gly Gly Ser Trp Leu Leu Ala
            20                  25                  30

Arg Val Leu Ala Trp Thr Tyr Thr Phe Tyr Asp Asn Cys Arg Arg Leu
        35                  40                  45

Gln Cys Phe Pro Gln Pro Pro Lys Gln Asn Trp Phe Trp Gly His Gln
    50                  55                  60

Gly Leu Val Thr Pro Thr Glu Glu Gly Met Lys Thr Leu Thr Gln Leu
65                  70                  75                  80

Val Thr Thr Tyr Pro Gln Gly Phe Lys Leu Trp Leu Gly Pro Thr Phe
                85                  90                  95

Pro Leu Leu Ile Leu Cys His Pro Asp Ile Ile Arg Pro Ile Thr Ser
            100                 105                 110

Ala Ser Ala Ala Val Ala Pro Lys Asp Met Ile Phe Tyr Gly Phe Leu
        115                 120                 125

Lys Pro Trp Leu Gly Asp Gly Leu Leu Leu Ser Gly Gly Asp Lys Trp
    130                 135                 140

Ser Arg His Arg Arg Met Leu Thr Pro Ala Phe His Phe Asn Ile Leu
145                 150                 155                 160

Lys Pro Tyr Met Lys Ile Phe Asn Lys Ser Val Asn Ile Met His Asp
                165                 170                 175

Lys Trp Gln Arg Leu Ala Ser Glu Gly Ser Ala Arg Leu Asp Met Phe
            180                 185                 190

Glu His Ile Ser Leu Met Thr Leu Asp Ser Leu Gln Lys Cys Val Phe
        195                 200                 205

Ser Phe Glu Ser Asn Cys Gln Glu Lys Pro Ser Glu Tyr Ile Ala Ala
    210                 215                 220

Ile Leu Glu Leu Ser Ala Phe Val Glu Lys Arg Asn Gln Gln Ile Leu
225                 230                 235                 240

Leu His Thr Asp Phe Leu Tyr Tyr Leu Thr Pro Asp Gly Gln Arg Phe
                245                 250                 255

Arg Arg Ala Cys His Leu Val His Asp Phe Thr Asp Ala Val Ile Gln
            260                 265                 270

Glu Arg Arg Cys Thr Leu Pro Thr Gln Gly Ile Asp Asp Phe Leu Lys
        275                 280                 285
```

```
Asn Lys Ala Lys Ser Lys Thr Leu Asp Phe Ile Asp Val Leu Leu Leu
    290                 295                 300

Ser Lys Asp Glu Asp Gly Lys Glu Leu Ser Asp Glu Asp Ile Arg Ala
305                 310                 315                 320

Glu Ala Asp Thr Phe Met Phe Glu Gly His Asp Thr Thr Ala Ser Gly
                325                 330                 335

Leu Ser Trp Val Leu Tyr His Leu Ala Lys His Pro Glu Tyr Gln Glu
            340                 345                 350

Gln Cys Arg Gln Glu Val Gln Glu Leu Leu Lys Asp Arg Glu Pro Ile
        355                 360                 365

Glu Ile Glu Trp Asp Asp Leu Ala Gln Leu Pro Phe Leu Thr Met Cys
    370                 375                 380

Ile Lys Glu Ser Leu Arg Leu His Pro Pro Val Pro Val Ile Ser Arg
385                 390                 395                 400

Cys Cys Thr Gln Asp Phe Val Leu Pro Asp Gly Arg Val Ile Pro Lys
                405                 410                 415

Gly Ile Val Cys Leu Ile Asn Ile Ile Gly Ile His Tyr Asn Pro Thr
            420                 425                 430

Val Trp Pro Asp Pro Glu Val Tyr Asp Pro Phe Arg Phe Asp Gln Glu
        435                 440                 445

Asn Ile Lys Glu Arg Ser Pro Leu Ala Phe Ile Pro Phe Ser Ala Gly
    450                 455                 460

Pro Arg Asn Cys Ile Gly Gln Ala Phe Ala Met Ala Glu Met Lys Val
465                 470                 475                 480

Val Leu Ala Leu Thr Leu Leu His Phe Arg Ile Leu Pro Thr His Thr
                485                 490                 495

Glu Pro Arg Arg Lys Pro Glu Leu Ile Leu Arg Ala Glu Gly Gly Leu
            500                 505                 510

Trp Leu Arg Val Glu Pro Leu Gly Ala Asn Ser Gln
        515                 520


<210> SEQ ID NO 41
<211> LENGTH: 423
<212> TYPE: PRT
<213> ORGANISM: Homo sapiens

<400> SEQUENCE: 41

Met Arg Ser Leu Gly Ala Asn Met Ala Ala Ala Leu Arg Ala Ala Gly
1               5                   10                  15

Val Leu Leu Arg Asp Pro Leu Ala Ser Ser Ser Trp Arg Val Cys Gln
            20                  25                  30

Pro Trp Arg Trp Lys Ser Gly Ala Ala Ala Ala Ala Val Thr Thr Glu
        35                  40                  45

Thr Ala Gln His Ala Gln Gly Ala Lys Pro Gln Val Gln Pro Gln Lys
    50                  55                  60

Arg Lys Pro Lys Thr Gly Ile Leu Met Leu Asn Met Gly Gly Pro Glu
65                  70                  75                  80

Thr Leu Gly Asp Val His Asp Phe Leu Leu Arg Leu Phe Leu Asp Arg
                85                  90                  95

Asp Leu Met Thr Leu Pro Ile Gln Asn Lys Leu Ala Pro Phe Ile Ala
            100                 105                 110

Lys Arg Arg Thr Pro Lys Ile Gln Glu Gln Tyr Arg Arg Ile Gly Gly
        115                 120                 125

Gly Ser Pro Ile Lys Ile Trp Thr Ser Lys Gln Gly Glu Gly Met Val
    130                 135                 140
```

```
Lys Leu Leu Asp Glu Leu Ser Pro Asn Thr Ala Pro His Lys Tyr Tyr
145                 150                 155                 160

Ile Gly Phe Arg Tyr Val His Pro Leu Thr Glu Glu Ala Ile Glu Glu
                165                 170                 175

Met Glu Arg Asp Gly Leu Glu Arg Ala Ile Ala Phe Thr Gln Tyr Pro
            180                 185                 190

Gln Tyr Ser Cys Ser Thr Thr Gly Ser Ser Leu Asn Ala Ile Tyr Arg
        195                 200                 205

Tyr Tyr Asn Gln Val Gly Arg Lys Pro Thr Met Lys Trp Ser Thr Ile
    210                 215                 220

Asp Arg Trp Pro Thr His His Leu Leu Ile Gln Cys Phe Ala Asp His
225                 230                 235                 240

Ile Leu Lys Glu Leu Asp His Phe Pro Leu Glu Lys Arg Ser Glu Val
                245                 250                 255

Val Ile Leu Phe Ser Ala His Ser Leu Pro Met Ser Val Val Asn Arg
            260                 265                 270

Gly Asp Pro Tyr Pro Gln Glu Val Ser Ala Thr Val Gln Lys Val Met
        275                 280                 285

Glu Arg Leu Glu Tyr Cys Asn Pro Tyr Arg Leu Val Trp Gln Ser Lys
    290                 295                 300

Val Gly Pro Met Pro Trp Leu Gly Pro Gln Thr Asp Glu Ser Ile Lys
305                 310                 315                 320

Gly Leu Cys Glu Arg Gly Arg Lys Asn Ile Leu Leu Val Pro Ile Ala
                325                 330                 335

Phe Thr Ser Asp His Ile Glu Thr Leu Tyr Glu Leu Asp Ile Glu Tyr
            340                 345                 350

Ser Gln Val Leu Ala Lys Glu Cys Gly Val Glu Asn Ile Arg Arg Ala
        355                 360                 365

Glu Ser Leu Asn Gly Asn Pro Leu Phe Ser Lys Ala Leu Ala Asp Leu
    370                 375                 380

Val His Ser His Ile Gln Ser Asn Glu Leu Cys Ser Lys Gln Leu Thr
385                 390                 395                 400

Leu Ser Cys Pro Leu Cys Val Asn Pro Val Cys Arg Glu Thr Lys Ser
                405                 410                 415

Phe Phe Thr Ser Gln Gln Leu
            420
```

<210> SEQ ID NO 42
<211> LENGTH: 175
<212> TYPE: PRT
<213> ORGANISM: Homo sapiens

<400> SEQUENCE: 42

```
Met Ser Ser Gln Ile Arg Gln Asn Tyr Ser Thr Asp Val Glu Ala Ala
1               5                   10                  15

Val Asn Ser Leu Val Asn Leu Tyr Leu Gln Ala Ser Tyr Thr Tyr Leu
            20                  25                  30

Ser Leu Gly Phe Tyr Phe Asp Arg Asp Asp Val Ala Leu Glu Gly Val
        35                  40                  45

Ser His Phe Phe Arg Glu Leu Ala Glu Glu Lys Arg Glu Gly Tyr Glu
    50                  55                  60

Arg Leu Leu Lys Met Gln Asn Gln Arg Gly Gly Arg Ala Leu Phe Gln
65                  70                  75                  80

Asp Ile Lys Lys Pro Ala Glu Asp Glu Trp Gly Lys Thr Pro Asp Ala
```

```
                85                  90                  95

Met Lys Ala Ala Met Ala Leu Glu Lys Lys Leu Asn Gln Ala Leu Leu
            100                 105                 110

Asp Leu His Ala Leu Gly Ser Ala Arg Thr Asp Pro His Leu Cys Asp
        115                 120                 125

Phe Leu Glu Thr His Phe Leu Asp Glu Glu Val Lys Leu Ile Lys Lys
    130                 135                 140

Met Gly Asp His Leu Thr Asn Leu His Arg Leu Gly Gly Pro Glu Ala
145                 150                 155                 160

Gly Leu Gly Glu Tyr Leu Phe Glu Arg Leu Thr Leu Lys His Asp
                165                 170                 175


<210> SEQ ID NO 43
<211> LENGTH: 274
<212> TYPE: PRT
<213> ORGANISM: Homo sapiens

<400> SEQUENCE: 43

Met Gly Thr Asp Ser Arg Ala Ala Lys Ala Leu Leu Ala Arg Ala Arg
1               5                   10                  15

Thr Leu His Leu Gln Thr Gly Asn Leu Leu Asn Trp Gly Arg Leu Arg
            20                  25                  30

Lys Lys Cys Pro Ser Thr His Ser Glu Glu Leu His Asp Cys Ile Gln
        35                  40                  45

Lys Thr Leu Asn Glu Trp Ser Ser Gln Ile Asn Pro Asp Leu Val Arg
    50                  55                  60

Glu Phe Pro Asp Val Leu Glu Cys Thr Val Ser His Ala Val Glu Lys
65                  70                  75                  80

Ile Asn Pro Asp Glu Arg Glu Glu Met Lys Val Ser Ala Lys Leu Phe
                85                  90                  95

Ile Val Glu Ser Asn Ser Ser Ser Ser Thr Arg Ser Ala Val Asp Met
            100                 105                 110

Ala Cys Ser Val Leu Gly Val Ala Gln Leu Asp Ser Val Ile Ile Ala
        115                 120                 125

Ser Pro Pro Ile Glu Asp Gly Val Asn Leu Ser Leu Glu His Leu Gln
    130                 135                 140

Pro Tyr Trp Glu Glu Leu Glu Asn Leu Val Gln Ser Lys Lys Ile Val
145                 150                 155                 160

Ala Ile Gly Thr Ser Asp Leu Asp Lys Thr Gln Leu Glu Gln Leu Tyr
                165                 170                 175

Gln Trp Ala Gln Val Lys Pro Asn Ser Asn Gln Val Asn Leu Ala Ser
            180                 185                 190

Cys Cys Val Met Pro Pro Asp Leu Thr Ala Phe Ala Lys Gln Phe Asp
        195                 200                 205

Ile Gln Leu Leu Thr His Asn Asp Pro Lys Glu Leu Leu Ser Glu Ala
    210                 215                 220

Ser Phe Gln Glu Ala Leu Gln Glu Ser Ile Pro Asp Ile Gln Ala His
225                 230                 235                 240

Glu Trp Val Pro Leu Trp Leu Leu Arg Tyr Ser Val Ile Val Lys Ser
                245                 250                 255

Arg Gly Ile Ile Lys Ser Lys Gly Tyr Ile Leu Gln Ala Lys Arg Arg
            260                 265                 270

Gly Ser
```

```
<210> SEQ ID NO 44
<211> LENGTH: 522
<212> TYPE: PRT
<213> ORGANISM: Homo sapiens

<400> SEQUENCE: 44

Met Ala Leu Leu Pro Arg Ala Leu Ser Ala Gly Ala Gly Pro Ser Trp
1               5                   10                  15

Arg Arg Ala Ala Arg Ala Phe Arg Gly Phe Leu Leu Leu Leu Pro Glu
            20                  25                  30

Pro Ala Ala Leu Thr Arg Ala Leu Ser Arg Ala Met Ala Cys Arg Gln
        35                  40                  45

Glu Pro Gln Pro Gln Gly Pro Pro Pro Ala Ala Gly Ala Val Ala Ser
    50                  55                  60

Tyr Asp Tyr Leu Val Ile Gly Gly Gly Ser Gly Gly Leu Ala Ser Ala
65                  70                  75                  80

Arg Arg Ala Ala Glu Leu Gly Ala Arg Ala Ala Val Val Glu Ser His
                85                  90                  95

Lys Leu Gly Gly Thr Cys Val Asn Val Gly Cys Val Pro Lys Lys Val
            100                 105                 110

Met Trp Asn Thr Ala Val His Ser Glu Phe Met His Asp His Ala Asp
        115                 120                 125

Tyr Gly Phe Pro Ser Cys Glu Gly Lys Phe Asn Trp Arg Val Ile Lys
    130                 135                 140

Glu Lys Arg Asp Ala Tyr Val Ser Arg Leu Asn Ala Ile Tyr Gln Asn
145                 150                 155                 160

Asn Leu Thr Lys Ser His Ile Glu Ile Ile Arg Gly His Ala Ala Phe
                165                 170                 175

Thr Ser Asp Pro Lys Pro Thr Ile Glu Val Ser Gly Lys Lys Tyr Thr
            180                 185                 190

Ala Pro His Ile Leu Ile Ala Thr Gly Gly Met Pro Ser Thr Pro His
        195                 200                 205

Glu Ser Gln Ile Pro Gly Ala Ser Leu Gly Ile Thr Ser Asp Gly Phe
    210                 215                 220

Phe Gln Leu Glu Glu Leu Pro Gly Arg Ser Val Ile Val Gly Ala Gly
225                 230                 235                 240

Tyr Ile Ala Val Glu Met Ala Gly Ile Leu Ser Ala Leu Gly Ser Lys
                245                 250                 255

Thr Ser Leu Met Ile Arg His Asp Lys Val Leu Arg Ser Phe Asp Ser
            260                 265                 270

Met Ile Ser Thr Asn Cys Thr Glu Glu Leu Glu Asn Ala Gly Val Glu
        275                 280                 285

Val Leu Lys Phe Ser Gln Val Lys Glu Val Lys Lys Thr Leu Ser Gly
    290                 295                 300

Leu Glu Val Ser Met Val Thr Ala Val Pro Gly Arg Leu Pro Val Met
305                 310                 315                 320

Thr Met Ile Pro Asp Val Asp Cys Leu Leu Trp Ala Ile Gly Arg Val
                325                 330                 335

Pro Asn Thr Lys Asp Leu Ser Leu Asn Lys Leu Gly Ile Gln Thr Asp
            340                 345                 350

Asp Lys Gly His Ile Ile Val Asp Glu Phe Gln Asn Thr Asn Val Lys
        355                 360                 365

Gly Ile Tyr Ala Val Gly Asp Val Cys Gly Lys Ala Leu Leu Thr Pro
    370                 375                 380
```

```
Val Ala Ile Ala Ala Gly Arg Lys Leu Ala His Arg Leu Phe Glu Tyr
385                 390                 395                 400

Lys Glu Asp Ser Lys Leu Asp Tyr Asn Asn Ile Pro Thr Val Val Phe
                405                 410                 415

Ser His Pro Pro Ile Gly Thr Val Gly Leu Thr Glu Asp Glu Ala Ile
            420                 425                 430

His Lys Tyr Gly Ile Glu Asn Val Lys Thr Tyr Ser Thr Ser Phe Thr
        435                 440                 445

Pro Met Tyr His Ala Val Thr Lys Arg Lys Thr Lys Cys Val Met Lys
    450                 455                 460

Met Val Cys Ala Asn Lys Glu Glu Lys Val Val Gly Ile His Met Gln
465                 470                 475                 480

Gly Leu Gly Cys Asp Glu Met Leu Gln Gly Phe Ala Val Ala Val Lys
                485                 490                 495

Met Gly Ala Thr Lys Ala Asp Phe Asp Asn Thr Val Ala Ile His Pro
            500                 505                 510

Thr Ser Ser Glu Glu Leu Val Thr Leu Arg
        515                 520


<210> SEQ ID NO 45
<211> LENGTH: 465
<212> TYPE: PRT
<213> ORGANISM: Homo sapiens

<400> SEQUENCE: 45

Met Glu Pro Ser Ser Leu Glu Leu Pro Ala Asp Thr Val Gln Arg Ile
1               5                   10                  15

Ala Ala Glu Leu Lys Cys His Pro Thr Asp Glu Arg Val Ala Leu His
            20                  25                  30

Leu Asp Glu Glu Asp Lys Leu Arg His Phe Arg Glu Cys Phe Tyr Ile
        35                  40                  45

Pro Lys Ile Gln Asp Leu Pro Pro Val Asp Leu Ser Leu Val Asn Lys
    50                  55                  60

Asp Glu Asn Ala Ile Tyr Phe Leu Gly Asn Ser Leu Gly Leu Gln Pro
65                  70                  75                  80

Lys Met Val Lys Thr Tyr Leu Glu Glu Glu Leu Asp Lys Trp Ala Lys
                85                  90                  95

Ile Ala Ala Tyr Gly His Glu Val Gly Lys Arg Pro Trp Ile Thr Gly
            100                 105                 110

Asp Glu Ser Ile Val Gly Leu Met Lys Asp Ile Val Gly Ala Asn Glu
        115                 120                 125

Lys Glu Ile Ala Leu Met Asn Ala Leu Thr Val Asn Leu His Leu Leu
    130                 135                 140

Met Leu Ser Phe Phe Lys Pro Thr Pro Lys Arg Tyr Lys Ile Leu Leu
145                 150                 155                 160

Glu Ala Lys Ala Phe Pro Ser Asp His Tyr Ala Ile Glu Ser Gln Leu
                165                 170                 175

Gln Leu His Gly Leu Asn Ile Glu Glu Ser Met Arg Met Ile Lys Pro
            180                 185                 190

Arg Glu Gly Glu Glu Thr Leu Arg Ile Glu Asp Ile Leu Glu Val Ile
        195                 200                 205

Glu Lys Glu Gly Asp Ser Ile Ala Val Ile Leu Phe Ser Gly Val His
    210                 215                 220

Phe Tyr Thr Gly Gln His Phe Asn Ile Pro Ala Ile Thr Lys Ala Gly
225                 230                 235                 240
```

Gln Ala Lys Gly Cys Tyr Val Gly Phe Asp Leu Ala His Ala Val Gly
245 250 255

Asn Val Glu Leu Tyr Leu His Asp Trp Gly Val Asp Phe Ala Cys Trp
260 265 270

Cys Ser Tyr Lys Tyr Leu Asn Ala Gly Ala Gly Gly Ile Ala Gly Ala
275 280 285

Phe Ile His Glu Lys His Ala His Thr Ile Lys Pro Ala Leu Val Gly
290 295 300

Trp Phe Gly His Glu Leu Ser Thr Arg Phe Lys Met Asp Asn Lys Leu
305 310 315 320

Gln Leu Ile Pro Gly Val Cys Gly Phe Arg Ile Ser Asn Pro Pro Ile
325 330 335

Leu Leu Val Cys Ser Leu His Ala Ser Leu Glu Ile Phe Lys Gln Ala
340 345 350

Thr Met Lys Ala Leu Arg Lys Lys Ser Val Leu Leu Thr Gly Tyr Leu
355 360 365

Glu Tyr Leu Ile Lys His Asn Tyr Gly Lys Asp Lys Ala Ala Thr Lys
370 375 380

Lys Pro Val Val Asn Ile Ile Thr Pro Ser His Val Glu Glu Arg Gly
385 390 395 400

Cys Gln Leu Thr Ile Thr Phe Ser Val Pro Asn Lys Asp Val Phe Gln
405 410 415

Glu Leu Glu Lys Arg Gly Val Val Cys Asp Lys Arg Asn Pro Asn Gly
420 425 430

Ile Arg Val Ala Pro Val Pro Leu Tyr Asn Ser Phe His Asp Val Tyr
435 440 445

Lys Phe Thr Asn Leu Leu Thr Ser Ile Leu Asp Ser Ala Glu Thr Lys
450 455 460

Asn
465

<210> SEQ ID NO 46
<211> LENGTH: 572
<212> TYPE: PRT
<213> ORGANISM: Homo sapiens

<400> SEQUENCE: 46

Met Glu Pro Glu Ala Pro Arg Arg Arg His Thr His Gln Arg Gly Tyr
1 5 10 15

Leu Leu Thr Arg Asn Pro His Leu Asn Lys Asp Leu Ala Phe Thr Leu
20 25 30

Glu Glu Arg Gln Gln Leu Asn Ile His Gly Leu Leu Pro Pro Ser Phe
35 40 45

Asn Ser Gln Glu Ile Gln Val Leu Arg Val Val Lys Asn Phe Glu His
50 55 60

Leu Asn Ser Asp Phe Asp Arg Tyr Leu Leu Leu Met Asp Leu Gln Asp
65 70 75 80

Arg Asn Glu Lys Leu Phe Tyr Arg Val Leu Thr Ser Asp Ile Glu Lys
85 90 95

Phe Met Pro Ile Val Tyr Thr Pro Thr Val Gly Leu Ala Cys Gln Gln
100 105 110

Tyr Ser Leu Val Phe Arg Lys Pro Arg Gly Leu Phe Ile Thr Ile His
115 120 125

Asp Arg Gly His Ile Ala Ser Val Leu Asn Ala Trp Pro Glu Asp Val

```
    130                 135                 140

Ile Lys Ala Ile Val Val Thr Asp Gly Glu Arg Ile Leu Gly Leu Gly
145                 150                 155                 160

Asp Leu Gly Cys Asn Gly Met Gly Ile Pro Val Gly Lys Leu Ala Leu
                165                 170                 175

Tyr Thr Ala Cys Gly Gly Met Asn Pro Gln Glu Cys Leu Pro Val Ile
            180                 185                 190

Leu Asp Val Gly Thr Glu Asn Glu Glu Leu Leu Lys Asp Pro Leu Tyr
        195                 200                 205

Ile Gly Leu Arg Gln Arg Arg Val Arg Gly Ser Glu Tyr Asp Asp Phe
    210                 215                 220

Leu Asp Glu Phe Met Glu Ala Val Ser Ser Lys Tyr Gly Met Asn Cys
225                 230                 235                 240

Leu Ile Gln Phe Glu Asp Phe Ala Asn Val Asn Ala Phe Arg Leu Leu
                245                 250                 255

Asn Lys Tyr Arg Asn Gln Tyr Cys Thr Phe Asn Asp Asp Ile Gln Gly
            260                 265                 270

Thr Ala Ser Val Ala Val Ala Gly Leu Leu Ala Ala Leu Arg Ile Thr
        275                 280                 285

Lys Asn Lys Leu Ser Asp Gln Thr Ile Leu Phe Gln Gly Ala Gly Glu
    290                 295                 300

Ala Ala Leu Gly Ile Ala His Leu Ile Val Met Ala Leu Glu Lys Glu
305                 310                 315                 320

Gly Leu Pro Lys Glu Lys Ala Ile Lys Lys Ile Trp Leu Val Asp Ser
                325                 330                 335

Lys Gly Leu Ile Val Lys Gly Arg Ala Ser Leu Thr Gln Glu Lys Glu
            340                 345                 350

Lys Phe Ala His Glu His Glu Glu Met Lys Asn Leu Glu Ala Ile Val
        355                 360                 365

Gln Glu Ile Lys Pro Thr Ala Leu Ile Gly Val Ala Ala Ile Gly Gly
    370                 375                 380

Ala Phe Ser Glu Gln Ile Leu Lys Asp Met Ala Ala Phe Asn Glu Arg
385                 390                 395                 400

Pro Ile Ile Phe Ala Leu Ser Asn Pro Thr Ser Lys Ala Glu Cys Ser
                405                 410                 415

Ala Glu Gln Cys Tyr Lys Ile Thr Lys Gly Arg Ala Ile Phe Ala Ser
            420                 425                 430

Gly Ser Pro Phe Asp Pro Val Thr Leu Pro Asn Gly Gln Thr Leu Tyr
        435                 440                 445

Pro Gly Gln Gly Asn Asn Ser Tyr Val Phe Pro Gly Val Ala Leu Gly
    450                 455                 460

Val Val Ala Cys Gly Leu Arg Gln Ile Thr Asp Asn Ile Phe Leu Thr
465                 470                 475                 480

Thr Ala Glu Val Ile Ala Gln Gln Val Ser Asp Lys His Leu Glu Glu
                485                 490                 495

Gly Arg Leu Tyr Pro Pro Leu Asn Thr Ile Arg Asp Val Ser Leu Lys
            500                 505                 510

Ile Ala Glu Lys Ile Val Lys Asp Ala Tyr Gln Glu Lys Thr Ala Thr
        515                 520                 525

Val Tyr Pro Glu Pro Gln Asn Lys Glu Ala Phe Val Arg Ser Gln Met
    530                 535                 540

Tyr Ser Thr Asp Tyr Asp Gln Ile Leu Pro Asp Cys Tyr Ser Trp Pro
545                 550                 555                 560
```

```
Glu Glu Val Gln Lys Ile Gln Thr Lys Val Asp Gln
                565                 570


<210> SEQ ID NO 47
<211> LENGTH: 605
<212> TYPE: PRT
<213> ORGANISM: Homo sapiens

<400> SEQUENCE: 47

Met Met Asp Leu Glu Leu Pro Pro Pro Gly Leu Pro Ser Gln Gln Asp
1               5                   10                  15

Met Asp Leu Ile Asp Ile Leu Trp Arg Gln Asp Ile Asp Leu Gly Val
            20                  25                  30

Ser Arg Glu Val Phe Asp Phe Ser Gln Arg Arg Lys Glu Tyr Glu Leu
        35                  40                  45

Glu Lys Gln Lys Lys Leu Glu Lys Glu Arg Gln Glu Gln Leu Gln Lys
    50                  55                  60

Glu Gln Glu Lys Ala Phe Phe Ala Gln Leu Gln Leu Asp Glu Glu Thr
65                  70                  75                  80

Gly Glu Phe Leu Pro Ile Gln Pro Ala Gln His Ile Gln Ser Glu Thr
                85                  90                  95

Ser Gly Ser Ala Asn Tyr Ser Gln Val Ala His Ile Pro Lys Ser Asp
            100                 105                 110

Ala Leu Tyr Phe Asp Asp Cys Met Gln Leu Leu Ala Gln Thr Phe Pro
        115                 120                 125

Phe Val Asp Asp Asn Glu Val Ser Ser Ala Thr Phe Gln Ser Leu Val
    130                 135                 140

Pro Asp Ile Pro Gly His Ile Glu Ser Pro Val Phe Ile Ala Thr Asn
145                 150                 155                 160

Gln Ala Gln Ser Pro Glu Thr Ser Val Ala Gln Val Ala Pro Val Asp
                165                 170                 175

Leu Asp Gly Met Gln Gln Asp Ile Glu Gln Val Trp Glu Glu Leu Leu
            180                 185                 190

Ser Ile Pro Glu Leu Gln Cys Leu Asn Ile Glu Asn Asp Lys Leu Val
        195                 200                 205

Glu Thr Thr Met Val Pro Ser Pro Glu Ala Lys Leu Thr Glu Val Asp
    210                 215                 220

Asn Tyr His Phe Tyr Ser Ser Ile Pro Ser Met Glu Lys Glu Val Gly
225                 230                 235                 240

Asn Cys Ser Pro His Phe Leu Asn Ala Phe Glu Asp Ser Phe Ser Ser
                245                 250                 255

Ile Leu Ser Thr Glu Asp Pro Asn Gln Leu Thr Val Asn Ser Leu Asn
            260                 265                 270

Ser Asp Ala Thr Val Asn Thr Asp Phe Gly Asp Glu Phe Tyr Ser Ala
        275                 280                 285

Phe Ile Ala Glu Pro Ser Ile Ser Asn Ser Met Pro Ser Pro Ala Thr
    290                 295                 300

Leu Ser His Ser Leu Ser Glu Leu Leu Asn Gly Pro Ile Asp Val Ser
305                 310                 315                 320

Asp Leu Ser Leu Cys Lys Ala Phe Asn Gln Asn His Pro Glu Ser Thr
                325                 330                 335

Ala Glu Phe Asn Asp Ser Asp Ser Gly Ile Ser Leu Asn Thr Ser Pro
            340                 345                 350

Ser Val Ala Ser Pro Glu His Ser Val Glu Ser Ser Ser Tyr Gly Asp
```

```
        355                 360                 365

Thr Leu Leu Gly Leu Ser Asp Ser Glu Val Glu Glu Leu Asp Ser Ala
    370                 375                 380

Pro Gly Ser Val Lys Gln Asn Gly Pro Lys Thr Pro Val His Ser Ser
385                 390                 395                 400

Gly Asp Met Val Gln Pro Leu Ser Pro Ser Gln Gly Gln Ser Thr His
                405                 410                 415

Val His Asp Ala Gln Cys Glu Asn Thr Pro Glu Lys Glu Leu Pro Val
            420                 425                 430

Ser Pro Gly His Arg Lys Thr Pro Phe Thr Lys Asp Lys His Ser Ser
        435                 440                 445

Arg Leu Glu Ala His Leu Thr Arg Asp Glu Leu Arg Ala Lys Ala Leu
    450                 455                 460

His Ile Pro Phe Pro Val Glu Lys Ile Ile Asn Leu Pro Val Val Asp
465                 470                 475                 480

Phe Asn Glu Met Met Ser Lys Glu Gln Phe Asn Glu Ala Gln Leu Ala
                485                 490                 495

Leu Ile Arg Asp Ile Arg Arg Arg Gly Lys Asn Lys Val Ala Ala Gln
            500                 505                 510

Asn Cys Arg Lys Arg Lys Leu Glu Asn Ile Val Glu Leu Glu Gln Asp
        515                 520                 525

Leu Asp His Leu Lys Asp Glu Lys Glu Lys Leu Leu Lys Glu Lys Gly
    530                 535                 540

Glu Asn Asp Lys Ser Leu His Leu Leu Lys Lys Gln Leu Ser Thr Leu
545                 550                 555                 560

Tyr Leu Glu Val Phe Ser Met Leu Arg Asp Glu Asp Gly Lys Pro Tyr
                565                 570                 575

Ser Pro Ser Glu Tyr Ser Leu Gln Gln Thr Arg Asp Gly Asn Val Phe
            580                 585                 590

Leu Val Pro Lys Ser Lys Lys Pro Asp Val Lys Lys Asn
        595                 600                 605


<210> SEQ ID NO 48
<211> LENGTH: 274
<212> TYPE: PRT
<213> ORGANISM: Homo sapiens

<400> SEQUENCE: 48

Met Val Gly Arg Arg Ala Leu Ile Val Leu Ala His Ser Glu Arg Thr
1               5                   10                  15

Ser Phe Asn Tyr Ala Met Lys Glu Ala Ala Ala Ala Ala Leu Lys Lys
            20                  25                  30

Lys Gly Trp Glu Val Val Glu Ser Asp Leu Tyr Ala Met Asn Phe Asn
        35                  40                  45

Pro Ile Ile Ser Arg Lys Asp Ile Thr Gly Lys Leu Lys Asp Pro Ala
    50                  55                  60

Asn Phe Gln Tyr Pro Ala Glu Ser Val Leu Ala Tyr Lys Glu Gly His
65                  70                  75                  80

Leu Ser Pro Asp Ile Val Ala Glu Gln Lys Lys Leu Glu Ala Ala Asp
                85                  90                  95

Leu Val Ile Phe Gln Phe Pro Leu Gln Trp Phe Gly Val Pro Ala Ile
            100                 105                 110

Leu Lys Gly Trp Phe Glu Arg Val Phe Ile Gly Glu Phe Ala Tyr Thr
        115                 120                 125
```

```
Tyr Ala Ala Met Tyr Asp Lys Gly Pro Phe Arg Ser Lys Lys Ala Val
    130                 135                 140

Leu Ser Ile Thr Thr Gly Gly Ser Gly Ser Met Tyr Ser Leu Gln Gly
145                 150                 155                 160

Ile His Gly Asp Met Asn Val Ile Leu Trp Pro Ile Gln Ser Gly Ile
                165                 170                 175

Leu His Phe Cys Gly Phe Gln Val Leu Glu Pro Gln Leu Thr Tyr Ser
            180                 185                 190

Ile Gly His Thr Pro Ala Asp Ala Arg Ile Gln Ile Leu Glu Gly Trp
        195                 200                 205

Lys Lys Arg Leu Glu Asn Ile Trp Asp Glu Thr Pro Leu Tyr Phe Ala
    210                 215                 220

Pro Ser Ser Leu Phe Asp Leu Asn Phe Gln Ala Gly Phe Leu Met Lys
225                 230                 235                 240

Lys Glu Val Gln Asp Glu Glu Lys Asn Lys Lys Phe Gly Leu Ser Val
                245                 250                 255

Gly His His Leu Gly Lys Ser Ile Pro Thr Asp Asn Gln Ile Lys Ala
            260                 265                 270

Arg Lys


<210> SEQ ID NO 49
<211> LENGTH: 470
<212> TYPE: PRT
<213> ORGANISM: Homo sapiens

<400> SEQUENCE: 49

Met Ala Gly Glu Asn His Gln Trp Gln Gly Ser Ile Leu Tyr Asn Met
1               5                   10                  15

Leu Met Ser Ala Lys Gln Thr Arg Ala Ala Pro Glu Ala Pro Glu Thr
            20                  25                  30

Arg Leu Val Asp Gln Cys Trp Gly Cys Ser Cys Gly Asp Glu Pro Gly
        35                  40                  45

Val Gly Arg Glu Gly Leu Leu Gly Gly Arg Asn Val Ala Leu Leu Tyr
    50                  55                  60

Arg Cys Cys Phe Cys Gly Lys Asp His Pro Arg Gln Gly Ser Ile Leu
65                  70                  75                  80

Tyr Ser Met Leu Thr Ser Ala Lys Gln Thr Tyr Ala Ala Pro Lys Ala
                85                  90                  95

Pro Glu Ala Thr Leu Gly Pro Cys Trp Gly Cys Ser Cys Gly Ser Asp
            100                 105                 110

Pro Gly Val Gly Arg Ala Gly Leu Pro Gly Gly Arg Pro Val Ala Leu
        115                 120                 125

Leu Tyr Arg Cys Cys Phe Cys Gly Glu Asp His Pro Arg Gln Gly Ser
    130                 135                 140

Ile Leu Tyr Ser Leu Leu Thr Ser Ser Lys Gln Thr His Val Ala Pro
145                 150                 155                 160

Ala Ala Pro Glu Ala Arg Pro Gly Gly Ala Trp Trp Asp Arg Ser Tyr
                165                 170                 175

Phe Ala Gln Arg Pro Gly Gly Lys Glu Ala Leu Pro Gly Gly Arg Ala
            180                 185                 190

Thr Ala Leu Leu Tyr Arg Cys Cys Phe Cys Gly Glu Asp His Pro Gln
        195                 200                 205

Gln Gly Ser Thr Leu Tyr Cys Val Pro Thr Ser Thr Asn Gln Ala Gln
    210                 215                 220
```

Ala Ala Pro Glu Glu Arg Pro Arg Ala Pro Trp Trp Asp Thr Ser Ser
225 230 235 240

Gly Ala Leu Arg Pro Val Ala Leu Lys Ser Pro Gln Val Val Cys Glu
245 250 255

Ala Ala Ser Ala Gly Leu Leu Lys Thr Leu Arg Phe Val Lys Tyr Leu
260 265 270

Pro Cys Phe Gln Val Leu Pro Leu Asp Gln Gln Leu Val Leu Val Arg
275 280 285

Asn Cys Trp Ala Ser Leu Leu Met Leu Glu Leu Ala Gln Asp Arg Leu
290 295 300

Gln Phe Glu Thr Val Glu Val Ser Glu Pro Ser Met Leu Gln Lys Ile
305 310 315 320

Leu Thr Thr Arg Arg Arg Glu Thr Gly Gly Asn Glu Pro Leu Pro Val
325 330 335

Pro Thr Leu Gln His His Leu Ala Pro Pro Ala Glu Ala Arg Lys Val
340 345 350

Pro Ser Ala Ser Gln Val Gln Ala Ile Lys Cys Phe Leu Ser Lys Cys
355 360 365

Trp Ser Leu Asn Ile Ser Thr Lys Glu Tyr Ala Tyr Leu Lys Gly Thr
370 375 380

Val Leu Phe Asn Pro Asp Val Pro Gly Leu Gln Cys Val Lys Tyr Ile
385 390 395 400

Gln Gly Leu Gln Trp Gly Thr Gln Gln Ile Leu Ser Glu His Thr Arg
405 410 415

Met Thr His Gln Gly Pro His Asp Arg Phe Ile Glu Leu Asn Ser Thr
420 425 430

Leu Phe Leu Leu Arg Phe Ile Asn Ala Asn Val Ile Ala Glu Leu Phe
435 440 445

Phe Arg Pro Ile Ile Gly Thr Val Ser Met Asp Asp Met Met Leu Glu
450 455 460

Met Leu Cys Thr Lys Ile
465 470

<210> SEQ ID NO 50
<211> LENGTH: 560
<212> TYPE: PRT
<213> ORGANISM: Homo sapiens

<400> SEQUENCE: 50

Met Gly Lys Trp Arg Pro Arg Gly Cys Cys Arg Gly Asn Met Gln Cys
1 5 10 15

Arg Gln Glu Val Pro Ala Thr Leu Thr Ser Ser Glu Leu Phe Ser Thr
20 25 30

Arg Asn Gln Pro Gln Pro Gln Pro Gln Pro Leu Leu Ala Asp Ala Pro
35 40 45

Val Pro Trp Ala Val Ala Ser Arg Met Cys Leu Thr Pro Gly Gln Gly
50 55 60

Cys Gly His Gln Gly Gln Asp Glu Gly Pro Leu Pro Ala Pro Ser Pro
65 70 75 80

Pro Pro Ala Met Ser Ser Ser Arg Lys Asp His Leu Gly Ala Ser Ser
85 90 95

Ser Glu Pro Leu Pro Val Ile Ile Val Gly Asn Gly Pro Ser Gly Ile
100 105 110

Cys Leu Ser Tyr Leu Leu Ser Gly Tyr Thr Pro Tyr Thr Lys Pro Asp
115 120 125

```
Ala Ile His Pro His Pro Leu Leu Gln Arg Lys Leu Thr Glu Ala Pro
    130                 135                 140

Gly Val Ser Ile Leu Asp Gln Asp Leu Asp Tyr Leu Ser Glu Gly Leu
145                 150                 155                 160

Glu Gly Arg Ser Gln Ser Pro Val Ala Leu Leu Phe Asp Ala Leu Leu
                165                 170                 175

Arg Pro Asp Thr Asp Phe Gly Gly Asn Met Lys Ser Val Leu Thr Trp
            180                 185                 190

Lys His Arg Lys Glu His Ala Ile Pro His Val Val Leu Gly Arg Asn
        195                 200                 205

Leu Pro Gly Gly Ala Trp His Ser Ile Glu Gly Ser Met Val Ile Leu
    210                 215                 220

Ser Gln Gly Gln Trp Met Gly Leu Pro Asp Leu Glu Val Lys Asp Trp
225                 230                 235                 240

Met Gln Lys Lys Arg Arg Gly Leu Arg Asn Ser Arg Ala Thr Ala Gly
                245                 250                 255

Asp Ile Ala His Tyr Tyr Arg Asp Tyr Val Val Lys Lys Gly Leu Gly
            260                 265                 270

His Asn Phe Val Ser Gly Ala Val Val Thr Ala Val Glu Trp Gly Thr
        275                 280                 285

Pro Asp Pro Ser Ser Cys Gly Ala Gln Asp Ser Ser Pro Leu Phe Gln
    290                 295                 300

Val Ser Gly Phe Leu Thr Arg Asn Gln Ala Gln Gln Pro Phe Ser Leu
305                 310                 315                 320

Trp Ala Arg Asn Val Val Leu Ala Thr Gly Thr Phe Asp Ser Pro Ala
                325                 330                 335

Arg Leu Gly Ile Pro Gly Glu Ala Leu Pro Phe Ile His His Glu Leu
            340                 345                 350

Ser Ala Leu Glu Ala Ala Thr Arg Val Gly Ala Val Thr Pro Ala Ser
        355                 360                 365

Asp Pro Val Leu Ile Ile Gly Ala Gly Leu Ser Ala Ala Asp Ala Val
    370                 375                 380

Leu Tyr Ala Arg His Tyr Asn Ile Pro Val Ile His Ala Phe Arg Arg
385                 390                 395                 400

Ala Val Asp Asp Pro Gly Leu Val Phe Asn Gln Leu Pro Lys Met Leu
                405                 410                 415

Tyr Pro Glu Tyr His Lys Val His Gln Met Met Arg Glu Gln Ser Ile
            420                 425                 430

Leu Ser Pro Ser Pro Tyr Glu Gly Tyr Arg Ser Leu Pro Arg His Gln
        435                 440                 445

Leu Leu Cys Phe Lys Glu Asp Cys Gln Ala Val Phe Gln Asp Leu Glu
    450                 455                 460

Gly Val Glu Lys Val Phe Gly Val Ser Leu Val Leu Val Leu Ile Gly
465                 470                 475                 480

Ser His Pro Asp Leu Ser Phe Leu Pro Gly Ala Gly Ala Asp Phe Ala
                485                 490                 495

Val Asp Pro Asp Gln Pro Leu Ser Ala Lys Arg Asn Pro Ile Asp Val
            500                 505                 510

Asp Pro Phe Thr Tyr Gln Ser Thr Arg Gln Glu Gly Leu Tyr Ala Met
        515                 520                 525

Gly Pro Leu Ala Gly Asp Asn Phe Val Arg Phe Val Gln Gly Gly Ala
    530                 535                 540
```

```
Leu Ala Val Ala Ser Ser Leu Leu Arg Lys Glu Thr Arg Lys Pro Pro
545                 550                 555                 560


<210> SEQ ID NO 51
<211> LENGTH: 483
<212> TYPE: PRT
<213> ORGANISM: Homo sapiens

<400> SEQUENCE: 51

Met Ala Gln Ala Asp Ile Ala Leu Ile Gly Leu Ala Val Met Gly Gln
1               5                   10                  15

Asn Leu Ile Leu Asn Met Asn Asp His Gly Phe Val Val Cys Ala Phe
            20                  25                  30

Asn Arg Thr Val Ser Lys Val Asp Asp Phe Leu Ala Asn Glu Ala Lys
        35                  40                  45

Gly Thr Lys Val Val Gly Ala Gln Ser Leu Lys Glu Met Val Ser Lys
    50                  55                  60

Leu Lys Lys Pro Arg Arg Ile Ile Leu Leu Val Lys Ala Gly Gln Ala
65                  70                  75                  80

Val Asp Asp Phe Ile Glu Lys Leu Val Pro Leu Leu Asp Thr Gly Asp
                85                  90                  95

Ile Ile Ile Asp Gly Gly Asn Ser Glu Tyr Arg Asp Thr Thr Arg Arg
            100                 105                 110

Cys Arg Asp Leu Lys Ala Lys Gly Ile Leu Phe Val Gly Ser Gly Val
        115                 120                 125

Ser Gly Gly Glu Glu Gly Ala Arg Tyr Gly Pro Ser Leu Met Pro Gly
    130                 135                 140

Gly Asn Lys Glu Ala Trp Pro His Ile Lys Thr Ile Phe Gln Gly Ile
145                 150                 155                 160

Ala Ala Lys Val Gly Thr Gly Glu Pro Cys Cys Asp Trp Val Gly Asp
                165                 170                 175

Glu Gly Ala Gly His Phe Val Lys Met Val His Asn Gly Ile Glu Tyr
            180                 185                 190

Gly Asp Met Gln Leu Ile Cys Glu Ala Tyr His Leu Met Lys Asp Val
        195                 200                 205

Leu Gly Met Ala Gln Asp Glu Met Ala Gln Ala Phe Glu Asp Trp Asn
    210                 215                 220

Lys Thr Glu Leu Asp Ser Phe Leu Ile Glu Ile Thr Ala Asn Ile Leu
225                 230                 235                 240

Lys Phe Gln Asp Thr Asp Gly Lys His Leu Leu Pro Lys Ile Arg Asp
                245                 250                 255

Ser Ala Gly Gln Lys Gly Thr Gly Lys Trp Thr Ala Ile Ser Ala Leu
            260                 265                 270

Glu Tyr Gly Val Pro Val Thr Leu Ile Gly Glu Ala Val Phe Ala Arg
        275                 280                 285

Cys Leu Ser Ser Leu Lys Asp Glu Arg Ile Gln Ala Ser Lys Lys Leu
    290                 295                 300

Lys Gly Pro Gln Lys Phe Gln Phe Asp Gly Asp Lys Lys Ser Phe Leu
305                 310                 315                 320

Glu Asp Ile Arg Lys Ala Leu Tyr Ala Ser Lys Ile Ile Ser Tyr Ala
                325                 330                 335

Gln Gly Phe Met Leu Leu Arg Gln Ala Ala Thr Glu Phe Gly Trp Thr
            340                 345                 350

Leu Asn Tyr Gly Gly Ile Ala Leu Met Trp Arg Gly Gly Cys Ile Ile
        355                 360                 365
```

```
Arg Ser Val Phe Leu Gly Lys Ile Lys Asp Ala Phe Asp Arg Asn Pro
    370                 375                 380

Glu Leu Gln Asn Leu Leu Leu Asp Asp Phe Phe Lys Ser Ala Val Glu
385                 390                 395                 400

Asn Cys Gln Asp Ser Trp Arg Arg Ala Val Ser Thr Gly Val Gln Ala
                405                 410                 415

Gly Ile Pro Met Pro Cys Phe Thr Thr Ala Leu Ser Phe Tyr Asp Gly
            420                 425                 430

Tyr Arg His Glu Met Leu Pro Ala Ser Leu Ile Gln Ala Gln Arg Asp
        435                 440                 445

Tyr Phe Gly Ala His Thr Tyr Glu Leu Leu Ala Lys Pro Gly Gln Phe
    450                 455                 460

Ile His Thr Asn Trp Thr Gly His Gly Gly Thr Val Ser Ser Ser Ser
465                 470                 475                 480

Tyr Asn Ala


<210> SEQ ID NO 52
<211> LENGTH: 272
<212> TYPE: PRT
<213> ORGANISM: Homo sapiens

<400> SEQUENCE: 52

Met His Leu Arg Leu Ile Ser Trp Leu Phe Ile Ile Leu Asn Phe Met
1               5                   10                  15

Glu Tyr Ile Gly Ser Gln Asn Ala Ser Arg Gly Arg Arg Gln Arg Arg
            20                  25                  30

Met His Pro Asn Val Ser Gln Gly Cys Gln Gly Gly Cys Ala Thr Cys
        35                  40                  45

Ser Asp Tyr Asn Gly Cys Leu Ser Cys Lys Pro Arg Leu Phe Phe Ala
    50                  55                  60

Leu Glu Arg Ile Gly Met Lys Gln Ile Gly Val Cys Leu Ser Ser Cys
65                  70                  75                  80

Pro Ser Gly Tyr Tyr Gly Thr Arg Tyr Pro Asp Ile Asn Lys Cys Thr
                85                  90                  95

Lys Cys Lys Ala Asp Cys Asp Thr Cys Phe Asn Lys Asn Phe Cys Thr
            100                 105                 110

Lys Cys Lys Ser Gly Phe Tyr Leu His Leu Gly Lys Cys Leu Asp Asn
        115                 120                 125

Cys Pro Glu Gly Leu Glu Ala Asn Asn His Thr Met Glu Cys Val Ser
    130                 135                 140

Ile Val His Cys Glu Val Ser Glu Trp Asn Pro Trp Ser Pro Cys Thr
145                 150                 155                 160

Lys Lys Gly Lys Thr Cys Gly Phe Lys Arg Gly Thr Glu Thr Arg Val
                165                 170                 175

Arg Glu Ile Ile Gln His Pro Ser Ala Lys Gly Asn Leu Cys Pro Pro
            180                 185                 190

Thr Asn Glu Thr Arg Lys Cys Thr Val Gln Arg Lys Lys Cys Gln Lys
        195                 200                 205

Gly Glu Arg Gly Lys Lys Gly Arg Glu Arg Lys Arg Lys Lys Pro Asn
    210                 215                 220

Lys Gly Glu Ser Lys Glu Ala Ile Pro Asp Ser Lys Ser Leu Glu Ser
225                 230                 235                 240

Ser Lys Glu Ile Pro Glu Gln Arg Glu Asn Lys Gln Gln Gln Lys Lys
                245                 250                 255
```

```
Arg Lys Val Gln Asp Lys Gln Lys Ser Val Ser Val Ser Thr Val His
            260                 265                 270


<210> SEQ ID NO 53
<211> LENGTH: 501
<212> TYPE: PRT
<213> ORGANISM: Homo sapiens

<400> SEQUENCE: 53

Met Val Arg Lys Pro Val Val Ser Thr Ile Ser Lys Gly Gly Tyr Leu
1               5                   10                  15

Gln Gly Asn Val Asn Gly Arg Leu Pro Ser Leu Gly Asn Lys Glu Pro
            20                  25                  30

Pro Gly Gln Glu Lys Val Gln Leu Lys Arg Lys Val Thr Leu Leu Arg
        35                  40                  45

Gly Val Ser Ile Ile Ile Gly Thr Ile Ile Gly Ala Gly Ile Phe Ile
    50                  55                  60

Ser Pro Lys Gly Val Leu Gln Asn Thr Gly Ser Val Gly Met Ser Leu
65                  70                  75                  80

Thr Ile Trp Thr Val Cys Gly Val Leu Ser Leu Phe Gly Ala Leu Ser
                85                  90                  95

Tyr Ala Glu Leu Gly Thr Thr Ile Lys Lys Ser Gly Gly His Tyr Thr
            100                 105                 110

Tyr Ile Leu Glu Val Phe Gly Pro Leu Pro Ala Phe Val Arg Val Trp
        115                 120                 125

Val Glu Leu Leu Ile Ile Arg Pro Ala Ala Thr Ala Val Ile Ser Leu
    130                 135                 140

Ala Phe Gly Arg Tyr Ile Leu Glu Pro Phe Phe Ile Gln Cys Glu Ile
145                 150                 155                 160

Pro Glu Leu Ala Ile Lys Leu Ile Thr Ala Val Gly Ile Thr Val Val
                165                 170                 175

Met Val Leu Asn Ser Met Ser Val Ser Trp Ser Ala Arg Ile Gln Ile
            180                 185                 190

Phe Leu Thr Phe Cys Lys Leu Thr Ala Ile Leu Ile Ile Ile Val Pro
        195                 200                 205

Gly Val Met Gln Leu Ile Lys Gly Gln Thr Gln Asn Phe Lys Asp Ala
    210                 215                 220

Phe Ser Gly Arg Asp Ser Ser Ile Thr Arg Leu Pro Leu Ala Phe Tyr
225                 230                 235                 240

Tyr Gly Met Tyr Ala Tyr Ala Gly Trp Phe Tyr Leu Asn Phe Val Thr
                245                 250                 255

Glu Glu Val Glu Asn Pro Glu Lys Thr Ile Pro Leu Ala Ile Cys Ile
            260                 265                 270

Ser Met Ala Ile Val Thr Ile Gly Tyr Val Leu Thr Asn Val Ala Tyr
        275                 280                 285

Phe Thr Thr Ile Asn Ala Glu Glu Leu Leu Leu Ser Asn Ala Val Ala
    290                 295                 300

Val Thr Phe Ser Glu Arg Leu Leu Gly Asn Phe Ser Leu Ala Val Pro
305                 310                 315                 320

Ile Phe Val Ala Leu Ser Cys Phe Gly Ser Met Asn Gly Gly Val Phe
                325                 330                 335

Ala Val Ser Arg Leu Phe Tyr Val Ala Ser Arg Glu Gly His Leu Pro
            340                 345                 350

Glu Ile Leu Ser Met Ile His Val Arg Lys His Thr Pro Leu Pro Ala
```

```
        355                 360                 365

Val Ile Val Leu His Pro Leu Thr Met Ile Met Leu Phe Ser Gly Asp
    370                 375                 380

Leu Asp Ser Leu Leu Asn Phe Leu Ser Phe Ala Arg Trp Leu Phe Ile
385                 390                 395                 400

Gly Leu Ala Val Ala Gly Leu Ile Tyr Leu Arg Tyr Lys Cys Pro Asp
                405                 410                 415

Met His Arg Pro Phe Lys Val Pro Leu Phe Ile Pro Ala Leu Phe Ser
            420                 425                 430

Phe Thr Cys Leu Phe Met Val Ala Leu Ser Leu Tyr Ser Asp Pro Phe
        435                 440                 445

Ser Thr Gly Ile Gly Phe Val Ile Thr Leu Thr Gly Val Pro Ala Tyr
    450                 455                 460

Tyr Leu Phe Ile Ile Trp Asp Lys Lys Pro Arg Trp Phe Arg Ile Met
465                 470                 475                 480

Ser Glu Lys Ile Thr Arg Thr Leu Gln Ile Ile Leu Glu Val Val Pro
                485                 490                 495

Glu Glu Asp Lys Leu
            500


<210> SEQ ID NO 54
<211> LENGTH: 137
<212> TYPE: PRT
<213> ORGANISM: Homo sapiens

<400> SEQUENCE: 54

Met Gly Leu Arg Ala Gly Gly Thr Leu Gly Arg Ala Gly Ala Gly Arg
1               5                   10                  15

Gly Ala Pro Glu Gly Pro Gly Pro Ser Gly Gly Ala Gln Gly Gly Ser
            20                  25                  30

Ile His Ser Gly Arg Ile Ala Ala Val His Asn Val Pro Leu Ser Val
        35                  40                  45

Leu Ile Arg Pro Leu Pro Ser Val Leu Asp Pro Ala Lys Val Gln Ser
    50                  55                  60

Leu Val Asp Thr Ile Arg Glu Asp Pro Asp Ser Val Pro Pro Ile Asp
65                  70                  75                  80

Val Leu Trp Ile Lys Gly Ala Gln Gly Gly Asp Tyr Phe Tyr Ser Phe
                85                  90                  95

Gly Gly Cys His Arg Tyr Ala Ala Tyr Gln Gln Leu Gln Arg Glu Thr
            100                 105                 110

Ile Pro Ala Lys Leu Val Gln Ser Thr Leu Ser Asp Leu Arg Val Tyr
        115                 120                 125

Leu Gly Ala Ser Thr Pro Asp Leu Gln
    130                 135


<210> SEQ ID NO 55
<211> LENGTH: 337
<212> TYPE: PRT
<213> ORGANISM: Homo sapiens

<400> SEQUENCE: 55

Met Ser Ser Ser Pro Val Lys Arg Gln Arg Met Glu Ser Ala Leu Asp
1               5                   10                  15

Gln Leu Lys Gln Phe Thr Thr Val Val Ala Asp Thr Gly Asp Phe His
            20                  25                  30

Ala Ile Asp Glu Tyr Lys Pro Gln Asp Ala Thr Thr Asn Pro Ser Leu
```

```
        35                  40                  45

Ile Leu Ala Ala Ala Gln Met Pro Ala Tyr Gln Glu Leu Val Glu Glu
    50                  55                  60

Ala Ile Ala Tyr Gly Arg Lys Leu Gly Gly Ser Gln Glu Asp Gln Ile
65                  70                  75                  80

Lys Asn Ala Ile Asp Lys Leu Phe Val Leu Phe Gly Ala Glu Ile Leu
                85                  90                  95

Lys Lys Ile Pro Gly Arg Val Ser Thr Glu Val Asp Ala Arg Leu Ser
            100                 105                 110

Phe Asp Lys Asp Ala Met Val Ala Arg Ala Arg Arg Leu Ile Glu Leu
        115                 120                 125

Tyr Lys Glu Ala Gly Ile Ser Lys Asp Arg Ile Leu Ile Lys Leu Ser
    130                 135                 140

Ser Thr Trp Glu Gly Ile Gln Ala Gly Lys Glu Leu Glu Glu Gln His
145                 150                 155                 160

Gly Ile His Cys Asn Met Thr Leu Leu Phe Ser Phe Ala Gln Ala Val
                165                 170                 175

Ala Cys Ala Glu Ala Gly Val Thr Leu Ile Ser Pro Phe Val Gly Arg
            180                 185                 190

Ile Leu Asp Trp His Val Ala Asn Thr Asp Lys Lys Ser Tyr Glu Pro
        195                 200                 205

Leu Glu Asp Pro Gly Val Lys Ser Val Thr Lys Ile Tyr Asn Tyr Tyr
    210                 215                 220

Lys Lys Phe Ser Tyr Lys Thr Ile Val Met Gly Ala Ser Phe Arg Asn
225                 230                 235                 240

Thr Gly Glu Ile Lys Ala Leu Ala Gly Cys Asp Phe Leu Thr Ile Ser
                245                 250                 255

Pro Lys Leu Leu Gly Glu Leu Leu Gln Asp Asn Ala Lys Leu Val Pro
            260                 265                 270

Val Leu Ser Ala Lys Ala Ala Gln Ala Ser Asp Leu Glu Lys Ile His
        275                 280                 285

Leu Asp Glu Lys Ser Phe Arg Trp Leu His Asn Glu Asp Gln Met Ala
    290                 295                 300

Val Glu Lys Leu Ser Asp Gly Ile Arg Lys Phe Ala Ala Asp Ala Val
305                 310                 315                 320

Lys Leu Glu Arg Met Leu Thr Glu Arg Met Phe Asn Ala Glu Asn Gly
                325                 330                 335

Lys


<210> SEQ ID NO 56
<211> LENGTH: 564
<212> TYPE: PRT
<213> ORGANISM: Homo sapiens

<400> SEQUENCE: 56

Met Ala Glu Leu Asp Leu Met Ala Pro Gly Pro Leu Pro Arg Ala Thr
1               5                   10                  15

Ala Gln Pro Pro Ala Pro Leu Ser Pro Asp Ser Gly Ser Pro Ser Pro
            20                  25                  30

Asp Ser Gly Ser Ala Ser Pro Val Glu Glu Glu Asp Val Gly Ser Ser
        35                  40                  45

Glu Lys Leu Gly Arg Glu Thr Glu Glu Gln Asp Ser Asp Ser Ala Glu
    50                  55                  60

Gln Gly Asp Pro Ala Gly Glu Gly Lys Glu Val Leu Cys Asp Phe Cys
```

-continued

```
65                  70                  75                  80

Leu Asp Asp Thr Arg Arg Val Lys Ala Val Lys Ser Cys Leu Thr Cys
                85                  90                  95

Met Val Asn Tyr Cys Glu Glu His Leu Gln Pro His Gln Val Asn Ile
            100                 105                 110

Lys Leu Gln Ser His Leu Leu Thr Glu Pro Val Lys Asp His Asn Trp
        115                 120                 125

Arg Tyr Cys Pro Ala His His Ser Pro Leu Ser Ala Phe Cys Cys Pro
    130                 135                 140

Asp Gln Gln Cys Ile Cys Gln Asp Cys Cys Gln Glu His Ser Gly His
145                 150                 155                 160

Thr Ile Val Ser Leu Asp Ala Ala Arg Arg Asp Lys Glu Ala Glu Leu
                165                 170                 175

Gln Cys Thr Gln Leu Asp Leu Glu Arg Lys Leu Lys Leu Asn Glu Asn
            180                 185                 190

Ala Ile Ser Arg Leu Gln Ala Asn Gln Lys Ser Val Leu Val Ser Val
        195                 200                 205

Ser Glu Val Lys Ala Val Ala Glu Met Gln Phe Gly Glu Leu Leu Ala
    210                 215                 220

Ala Val Arg Lys Ala Gln Ala Asn Val Met Leu Phe Leu Glu Glu Lys
225                 230                 235                 240

Glu Gln Ala Ala Leu Ser Gln Ala Asn Gly Ile Lys Ala His Leu Glu
                245                 250                 255

Tyr Arg Ser Ala Glu Met Glu Lys Ser Lys Gln Glu Leu Glu Arg Met
            260                 265                 270

Ala Ala Ile Ser Asn Thr Val Gln Phe Leu Glu Glu Tyr Cys Lys Phe
        275                 280                 285

Lys Asn Thr Glu Asp Ile Thr Phe Pro Ser Val Tyr Val Gly Leu Lys
    290                 295                 300

Asp Lys Leu Ser Gly Ile Arg Lys Val Ile Thr Glu Ser Thr Val His
305                 310                 315                 320

Leu Ile Gln Leu Leu Glu Asn Tyr Lys Lys Lys Leu Gln Glu Phe Ser
                325                 330                 335

Lys Glu Glu Glu Tyr Asp Ile Arg Thr Gln Val Ser Ala Val Val Gln
            340                 345                 350

Arg Lys Tyr Trp Thr Ser Lys Pro Glu Pro Ser Thr Arg Glu Gln Phe
        355                 360                 365

Leu Gln Tyr Ala Tyr Asp Ile Thr Phe Asp Pro Asp Thr Ala His Lys
    370                 375                 380

Tyr Leu Arg Leu Gln Glu Glu Asn Arg Lys Val Thr Asn Thr Thr Pro
385                 390                 395                 400

Trp Glu His Pro Tyr Pro Asp Leu Pro Ser Arg Phe Leu His Trp Arg
                405                 410                 415

Gln Val Leu Ser Gln Gln Ser Leu Tyr Leu His Arg Tyr Tyr Phe Glu
            420                 425                 430

Val Glu Ile Phe Gly Ala Gly Thr Tyr Val Gly Leu Thr Cys Lys Gly
        435                 440                 445

Ile Asp Arg Lys Gly Glu Glu Arg Asn Ser Cys Ile Ser Gly Asn Asn
    450                 455                 460

Phe Ser Trp Ser Leu Gln Trp Asn Gly Lys Glu Phe Thr Ala Trp Tyr
465                 470                 475                 480

Ser Asp Met Glu Thr Pro Leu Lys Ala Gly Pro Phe Arg Arg Leu Gly
                485                 490                 495
```

```
Val Tyr Ile Asp Phe Pro Gly Gly Ile Leu Ser Phe Tyr Gly Val Glu
            500                 505                 510

Tyr Asp Thr Met Thr Leu Val His Lys Phe Ala Cys Lys Phe Ser Glu
        515                 520                 525

Pro Val Tyr Ala Ala Phe Trp Leu Ser Lys Lys Glu Asn Ala Ile Arg
    530                 535                 540

Ile Val Asp Leu Gly Glu Glu Pro Glu Lys Pro Ala Pro Ser Leu Val
545                 550                 555                 560

Gly Thr Ala Pro


<210> SEQ ID NO 57
<211> LENGTH: 348
<212> TYPE: PRT
<213> ORGANISM: Homo sapiens

<400> SEQUENCE: 57

Met Gln Phe Gly Glu Leu Leu Ala Ala Val Arg Lys Ala Gln Ala Asn
1               5                   10                  15

Val Met Leu Phe Leu Glu Glu Lys Glu Gln Ala Ala Leu Ser Gln Ala
            20                  25                  30

Asn Gly Ile Lys Ala His Leu Glu Tyr Arg Ser Ala Glu Met Glu Lys
        35                  40                  45

Ser Lys Gln Glu Leu Glu Thr Met Ala Ala Ile Ser Asn Thr Val Gln
    50                  55                  60

Phe Leu Glu Glu Tyr Cys Lys Phe Lys Asn Thr Glu Asp Ile Thr Phe
65                  70                  75                  80

Pro Ser Val Tyr Ile Gly Leu Lys Asp Lys Leu Ser Gly Ile Arg Lys
                85                  90                  95

Val Ile Thr Glu Ser Thr Val His Leu Ile Gln Leu Leu Glu Asn Tyr
            100                 105                 110

Lys Lys Lys Leu Gln Glu Phe Ser Lys Glu Glu Glu Tyr Asp Ile Arg
        115                 120                 125

Thr Gln Val Ser Ala Ile Val Gln Arg Lys Tyr Trp Thr Ser Lys Pro
    130                 135                 140

Glu Pro Ser Thr Arg Glu Gln Phe Leu Gln Tyr Val His Asp Ile Thr
145                 150                 155                 160

Phe Asp Pro Asp Thr Ala His Lys Tyr Leu Arg Leu Gln Glu Glu Asn
                165                 170                 175

Arg Lys Val Thr Asn Thr Thr Pro Trp Glu His Pro Tyr Pro Asp Leu
            180                 185                 190

Pro Ser Arg Phe Leu His Trp Arg Gln Val Leu Ser Gln Gln Ser Leu
        195                 200                 205

Tyr Leu His Arg Tyr Tyr Phe Glu Val Glu Ile Phe Gly Ala Gly Thr
    210                 215                 220

Tyr Val Gly Leu Thr Cys Lys Gly Ile Asp Gln Lys Gly Glu Glu Arg
225                 230                 235                 240

Ser Ser Cys Ile Ser Gly Asn Asn Phe Ser Trp Ser Leu Gln Trp Asn
                245                 250                 255

Gly Lys Glu Phe Thr Ala Trp Tyr Ser Asp Met Glu Thr Pro Leu Lys
            260                 265                 270

Ala Gly Pro Phe Trp Arg Leu Gly Val Tyr Ile Asp Phe Pro Gly Gly
        275                 280                 285

Ile Leu Ser Phe Tyr Gly Val Glu Tyr Asp Ser Met Thr Leu Val His
    290                 295                 300
```

```
Lys Phe Ala Cys Lys Phe Ser Glu Pro Val Tyr Ala Ala Phe Trp Leu
305                 310                 315                 320

Ser Lys Lys Glu Asn Ala Ile Arg Ile Val Asp Leu Gly Glu Glu Pro
                325                 330                 335

Glu Lys Pro Ala Pro Ser Leu Val Gly Thr Ala Pro
            340                 345


<210> SEQ ID NO 58
<211> LENGTH: 105
<212> TYPE: PRT
<213> ORGANISM: Homo sapiens

<400> SEQUENCE: 58

Met Val Lys Gln Ile Glu Ser Lys Thr Ala Phe Gln Glu Ala Leu Asp
1               5                   10                  15

Ala Ala Gly Asp Lys Leu Val Val Val Asp Phe Ser Ala Thr Trp Cys
            20                  25                  30

Gly Pro Cys Lys Met Ile Lys Pro Phe Phe His Ser Leu Ser Glu Lys
        35                  40                  45

Tyr Ser Asn Val Ile Phe Leu Glu Val Asp Val Asp Asp Cys Gln Asp
    50                  55                  60

Val Ala Ser Glu Cys Glu Val Lys Cys Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val
            100                 105


<210> SEQ ID NO 59
<211> LENGTH: 649
<212> TYPE: PRT
<213> ORGANISM: Homo sapiens
<220> FEATURE:
<221> NAME/KEY: MISC_FEATURE
<222> LOCATION: (648)..(648)
<223> OTHER INFORMATION: Xaa is pyrrolidone carboxylic acid

<400> SEQUENCE: 59

Met Gly Cys Ala Glu Gly Lys Ala Val Ala Ala Ala Ala Pro Thr Glu
1               5                   10                  15

Leu Gln Thr Lys Gly Lys Asn Gly Asp Gly Arg Arg Arg Ser Ala Lys
            20                  25                  30

Asp His His Pro Gly Lys Thr Leu Pro Glu Asn Pro Ala Gly Phe Thr
        35                  40                  45

Ser Thr Ala Thr Ala Asp Ser Arg Ala Leu Leu Gln Ala Tyr Ile Asp
    50                  55                  60

Gly His Ser Val Val Ile Phe Ser Arg Ser Thr Cys Thr Arg Cys Thr
65                  70                  75                  80

Glu Val Lys Lys Leu Phe Lys Ser Leu Cys Val Pro Tyr Phe Val Leu
                85                  90                  95

Glu Leu Asp Gln Thr Glu Asp Gly Arg Ala Leu Glu Gly Thr Leu Ser
            100                 105                 110

Glu Leu Ala Ala Glu Thr Asp Leu Pro Val Val Phe Val Lys Gln Arg
        115                 120                 125

Lys Ile Gly Gly His Gly Pro Thr Leu Lys Ala Tyr Gln Glu Gly Arg
    130                 135                 140

Leu Gln Lys Leu Leu Lys Met Asn Gly Pro Glu Asp Leu Pro Lys Ser
```

```
145                 150                 155                 160

Tyr Asp Tyr Asp Leu Ile Ile Ile Gly Gly Gly Ser Gly Gly Leu Ala
                165                 170                 175

Ala Ala Lys Glu Ala Ala Gln Tyr Gly Lys Lys Val Met Val Leu Asp
            180                 185                 190

Phe Val Thr Pro Thr Pro Leu Gly Thr Arg Trp Gly Leu Gly Gly Thr
        195                 200                 205

Cys Val Asn Val Gly Cys Ile Pro Lys Lys Leu Met His Gln Ala Ala
    210                 215                 220

Leu Leu Gly Gln Ala Leu Gln Asp Ser Arg Asn Tyr Gly Trp Lys Val
225                 230                 235                 240

Glu Glu Thr Val Lys His Asp Trp Asp Arg Met Ile Glu Ala Val Gln
                245                 250                 255

Asn His Ile Gly Ser Leu Asn Trp Gly Tyr Arg Val Ala Leu Arg Glu
            260                 265                 270

Lys Lys Val Val Tyr Glu Asn Ala Tyr Gly Gln Phe Ile Gly Pro His
        275                 280                 285

Arg Ile Lys Ala Thr Asn Asn Lys Gly Lys Glu Lys Ile Tyr Ser Ala
    290                 295                 300

Glu Arg Phe Leu Ile Ala Thr Gly Glu Arg Pro Arg Tyr Leu Gly Ile
305                 310                 315                 320

Pro Gly Asp Lys Glu Tyr Cys Ile Ser Ser Asp Asp Leu Phe Ser Leu
                325                 330                 335

Pro Tyr Cys Pro Gly Lys Thr Leu Val Val Gly Ala Ser Tyr Val Ala
            340                 345                 350

Leu Glu Cys Ala Gly Phe Leu Ala Gly Ile Gly Leu Asp Val Thr Val
        355                 360                 365

Met Val Arg Ser Ile Leu Leu Arg Gly Phe Asp Gln Asp Met Ala Asn
    370                 375                 380

Lys Ile Gly Glu His Met Glu Glu His Gly Ile Lys Phe Ile Arg Gln
385                 390                 395                 400

Phe Val Pro Ile Lys Val Glu Gln Ile Glu Ala Gly Thr Pro Gly Arg
                405                 410                 415

Leu Arg Val Val Ala Gln Ser Thr Asn Ser Glu Glu Ile Ile Glu Gly
            420                 425                 430

Glu Tyr Asn Thr Val Met Leu Ala Ile Gly Arg Asp Ala Cys Thr Arg
        435                 440                 445

Lys Ile Gly Leu Glu Thr Val Gly Val Lys Ile Asn Glu Lys Thr Gly
    450                 455                 460

Lys Ile Pro Val Thr Asp Glu Glu Gln Thr Asn Val Pro Tyr Ile Tyr
465                 470                 475                 480

Ala Ile Gly Asp Ile Leu Glu Asp Lys Val Glu Leu Thr Pro Val Ala
                485                 490                 495

Ile Gln Ala Gly Arg Leu Leu Ala Gln Arg Leu Tyr Ala Gly Ser Thr
            500                 505                 510

Val Lys Cys Asp Tyr Glu Asn Val Pro Thr Thr Val Phe Thr Pro Leu
        515                 520                 525

Glu Tyr Gly Ala Cys Gly Leu Ser Glu Glu Lys Ala Val Glu Lys Phe
    530                 535                 540

Gly Glu Glu Asn Ile Glu Val Tyr His Ser Tyr Phe Trp Pro Leu Glu
545                 550                 555                 560

Trp Thr Ile Pro Ser Arg Asp Asn Asn Lys Cys Tyr Ala Lys Ile Ile
                565                 570                 575
```

```
Cys Asn Thr Lys Asp Asn Glu Arg Val Val Gly Phe His Val Leu Gly
            580                 585                 590

Pro Asn Ala Gly Glu Val Thr Gln Gly Phe Ala Ala Ala Leu Lys Cys
        595                 600                 605

Gly Leu Thr Lys Lys Gln Leu Asp Ser Thr Ile Gly Ile His Pro Val
    610                 615                 620

Cys Ala Glu Val Phe Thr Thr Leu Ser Val Thr Lys Arg Ser Gly Ala
625                 630                 635                 640

Ser Ile Leu Gln Ala Gly Cys Xaa Gly
                645


<210> SEQ ID NO 60
<211> LENGTH: 494
<212> TYPE: PRT
<213> ORGANISM: Homo sapiens

<400> SEQUENCE: 60

Met Phe Glu Ile Lys Lys Ile Cys Cys Ile Gly Ala Gly Tyr Val Gly
1               5                   10                  15

Gly Pro Thr Cys Ser Val Ile Ala His Met Cys Pro Glu Ile Arg Val
            20                  25                  30

Thr Val Val Asp Val Asn Glu Ser Arg Ile Asn Ala Trp Asn Ser Pro
        35                  40                  45

Thr Leu Pro Ile Tyr Glu Pro Gly Leu Lys Glu Val Val Glu Ser Cys
    50                  55                  60

Arg Gly Lys Asn Leu Phe Phe Ser Thr Asn Ile Asp Asp Ala Ile Lys
65                  70                  75                  80

Glu Ala Asp Leu Val Phe Ile Ser Val Asn Thr Pro Thr Lys Thr Tyr
                85                  90                  95

Gly Met Gly Lys Gly Arg Ala Ala Asp Leu Lys Tyr Ile Glu Ala Cys
            100                 105                 110

Ala Arg Arg Ile Val Gln Asn Ser Asn Gly Tyr Lys Ile Val Thr Glu
        115                 120                 125

Lys Ser Thr Val Pro Val Arg Ala Ala Glu Ser Ile Arg Arg Ile Phe
    130                 135                 140

Asp Ala Asn Thr Lys Pro Asn Leu Asn Leu Gln Val Leu Ser Asn Pro
145                 150                 155                 160

Glu Phe Leu Ala Glu Gly Thr Ala Ile Lys Asp Leu Lys Asn Pro Asp
                165                 170                 175

Arg Val Leu Ile Gly Gly Asp Glu Thr Pro Glu Gly Gln Arg Ala Val
            180                 185                 190

Gln Ala Leu Cys Ala Val Tyr Glu His Trp Val Pro Arg Glu Lys Ile
        195                 200                 205

Leu Thr Thr Asn Thr Trp Ser Ser Glu Leu Ser Lys Leu Ala Ala Asn
    210                 215                 220

Ala Phe Leu Ala Gln Arg Ile Ser Ser Ile Asn Ser Ile Ser Ala Leu
225                 230                 235                 240

Cys Glu Ala Thr Gly Ala Asp Val Glu Glu Val Ala Thr Ala Ile Gly
                245                 250                 255

Met Asp Gln Arg Ile Gly Asn Lys Phe Leu Lys Ala Ser Val Gly Phe
            260                 265                 270

Gly Gly Ser Cys Phe Gln Lys Asp Val Leu Asn Leu Val Tyr Leu Cys
        275                 280                 285

Glu Ala Leu Asn Leu Pro Glu Val Ala Arg Tyr Trp Gln Gln Val Ile
```

```
    290                 295                 300

Asp Met Asn Asp Tyr Gln Arg Arg Arg Phe Ala Ser Arg Ile Ile Asp
305                 310                 315                 320

Ser Leu Phe Asn Thr Val Thr Asp Lys Lys Ile Ala Ile Leu Gly Phe
                325                 330                 335

Ala Phe Lys Lys Asp Thr Gly Asp Thr Arg Glu Ser Ser Ser Ile Tyr
            340                 345                 350

Ile Ser Lys Tyr Leu Met Asp Glu Gly Ala His Leu His Ile Tyr Asp
        355                 360                 365

Pro Lys Val Pro Arg Glu Gln Ile Val Val Asp Leu Ser His Pro Gly
    370                 375                 380

Val Ser Glu Asp Asp Gln Val Ser Arg Leu Val Thr Ile Ser Lys Asp
385                 390                 395                 400

Pro Tyr Glu Ala Cys Asp Gly Ala His Ala Val Val Ile Cys Thr Glu
                405                 410                 415

Trp Asp Met Phe Lys Glu Leu Asp Tyr Glu Arg Ile His Lys Lys Met
            420                 425                 430

Leu Lys Pro Ala Phe Ile Phe Asp Gly Arg Arg Val Leu Asp Gly Leu
        435                 440                 445

His Asn Glu Leu Gln Thr Ile Gly Phe Gln Ile Glu Thr Ile Gly Lys
    450                 455                 460

Lys Val Ser Ser Lys Arg Ile Pro Tyr Ala Pro Ser Gly Glu Ile Pro
465                 470                 475                 480

Lys Phe Ser Leu Gln Asp Pro Pro Asn Lys Lys Pro Lys Val
                485                 490
```

<210> SEQ ID NO 61
<211> LENGTH: 78
<212> TYPE: DNA
<213> ORGANISM: Homo sapiens

<400> SEQUENCE: 61

```
aaacctgcca taactttccc aagaactgag tactctgtac ctgggagtag ttggcagatc     60

cactggtttc tgactgga                                                   78
```

<210> SEQ ID NO 62
<211> LENGTH: 78
<212> TYPE: DNA
<213> ORGANISM: Homo sapiens

<400> SEQUENCE: 62

```
tgtggaccta actaggggga gcctaaaata atgttgggac tacctagatg gtcagaaaga     60

atgagccaat taacttct                                                   78
```

<210> SEQ ID NO 63
<211> LENGTH: 78
<212> TYPE: DNA
<213> ORGANISM: Homo sapiens

<400> SEQUENCE: 63

```
aaacctgcca taactttccc aagaactgag tactctgtac tacctagatg gtcagaaaga     60

atgagccaat taacttct                                                   78
```

<210> SEQ ID NO 64
<211> LENGTH: 79
<212> TYPE: DNA
<213> ORGANISM: Homo sapiens

<400> SEQUENCE: 64
aggttaggta ctgaactcat caggaggctg aggttggaaa gtagatttga caaggttaag 60
taaaagaaag gcaaagctg 79

<210> SEQ ID NO 65
<211> LENGTH: 79
<212> TYPE: DNA
<213> ORGANISM: Homo sapiens

<400> SEQUENCE: 65 atttttcgg gtttttttc cactttttc cttttgaaat tttattattt atttactcat 60
tttgagatag ggtctcact 79

<210> SEQ ID NO 66
<211> LENGTH: 79
<212> TYPE: DNA
<213> ORGANISM: Homo sapiens

<400> SEQUENCE: 66
aggttgggta ctgaactcat caggaggctg agtttgaaat tttattattt atttactcat 60
tttgagatag ggtctcact 79

<210> SEQ ID NO 67
<211> LENGTH: 79
<212> TYPE: DNA
<213> ORGANISM: Homo sapiens

<400> SEQUENCE: 67
cttggttctc ctgctactac ttctgttgct gctacttgat ccttacagga tgtttctata 60
ctttacaaaa ctctttggt 79

<210> SEQ ID NO 68
<211> LENGTH: 79
<212> TYPE: DNA
<213> ORGANISM: Homo sapiens

<400> SEQUENCE: 68
gtgatggcag tgggcacgcc catatacatt tgcatacact ctaatataaa tgtttacaaa 60
catacacaca cacacattc 79

<210> SEQ ID NO 69
<211> LENGTH: 79
<212> TYPE: DNA
<213> ORGANISM: Homo sapiens

<400> SEQUENCE: 69
cttggttctc ctgctactac ttctgttgct gctacttgat ctaatataaa tgtttacaaa 60
catacacaca cacacattc 79

<210> SEQ ID NO 70
<211> LENGTH: 39
<212> TYPE: DNA
<213> ORGANISM: Homo sapiens

<400> SEQUENCE: 70
tttgggaatg tgggcaacct gctgggacgg gagtcccgg 39

<210> SEQ ID NO 71

<211> LENGTH: 1551
<212> TYPE: DNA
<213> ORGANISM: Homo sapiens

<400> SEQUENCE: 71

```
atgatggact tggagctgcc gccgccggga ctcccgtccc agcaggttgc ccacattccc     60
aaatcagatg ctttgtactt tgatgactgc atgcagcttt tggcgcagac attcccgttt    120
gtagatgaca atgaggtttc ttcggctacg tttcagtcac ttgttcctga tattcccggt    180
cacatcgaga gcccagtctt cattgctact aatcaggctc agtcacctga aacttctgtt    240
gctcaggtag cccctgttga tttagacggt atgcaacagg acattgagca agtttgggag    300
gagctattat ccattcctga gttacagtgt cttaatattg aaaatgacaa gctggttgag    360
actaccatgg ttccaagtcc agaagccaaa ctgacagaag ttgacaatta tcatttttac    420
tcatctatac cctcaatgga aaaagaagta ggtaactgta gtccacattt tcttaatgct    480
tttgaggatt ccttcagcag catcctctcc acagaagacc ccaaccagtt gacagtgaac    540
tcattaaatt cagatgccac agtcaacaca gattttggtg atgaatttta ttctgctttc    600
atagctgagc ccagtatcag caacagcatg ccctcacctg ctactttaag ccattcactc    660
tctgaacttc taaatgggcc cattgatgtt tctgatctat cactttgcaa agctttcaac    720
caaaaccacc ctgaaagcac agcagaattc aatgattctg actccggcat ttcactaaac    780
acaagtccca gtgtggcatc accagaacac tcagtggaat cttccagcta tggagacaca    840
ctacttggcc tcagtgattc tgaagtggaa gagctagata gtgcccctgg aagtgtcaaa    900
cagaatggtc ctaaaacacc agtacattct tctggggata tggtacaacc cttgtcacca    960
tctcaggggc agagcactca cgtgcatgat gcccaatgtg agaacacacc agagaaagaa   1020
ttgcctgtaa gtcctggtca tcggaaaacc ccattcacaa aagacaaaca ttcaagccgc   1080
ttggaggctc atctcacaag agatgaactt agggcaaaag ctctccatat cccattccct   1140
gtagaaaaaa tcattaacct ccctgttgtt gacttcaacg aaatgatgtc caaagagcag   1200
ttcaatgaag ctcaacttgc attaattcgg gatatacgta ggaggggtaa gaataaagtg   1260
gctgctcaga attgcagaaa aagaaaactg gaaaatatag tagaactaga gcaagattta   1320
gatcatttga aagatgaaaa agaaaaattg ctcaaagaaa aaggagaaaa tgacaaaagc   1380
cttcacctac tgaaaaaaca actcagcacc ttatatctcg aagttttcag catgctacgt   1440
gatgaagatg gaaaacctta ttctcctagt gaatactccc tgcagcaaac aagagatggc   1500
aatgttttcc ttgttcccaa aagtaagaag ccagatgtta agaaaaacta g            1551
```

<210> SEQ ID NO 72
<211> LENGTH: 516
<212> TYPE: PRT
<213> ORGANISM: Homo sapiens

<400> SEQUENCE: 72

```
Met Met Asp Leu Glu Leu Pro Pro Pro Gly Leu Pro Ser Gln Gln Val
1               5                   10                  15

Ala His Ile Pro Lys Ser Asp Ala Leu Tyr Phe Asp Asp Cys Met Gln
            20                  25                  30

Leu Leu Ala Gln Thr Phe Pro Phe Val Asp Asp Asn Glu Val Ser Ser
        35                  40                  45

Ala Thr Phe Gln Ser Leu Val Pro Asp Ile Pro Gly His Ile Glu Ser
    50                  55                  60

Pro Val Phe Ile Ala Thr Asn Gln Ala Gln Ser Pro Glu Thr Ser Val
```

```
65                  70                  75                  80

Ala Gln Val Ala Pro Val Asp Leu Asp Gly Met Gln Gln Asp Ile Glu
                85                  90                  95

Gln Val Trp Glu Glu Leu Leu Ser Ile Pro Glu Leu Gln Cys Leu Asn
            100                 105                 110

Ile Glu Asn Asp Lys Leu Val Glu Thr Thr Met Val Pro Ser Pro Glu
        115                 120                 125

Ala Lys Leu Thr Glu Val Asp Asn Tyr His Phe Tyr Ser Ser Ile Pro
    130                 135                 140

Ser Met Glu Lys Glu Val Gly Asn Cys Ser Pro His Phe Leu Asn Ala
145                 150                 155                 160

Phe Glu Asp Ser Phe Ser Ser Ile Leu Ser Thr Glu Asp Pro Asn Gln
                165                 170                 175

Leu Thr Val Asn Ser Leu Asn Ser Asp Ala Thr Val Asn Thr Asp Phe
            180                 185                 190

Gly Asp Glu Phe Tyr Ser Ala Phe Ile Ala Glu Pro Ser Ile Ser Asn
        195                 200                 205

Ser Met Pro Ser Pro Ala Thr Leu Ser His Ser Leu Ser Glu Leu Leu
    210                 215                 220

Asn Gly Pro Ile Asp Val Ser Asp Leu Ser Leu Cys Lys Ala Phe Asn
225                 230                 235                 240

Gln Asn His Pro Glu Ser Thr Ala Glu Phe Asn Asp Ser Asp Ser Gly
                245                 250                 255

Ile Ser Leu Asn Thr Ser Pro Ser Val Ala Ser Pro Glu His Ser Val
            260                 265                 270

Glu Ser Ser Ser Tyr Gly Asp Thr Leu Leu Gly Leu Ser Asp Ser Glu
        275                 280                 285

Val Glu Glu Leu Asp Ser Ala Pro Gly Ser Val Lys Gln Asn Gly Pro
    290                 295                 300

Lys Thr Pro Val His Ser Ser Gly Asp Met Val Gln Pro Leu Ser Pro
305                 310                 315                 320

Ser Gln Gly Gln Ser Thr His Val His Asp Ala Gln Cys Glu Asn Thr
                325                 330                 335

Pro Glu Lys Glu Leu Pro Val Ser Pro Gly His Arg Lys Thr Pro Phe
            340                 345                 350

Thr Lys Asp Lys His Ser Ser Arg Leu Glu Ala His Leu Thr Arg Asp
        355                 360                 365

Glu Leu Arg Ala Lys Ala Leu His Ile Pro Phe Pro Val Glu Lys Ile
    370                 375                 380

Ile Asn Leu Pro Val Val Asp Phe Asn Glu Met Met Ser Lys Glu Gln
385                 390                 395                 400

Phe Asn Glu Ala Gln Leu Ala Leu Ile Arg Asp Ile Arg Arg Arg Gly
                405                 410                 415

Lys Asn Lys Val Ala Ala Gln Asn Cys Arg Lys Arg Lys Leu Glu Asn
            420                 425                 430

Ile Val Glu Leu Glu Gln Asp Leu Asp His Leu Lys Asp Glu Lys Glu
        435                 440                 445

Lys Leu Leu Lys Glu Lys Gly Glu Asn Asp Lys Ser Leu His Leu Leu
    450                 455                 460

Lys Lys Gln Leu Ser Thr Leu Tyr Leu Glu Val Phe Ser Met Leu Arg
465                 470                 475                 480

Asp Glu Asp Gly Lys Pro Tyr Ser Pro Ser Glu Tyr Ser Leu Gln Gln
                485                 490                 495
```

```
Thr Arg Asp Gly Asn Val Phe Leu Val Pro Lys Ser Lys Lys Pro Asp
            500                 505                 510

Val Lys Lys Asn
        515


<210> SEQ ID NO 73
<211> LENGTH: 1700
<212> TYPE: DNA
<213> ORGANISM: Homo sapiens

<400> SEQUENCE: 73

atgatggact tggagctgcc gccgccggga ctcccgtccc agcaggacat ggatttgatt      60

gacatacttt ggaggcaaga tatagatctt ggagtaagtc gagaagtatt tgacttcagt     120

cagcgacgga aagagtatga gctggaaaaa cagaaaaaac ttgaaaagga aagacaagaa     180

caactccaaa aggagcaaga gaaagccttt ttcgctcagt tacaactaga tgaagagaca     240

ggtgaatttc tcccaattca gccagcccag cacatccagt cagaaaccag tggatctgcc     300

aactactccc aggttgccca cattcccaaa tcagatgctt tgtactttga tgactgcatg     360

cagcttttgg cgcagacatt cccgtttgta gatgacaatg aggtttcttc ggctacgttt     420

cagtcacttg ttcctgatat tcccggtcac atcgagagcc cagtcttcat tgctactaat     480

caggctcagt cacctgaaac ttctgttgct caggtagccc ctgttgattt agacggtatg     540

caacaggaca ttgagcaagt ttgggaggag ctattatcca ttcctgagtt acagtgtctt     600

aatattgaaa atgacaagct ggttgagact accatggttc caagtccaga agccaaactg     660

acagaagttg acaattatca tttttactca tctataccct caatggaaaa agaagtaggt     720

aactgtagtc cacattttct taatgctttt gaggattcct tcagcagcat cctctccaca     780

gaagacccca accagttgac agtgaactca ttaaattcag atgccacagt caacacagat     840

tttggtgatg aattttattc tgctttcata gctgagccca gtatcagcaa cagcatgccc     900

tcacctgcta ctttaagcca ttcactctct gaacttctaa atgggcccat tgatgtttct     960

gatctatcac tttgcaaagc tttcaaccaa aaccaccctg aaagcacagc agaattcaat    1020

gattctgact ccggcatttc actaaacaca agtcccagtg tggcatcacc agaacactca    1080

gtggaatctt ccagctatgg agacacacta cttggcctca gtgattctga agtggaagag    1140

ctagatagtg cccctggaag tgtcaaacag aatggtccta aaacaccagt acattcttct    1200

ggggatatgg tacaaccctt gtcaccatct caggggcaga gcactcacgt gcatgatgcc    1260

caatgtgaga acacaccaga gaaagaattg cctgtaagtc ctggtcatcg gaaaacccca    1320

ttcacaaaag acaaacattc aagccgcttg gaggctcatc tcacaagaga tgaacttagg    1380

gcaaaagctc tccatatccc attccctgta gaaaaaatca ttaacctccc tgttgttgac    1440

ttcaacgaaa tgatgtccaa agagcagttc aatgaagctc aacttgcatt aattcgggat    1500

atacgtagga ggggtaagaa taaagtggct gctcagaatt gcagaaaaag aaaactggaa    1560

aatatagtag aactagagca agatttagat catttgaaag atgaaaaaga aaaattgctc    1620

aaagaaaaag gagaaaatga caaaagcctt cacctactga aaaaacaact cagcacctta    1680

tatctcgaag ttttcagcat                                                1700


<210> SEQ ID NO 74
<211> LENGTH: 567
<212> TYPE: PRT
<213> ORGANISM: Homo sapiens
```

<400> SEQUENCE: 74

```
Met Met Asp Leu Glu Leu Pro Pro Pro Gly Leu Pro Ser Gln Gln Asp
1               5                   10                  15

Met Asp Leu Ile Asp Ile Leu Trp Arg Gln Asp Ile Asp Leu Gly Val
            20                  25                  30

Ser Arg Glu Val Phe Asp Phe Ser Gln Arg Arg Lys Glu Tyr Glu Leu
        35                  40                  45

Glu Lys Gln Lys Lys Leu Glu Lys Glu Arg Gln Glu Gln Leu Gln Lys
    50                  55                  60

Glu Gln Glu Lys Ala Phe Phe Ala Gln Leu Gln Leu Asp Glu Glu Thr
65                  70                  75                  80

Gly Glu Phe Leu Pro Ile Gln Pro Ala Gln His Ile Gln Ser Glu Thr
                85                  90                  95

Ser Gly Ser Ala Asn Tyr Ser Gln Val Ala His Ile Pro Lys Ser Asp
            100                 105                 110

Ala Leu Tyr Phe Asp Asp Cys Met Gln Leu Leu Ala Gln Thr Phe Pro
        115                 120                 125

Phe Val Asp Asp Asn Glu Val Ser Ser Ala Thr Phe Gln Ser Leu Val
    130                 135                 140

Pro Asp Ile Pro Gly His Ile Glu Ser Pro Val Phe Ile Ala Thr Asn
145                 150                 155                 160

Gln Ala Gln Ser Pro Glu Thr Ser Val Ala Gln Val Ala Pro Val Asp
                165                 170                 175

Leu Asp Gly Met Gln Gln Asp Ile Glu Gln Val Trp Glu Glu Leu Leu
            180                 185                 190

Ser Ile Pro Glu Leu Gln Cys Leu Asn Ile Glu Asn Asp Lys Leu Val
        195                 200                 205

Glu Thr Thr Met Val Pro Ser Pro Glu Ala Lys Leu Thr Glu Val Asp
    210                 215                 220

Asn Tyr His Phe Tyr Ser Ser Ile Pro Ser Met Glu Lys Glu Val Gly
225                 230                 235                 240

Asn Cys Ser Pro His Phe Leu Asn Ala Phe Glu Asp Ser Phe Ser Ser
                245                 250                 255

Ile Leu Ser Thr Glu Asp Pro Asn Gln Leu Thr Val Asn Ser Leu Asn
            260                 265                 270

Ser Asp Ala Thr Val Asn Thr Asp Phe Gly Asp Glu Phe Tyr Ser Ala
        275                 280                 285

Phe Ile Ala Glu Pro Ser Ile Ser Asn Ser Met Pro Ser Pro Ala Thr
    290                 295                 300

Leu Ser His Ser Leu Ser Glu Leu Leu Asn Gly Pro Ile Asp Val Ser
305                 310                 315                 320

Asp Leu Ser Leu Cys Lys Ala Phe Asn Gln Asn His Pro Glu Ser Thr
                325                 330                 335

Ala Glu Phe Asn Asp Ser Asp Ser Gly Ile Ser Leu Asn Thr Ser Pro
            340                 345                 350

Ser Val Ala Ser Pro Glu His Ser Val Glu Ser Ser Ser Tyr Gly Asp
        355                 360                 365

Thr Leu Leu Gly Leu Ser Asp Ser Glu Val Glu Glu Leu Asp Ser Ala
    370                 375                 380

Pro Gly Ser Val Lys Gln Asn Gly Pro Lys Thr Pro Val His Ser Ser
385                 390                 395                 400

Gly Asp Met Val Gln Pro Leu Ser Pro Ser Gln Gly Gln Ser Thr His
                405                 410                 415
```

```
Val His Asp Ala Gln Cys Glu Asn Thr Pro Glu Lys Glu Leu Pro Val
            420                 425                 430

Ser Pro Gly His Arg Lys Thr Pro Phe Thr Lys Asp Lys His Ser Ser
        435                 440                 445

Arg Leu Glu Ala His Leu Thr Arg Asp Glu Leu Arg Ala Lys Ala Leu
    450                 455                 460

His Ile Pro Phe Pro Val Glu Lys Ile Ile Asn Leu Pro Val Val Asp
465                 470                 475                 480

Phe Asn Glu Met Met Ser Lys Glu Gln Phe Asn Glu Ala Gln Leu Ala
                485                 490                 495

Leu Ile Arg Asp Ile Arg Arg Arg Gly Lys Asn Lys Val Ala Ala Gln
            500                 505                 510

Asn Cys Arg Lys Arg Lys Leu Glu Asn Ile Val Glu Leu Glu Gln Asp
        515                 520                 525

Leu Asp His Leu Lys Asp Glu Lys Glu Lys Leu Leu Lys Glu Lys Gly
    530                 535                 540

Glu Asn Asp Lys Ser Leu His Leu Leu Lys Lys Gln Leu Ser Thr Leu
545                 550                 555                 560

Tyr Leu Glu Val Phe Ser Met
                565
```

METHODS FOR DIAGNOSING AND TREATING CANCER BY MEANS OF THE EXPRESSION STATUS AND MUTATIONAL STATUS OF NRF2 AND DOWNSTREAM TARGET GENES OF SAID GENE

SEQUENCE LISTING

The instant application contains a Sequence Listing which has been submitted electronically in ASCII format and is hereby incorporated by reference in its entirety. Said ASCII copy, created on Jan. 14, 2021 is named 50474-127002 Sequence Listing 1 7 25 ST25 and is 230,245 bytes in size.

FIELD OF THE INVENTION

The present invention relates generally to methods for diagnosing, treating, and providing prognoses for cancer, e.g., lung cancer.

BACKGROUND OF THE INVENTION

Cancer remains one of the most deadly threats to human health. Lung cancer, in particular, is the primary cause of cancer-related death for men and women in the United States, despite recent advances in therapeutic treatments. The majority of lung cancers are non-small cell lung cancers (NSCLC), and most often of either the adenomatous or squamous subtype. Recent studies have identified patterns of point mutations that underlie these indications (Imielinski et al. *Cell.* 150(6):1107-1120, 2012), but despite an increasing number of identified mutations associated with various cellular pathways, a comprehensive understanding of the nature and influence of these mutations on these cellular pathways is lacking.

Thus, there is an unmet need in the field to develop effective diagnostic and therapeutic strategies for cancers, such as lung cancer.

SUMMARY OF THE INVENTION

The present invention provides compositions and methods for diagnosing, treating, and providing prognoses for cancer, for example, lung cancer (e.g., non-small cell lung cancer (NSCLC)) and head and neck carcinoma.

In one aspect, the invention features a method of diagnosing a cancer in a subject, the method comprising: (a) determining the expression level of at least one (e.g., 1, 2, 3, 4, 5, 6, 7, 8, 9, 10, 11, 12, 13, 14, 15, 16, 17, 18, 19, 20, 21, 22, 23, 24, 25, 26, or 27) gene selected from the group consisting of AKR1B10, AKR1C2, SRXN1, OSGIN1, FECH, GCLM, TRIM16, ME1, KYNU, CABYR, SLC7A11, TRIM16L, AKR1C4, CYP4F11, RSPO3, ABCC2, AKR1B15, NR0B1, UGDH, TXNRD1, GSR, AKR1C3, TALDO1, PGD, TXN, NQO1, and FTL in a sample obtained from the subject; and (b) comparing the expression level of the at least one gene to a reference expression level of the at least one gene, wherein an increase in the expression level of the at least one gene in the sample relative to the reference expression level of the at least one gene identifies a subject having a cancer.

In another aspect, the invention features a method of identifying a subject having a cancer that is a NRF2-dependent cancer, the method comprising: (a) determining the expression level of at least one (e.g., 1, 2, 3, 4, 5, 6, 7, 8, 9, 10, 11, 12, 13, 14, 15, 16, 17, 18, 19, 20, 21, 22, 23, 24, 25, 26, or 27) gene selected from the group consisting of AKR1B10, AKR1C2, SRXN1, OSGIN1, FECH, GCLM, TRIM16, ME1, KYNU, CABYR, SLC7A11, TRIM16L, AKR1C4, CYP4F11, RSPO3, ABCC2, AKR1B15, NR0B1, UGDH, TXNRD1, GSR, AKR1C3, TALDO1, PGD, TXN, NQO1, and FTL in a sample obtained from the subject; (b) comparing the expression level of the at least one gene to a reference expression level of the at least one gene; and (c) determining if the subject's cancer is a NRF2-dependent cancer, wherein an increase in the expression level of the at least one gene in the sample relative to the reference expression level of the at least one gene identifies a subject having a NRF2-dependent cancer. In some embodiments of either of the preceding aspects, the expression level of at least two (e.g., 2, 3, 4, 5, 6, 7, 8, 9, 10, 11, 12, 13, 14, 15, 16, 17, 18, 19, 20, 21, 22, 23, 24, 25, 26, or 27) genes selected from the group consisting of AKR1B10, AKR1C2, SRXN1, OSGIN1, FECH, GCLM, TRIM16, ME1, KYNU, CABYR, SLC7A11, TRIM16L, AKR1C4, CYP4F11, RSPO3, ABCC2, AKR1B15, NR0B1, UGDH, TXNRD1, GSR, AKR1C3, TALDO1, PGD, TXN, NQO1, and FTL in a sample obtained from the subject is determined. In some embodiments, the expression level of at least three (e.g., 3, 4, 5, 6, 7, 8, 9, 10, 11, 12, 13, 14, 15, 16, 17, 18, 19, 20, 21, 22, 23, 24, 25, 26, or 27) genes selected from the group consisting of AKR1B10, AKR1C2, SRXN1, OSGIN1, FECH, GCLM, TRIM16, ME1, KYNU, CABYR, SLC7A11, TRIM16L, AKR1C4, CYP4F11, RSPO3, ABCC2, AKR1B15, NR0B1, UGDH, TXNRD1, GSR, AKR1C3, TALDO1, PGD, TXN, NQO1, and FTL in a sample obtained from the subject is determined. In some embodiments, the expression level of at least four (e.g., 4, 5, 6, 7, 8, 9, 10, 11, 12, 13, 14, 15, 16, 17, 18, 19, 20, 21, 22, 23, 24, 25, 26, or 27) genes selected from the group consisting of AKR1B10, AKR1C2, SRXN1, OSGIN1, FECH, GCLM, TRIM16, ME1, KYNU, CABYR, SLC7A11, TRIM16L, AKR1C4, CYP4F11, RSPO3, ABCC2, AKR1B15, NR0B1, UGDH, TXNRD1, GSR, AKR1C3, TALDO1, PGD, TXN, NQO1, and FTL in a sample obtained from the subject is determined. In some embodiments, the expression level of AKR1B10, AKR1C2, SRXN1, OSGIN1, FECH, GCLM, TRIM16, ME1, KYNU, CABYR, SLC7A11, TRIM16L, AKR1C4, CYP4F11, RSPO3, ABCC2, AKR1B15, NR0B1, UGDH, TXNRD1, GSR, AKR1C3, TALDO1, PGD, TXN, NQO1, and FTL in a sample obtained from the subject is determined.

In some embodiments, the expression level of one or more (e.g., 1, 2, 3, 4, 5, 6, 7, 8, 9, 10, 11, 12, 13, 14, 15, 16, 17, 18, 19, 20, or 21) of AKR1B10, AKR1C2, SRXN1, OSGIN1, FECH, GCLM, TRIM16, KYNU, CABYR, SLC7A11, TRIM16L, AKR1C4, NR0B1, UGDH, TXNRD1, GSR, AKR1C3, TALDO1, PGD, TXN, or NQO1 is determined. In some embodiments, the expression level of one or more (e.g., 1, 2, 3, 4, 5, 6, 7, 8, 9, 10, 11, or 12) of AKR1B10, AKR1C2, ME1, KYNU, CABYR, TRIM16L, AKR1C4, CYP4F11, RSPO3, AKR1B15, NR0B1, and AKR1C3 is determined.

In some embodiments, (a) the expression level of the at least two genes in the sample is an average (e.g., mean or median) of the at least two genes of the sample; (b) the reference expression level of the at least two genes is an average (e.g., mean or median) of the at least two genes of the reference; and (c) the average (e.g., mean or median) of the at least two genes of the sample is compared to the average of the at least two genes of the reference.

In some embodiments, the reference expression level is the mean level of expression of the at least one gene in a population of subjects. In some embodiments, the population of subjects is a population of subjects sharing a common ethnicity.

In some embodiments, the reference expression level is the mean level of expression of the at least one gene in a population of subjects having cancer (e.g., lung cancer, e.g., non-small cell lung cancer (NSCLC), e.g., squamous NSCLC).

In some embodiments, the expression level is an mRNA expression level. In some embodiments, the mRNA expression level is determined by PCR, RT-PCR, RNA-seq, gene expression profiling, serial analysis of gene expression, or microarray analysis.

In other embodiments, the expression level is a protein expression level. In some embodiments, the protein expression level is determined by western blot, immunohistochemistry, or mass spectrometry.

In some embodiments, any of the preceding methods further comprises determining a DNA sequence of NRF2. In some embodiments, the DNA sequence is determined by PCR, exome-seq, microarray analysis, or whole genome sequencing.

In another aspect, the invention features a method of diagnosing a cancer in a subject, the method comprising determining a DNA sequence of in a sample obtained from the subject, wherein the presence of NRF2 DNA comprising a deletion of all or a portion of its exon 2 identifies the subject as having a cancer. In some embodiments, the DNA sequence is determined by PCR, exome-seq, microarray analysis, or whole genome sequencing.

In another aspect, the invention features a method of identifying a subject having cancer, the method comprising determining the mRNA expression level of NRF2 comprising a deletion of all or a portion of its exon 2 in a sample obtained from the subject, wherein the presence of NRF2 comprising a deletion of all or a portion of its exon 2 identifies the subject as having a cancer. In some embodiments, the mRNA expression level is determined by PCR, RT-PCR, RNA-seq, gene expression profiling, serial analysis of gene expression, or microarray analysis. In some embodiments, the method further comprises determining a DNA sequence of the NRF2. In some embodiments, the DNA sequence is determined by PCR, exome-seq, microarray analysis, or whole genome sequencing.

In some embodiments of any of the preceding aspects, the NRF2 further comprises a deletion of all or a portion of its exon 3.

In another aspect, the invention features a method of diagnosing a cancer in a subject, the method comprising determining the protein expression level of NRF2 comprising a deletion of all or a portion of its Neh2 domain in a sample obtained from the subject, wherein the presence of NRF2 comprising a deletion of all or a portion of its Neh2 domain identifies the subject as having a cancer.

In another aspect, the invention features a method of identifying a subject having cancer, the method comprising determining the protein expression level of NRF2 comprising a deletion of all or a portion of its Neh2 domain in a sample obtained from the subject, wherein the presence of NRF2 comprising a deletion of all or a portion of its Neh2 domain identifies the subject as having a cancer.

In some embodiments of any of the preceding aspects, the NRF2 further comprises a deletion in all or a portion of its Neh4 domain. In some embodiments, the protein expression is determined by western blot, immunohistochemistry, or mass spectrometry.

In some embodiments, the method further comprises administering to the subject a therapeutically effective amount of a NRF2 pathway antagonist. In some embodiments, the method further comprises administering to the subject a therapeutically effective amount of an anti-cancer agent. In other embodiments, the method comprises administering an anti-cancer agent and a NRF2 pathway antagonist. In some embodiments, the anti-cancer agent and the NRF2 pathway antagonist are co-administered. In other embodiments, the anti-cancer agent and the NRF2 pathway antagonist are sequentially administered. In some embodiments, the anti-cancer agent is selected from the group consisting of an anti-angiogenic agent, a chemotherapeutic agent, a growth inhibitory agent, a cytotoxic agent, and an immunotherapy. In some embodiments, the anti-angiogenic agent is a VEGF antagonist. In some embodiments, the NRF2 pathway antagonist is selected from the group consisting of a CREB antagonist, a CREB Binding Protein (CBP) antagonist, a Maf antagonist, an activating transcription factor 4 (ATF4) antagonist, a protein kinase C (PKC) antagonist, a Jun antagonist, a glucocorticoid receptor antagonist, a UbcM2 antagonist, a HACE1 antagonist, a c-Myc agonist, a SUMO agonist, a KEAP1 agonist, a CUL3 agonist, or a retinoic acid receptor α (RARα) agonist.

In another aspect, the invention features a method of treating a subject having a cancer, the method comprising administering to the subject a therapeutically effective amount of a NRF2 pathway antagonist, wherein the expression level of at least one (e.g., 1, 2, 3, 4, 5, 6, 7, 8, 9, 10, 11, 12, 13, 14, 15, 16, 17, 18, 19, 20, 21, 22, 23, 24, 25, 26, or 27) of the following genes AKR1B10, AKR1C2, SRXN1, OSGIN1, FECH, GCLM, TRIM16, ME1, KYNU, CABYR, SLC7A11, TRIM16L, AKR1C4, CYP4F11, RSPO3, ABCC2, AKR1B15, NR0B1, UGDH, TXNRD1, GSR, AKR1C3, TALDO1, PGD, TXN, NQO1, and FTL in a sample obtained from the subject has been determined to be increased relative to a reference expression level of the at least one gene. In other embodiments, the expression level of at least two (e.g., 2, 3, 4, 5, 6, 7, 8, 9, 10, 11, 12, 13, 14, 15, 16, 17, 18, 19, 20, 21, 22, 23, 24, 25, 26, or 27) genes selected from the group consisting of AKR1B10, AKR1C2, SRXN1, OSGIN1, FECH, GCLM, TRIM16, ME1, KYNU, CABYR, SLC7A11, TRIM16L, AKR1C4, CYP4F11, RSPO3, ABCC2, AKR1B15, NR0B1, UGDH, TXNRD1, GSR, AKR1C3, TALDO1, PGD, TXN, NQO1, and FTL in a sample obtained from the subject is determined. In other embodiments, the expression level of at least three (e.g., 3, 4, 5, 6, 7, 8, 9, 10, 11, 12, 13, 14, 15, 16, 17, 18, 19, 20, 21, 22, 23, 24, 25, 26, or 27) genes selected from the group consisting of AKR1B10, AKR1C2, SRXN1, OSGIN1, FECH, GCLM, TRIM16, ME1, KYNU, CABYR, SLC7A11, TRIM16L, AKR1C4, CYP4F11, RSPO3, ABCC2, AKR1B15, NR0B1, UGDH, TXNRD1, GSR, AKR1C3, TALDO1, PGD, TXN, NQO1, and FTL in a sample obtained from the subject is determined. In other embodiments, the expression level of at least four (e.g., 4, 5, 6, 7, 8, 9, 10, 11, 12, 13, 14, 15, 16, 17, 18, 19, 20, 21, 22, 23, 24, 25, 26, or 27) genes selected from the group consisting of AKR1B10, AKR1C2, SRXN1, OSGIN1, FECH, GCLM, TRIM16, ME1, KYNU, CABYR, SLC7A11, TRIM16L, AKR1C4, CYP4F11, RSPO3, ABCC2, AKR1B15, NR0B1, UGDH, TXNRD1, GSR, AKR1C3, TALDO1, PGD, TXN, NQO1, and FTL in a sample obtained from the subject is determined. In other embodiments, the expression level of AKR1B10, AKR1C2, SRXN1, OSGIN1, FECH, GCLM, TRIM16, ME1, KYNU, CABYR, SLC7A11, TRIM16L, AKR1C4, CYP4F11, RSPO3, ABCC2, AKR1B15, NR0B1, UGDH, TXNRD1, GSR, AKR1C3, TALDO1, PGD, TXN, NQO1, and FTL in a sample obtained from the subject is determined.

In some embodiments, the expression level of one or more (e.g., 1, 2, 3, 4, 5, 6, 7, 8, 9, 10, 11, 12, 13, 14, 15, 16, 17, 18, 19, 20, or 21) of AKR1B10, AKR1C2, SRXN1, OSGIN1, FECH, GCLM, TRIM16, KYNU, CABYR, SLC7A11, TRIM16L, AKR1C4, NR0B1, UGDH, TXNRD1, GSR, AKR1C3, TALDO1, PGD, TXN, or NQO1 is determined. In other embodiments, the expression level of one or more (e.g., 1, 2, 3, 4, 5, 6, 7, 8, 9, 10, 11, or 12) of AKR1B10, AKR1C2, ME1, KYNU, CABYR, TRIM16L, AKR1C4, CYP4F11, RSPO3, AKR1B15, NR0B1, and AKR1C3 is determined.

In some embodiments, (a) the expression level of at least two genes in the sample is an average of the at least two genes of the sample; (b) the reference expression level of the at least two genes is an average of the at least two genes of the reference; and (c) the average of the at least two genes of the sample is compared to the average of the at least two genes of the reference. In some embodiments, the reference expression level is the mean level of expression of the at least one gene in a population of subjects. In some embodiments, the population of subjects is a population of subjects sharing a common ethnicity. In some embodiments, the reference expression level is the mean level of expression of the at least one gene in a population of subjects having cancer.

In some embodiments, the lung cancer is a non-small cell lung cancer (NSCLC), e.g., squamous NSCLC.

In some embodiments, the expression level is an mRNA expression level. In some embodiments, the mRNA expression level is determined by PCR, RT-PCR, RNA-seq, gene expression profiling, serial analysis of gene expression, or microarray analysis. In some embodiments, the mRNA expression level is determined by RNA-seq.

In some embodiments, the method further comprises determining a DNA sequence of the NRF2 (e.g., by PCR, exome-seq, microarray analysis, or whole genome sequencing).

In some embodiments, the expression level is a protein expression level. In some embodiments, the protein expression is determined by western blot, immunohistochemistry, or mass spectrometry.

In another aspect, the invention features a method of treating a subject having a cancer, the method comprising: (a) determining the mRNA expression level of NRF2 comprising a deletion of all or a portion of its exon 2 in a sample obtained from the subject, wherein the presence of NRF2 mRNA comprising a deletion of all or a portion of its exon 2 identifies the subject as having a cancer; and (b) administering to the subject a therapeutically effective amount of a NRF2 pathway antagonist.

In some embodiments, the mRNA expression is determined by PCR, RT-PCR, RNA-seq, gene expression profiling, serial analysis of gene expression, or microarray analysis. In some embodiments, the mRNA expression is determined by RNA-seq. In some embodiments, the method further comprises determining a DNA sequence of the NRF2 (e.g., by PCR, exome-seq, microarray analysis, or whole genome sequencing).

In another aspect, the invention features a method of treating a subject having a cancer, the method comprising: (a) determining a DNA sequence of NRF2 comprising a deletion of all or a portion of its exon 2 in a sample obtained from the subject, wherein the presence of NRF2 DNA comprising a deletion of all or a portion of its exon 2 identifies the subject as having a cancer; and (b) administering to the subject a therapeutically effective amount of a NRF2 pathway antagonist. In some embodiments, the DNA sequence is determined by PCR, exome-seq, microarray analysis, or whole genome sequencing. In some embodiments, the NRF2 (e.g., mRNA or DNA) further comprises a deletion in all or a portion of its exon 3.

In another aspect, the invention features a method of treating a subject having a cancer, the method comprising: (a) determining the protein expression level of NRF2 comprising a deletion of all or a portion of its Neh2 in a sample obtained from the subject, wherein the presence of NRF2 protein comprising a deletion of all or a portion of its Neh2 identifies the subject as having a cancer; and (b) administering to the subject a therapeutically effective amount of a NRF2 pathway antagonist.

In some embodiments, the NRF2 protein further comprises a deletion of all or a portion of its Neh4 domain. In some embodiments, the protein expression is determined by western blot, immunohistochemistry, or mass spectrometry. In some embodiments, the method further comprises determining a DNA sequence of the NRF2 (e.g., by PCR, exome-seq, microarray analysis, or whole genome sequencing).

In some embodiments, the method comprises administering to the subject a therapeutically effective amount of an anti-cancer agent. In some embodiments, the anti-cancer agent and the NRF2 pathway antagonist are co-administered. In other embodiments, the anti-cancer agent and the NRF2 pathway antagonist are sequentially administered. In some embodiments, the anti-cancer agent is selected from the group consisting of an anti-angiogenic agent, a chemotherapeutic agent, a growth inhibitory agent, a cytotoxic agent, and an immunotherapy. In some embodiments, the anti-angiogenic agent is a VEGF antagonist. In some embodiments, the NRF2 pathway antagonist is selected from the group consisting of a CREB antagonist, a CREB Binding Protein (CBP) antagonist, a Maf antagonist, an activating transcription factor 4 (ATF4) antagonist, a protein kinase C (PKC) antagonist, a Jun antagonist, a glucocorticoid receptor antagonist, a UbcM2 antagonist, a HACE1 antagonist, a c-Myc agonist, a SUMO agonist, a KEAP1 agonist, a CUL3 agonist, or a retinoic acid receptor α (RARα) agonist.

In some embodiments, the sample obtained from the subject is a tumor sample, e.g., from a biopsy sample. In some embodiments, the sample is obtained from a previously untreated subject. In some embodiments, the subject has a lung cancer (e.g., non-small cell lung cancer (NSCLC), e.g., squamous NSCLC) or a head and neck cancer (e.g., squamous head and neck cancer).

BRIEF DESCRIPTION OF THE DRAWINGS

FIG. 1D is an image of the crystal structure of the KEAP1/NRF2 peptide complex.

FIG. 12A is a graph showing the sequencing results (SEQ ID NO: 70) of the PCR products from JHH-6 and KMS-27 cells, indicating the deletion of exon 2 in NRF2.

FIG. 12B shows the nucleic acid (SEQ ID NO: 71) and amino acid (SEQ ID NO: 72) sequences for Δe2 NRF2.

FIG. 12C shows the nucleic acid (SEQ ID NO: 73) and amino acid (SEQ ID NO: 74) sequences for wild-type NRF2. The exon 2 sequence is shaded.

FIG. 20 is a series of bar graphs showing the effect of transfection reagents on relative NRF2 expression by HUH-1, JHH-6, and HuCCT1 cells. Cells were grown in 6-well dishes and transfected with siRNA targeting NRF2 exon 5 of NRF2. Total RNA was isolated after 48 hours, and NRF2 expression was measured using Taqman probes targeting exon 5.

FIG. 28B-1 is a set of graphs showing the copy number analyses of chromosome 2 showing two tumor samples with NRF2 exon 2 focal deletions. Arrows point to NRF2 exon 2. The log-ratio of target regions are shown in black and control regions are shown in gray.

FIG. 28B-2 is a set of graphs showing the copy number analyses of chromosome 2 showing two tumor samples with NRF2 exon 2+3 focal deletions. Arrows point to NRF2 exon 2 and exon 3. The log-ratio of target regions are shown in black and control regions are shown in gray.

FIG. 34 is a series of junction read sequences showing the structure of the deletions in JHH-6 cells, KMS-26 cells, and primary tumor, identified by WGS. The DNA sequences of the 3' end, 5' end, and junction read of JHH-6 cells are provided by SEQ ID NOs: 61-63, respectively. The DNA sequences of the 3' end, 5' end, and junction read of KMS-27 cells are provided by SEQ ID NOs: 64-66, respectively. The DNA sequences of the 3' end, 5' end, and junction read of primary tumor cells are provided by SEQ ID NOs: 67-69, respectively.

DETAILED DESCRIPTION OF EMBODIMENTS OF THE INVENTION

I. Introduction

Figure 1A:
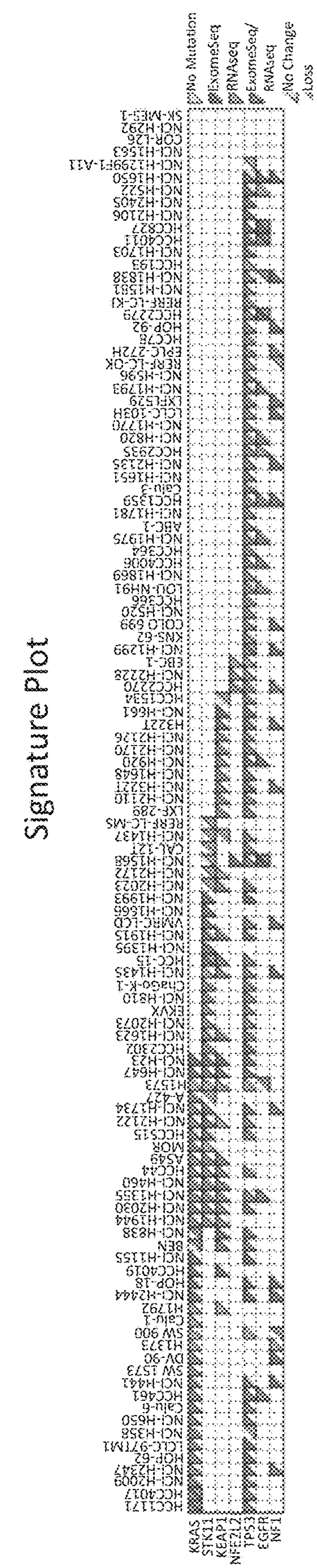
FIG. 1A is a plot showing 96 lung cancer cell lines subjected to RNA-seq, exome-seq, and SNP array analysis. Alterations in KRAS, TP53, KEAP1, EGFR, STK11, NFE2L2, and NF1 are shown.

The present invention provides diagnostic and accompanying therapeutic methods for cancer, such as lung cancer (e.g., NSCLC) or head and neck squamous cancer (e.g., HNSC). The invention is based, at least in part, on the discovery that splice variants in NRF2 that remove exon 2 or exons 2+3 result in an unexpected mechanism for conferring NRF2 activation in cancers. The NRF2 splice variants result in NRF2 activation by a mutually exclusive mechanism from mutations in KEAP1 or NRF2, yet result in a similar NRF2 target gene expression profile. In cell lines with microdeletions that result in these NRF2 splice variants, there is a loss of NRF2-KEAP1 interaction, increased NRF2 stabilization, induction of a NRF2 transcriptional response, and NRF2 pathway dependency. This occurs in 3-6% of squamous NSCLC and 1-2% of HNSC and results in a similar activation of NRF2 target genes and dependency on the pathway as KEAP1 mutations.

This discovery is useful for diagnosing a subject suffering from cancer (e.g., by detecting a NRF2 splice variant or by detecting a gene or protein expression profile consistent with the presence of a NRF2 splice variant) and for treating a subject according to such a diagnosis (e.g., by administering a therapeutically effective amount of a NRF2 pathway antagonist, e.g., a cAMP Responsive Element Binding Protein (CREB) Binding Protein (CBP) inhibitor).

II. Definitions

The terms “diagnose,” “diagnosing,” or “diagnosis” are used herein to refer to the identification or classification of a molecular or pathological state, disease or condition (e.g., cancer). For example, “diagnosis” may refer to identification of a particular type of cancer. “Diagnosis” may also refer to the classification of a particular subtype of cancer, e.g., by histopathological criteria, or by molecular features (e.g., a subtype characterized by expression of one or a combination of biomarkers (e.g., particular genes or proteins encoded by said genes)).

The terms “cancer” and “cancerous” refer to or describe the physiological condition in mammals that is typically characterized by unregulated cell growth. Included in this definition are benign and malignant cancers as well as dormant tumors or micrometastatses. Examples of cancer include, but are not limited to, carcinoma, lymphoma, blastoma, glioblastoma, sarcoma, and leukemia. Cancers may include, for example, breast cancer, squamous cell cancer, lung cancer (including small-cell lung cancer, non-small cell lung cancer (NSCLC), adenocarcinoma of the lung, and squamous carcinoma of the lung (e.g., squamous NSCLC)), various types of head and neck cancer (e.g., HNSC), cancer of the peritoneum, hepatocellular cancer, gastric or stomach cancer (including gastrointestinal cancer), pancreatic cancer, ovarian cancer, cervical cancer, liver cancer, bladder cancer, hepatoma, colon cancer, colorectal cancer, endometrial or uterine carcinoma, salivary gland carcinoma, kidney or renal cancer, liver cancer, prostate cancer, vulval cancer, thyroid cancer, and hepatic carcinoma, as well as B-cell lymphoma (including low grade/follicular non-Hodgkin’s lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, and Waldenstrom's Macroglobulinemia), chronic lymphocytic leukemia (CLL), acute lymphoblastic leukemia (ALL), hairy cell leukemia, chronic myeloblastic leukemia, and post-transplant lymphoproliferative disorder (PTLD), as well as abnormal vascular proliferation associated with phakomatoses, edema (such as that associated with brain tumors), and Meigs' syndrome.

A "patient" or "subject" herein refers to any single animal (including, e.g., a mammal, such as a dog, a cat, a horse, a rabbit, a zoo animal, a cow, a pig, a sheep, a non-human primate, and a human), such as a human, eligible for treatment who is experiencing or has experienced one or more signs, symptoms, or other indicators of a disease or disorder, such as a cancer. Intended to be included as a patient are any patients involved in clinical research trials not showing any clinical sign of disease, patients involved in epidemiological studies, or patients once used as controls. The patient may have been previously treated with a NRF2 pathway antagonist or another drug, or not so treated. The patient may be naive to an additional drug(s) being used when the treatment herein is started, i.e., the patient may not have been previously treated with, for example, a therapy other than a NRF2 pathway antagonist (e.g., a VEGF antagonist or a PD-1 axis binding antagonist) at "baseline" (i.e., at a set point in time before the administration of a first dose of a NRF2 pathway antagonist in the treatment method herein, such as the day of screening the subject before treatment is commenced). Such "naive" patients or subjects are generally considered to be candidates for treatment with such additional drug(s).

The terms "level of expression" or "expression level" in general are used interchangeably and generally refer to the amount of a biomarker in a biological sample. "Expression" generally refers to the process by which information (e.g., gene-encoded and/or epigenetic information) is converted into the structures present and operating in the cell. Therefore, as used herein, "expression" may refer to transcription into a polynucleotide, translation into a polypeptide, or even polynucleotide and/or polypeptide modifications (e.g., post-translational modification of a polypeptide). Fragments of the transcribed polynucleotide, the translated polypeptide, or polynucleotide and/or polypeptide modifications (e.g., post-translational modification of a polypeptide) shall also be regarded as expressed whether they originate from a transcript generated by alternative splicing or a degraded transcript, or from a post-translational processing of the polypeptide, e.g., by proteolysis. "Expressed genes" include those that are transcribed into a polynucleotide as mRNA and then translated into a polypeptide, and also those that are transcribed into RNA but not translated into a polypeptide (for example, transfer and ribosomal RNAs).

The terms "biomarker" and "marker" are used interchangeably herein to refer to a DNA, RNA, protein, carbohydrate, or glycolipid-based molecular marker, the expression or presence of which in a subjects or patients sample can be detected by standard methods (or methods disclosed herein). Such biomarkers include, but are not limited to, the mRNA sequences set forth in Table 1 and encoded proteins thereof. Expression of such a biomarker may be determined to be higher or lower in a sample obtained from a patient sensitive or responsive to a NRF2 pathway antagonist than a reference level (including, e.g., the average (e.g., mean or median) expression level of the biomarker in a sample from a group/population of patients, e.g., patients having cancer, and being tested for responsiveness to a NRF2 pathway antagonist; the median expression level of the biomarker in a sample from a group/population of patients, e.g., patients having cancer, and identified as not responding to NRF2 pathway antagonists; the level in a sample previously obtained from the individual at a prior time; or the level in a sample from a patient who received prior treatment with a NRF2 pathway antagonist in a primary tumor setting, and who now may be experiencing metastasis). Individuals having an expression level that is greater than or less than the reference expression level of at least one gene, such as those set forth in Table 1 can be identified as subjects/patients likely to respond to treatment with a NRF2 pathway antagonist. For example, such subjects/patients who exhibit gene expression levels at the most extreme 50%, 45%, 40%, 35%, 30%, 25%, 20%, 15%, 10%, or 5% relative to (i.e., higher or lower than) the reference level (such as the mean level), can be identified as subjects/patients (e.g., patients having cancer) likely to respond to treatment with a NRF2 pathway antagonist.

TABLE 1

| SEQ ID NO | Biomarker |
|---|---|
| 1 | ABCC2 |
| 2 | AKR1B10 |
| 3 | AKR1B15 |
| 4 | AKR1C2 |
| 5 | AKR1C3 |
| 6 | AKR1C4 |
| 7 | CABYR |
| 8 | CYP4F11 |
| 9 | FECH |
| 10 | FTL |
| 11 | GCLM |
| 12 | GSR |
| 13 | KYNU |
| 14 | ME1 |
| 15 | NRF2/NFE2L2 |
| 16 | NQO1 |
| 17 | NR0B1 |
| 18 | OSGIN1 |
| 19 | PGD |
| 20 | RSPO3 |
| 21 | SLC7A11 |
| 22 | SRXN1 |
| 23 | TALDO1 |
| 24 | TRIM16 |
| 25 | TRIM16L |
| 26 | TXN |
| 27 | TXNRD1 |
| 28 | UGDH |

The term "ABCC2" as used herein, refers to any native ABCC2 (ATP-Binding Cassette Sub-Family C, Member 2) from any vertebrate source, including mammals such as primates (e.g., humans) and rodents (e.g., mice and rats), unless otherwise indicated. The term encompasses "full-length," unprocessed ABCC2 as well as any form of ABCC2 that results from processing in the cell. The term also encompasses naturally occurring variants of ABCC2, e.g., splice variants or allelic variants. The nucleic acid sequence of an exemplary human ABCC2 is set forth in SEQ ID NO: 1. The amino acid sequence of an exemplary protein encoded by human ABCC2 is shown in SEQ ID NO: 33.

The term "AKR1 B10" as used herein, refers to any native AKR1 B10 (Aldo-Keto Reductase Family 1, Member B10) from any vertebrate source, including mammals such as primates (e.g., humans) and rodents (e.g., mice and rats), unless otherwise indicated. The term encompasses "full-length," unprocessed AKR1B10 as well as any form of AKR1B10 that results from processing in the cell. The term also encompasses naturally occurring variants of AKR1B10, e.g., splice variants or allelic variants. The nucleic acid sequence of an exemplary human AKR1 B10 is set forth in SEQ ID NO: 2. The amino acid sequence of an exemplary protein encoded by human AKR1 B10 is shown in SEQ ID NO: 34.

The term "AKR1 B15" as used herein, refers to any native AKR1 B15 (Aldo-Keto Reductase Family 1, Member B15) from any vertebrate source, including mammals such as primates (e.g., humans) and rodents (e.g., mice and rats), unless otherwise indicated. The term encompasses "full-length," unprocessed AKR1B15 as well as any form of AKR1B15 that results from processing in the cell. The term also encompasses naturally occurring variants of AKR1B15, e.g., splice variants or allelic variants. The nucleic acid sequence of an exemplary human AKR1 B15 is set forth in SEQ ID NO: 3. The amino acid sequence of an exemplary protein encoded by human AKR1 B15 is shown in SEQ ID NO: 35.

The term "AKR1C2" as used herein, refers to any native AKR1C2 (Aldo-Keto Reductase Family 1, Member C2) from any vertebrate source, including mammals such as primates (e.g., humans) and rodents (e.g., mice and rats), unless otherwise indicated. The term encompasses "full-length," unprocessed AKR1C2 as well as any form of AKR1C2 that results from processing in the cell. The term also encompasses naturally occurring variants of AKR1C2, e.g., splice variants or allelic variants. The nucleic acid sequence of an exemplary human AKR1C2 is set forth in SEQ ID NO: 4. The amino acid sequence of an exemplary protein encoded by human AKR1C2 is shown in SEQ ID NO: 36.

The term "AKR1C3" as used herein, refers to any native AKR1C3 (Aldo-Keto Reductase Family 1, Member C3) from any vertebrate source, including mammals such as primates (e.g., humans) and rodents (e.g., mice and rats), unless otherwise indicated. The term encompasses "full-length," unprocessed AKR1C3 as well as any form of AKR1C3 that results from processing in the cell. The term also encompasses naturally occurring variants of AKR1C3, e.g., splice variants or allelic variants. The nucleic acid sequence of an exemplary human AKR1C3 is set forth in SEQ ID NO: 5. The amino acid sequence of an exemplary protein encoded by human AKR1C3 is shown in SEQ ID NO: 37.

The term "AKR1C4" as used herein, refers to any native AKR1C4 (Aldo-Keto Reductase Family 1, Member C4) from any vertebrate source, including mammals such as primates (e.g., humans) and rodents (e.g., mice and rats), unless otherwise indicated. The term encompasses "full-length," unprocessed AKR1C4 as well as any form of AKR1C4 that results from processing in the cell. The term also encompasses naturally occurring variants of AKR1C4, e.g., splice variants or allelic variants. The nucleic acid sequence of an exemplary human AKR1C4 is set forth in SEQ ID NO: 6. The amino acid sequence of an exemplary protein encoded by human AKR1C4 is shown in SEQ ID NO: 38.

The term "CABYR" as used herein, refers to any native CABYR (Calcium Binding Tyrosine-(Y)-Phosphorylation Regulated) from any vertebrate source, including mammals such as primates (e.g., humans) and rodents (e.g., mice and rats), unless otherwise indicated. The term encompasses "full-length," unprocessed CABYR as well as any form of CABYR that results from processing in the cell. The term also encompasses naturally occurring variants of CABYR, e.g., splice variants or allelic variants. The nucleic acid sequence of an exemplary human CABYR is set forth in SEQ ID NO: 7. The amino acid sequence of an exemplary protein encoded by human CABYR is shown in SEQ ID NO: 39.

The term "CYP4F11" as used herein, refers to any native CYP4F11 (Cytochrome P450, Family 4, Subfamily F, Polypeptide 11) from any vertebrate source, including mammals such as primates (e.g., humans) and rodents (e.g., mice and rats), unless otherwise indicated. The term encompasses "full-length," unprocessed CYP4F11 as well as any form of CYP4F11 that results from processing in the cell. The term also encompasses naturally occurring variants of CYP4F11, e.g., splice variants or allelic variants. The nucleic acid sequence of an exemplary human CYP4F11 is set forth in SEQ ID NO: 8. The amino acid sequence of an exemplary protein encoded by human CYP4F11 is shown in SEQ ID NO: 40.

The term "FECH" as used herein, refers to any native FECH (Ferrochelatase) from any vertebrate source, including mammals such as primates (e.g., humans) and rodents (e.g., mice and rats), unless otherwise indicated. The term encompasses "full-length," unprocessed FECH as well as any form of FECH that results from processing in the cell. The term also encompasses naturally occurring variants of FECH, e.g., splice variants or allelic variants. The nucleic acid sequence of an exemplary human FECH is set forth in SEQ ID NO: 9. The amino acid sequence of an exemplary protein encoded by human FECH is shown in SEQ ID NO: 41.

The term "FTL" as used herein, refers to any native FTL (Ferritin, Light Polypeptide) from any vertebrate source, including mammals such as primates (e.g., humans) and rodents (e.g., mice and rats), unless otherwise indicated. The term encompasses "full-length," unprocessed FTL as well as any form of FTL that results from processing in the cell. The term also encompasses naturally occurring variants of FTL, e.g., splice variants or allelic variants. The nucleic acid sequence of an exemplary human FTL is set forth in SEQ ID NO: 10. The amino acid sequence of an exemplary protein encoded by human FTL is shown in SEQ ID NO: 42.

The term "GCLM" as used herein, refers to any native GCLM (Glutamate-Cysteine Ligase, Modifier Subunit) from any vertebrate source, including mammals such as primates (e.g., humans) and rodents (e.g., mice and rats), unless otherwise indicated. The term encompasses "full-length," unprocessed GCLM as well as any form of GCLM that results from processing in the cell. The term also encompasses naturally occurring variants of GCLM, e.g., splice variants or allelic variants. The nucleic acid sequence of an exemplary human GCLM is set forth in SEQ ID NO: 11. The amino acid sequence of an exemplary protein encoded by human GCLM is shown in SEQ ID NO: 43.

The term "GSR" as used herein, refers to any native GSR (Glutathione Reductase) from any vertebrate source, including mammals such as primates (e.g., humans) and rodents (e.g., mice and rats), unless otherwise indicated. The term encompasses "full-length," unprocessed GSR as well as any form of GSR that results from processing in the cell. The term also encompasses naturally occurring variants of GSR, e.g., splice variants or allelic variants. The nucleic acid sequence of an exemplary human GSR is set forth in SEQ ID NO: 12. The amino acid sequence of an exemplary protein encoded by human GSR is shown in SEQ ID NO: 44.

The term "KYNU" as used herein, refers to any native KYNU (Kynureninase) from any vertebrate source, including mammals such as primates (e.g., humans) and rodents (e.g., mice and rats), unless otherwise indicated. The term encompasses "full-length," unprocessed KYNU as well as any form of KYNU that results from processing in the cell. The term also encompasses naturally occurring variants of KYNU, e.g., splice variants or allelic variants. The nucleic acid sequence of an exemplary human KYNU is set forth in SEQ ID NO: 13. The amino acid sequence of an exemplary protein encoded by human KYNU is shown in SEQ ID NO: 45.

The term "ME1" as used herein, refers to any native ME1 (Malic Enzyme 1, NADP(+)-Dependent, Cytosolic) from any vertebrate source, including mammals such as primates (e.g., humans) and rodents (e.g., mice and rats), unless otherwise indicated. The term encompasses "full-length," unprocessed ME1 as well as any form of ME1 that results from processing in the cell. The term also encompasses naturally occurring variants of ME1, e.g., splice variants or allelic variants. The nucleic acid sequence of an exemplary human ME1 is set forth in SEQ ID NO: 14. The amino acid sequence of an exemplary protein encoded by human ME1 is shown in SEQ ID NO: 46.

The term "NFE2L2" or "NRF2" as used herein, refers to any native NFE2L2 or NRF2 (Nuclear Factor, Erythroid 2-Like 2) from any vertebrate source, including mammals such as primates (e.g., humans) and rodents (e.g., mice and rats), unless otherwise indicated. The term encompasses "full-length," unprocessed NFE2L2 as well as any form of NFE2L2 that results from processing in the cell. The term also encompasses naturally occurring variants of NFE2L2, e.g., splice variants or allelic variants. The nucleic acid sequence of an exemplary human NFE2L2 is set forth in SEQ ID NO: 15. The amino acid sequence of an exemplary protein encoded by human NFE2L2 is shown in SEQ ID NO: 47.

The term "NQO1" as used herein, refers to any native NQO1 (NAD(P)H Dehydrogenase, Quinone 1) from any vertebrate source, including mammals such as primates (e.g., humans) and rodents (e.g., mice and rats), unless otherwise indicated. The term encompasses "full-length," unprocessed NQO1 as well as any form of NQO1 that results from processing in the cell. The term also encompasses naturally occurring variants of NQO1, e.g., splice variants or allelic variants. The nucleic acid sequence of an exemplary human NQO1 is set forth in SEQ ID NO: 16. The amino acid sequence of an exemplary protein encoded by human NQO1 is shown in SEQ ID NO: 48.

The term "NR0B1" as used herein, refers to any native NR0B1 (Nuclear Receptor Subfamily 0, Group B, Member 1) from any vertebrate source, including mammals such as primates (e.g., humans) and rodents (e.g., mice and rats), unless otherwise indicated. The term encompasses "full-length," unprocessed NR0B1 as well as any form of NR0B1 that results from processing in the cell. The term also encompasses naturally occurring variants of NR0B1, e.g., splice variants or allelic variants. The nucleic acid sequence of an exemplary human NR0B1 is set forth in SEQ ID NO: 17. The amino acid sequence of an exemplary protein encoded by human NR0B1 is shown in SEQ ID NO: 49.

The term "OSGIN1" as used herein, refers to any native OSGIN1 (Oxidative Stress Induced Growth Inhibitor 1) from any vertebrate source, including mammals such as primates (e.g., humans) and rodents (e.g., mice and rats), unless otherwise indicated. The term encompasses "full-length," unprocessed OSGIN1 as well as any form of OSGIN1 that results from processing in the cell. The term also encompasses naturally occurring variants of OSGIN1, e.g., splice variants or allelic variants. The nucleic acid sequence of an exemplary human OSGIN1 is set forth in SEQ ID NO: 18. The amino acid sequence of an exemplary protein encoded by human OSGIN1 is shown in SEQ ID NO: 50.

The term "PGD" as used herein, refers to any native PGD (Phosphogluconate Dehydrogenase) from any vertebrate source, including mammals such as primates (e.g., humans) and rodents (e.g., mice and rats), unless otherwise indicated. The term encompasses "full-length," unprocessed PGD as well as any form of PGD that results from processing in the cell. The term also encompasses naturally occurring variants of PGD, e.g., splice variants or allelic variants. The nucleic acid sequence of an exemplary human PGD is set forth in SEQ ID NO: 19. The amino acid sequence of an exemplary protein encoded by human PGD is shown in SEQ ID NO: 51.

The term "RSPO3" as used herein, refers to any native RSPO3 (R-Spondin 3) from any vertebrate source, including mammals such as primates (e.g., humans) and rodents (e.g., mice and rats), unless otherwise indicated. The term encompasses "full-length," unprocessed RSPO3 as well as any form of RSPO3 that results from processing in the cell. The term also encompasses naturally occurring variants of RSPO3, e.g., splice variants or allelic variants. The nucleic acid sequence of an exemplary human RSPO3 is set forth in SEQ ID NO: 20. The amino acid sequence of an exemplary protein encoded by human RSPO3 is shown in SEQ ID NO: 52.

The term "SLC7A11" as used herein, refers to any native SLC7A11 (Solute Carrier Family 7 (Anionic Amino Acid Transporter Light Chain, Xc-System), Member 11) from any vertebrate source, including mammals such as primates (e.g., humans) and rodents (e.g., mice and rats), unless otherwise indicated. The term encompasses "full-length," unprocessed SLC7A11 as well as any form of SLC7A11 that results from processing in the cell. The term also encompasses naturally occurring variants of SLC7A11, e.g., splice variants or allelic variants. The nucleic acid sequence of an exemplary human SLC7A11 is set forth in SEQ ID NO: 21. The amino acid sequence of an exemplary protein encoded by human SLC7A11 is shown in SEQ ID NO: 53.

The term "SRXN1" as used herein, refers to any native SRXN1 (Sulfiredoxin 1) from any vertebrate source, including mammals such as primates (e.g., humans) and rodents (e.g., mice and rats), unless otherwise indicated. The term encompasses "full-length," unprocessed SRXN1 as well as any form of SRXN1 that results from processing in the cell. The term also encompasses naturally occurring variants of SRXN1, e.g., splice variants or allelic variants. The nucleic acid sequence of an exemplary human SRXN1 is set forth in SEQ ID NO: 22. The amino acid sequence of an exemplary protein encoded by human SRXN1 is shown in SEQ ID NO: 54.

The term "TALDO1" as used herein, refers to any native TALDO1 (Transaldolase 1) from any vertebrate source, including mammals such as primates (e.g., humans) and rodents (e.g., mice and rats), unless otherwise indicated. The term encompasses "full-length," unprocessed TALDO1 as well as any form of TALDO1 that results from processing in the cell. The term also encompasses naturally occurring variants of TALDO1, e.g., splice variants or allelic variants. The nucleic acid sequence of an exemplary human TALDO1 is set forth in SEQ ID NO: 23. The amino acid sequence of an exemplary protein encoded by human TALDO1 is shown in SEQ ID NO: 55.

The term "TRIM16" as used herein, refers to any native TRIM16 (Tripartite Motif Containing 16) from any vertebrate source, including mammals such as primates (e.g., humans) and rodents (e.g., mice and rats), unless otherwise indicated. The term encompasses "full-length," unprocessed TRIM16 as well as any form of TRIM16 that results from processing in the cell. The term also encompasses naturally occurring variants of TRIM16, e.g., splice variants or allelic variants. The nucleic acid sequence of an exemplary human TRIM16 is set forth in SEQ ID NO: 24. The amino acid sequence of an exemplary protein encoded by human TRIM16 is shown in SEQ ID NO: 56.

The term "TRIM16L" as used herein, refers to any native TRIM16L (Tripartite Motif Containing 16-Like) from any vertebrate source, including mammals such as primates (e.g., humans) and rodents (e.g., mice and rats), unless otherwise indicated. The term encompasses "full-length," unprocessed TRIM16L as well as any form of TRIM16L that results from processing in the cell. The term also encompasses naturally occurring variants of TRIM16L, e.g., splice variants or allelic variants. The nucleic acid sequence of an exemplary human TRIM16L is set forth in SEQ ID NO: 25. The amino acid sequence of an exemplary protein encoded by human TRIM16L is shown in SEQ ID NO: 57.

The term "TXN" as used herein, refers to any native TXN (Thioredoxin) from any vertebrate source, including mammals such as primates (e.g., humans) and rodents (e.g., mice and rats), unless otherwise indicated. The term encompasses "full-length," unprocessed TXN as well as any form of TXN that results from processing in the cell. The term also encompasses naturally occurring variants of TXN, e.g., splice variants or allelic variants. The nucleic acid sequence of an exemplary human TXN is set forth in SEQ ID NO: 26. The amino acid sequence of an exemplary protein encoded by human TXN is shown in SEQ ID NO: 58.

The term "TXNRD1" as used herein, refers to any native TXNRD1 (Thioredoxin Reductase 1) from any vertebrate source, including mammals such as primates (e.g., humans) and rodents (e.g., mice and rats), unless otherwise indicated. The term encompasses "full-length," unprocessed TXNRD1 as well as any form of TXNRD1 that results from processing in the cell. The term also encompasses naturally occurring variants of TXNRD1, e.g., splice variants or allelic variants. The nucleic acid sequence of an exemplary human TXNRD1 is set forth in SEQ ID NO: 27. The amino acid sequence of an exemplary protein encoded by human TXNRD1 is shown in SEQ ID NO: 59.

The term "UGDH" as used herein, refers to any native UGDH (Uridine Diphospho (UDP)-Glucose 6-Dehydrogenase) from any vertebrate source, including mammals such as primates (e.g., humans) and rodents (e.g., mice and rats), unless otherwise indicated. The term encompasses "full-length," unprocessed UGDH as well as any form of UGDH that results from processing in the cell. The term also encompasses naturally occurring variants of UGDH, e.g., splice variants or allelic variants. The nucleic acid sequence of an exemplary human UGDH is set forth in SEQ ID NO: 28. The amino acid sequence of an exemplary protein encoded by human UGDH is shown in SEQ ID NO: 60.

The terms "sample" and "biological sample" are used interchangeably to refer to any biological sample obtained from an individual including body fluids, body tissue (e.g., tumor tissue), cells, or other sources. Body fluids are, e.g., lymph, sera, whole fresh blood, peripheral blood mononuclear cells, frozen whole blood, plasma (including fresh or frozen), urine, saliva, semen, synovial fluid and spinal fluid. Samples also include breast tissue, renal tissue, colonic tissue, brain tissue, muscle tissue, synovial tissue, skin, hair follicle, bone marrow, and tumor tissue. Methods for obtaining tissue biopsies and body fluids from mammals are well known in the art.

By "tissue sample" or "cell sample" is meant a collection of similar cells obtained from a tissue of a subject or individual. The source of the tissue or cell sample may be solid tissue as from a fresh, frozen and/or preserved organ, tissue sample, biopsy, and/or aspirate; blood or any blood constituents such as plasma; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

A "reference sample," "reference cell," "reference tissue," "control sample," "control cell," or "control tissue," as used herein, refers to a sample, cell, tissue, standard, or level that is used for comparison purposes. In one embodiment, a reference sample, reference cell, reference tissue, control sample, control cell, or control tissue is obtained from a healthy and/or non-diseased part of the body (e.g., tissue or cells) of the same subject or individual. For example, healthy and/or non-diseased cells or tissue adjacent to the diseased cells or tissue (e.g., cells or tissue adjacent to a tumor). In another embodiment, a reference sample is obtained from an untreated tissue and/or cell of the body of the same subject or individual. In yet another embodiment, a reference sample, reference cell, reference tissue, control sample, control cell, or control tissue is obtained from a healthy and/or non-diseased part of the body (e.g., tissues or cells) of an individual who is not the subject or individual. In even another embodiment, a reference sample, reference cell, reference tissue, control sample, control cell, or control tissue is obtained from an untreated tissue and/or cell of the body of an individual who is not the subject or individual. In another embodiment, a reference sample, reference cell, reference tissue, control sample, control cell, or control tissue is obtained from one or more cell lines (e.g., one or more normal cell lines).

The phrase "identifying a patient" or "identifies a patient" as used herein, refers to using the information or data generated relating to the level of at least one of the genes set forth in Table 1, the presence of NRF2 mRNA having deletion of all or a portion of its exon 2 or exon 2+3, or the presence of NRF2 protein having a deletion of all or a portion of its Neh2 or Neh2+4 in a sample of a patient to identify or select the patient as more likely to benefit or less likely to benefit from a therapy comprising a NRF2 pathway antagonist. The information or data used or generated may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional. In some embodiments, the information or data includes a comparison of the level of at least one of the genes set forth in Table 1 to a reference level. In some embodiments, the information or data includes an indication that at least one of the genes set forth in Table 1 is present or absent in the sample. In some embodiments, the information or data includes an indication that the NRF2 mRNA has a deletion of all or a portion of its exon 2 or exon 2+3. In some embodiments, the information or data includes an indication that the NRF2 protein has a deletion of all or a portion of its Neh2 or Neh2+4. In some embodiments, the information or data includes an indication that the patient is more likely or less likely to respond to a therapy comprising a NRF2 pathway antagonist).

The term "primer" refers to a single-stranded polynucleotide that is capable of hybridizing to a nucleic acid and allowing polymerization of a complementary nucleic acid, generally by providing a free 3'-OH group.

As used herein, the term "treatment" (and variations thereof, such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

As used herein, "administering" is meant a method of giving a dosage of a compound (e.g., a NRF2 pathway antagonist) to a subject. The compositions utilized in the methods described herein can be administered, for example, intravitreally (e.g., by intravitreal injection), by eye drop, intramuscularly, intravenously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subcutaneously, subconjunctivally, intravesicularly, mucosally, intrapericardially, intraumbilically, intraocularly, intraorbitally, orally, topically, transdermally, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered and the severity of the condition, disease, or disorder being treated).

An "effective amount" of an agent, e.g., a pharmaceutical formulation, refers to an amount effective, at dosages and for periods of time necessary, to achieve the desired therapeutic or prophylactic result.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "anti-neoplastic" refers to a composition useful in treating cancer comprising at least one active therapeutic agent, e.g., "anti-cancer agent." Examples of therapeutic agents (anti-cancer agents) include, but are limited to, e.g., chemotherapeutic agents, growth inhibitory agents, cytotoxic agents, agents used in radiation therapy, anti-angiogenesis agents, apoptotic agents, anti-tubulin agents, and other-agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (TARCEVA™), platelet derived growth factor inhibitors (e.g., GLEEVEC™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, and the like. Combinations thereof are also included in the invention.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes, antibiotics, toxins such as small molecule toxins or enzymatically active toxins of bacterial, fungal, plant or animal origin, including fragments and/or variants thereof, and the various antitumor or anticancer agents disclosed below.

A “chemotherapeutic agent” is a chemical compound useful in the treatment of cancer. Examples of chemotherapeutic agents include is a chemical compound useful in the treatment of cancer. Examples of chemotherapeutic agents include alkylating agents, such as, for example, temozolomide (TMZ), the imidazotetrazine derivative of the alkylating agent dacarbazine. Additional examples of chemotherapeutics agents include, e.g., paclitaxel or topotecan or pegylated liposomal doxorubicin (PLD). Other examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin; bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethyl hydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside (“Ara-C”); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® docetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb.RTM.); inhibitors of PKC-alpha, Raf, H-Ras, EGFR (e.g., erlotinib (Tarceva.RTM.)) and VEGF that reduce cell proliferation and pharmaceutically acceptable salts, acids, or derivatives of any of the above.

The terms “Programmed Death Ligand 1” and “PD-L1” refer herein to a native sequence PD-L1 polypeptide, polypeptide variants, and fragments of a native sequence polypeptide and polypeptide variants. The PD-L1 polypeptide described herein may be that which is isolated from a variety of sources, such as from human tissue types or from another source, or prepared by recombinant or synthetic methods.

The term “PD-L1 axis binding antagonist” refers to a molecule that inhibits the interaction of a PD-L1 axis binding partner with one or more of its binding partners, so as to remove T-cell dysfunction resulting from signaling on the PD-1 signaling axis, with a result being restored or enhanced T-cell function. As used herein, a PD-L1 axis binding antagonist includes a PD-L1 binding antagonist and a PD-1 binding antagonist as well as molecules that interfere with the interaction between PD-L1 and PD-1 (e.g., a PD-L2-Fc fusion).

As used herein, a “PD-L1 binding antagonist” is a molecule that decreases, blocks, inhibits, abrogates or interferes with signal transduction resulting from the interaction of PD-L1 with either one or more of its binding partners, such as PD-1 and/or B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, PD-L1 binding antagonists include anti-PD-L1 antibodies and antigen-binding fragments thereof, immunoadhesins, fusion proteins, oligopeptides, small molecule antagonists, polynucleotide antagonists, and other molecules that decrease, block, inhibit, abrogate or interfere with signal transduction resulting from the interaction of PD-L1 with one or more of its binding partners, such as PD-1 and/or B7-1. In one embodiment, a PD-L1 binding antagonist reduces the negative signal mediated by or through cell surface proteins expressed on T lymphocytes, and other cells, mediated signaling through PD-L1 or PD-1 so as render a dysfunctional T-cell less dysfunctional. In some embodiments, a PD-L1 binding antagonist is an anti-PD-L1 antibody. In a specific aspect, an anti-PD-L1 antibody is YW243.55.570. In another specific aspect, an anti-PD-L1 antibody is MDX-1105. In still another specific aspect, an anti-PD-L1 antibody is atezolizumab (MPDL3280A). In still another specific aspect, an anti-PD-L1 antibody is MED14736 (druvalumab). In still another specific aspect, an anti-PD-L1 antibody is MSB0010718C (avelumab).

As used herein, a "PD-1 binding antagonist" is a molecule that decreases, blocks, inhibits, abrogates or interferes with signal transduction resulting from the interaction of PD-1 with one or more of its binding partners, such as PD-L1 and/or PD-L2. In some embodiments, the PD-1 binding antagonist is a molecule that inhibits the binding of PD-1 to its binding partners. In a specific aspect, the PD-1 binding antagonist inhibits the binding of PD-1 to PD-L1 and/or PD-L2. For example, PD-1 binding antagonists include anti-PD-1 antibodies and antigen-binding fragments thereof, immunoadhesins, fusion proteins, oligopeptides, small molecule antagonists, polynucleotide antagonists, and other molecules that decrease, block, inhibit, abrogate or interfere with signal transduction resulting from the interaction of PD-1 with PD-L1 and/or PD-L2. In one embodiment, a PD-1 binding antagonist reduces the negative signal mediated by or through cell surface proteins expressed on T lymphocytes, and other cells, mediated signaling through PD-1 or PD-L1 so as render a dysfunctional T-cell less dysfunctional. In some embodiments, the PD-1 binding antagonist is an anti-PD-1 antibody. In a specific aspect, a PD-1 binding antagonist is MDX-1106 (nivolumab). In another specific aspect, a PD-1 binding antagonist is MK-3475 (pembrolizumab). In another specific aspect, a PD-1 binding antagonist is CT-011 (pidilizumab). In another specific aspect, a PD-1 binding antagonist is MEDI-0680 (AMP-514). In another specific aspect, a PD-1 binding antagonist is PDR001. In another specific aspect, a PD-1 binding antagonist is REGN2810 described herein. In another specific aspect, a PD-1 binding antagonist is BGB-108 described herein. In another specific aspect, a PD-1 binding antagonist is AMP-224.

The term "vascular endothelial growth factor" or "VEGF" refers to vascular endothelial growth factor. The term "VEGF" encompasses homologues and isoforms thereof. The term "VEGF" also encompasses the known isoforms, e.g., splice isoforms, of VEGF, e.g., $VEGF_{111}$, $VEGF_{121}$, $VEGF_{145}$, $VEGF_{165}$, $VEGF_{189}$, and $VEGF_{206}$, together with the naturally-occurring allelic and processed forms thereof, including the 110-amino acid human vascular endothelial cell growth factor generated by plasmin cleavage of VEGF165 as described in Ferrara *Mol. Biol. Cell.* 21:687 (2010), Leung et al., *Science,* 246:1306 (1989), and Houck et al., *Mol. Endocrin.,* 5:1806 (1991). The term "VEGF" also refers to VEGFs from non-human species such as mouse, rat or primate. Sometimes the VEGF from a specific species are indicated by terms such as hVEGF for human VEGF, mVEGF for murine VEGF, and the like. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "$VEGF_{109}$," "VEGF (8-109)," "VEGF (1-109)" or "$VEGF_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF. The term "VEGF variant" as used herein refers to a VEGF polypeptide which includes one or more amino acid mutations in the native VEGF sequence. Optionally, the one or more amino acid mutations include amino acid substitution(s). For purposes of shorthand designation of VEGF variants described herein, it is noted that numbers refer to the amino acid residue position along the amino acid sequence of the putative native VEGF (provided in Leung et al., supra and Houck et al., supra).

The term "VEGF antagonist," as used herein, refers to a molecule capable of binding to VEGF, reducing VEGF expression levels, or neutralizing, blocking, inhibiting, abrogating, reducing, or interfering with VEGF biological activities, including, but not limited to, VEGF binding to one or more VEGF receptors, VEGF signaling, and VEGF-mediated angiogenesis and endothelial cell survival or proliferation. For example, a molecule capable of neutralizing, blocking, inhibiting, abrogating, reducing, or interfering with VEGF biological activities can exert its effects by binding to one or more VEGF receptor (VEGFR) (e.g., VEGFR1, VEGFR2, VEGFR3, membrane-bound VEGF receptor (mbVEGFR), or soluble VEGF receptor (sVEGFR)). Included as VEGF antagonists useful in the methods of the invention are polypeptides that specifically bind to VEGF, anti-VEGF antibodies and antigen-binding fragments thereof, receptor molecules and derivatives which bind specifically to VEGF thereby sequestering its binding to one or more receptors, fusions proteins (e.g., VEGF-Trap (Regeneron)), and $VEGF_{121}$-gelonin (Peregrine). VEGF antagonists also include antagonist variants of VEGF polypeptides, antisense nucleobase oligomers complementary to at least a fragment of a nucleic acid molecule encoding a VEGF polypeptide; small RNAs complementary to at least a fragment of a nucleic acid molecule encoding a VEGF polypeptide; ribozymes that target VEGF; peptibodies to VEGF; and VEGF aptamers. VEGF antagonists also include polypeptides that bind to VEGFR, anti-VEGFR antibodies, and antigen-binding fragments thereof, and derivatives which bind to VEGFR thereby blocking, inhibiting, abrogating, reducing, or interfering with VEGF biological activities (e.g., VEGF signaling), or fusions proteins. VEGF antagonists also include nonpeptide small molecules that bind to VEGF or VEGFR and are capable of blocking, inhibiting, abrogating, reducing, or interfering with VEGF biological activities. Thus, the term "VEGF activities" specifically includes VEGF-mediated biological activities of VEGF. In certain embodiments, the VEGF antagonist reduces or inhibits, by at least 10%, 20%, 30%, 40%, 50%, 60%, 70%, 80%, 90% or more, the expression level or biological activity of VEGF. In some embodiments, the VEGF inhibited by the VEGF-specific antagonist is VEGF (8-109), VEGF (1-109), or $VEGF_{165}$.

As used herein, VEGF antagonists can include, but are not limited to, anti-VEGFR2 antibodies and related molecules (e.g., ramucirumab, tanibirumab, aflibercept), anti-VEGFR1 antibodies and related molecules (e.g., icrucumab, aflibercept (VEGF Trap-Eye; EYLEA®), and ziv-aflibercept (VEGF Trap; ZALTRAP®)), bispecific VEGF antibodies (e.g., MP-0250, vanucizumab (VEGF-ANG2), and bispecific antibodies disclosed in US 2001/0236388), bispecific antibodies including combinations of two of anti-VEGF, anti-VEGFR1, and anti-VEGFR2 arms, anti-VEGF antibodies (e.g., bevacizumab, sevacizumab, and ranibizumab), and nonpeptide small molecule VEGF antagonists (e.g., pazopanib, axitinib, vandetanib, stivarga, cabozantinib, lenvatinib, nintedanib, orantinib, telatinib, dovitinig, cediranib, motesanib, sulfatinib, apatinib, foretinib, famitinib, and tivozanib).

The terms "anti-VEGF antibody," an "antibody that binds to VEGF," and "antibody that specifically binds VEGF" refer to an antibody that is capable of binding VEGF with sufficient affinity such that the antibody is useful as a diagnostic and/or therapeutic agent in targeting VEGF. In one embodiment, the extent of binding of an anti-VEGF antibody to an unrelated, non-VEGF protein is less than about 10% of the binding of the antibody to VEGF as measured, for example, by a radioimmunoassay (RIA). In certain embodiments, an antibody that binds to VEGF has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g., from $10^{-8}$ M to $10^{-13}$ M, e.g., from $10^{-9}$M to $10^{-13}$ M). In certain embodiments, an anti-VEGF antibody binds to an epitope of VEGF that is conserved among VEGF from different species.

In certain embodiments, the anti-VEGF antibody can be used as a therapeutic agent in targeting and interfering with diseases or conditions wherein the VEGF activity is involved. Also, the antibody may be subjected to other biological activity assays, e.g., in order to evaluate its effectiveness as a therapeutic. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). An anti-VEGF antibody will usually not bind to other VEGF homologues such as VEGF-B or VEGF-C, nor other growth factors such as PIGF, PDGF, or bFGF. In one embodiment, anti-VEGF antibody is a monoclonal antibody that binds to the same epitope as the monoclonal anti-VEGF antibody A4.6.1 produced by hybridoma ATCC HB 10709. In another embodiment, the anti-VEGF antibody is a recombinant humanized anti-VEGF monoclonal antibody generated according to Presta et al. (1997) *Cancer Res.* 57:4593-4599, including but not limited to the antibody known as bevacizumab (BV; AVASTIN®).

The anti-VEGF antibody "ranibizumab" also known as "LUCENTIS®" or "rhuFab V2" is a humanized, affinity-matured anti-human VEGF Fab fragment. Ranibizumab is produced by standard recombinant technology methods in *Escherichia coli* expression vector and bacterial fermentation. Ranibizumab is not glycosylated and has a molecular mass of 48,000 daltons. See WO 98/45331 and US 2003/0190317. Additional preferred antibodies include the G6 or B20 series antibodies (e.g., G6-31, B20-4.1), as described in PCT Application Publication Nos. WO 2005/012359 and WO 2005/044853, which are each incorporated herein by reference in their entirety. For additional preferred antibodies see U.S. Pat. Nos. 7,060,269, 6,582,959, 6,703,020; 6,054,297; WO98/45332; WO 96/30046; WO94/10202; EP 066686861; U.S. Patent Application Publication Nos. 2006009360, 20050186208, 20030206899, 20030190317, 20030203409, and 20050112126; and Popkov et al., *Journal of Immunological Methods* 288:149-164 (2004). Other preferred antibodies include those that bind to a functional epitope on human VEGF comprising of residues F17, M18, D19, Y21, Y25, Q89, 191, K101, E103, and C104 or, alternatively, comprising residues F17, Y21, Q22, Y25, D63, 183, and Q89. Additional anti-VEGF antibodies include anti-VEGF antibodies described in PCT Application Publication No. WO 2009/155724.

The term "co-administered" is used herein to refer to administration of two or more therapeutic agents, where at least part of the administration overlaps in time. Accordingly, co-administration includes a dosing regimen when the administration of one or more agent(s) continues after discontinuing the administration of one or more other agent(s).

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

III. Methods

A. Diagnostic Methods

Provided herein are methods for diagnosing cancer (e.g., a lung cancer (e.g., squamous NSCLC or non-squamous NSCLC) or a head and neck cancer (e.g., HNSC)) in a subject. Also provided herein are methods for identifying a subject having a cancer that is a NRF2-dependent cancer (e.g., lung cancer, e.g., squamous non-small cell lung cancer or non-squamous non-small cell lung cancer, or head and neck cancer). Any of the methods may be based on the expression level of a biomarker provided herein, for example, a splice variant of NRF2 (e.g., NRF2 mRNA or NRF2 protein), or an increased expression of one or more NRF2 target genes. Any of the methods may further include administering to the subject a NRF2 pathway antagonist. Any of the methods may further include administering an effective amount of a second therapeutic (e.g., one or more (e.g., 1, 2, 3, or 4 or more) additional NRF2 pathway antagonists or one or more (e.g., 1, 2, 3, or 4 or more) anti-cancer agents) to the subject.

The invention provides a method of diagnosing a cancer in a subject, the method comprising determining the expression level of at least one gene (e.g., 1, 2, 3, 4, 5, 6, 7, 8, 9, 10, 11, 12, 13, 14, 15, 16, 17, 18, 19, 20, 21, 22, 23, 24, 25, 26, or 27 genes) selected from the group consisting of AKR1B10, AKR1C2, SRXN1, OSGIN1, FECH, GCLM, TRIM16, ME1, KYNU, CABYR, SLC7A11, TRIM16L, AKR1C4, CYP4F11, RSPO3, ABCC2, AKR1B15, NR0B1, UGDH, TXNRD1, GSR, AKR1C3, TALDO1, PGD, TXN, NQO1, and FTL in a sample obtained from the subject; and comparing the expression level of the at least one gene to a reference expression level of the at least one gene, wherein an increase in the expression level of the at least one gene in the sample relative to the reference expression level of the at least one gene identifies a subject having a cancer.

The invention further provides a method of identifying a subject having a cancer that is a NRF2-dependent cancer, the method comprising determining the expression level of at least one gene (e.g., 1, 2, 3, 4, 5, 6, 7, 8, 9, 10, 11, 12, 13, 14, 15, 16, 17, 18, 19, 20, 21, 22, 23, 24, 25, 26, or 27 genes) selected from the group consisting of AKR1B10, AKR1C2, SRXN1, OSGIN1, FECH, GCLM, TRIM16, ME1, KYNU, CABYR, SLC7A11, TRIM16L, AKR1C4, CYP4F11, RSPO3, ABCC2, AKR1B15, NR0B1, UGDH, TXNRD1, GSR, AKR1C3, TALDO1, PGD, TXN, NQO1, and FTL in a sample obtained from the subject; comparing the expression level of the at least one gene to a reference expression level of the at least one gene; and determining if the subject's cancer is a NRF2-dependent cancer, wherein an increase in the expression level of the at least one gene in the sample relative to the reference expression level of the at least one gene identifies a subject having a NRF2-dependent cancer.

In any of the preceding methods, the expression level of one or more (e.g., 1, 2, 3, 4, 5, 6, 7, 8, 9, 10, 11, 12, 13, 14, 15, 16, 17, 18, 19, 20, or 21) of AKR1B10, AKR1C2, SRXN1, OSGIN1, FECH, GCLM, TRIM16, KYNU, CABYR, SLC7A11, TRIM16L, AKR1C4, NR0B1, UGDH, TXNRD1, GSR, AKR1C3, TALDO1, PGD, TXN, or NQO1 is determined.

In any of the preceding methods, the expression level of one or more (e.g., 1, 2, 3, 4, 5, 6, 7, 8, 9, 10, 11, or 12) newly identified NRF2 target genes is determined. Newly identified NRF2 target genes include AKR1B10, AKR1C2, ME1, KYNU, CABYR, TRIM16L, AKR1C4, CYP4F11, RSPO3, AKR1B15, NR0B1, and AKR1C3.

The invention further provides a method of diagnosing a cancer in a subject, the method comprising determining the mRNA expression level of NRF2 comprising a deletion in all or a portion of its exon 2 in a sample obtained from the subject (e.g., a tumor sample), wherein the presence of NRF2 comprising a deletion in all or a portion of its exon 2 identifies the subject as having a cancer. In some embodiments, the NRF2 further comprises a deletion in all or a portion of its exon 3. Presence and/or expression levels of a gene (e.g., NRF2, KEAP1, AKR1B10, AKR1C2, SRXN1, OSGIN1, FECH, GCLM, TRIM16, ME1, KYNU, CABYR, SLC7A11, TRIM16L, AKR1C4, CYP4F11, RSPO3, ABCC2, AKR1B15, NR0B1, UGDH, TXNRD1, GSR, AKR1C3, TALDO1, PGD, TXN, NQO1, or FTL) may be determined qualitatively or quantitatively based on any suitable criterion known in the art, including, but not limited to DNA, mRNA, cDNA, protein fragments, and/or gene copy number.

The invention further provides a method of diagnosing a cancer in a subject, the method comprising determining the protein expression level of NRF2 comprising a deletion in all or a portion of its Neh2 domain in a sample obtained from the subject, wherein the presence of NRF2 comprising a deletion in all or a portion of its Neh2 domain identifies the subject as having a cancer. In some embodiments, the NRF2 further comprises a deletion in all or a portion of its Neh4 domain.

The invention further provides a method of identifying a subject having cancer, the method comprising determining the mRNA expression level of NRF2 comprising a deletion in all or a portion of its exon 2 in a sample obtained from the subject (e.g., a tumor sample), wherein the presence of NRF2 comprising a deletion in all or a portion of its exon 2 identifies the subject as having a cancer. In some embodiments, the NRF2 further comprises a deletion in all or a portion of its exon 3. Presence and/or expression levels of a gene (e.g., NRF2, KEAP1, AKR1B10, AKR1C2, SRXN1, OSGIN1, FECH, GCLM, TRIM16, ME1, KYNU, CABYR, SLC7A11, TRIM16L, AKR1C4, CYP4F11, RSPO3, ABCC2, AKR1B15, NR0B1, UGDH, TXNRD1, GSR, AKR1C3, TALDO1, PGD, TXN, NQO1, or FTL) may be determined qualitatively or quantitatively based on any suitable criterion known in the art, including, but not limited to DNA, mRNA, cDNA, protein fragments, and/or gene copy number.

The invention further provides a method of identifying a subject having cancer, the method comprising determining the protein expression level of NRF2 comprising a deletion in all or a portion of its Neh2 domain in a sample obtained from the subject, wherein the presence of NRF2 comprising a deletion in all or a portion of its Neh2 domain identifies the subject as having a cancer. In some embodiments, the NRF2 further comprises a deletion in all or a portion of its Neh4 domain.

The presence and/or expression level/amount of various biomarkers described herein in a sample can be analyzed by a number of methodologies, many of which are known in the art and understood by the skilled artisan, including, but not limited to, immunohistochemistry ("IHC"), Western blot analysis, immunoprecipitation, molecular binding assays, ELISA, ELIFA, fluorescence activated cell sorting ("FACS"), MassARRAY, proteomics, quantitative blood based assays (e.g., Serum ELISA), biochemical enzymatic activity assays, in situ hybridization, fluorescence in situ hybridization (FISH), Southern analysis, Northern analysis, whole genome sequencing, massively parallel DNA sequencing (e.g., next-generation sequencing), NANOSTRING®, polymerase chain reaction (PCR) including quantitative real time PCR (qRT-PCR) and other amplification type detection methods, such as, for example, branched DNA, SISBA, TMA and the like, RNA-seq, microarray analysis, gene expression profiling, and/or serial analysis of gene expression ("SAGE"), as well as any one of the wide variety of assays that can be performed by protein, gene, and/or tissue array analysis. Typical protocols for evaluating the status of genes and gene products are found, for example in Ausubel et al., eds., 1995, *Current Protocols In Molecular Biology*, Units 2 (Northern Blotting), 4 (Southern Blotting), 15 (Immunoblotting) and 18 (PCR Analysis). Multiplexed immunoassays such as those available from Rules Based Medicine or Meso Scale Discovery ("MSD") may also be used.

In some embodiments of any of the methods described herein, DNA from clinical tumor samples can be sequenced using a next-generation sequencing method, such as the targeted gene pulldown and sequencing method described in Frampton et al. (*Nature Biotechnology.* 31(11): 1023-1033, 2013), which is incorporated by reference herein in its entirety. Such a next-generation sequencing method can be used with any of the methods disclosed herein to detect various mutations (e.g., insertions, deletions, base substitutions, focal gene amplifications, and/or homozygous gene deletions), while enabling the use of small samples (e.g., from small-core needle biopsies, fine-needle aspirations, and/or cell blocks) or fixed samples (e.g., formalin-fixed and paraffin-embedded (FFPE) samples).

In any of the preceding methods, the presence and/or expression level/amount of a biomarker (e.g., NRF2, KEAP1, AKR1B10, AKR1C2, SRXN1, OSGIN1, FECH, GCLM, TRIM16, ME1, KYNU, CABYR, SLC7A11, TRIM16L, AKR1C4, CYP4F11, RSPO3, ABCC2, AKR1B15, NR0B1, UGDH, TXNRD1, GSR, AKR1C3, TALDO1, PGD, TXN, NQO1, or FTL) is measured by determining protein expression levels of the biomarker. In certain embodiments, the method comprises contacting the biological sample with antibodies that specifically bind to a biomarker (e.g., anti-NRF2 antibodies) under conditions permissive for binding of the biomarker, and detecting whether a complex is formed between the antibodies and biomarker. Such method may be an in vitro or in vivo method. Any method of measuring protein expression levels known in the art or provided herein may be used. For example, in some embodiments, a protein expression level of a biomarker is determined using a method selected from the group consisting of flow cytometry (e.g., fluorescence-activated cell sorting (FACS™)), Western blot, enzyme-linked immunosorbent assay (ELISA), immunoprecipitation, immunohistochemistry (IHC), immunofluorescence, radioimmunoassay, dot blotting, immunodetection methods, HPLC, surface plasmon resonance, optical spectroscopy, mass spectrometry, and HPLC. In some embodiments, the protein expression level of the biomarker is determined in tumor cells.

In some embodiments, the presence and/or expression level/amount of a biomarker (e.g., NRF2, KEAP1, AKR1B10, AKR1C2, SRXN1, OSGIN1, FECH, GCLM, TRIM16, ME1, KYNU, CABYR, SLC7A11, TRIM16L, AKR1C4, CYP4F11, RSPO3, ABCC2, AKR1B15, NR0B1, UGDH, TXNRD1, GSR, AKR1C3, TALDO1, PGD, TXN, NQO1, or FTL) is measure by determining mRNA expression levels of the biomarker. In certain embodiments, presence and/or expression level/amount of a gene is determined using a method comprising: (a) performing gene expression profiling, PCR (such as RT-PCR), RNA-seq, microarray analysis, SAGE, MassARRAY technique, or FISH on a sample (such as a subject cancer sample); and b) determining presence and/or expression level/amount of a biomarker in the sample. In one embodiment, the PCR method is qRT-PCR. In one embodiment, the PCR method is multiplex-PCR. In some embodiments, gene expression is measured by microarray. In some embodiments, gene expression is measured by qRT-PCR. In some embodiments, expression is measured by multiplex-PCR.

Methods for the evaluation of mRNAs in cells are well known and include, for example, hybridization assays using complementary DNA probes (such as in situ hybridization using labeled riboprobes specific for the one or more genes, Northern blot and related techniques) and various nucleic acid amplification assays (such as RT-PCR using complementary primers specific for one or more of the genes, and other amplification type detection methods, such as, for example, branched DNA, SISBA, TMA and the like). Samples from mammals can be conveniently assayed for mRNAs using Northern, dot blot, or PCR analysis. In addition, such methods can include one or more steps that allow one to determine the levels of target mRNA in a biological sample (e.g., by simultaneously examining the levels a comparative control mRNA sequence of a “housekeeping” gene such as an actin family member).

In some embodiments of any of the methods, the biomarker is NRF2 (e.g., exon 2-deleted NRF2 or exon 2+3-deleted NRF2). In one embodiment, expression level of biomarker is determined using a method comprising performing WGS analysis on a sample (such as a tumor sample obtained from a patient) and determining expression level of a biomarker in the sample. In some embodiments, presence of exon 2-deleted NRF2 or exon 2+3-deleted NRF2 is determined relative to a reference. In some embodiments, the reference is a reference value. In some embodiments, the reference is a reference sample (e.g., a control cell line sample, a tissue sample from non-cancerous patient, or a wild-type NRF2 tissue sample).

Additionally or alternatively to mRNA expression analysis, other biomarkers, such as protein expression, may be quantified according to methods described above. For example, methods of the invention include testing a sample for a genomic biomarker (e.g., the presence of exon 2-deleted NRF2 or exon 2+3-deleted NRF2, or the upregulation of one or more NRF2 target genes, e.g., AKR1B10, AKR1C2, SRXN1, OSGIN1, FECH, GCLM, TRIM16, ME1, KYNU, CABYR, SLC7A11, TRIM16L, AKR1C4, CYP4F11, RSPO3, ABCC2, AKR1B15, NR0B1, UGDH, TXNRD1, GSR, AKR1C3, TALDO1, PGD, TXN, NQO1, or FTL) and additionally testing a sample for a protein biomarker (e.g., protein transcripts of one or more of AKR1B10, AKR1C2, SRXN1, OSGIN1, FECH, GCLM, TRIM16, ME1, KYNU, CABYR, SLC7A11, TRIM16L, AKR1C4, CYP4F11, RSPO3, ABCC2, AKR1B15, NR0B1, UGDH, TXNRD1, GSR, AKR1C3, TALDO1, PGD, TXN, NQO1, or FTL).

In some embodiments of any of the methods, a DNA sequence may serve as a biomarker. DNA can be quantified according to any method known in the art, including, but not limited to, PCR, exome-seq (e.g., whole exome sequencing), DNA microarray analysis, NANOSTRING®, or whole genome sequencing.

In some instances, the expression level of the genes in the sample is an average (e.g., mean expression or median expression) of the genes, the reference expression level of the genes is an average (e.g., mean expression or median expression) of the genes of the reference, and the average of the genes of the sample is compared to the average of the genes of the reference.

In certain embodiments, the presence and/or expression levels/amount of a biomarker in a first sample is increased or elevated as compared to presence/absence and/or expression levels/amount in a second sample. In certain embodiments, the presence/absence and/or expression levels/amount of a biomarker in a first sample is decreased or reduced as compared to presence and/or expression levels/amount in a second sample. In certain embodiments, the second sample is a reference sample, reference cell, reference tissue, control sample, control cell, or control tissue. Additional disclosures for determining the presence/absence and/or expression levels/amount of a gene are described herein.

In certain embodiments, a reference sample, reference cell, reference tissue, control sample, control cell, or control tissue is a single sample or combined multiple samples from the same subject or individual that are obtained at one or more different time points than when the test sample is obtained. For example, a reference sample, reference cell, reference tissue, control sample, control cell, or control tissue is obtained at an earlier time point from the same subject or individual than when the test sample is obtained. Such reference sample, reference cell, reference tissue, control sample, control cell, or control tissue may be useful if the reference sample is obtained during initial diagnosis of cancer and the test sample is later obtained when the cancer becomes metastatic.

In certain embodiments, a reference sample, reference cell, reference tissue, control sample, control cell, or control tissue is a combined multiple samples from one or more healthy individuals who are not the patient. In certain embodiments, a reference sample, reference cell, reference tissue, control sample, control cell, or control tissue is a combined multiple samples from one or more individuals with a disease or disorder (e.g., cancer) who are not the subject or individual. In certain embodiments, a reference sample, reference cell, reference tissue, control sample, control cell, or control tissue is pooled RNA samples from normal tissues or pooled plasma or serum samples from one or more individuals who are not the patient. In certain embodiments, a reference sample, reference cell, reference tissue, control sample, control cell, or control tissue is pooled RNA samples from tumor tissues or pooled plasma or serum samples from one or more individuals with a disease or disorder (e.g., cancer) who are not the patient.

In some embodiments of any of the methods, elevated or increased expression refers to an overall increase of about any of 10%, 20%, 30%, 40%, 50%, 60%, 70%, 80%, 90%, 95%, 96%, 97%, 98%, 99% or greater, in the level of biomarker (e.g., protein or nucleic acid (e.g., gene (DNA or mRNA))), detected by standard art-known methods such as those described herein, as compared to a reference sample, reference cell, reference tissue, control sample, control cell, or control tissue. In certain embodiments, the elevated expression refers to the increase in expression level/amount of a biomarker in the sample wherein the increase is at least about any of 1.5×, 1.75×, 2×, 3×, 4×, 5×, 6×, 7×, 8×, 9×, 10×, 25×, 50×, 75×, or 100× the expression level/amount of the respective biomarker in a reference sample, reference cell, reference tissue, control sample, control cell, or control tissue. In some embodiments, elevated expression refers to an overall increase of greater than about 1.5 fold, about 1.75 fold, about 2 fold, about 2.25 fold, about 2.5 fold, about 2.75 fold, about 3.0 fold, or about 3.25 fold as compared to a reference sample, reference cell, reference tissue, control sample, control cell, control tissue, or internal control (e.g., housekeeping gene).

In some embodiments of any of the methods, reduced expression refers to an overall reduction of about any of 10%, 20%, 30%, 40%, 50%, 60%, 70%, 80%, 90%, 95%, 96%, 97%, 98%, 99% or greater, in the level of biomarker (e.g., protein or nucleic acid (e.g., gene (DNA or mRNA))), detected by standard art known methods such as those described herein, as compared to a reference sample, reference cell, reference tissue, control sample, control cell, or control tissue. In certain embodiments, reduced expression refers to the decrease in expression level/amount of a biomarker in the sample wherein the decrease is at least about any of 0.9×, 0.8×, 0.7×, 0.6×, 0.5×, 0.4×, 0.3×, 0.2×, 0.1×, 0.05×, or 0.01× the expression level/amount of the respective biomarker in a reference sample, reference cell, reference tissue, control sample, control cell, or control tissue.

B. Therapeutic Methods

The present invention provides methods for treating a patient suffering from a cancer (e.g., a lung cancer (e.g., squamous NSCLC or non-squamous NSCLC) or a head and neck cancer (e.g., HNSC)). In some instances, the methods of the invention include administering to the patient an effective amount of a NRF2 pathway antagonist. Any of the NRF2 pathway antagonists described herein or otherwise known in the art may be used in the methods. In some instances, the methods involve determining the presence and/or expression level of a NRF2 splice variant (e.g., exon 2-deleted NRF2 or exon 2+3-deleted NRF2) or a NRF2 target gene in a sample obtained from a patient and administering an NRF2 pathway antagonist to the patient based on the presence and/or expression level of a NRF2 splice variant (e.g., exon 2-deleted NRF2 or exon 2+3-deleted NRF2) or a NRF2 target gene, e.g., using any of the methods described herein, in the Examples below, or known in the art.

The invention provides a method of treating a subject suffering from a cancer (e.g., a lung cancer (e.g., squamous NSCLC or non-squamous NSCLC) or a head and neck cancer (e.g., HNSC)), the method comprising determining the expression level of at least one gene (e.g., 1, 2, 3, 4, 5, 6, 7, 8, 9, 10, 11, 12, 13, 14, 15, 16, 17, 18, 19, 20, 21, 22, 23, 24, 25, 26, or 27 genes) selected from the group consisting of AKR1B10, AKR1C2, SRXN1, OSGIN1, FECH, GCLM, TRIM16, ME1, KYNU, CABYR, SLC7A11, TRIM16L, AKR1C4, CYP4F11, RSPO3, ABCC2, AKR1B15, NR0B1, UGDH, TXNRD1, GSR, AKR1C3, TALDO1, PGD, TXN, NQO1, and FTL in a sample obtained from the subject; and comparing the expression level of the at least one gene to a reference expression level of the at least one gene, wherein an increase in the expression level of the at least one gene in the sample relative to the reference expression level of the at least one gene identifies a subject having a cancer, and administering to the subject a therapeutically effective amount of one or more NRF2 pathway antagonists.

The invention further provides a method of treating a subject suffering from a cancer (e.g., lung cancer (e.g., squamous NSCLC or non-squamous NSCLC) or head and neck cancer), wherein the expression level of one or more (e.g., 1, 2, 3, 4, 5, 6, 7, 8, 9, 10, 11, or 12) newly identified NRF2 target genes is determined. Newly identified NRF2 target genes include AKR1B10, AKR1C2, ME1, KYNU, CABYR, TRIM16L, AKR1C4, CYP4F11, RSPO3, AKR1B15, NR0B1, and AKR1C3.

In some instances, the invention further provides a method of treating a subject suffering from a cancer (e.g., lung cancer (e.g., squamous NSCLC or non-squamous NSCLC) or head and neck cancer), wherein the mRNA expression level of NRF2 comprises a deletion in all, or a portion of, its exon 2 in a sample obtained from the subject, and wherein the presence of NRF2 comprising a deletion in all or a portion of its exon 2 identifies the subject as having a cancer; and administering to the subject a therapeutically effective amount of one or more NRF2 pathway antagonists. In some embodiments, the NRF2 further comprises a deletion in all, or a portion of, its exon 3.

In some instances, the invention further provides a method of treating a subject suffering from a cancer (e.g., a lung cancer (e.g., squamous NSCLC or non-squamous NSCLC) or a head and neck cancer (e.g., HNSC)), wherein the NRF2 protein comprises a deletion in all, or a portion of, its Neh2 domain in a sample obtained from the subject, and wherein the presence of NRF2 comprising a deletion in all, or a portion of, its Neh2 domain identifies the subject as having a cancer; and administering to the subject a therapeutically effective amount of one or more NRF2 pathway antagonists. In some embodiments, the NRF2 further comprises a deletion in all or a portion of its Neh4 domain.

In any of the preceding methods, the NRF2 pathway antagonist may be any NRF2 pathway antagonist known in the art or described herein.

In some instances, the method further includes administering to the subject an effective amount of a second therapeutic agent (e.g., one or more anti-cancer agents). In some instances, the second therapeutic agent is selected from the group consisting of an anti-angiogenic agent, a chemotherapeutic agent, a growth inhibitory agent, a cytotoxic agent, an immunotherapy, and combinations thereof. In some embodiments, the immunotherapy is a VEGF antagonist (e.g., anti-VEGFR2 antibodies and related molecules (e.g., ramucirumab, tanibirumab, aflibercept), anti-VEGFR1 antibodies and related molecules (e.g., icrucumab, aflibercept (VEGF Trap-Eye; EYLEA®), and ziv-aflibercept (VEGF Trap; ZALTRAP®)), bispecific VEGF antibodies (e.g., MP-0250, vanucizumab (VEGF-ANG2), and bispecific antibodies disclosed in US 2001/0236388), bispecific antibodies including combinations of two of anti-VEGF, anti-VEGFR1, and anti-VEGFR2 arms, anti-VEGF antibodies (e.g., bevacizumab, sevacizumab, and ranibizumab), and nonpeptide small molecule VEGF antagonists (e.g., pazopanib, axitinib, vandetanib, stivarga, cabozantinib, lenvatinib, nintedanib, orantinib, telatinib, dovitinig, cediranib, motesanib, sulfatinib, apatinib, foretinib, famitinib, and tivozanib)). In other embodiments, the immunotherapy is a PD-1 axis binding antagonist (e.g., YW243.55.570, MDX-1105, MPDL3280A (atezolizumab), MED14736 (druvalumab), MSB0010718C (avelumab), MDX-1106 (nivolumab), MK-3475 (pembrolizumab), CT-011 (pidilizumab), MEDI-0680 (AMP-514), PDR001, REGN2810, BGB-108 or AMP-224).

The compositions used in the methods described herein (e.g., NRF2 pathway antagonists) can be administered by any suitable method, including, for example, intravenously, intramuscularly, subcutaneously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subconjunctivally, intravesicularly, mucosally, intrapericardially, intraumbilically, intraocularly, intraorbitally, orally, topically, transdermally, intravitreally (e.g., by intravitreal injection), by eye drop, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered and the severity of the condition, disease, or disorder being treated). In some embodiments, the NRF2 pathway antagonist is administered intravenously, intramuscularly, subcutaneously, topically, orally, transdermally, intraperitoneally, intraorbitally, by implantation, by inhalation, intrathecally, intraventricularly, or intranasally. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

NRF2 pathway antagonists described herein (and any additional anti-cancer agents) may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The NRF2 pathway antagonist need not be, but is optionally formulated with and/or administered concurrently with one or more agents currently used to prevent or treat the disorder in question. The effective amount of such other agents depends on the amount of the Nrd2 pathway inhibitor present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

In some embodiments, the methods further involve administering to the patient an effective amount of a second therapeutic agent (e.g., one or more anti-cancer agents). In some embodiments, the second therapeutic agent is selected from the group consisting of an anti-angiogenic agent, a chemotherapeutic agent, a growth inhibitory agent, a cytotoxic agent, an immunotherapy, and combinations thereof.

Such combination therapies noted above encompass combined administration (where two or more therapeutic agents (e.g., a NRF2 pathway antagonist and an anti-cancer agent) are included in the same or separate formulations), and separate administration, in which case, administration of a NRF2 pathway antagonist can occur prior to, simultaneously, and/or following, administration of the additional anti-cancer agent or agents. In one embodiment, administration of NRF2 pathway antagonist and administration of an additional anti-cancer agent occur within about one month, or within about one, two or three weeks, or within about one, two, three, four, five, or six days, of each other.

C. NRF2 Pathway Antagonists for Use in the Methods of the Invention

Provided herein are methods for treating or delaying progression of a cancer (e.g., a lung cancer (e.g., squamous NSCLC) or head and neck cancer) in a subject comprising administering to the subject a therapeutically effective amount of a NRF2 pathway antagonist. Any of the preceding methods may be based on the expression level of a biomarker provided herein, for example, NRF2 expression or expression of any protein or mRNA involved in a NRF2 pathway in a tumor sample, e.g., a biopsy containing tumor cells.

In some embodiments, a NRF2 pathway antagonist is a small molecule, e.g., a small molecule capable of binding to NRF2 or protein or gene that regulates the expression, stability, or activity of NRF2.

In some embodiments, the NRF2 pathway antagonist is an antagonist of a NRF2 agonist. Examples of NRF2 agonists include, but are not limited to, cAMP response element-binding protein (CREB), CREB Binding Protein (CBP), Maf, activating transcription factor 4 (ATF4), protein kinase C (PKC), Jun, glucocorticoid receptor, UbcM2, and homologous to the E6-AP carboxyl terminus domain and Ankyrin repeat containing E3 ubiquitin protein ligase 1 (HACE1). Therefore, examples of NRF2 pathway antagonists include, but are not limited to, CREB antagonists, CBP antagonists, Maf antagonists, ATF4 antagonists, PKC antagonists, Jun antagonists, glucocorticoid receptor antagonists, UbcM2 antagonists, and HACE1 antagonists, such as those set forth in Table 2.

In some embodiments, the NRF2 pathway antagonist is an agonist of a NRF2 antagonist. Examples of NRF2 antagonists include, but are not limited to, c-Myc, SUMO, KEAP1, CUL3, retinoic acid receptor α (RARα). Therefore, examples of NRF2 pathway antagonists include, but are not limited to, c-Myc agonists, SUMO, KEAP1 agonists, CUL3 agonists, and RARα agonists, such as those set forth in Table 3.

TABLE 2

| Compound | Target |
|---|---|
| KG-501<br>2-naphthol-AS-E-phosphate | CREB |
| C646<br>4-[4-[[5-(4,5-Dimethyl-2-nitrophenyl)-2-furanyl]methylene]-4,5-dihydro-3-methyl-5-oxo-1H-pyrazol-1-yl]benzoic acid | CBP |
| CBP30<br>8-(3-chloro-4-methoxy-phenethyl)-4-(3,5-dimethyl-isoxazol-4-yl)-9-(2-(morpholin-4-yl)-propyl)-7,9-diaza-bicyclo[4.3.0]nona-1(6),2,4,7-tetraene | CBP |
| nivalenol<br>3,4,7,15-Tetrahydroxy-12,13-epoxytrichothec-9-en-8-on | c-maf |
| tomatidine<br>(3β,5α,22β,25S)-spirosolan-3-ol | ATF4 |

TABLE 2-continued

| Compound | Target |
|---|---|
| ruboxistaurin<br>(9S)-9-[(dimethylamino)methyl]-6,7,10,11-tetrahydro-9H,18H-5,21:12,17-di(metheno)dibenzo[e,k]pyrrolo[3,4-h][1,4,13]oxadiazacyclohexadecine-18,20-dione | PKC |
| SP600125<br>1,9-Pyrazoloanthrone | Jun |
| mifepristone<br>(11β,17β)-11-[4-(Dimethylamino)phenyl]-17-hydroxy-17-(1-propynyl)-estra-4,9-dien-3-one | Glucocorticoid receptor |
| CORT 108297<br>1H-Pyrazolo[3,4-g]isoquinoline, 4a-(ethoxymethyl)-1-(4-fluorophenyl)-4,4a,5,6,7,8-hexahydro-6-[[4-(trifluoromethyl)phenyl]sulfonyl]-, (4aR)- | Glucocorticoid receptor |

TABLE 3

| Compound | Target |
|---|---|
| AI-1<br>4-Chloro-1,2-dihydro-1-methyl-2-oxo-3-quinolinecarboxylic acid ethyl ester, Ethyl 4-chloro-1-methyl-2-oxo-1,2-dihydroquinoline-3-carboxylate | KEAP1 |
| retinoic acid<br>3,7-Dimethyl-9-(2,6,6-trimethyl-1-cyclohexen-1-yl)-2E,4E,6E,8E,-nonatetraenoic acid | RARα |
| CD437<br>6-(4-Hydroxy-3-tricyclo[3.3.1.13,7]dec-1-ylphenyl)-2-naphthalenecarboxylic acid | RARα |
| TTNPB<br>4-[(E)-2-(5,6,7,8-Tetrahydro-5,5,8,8-tetramethyl-2-naphthalenyl)-1-propenyl]benzoic acid | RARα |

In some embodiments of the invention, derivatives of the compounds listed in Table 2 or 3 may also be administered as NRF2 pathway antagonists. A derivative of a compound listed in Table 2 or 3 is a small molecule that differs in structure from the parent compound, but retains the ability to antagonize a NRF2 pathway. A derivative of a compound may change its interaction with certain other molecules or proteins relative to the parent compound. A derivative of a compound may also include a salt, an adduct, or other variant of the parent compound. In some embodiments of the invention, any derivative of a compound described herein (e.g., any one compound of the compounds listed in Table 2 or 3 may be used instead of the parent compound. In some embodiments, any derivative of a compound listed in Table 2 or 3 may be used in a method of treating a subject having cancer, such as lung cancer.

In some embodiments, a NRF2 pathway antagonist is an antibody (e.g., an anti-NRF2 antibody or an antibody directed against a protein or gene that regulates NRF2 expression, stability, or activity, e.g., a target listed in Table 2 or 3). In some embodiments, the anti-NRF2 antibody is capable of inhibiting binding between NRF2 and antioxidant response element. In some embodiments, the anti-NRF2 antibody is capable of inhibiting binding between NRF2 and a cofactor (e.g., Maf, PKC, Jun, ATF4, or CBP). In some embodiments, the antibody of the invention is an antibody fragment selected from the group consisting of Fab, Fab'-SH, Fv, scFv, and (Fab')2 fragments. In some embodiments, the antibody is a humanized antibody. In some embodiments, the antibody is a human antibody. In some embodiments, the antibody is a derivative of a known antibody having any of the above-mentioned properties. Derivatives of antibodies include antibody variants having about 99%, 98%, 97%, 96%, 95%, 94%, 93%, 92%, 91%, 90%, 85%, 80% or lower sequence identity to its parent antibody. Percent (%) amino acid sequence identity is determined according to methods known in the art, including by ALIGN-2, as described above.

In some embodiments, a NRF2 pathway antagonist includes an inhibitor of any downstream biomarker (e.g., gene or protein, e.g., a gene or protein involved in iron sequestration (e.g., Ferritin, Light Polypeptide (FTL), Ferritin, Heavy Polypeptide 1 (FTH), or Heme Oxygenase 1 (HMOX1)), GSH utilization (e.g., Glutathione Peroxidase 2 (GPX2), Glutathione S-Transferase Alpha 1 (GSTA1), Glutathione S-Transferase Alpha 2 (GSTA2), Glutathione S-Transferase Alpha 3 (GSTA3), Glutathione S-Transferase Alpha 5 (GSTA5), Glutathione S-Transferase Mu 1 (GSTM1), Glutathione S-Transferase Mu 2 (GSTM2), Glutathione S-Transferase Mu 3 (GSTM3), or Glutathione S-Transferase Pi 1 (GSTP1)), quinine detoxification (e.g., NAD(P)H Dehydrogenase, Quinone 1 (NQO1)), GSH production and regeneration (e.g., Glutamate-Cysteine Ligase, Modifier Subunit (GCLM), Glutamate-Cysteine Ligase, Catalytic Subunit (GCLC), Glutathione Reductase (GSR), or Solute Carrier Family 7 (Anionic Amino Acid Transporter Light Chain, Xc-System), Member 11 (SLC7A11, or XCT)), thioredoxin (TXN) production, regeneration, and utilization (e.g., Thioredoxin 1, (TXN1), Thioredoxin Reductase 1 (TXNRD1), or Peroxiredoxin 1 (PRDX1)), NADPH production (e.g., Glucose-6-Phosphate Dehydrogenase (G6PD), Phosphogluconate Dehydrogenase (PGD), Malic Enzyme 1, NADP(+)-Dependent, Cytosolic (ME1), Isocitrate Dehydrogenase 1 (NADP+), Soluble (IDH1)) or any of the genes or proteins thereof of Table 1).

In some embodiments, a NRF2 pathway antagonist includes a compound that inhibits NRF2 from binding to antioxidant response element (ARE) (e.g., by competitively binding to the ARE binding site on NRF2, by competitively binding to ARE, or by otherwise interfering with a transcriptional cofactor (e.g., small Maf proteins).

In some embodiments, a NRF2 pathway antagonist includes an agonist or antagonist of NRF2-related genes, such that the pharmacological effect of compound involves the downregulation of one or more pathways downstream of NRF2-mediated transcription. Such NRF2-related genes include, e.g., Kelch-Like ECH-Associated Protein 1 (KEAP1), Ectodermal-Neural Cortex 1 (With BTB Domain) (ENC1), Protein Kinase C, Delta (PRKCD), Protein Kinase C, Beta (PRKCB), Polyamine-Modulated Factor 1 (PMF1), Cullin 3 (CUL3), Nuclear Factor, Erythroid 2 (NFE2), Activating Transcription Factor 4 (ATF4), Heme Oxygenase 1 (HMOX1), Heme Oxygenase 2 (HMOX2), Ubiquitin C (UBC), V-Maf Avian Musculoaponeurotic Fibrosarcoma Oncogene Homolog K (MAFK), UDP Glucuronosyltransferase 1 Family, Polypeptide A6 (UGT1A6), V-Maf Avian Musculoaponeurotic Fibrosarcoma Oncogene Homolog F (MAFF), CREB Binding Protein (CREBBP), V-Maf Avian Musculoaponeurotic Fibrosarcoma Oncogene Homolog G (MAFG), CAMP Responsive Element Binding Protein 1 (CREB1), FXYD Domain Containing Ion Transport Regulator 2 (FXYD2), Jun Proto-Oncogene (JUN), Small Ubiquitin-Like Modifier 2 (SUMO2), Small Ubiquitin-Like Modifier 1 (SUMO1), V-Myc Avian Myelocytomatosis Viral Oncogene Homolog (MYC), Crystallin, Zeta (Quinone Reductase) (CRYZ), Aldo-Keto Reductase Family 7, Member A2 (Aflatoxin Aldehyde Reductase) (AKR7A2), and Glutathione S-Transferase Alpha 2 (GSTA2).

In some embodiments, a method of increasing ubiquitination of NRF2 in a cell is provided, the method comprising contacting the cell with an inhibitor of a NRF2 pathway under conditions allowing inhibition of a NRF2 pathway in a cell. Increased ubiquitination of NRF2 can be determined, e.g., by immunoaffinity enrichment of ubiquitinated NRF2 following trypsin digestion, followed by mass spectrometry, according to known methods. In some embodiments, an increase in ubiquitation may be determined by comparing the ubiquitination of a wild-type NRF2 in a cell or population of cells contacted with a NRF2 pathway antagonist with the ubiquitination of an exon 2 or exon 2+3 deleted NRF2 in a cell or a population of cells contacted with a NRF2 pathway antagonist and/or the ubiquitination of an exon 2 or exon 2+3 deleted NRF2 in a cell or a population of cells not contacted with a NRF2 pathway antagonist.

In some embodiments of the invention, the NRF2 pathway antagonist is ascorbic acid, brusatol, luteolin, or ochratoxin A.

EXAMPLES

Example 1

Materials and Experimental Methods

A. Mutation and Copy Number Analysis

For 99 NSCLC cell lines, non-synonymous mutations and copy number data for KRas, LKB1, KEAP1, and NRF2 were obtained from Klijn et al. (*Nat Biotechnol.* 33(3):306-312, 2015). Thirteen additional NSCLC cell lines were subjected to copy number analysis. In addition, exome sequencing was applied to 104 NSCLC cell lines. For the cancer genome atlas (TCGA) tumors mutation and copy number data were retrieved from cBioPortal using the R software package CGDS-R (Cerami et al. *Cancer Discovery.* 2:401-404, 2012; Gao et al. *Sci. Signal.* 6:11, 2013).

B. RNA-seq Analysis and Derivation of a Mutant KEAP1 Gene Expression Signature

Raw RNA-seq data for 99 NSCLC cell lines were retrieved from the European Genome-phenome Archive (accession number EGAS00001000610) (PMID: 25485619). Mutations in KEAP1 and NRF2 in each of the NSCLC cell lines are provided in Table 4. Raw RNA-seq data were downloaded from TCGA and aligned to the human reference genome (GRCh37/hg19) using GSNAP version 2013-10-10 (Wu and Nacu. *Bioinformatics* 26:873-881, 2010), allowing maximum of 2 mismatches (parameters: "-M 2 -n 10 -B 2 -i 1 -N 1 -w 200000 -E 1—pairmax-rna=200000"). Gene expression levels were quantified with RPKM (reads per kilobase of target and million reads sequenced) values derived from the number of reads mapped to each RefSeq gene. Using the DESeq R package (PMID: 20979621) differential gene expression was measured between KEAP1 mutant and KEAP1 wild-type cell lines, reported as fold-change and associated adjusted p-values. For ward clustering of samples and genes (using Euclidean distance) in variance stabilized count data were used. The 'NMF' R package was used to create associated heatmaps.

TABLE 4

| Name | Sample Type | Gene | Mutation |
|---|---|---|---|
| BEN | Carcinoma | KEAP1 | A556T |
| NCI-H460 | Carcinoma Large Cell | KEAP1 | D236H |
| NCI-H838 | Carcinoma Non-Small Cell | KEAP1 | E444* |
| HCC44 | Carcinoma Non-Small Cell | KEAP1 | F211C |
| A549 | Carcinoma | KEAP1 | G333C |
| HCC-15 | Carcinoma Non-Small Cell | KEAP1 | G364C |
| NCI-H1648 | Adenocarcinoma | KEAP1 | G364C |
| NCI-H2110 | Carcinoma Non-Small Cell | KEAP1 | G429C |
| LXF-289 | Adenocarcinoma | KEAP1 | G430V |
| NCI-H647 | Carcinoma Non-Small Cell | KEAP1 | G523W |
| NCI-H920 | Carcinoma Non-Small Cell | KEAP1 | G603V |
| HCC4019 | Adenocarcinoma | KEAP1 | K131* |
| NCI-H23 | Carcinoma Non-Small Cell | KEAP1 | Q193H |
| NCI-H1355 | Adenocarcinoma | KEAP1 | Q75* |
| NCI-H1915 | Carcinoma Non-Small Cell | KEAP1 | R135L |
| NCI-H2126 | Carcinoma Non-Small Cell | KEAP1 | R272C |
| NCI-H1944 | Carcinoma Non-Small Cell | KEAP1 | R272L |
| NCI-H1623 | Carcinoma Non-Small Cell | KEAP1 | R320L |
| NCI-H2170 | Carcinoma Squamous Cell | KEAP1 | R336* |
| NCI-H1435 | Carcinoma Non-Small Cell | KEAP1 | R413L |
| NCI-H322T | Unknown | KEAP1 | R460S |
| H322T | Carcinoma Non-Small Cell | KEAP1 | R460S |
| NCI-H661 | Carcinoma Large Cell | KEAP1 | V168I |
| NCI-H2030 | Carcinoma Non-Small Cell | KEAP1 | V568F |
| NCI-H2023 | Carcinoma Non-Small Cell | KEAP1 | W252C |
| H1573 | Adenocarcinoma | KEAP1 | A143P |
| NCI-H2172 | Carcinoma Non-Small Cell | KEAP1 | G430C |
| H1792 | Adenocarcinoma | KEAP1 | G462W |
| NCI-H2122 | Carcinoma Non-Small Cell | KEAP1 | R202G |
| HCC2270 | Adenocarcinoma | NRF2 | G31E |
| NCI-H2228 | Carcinoma Non-Small Cell | NRF2 | G31A |
| NCI-H1568 | Carcinoma Non-Small Cell | NRF2 | DEE77-79 |
| EBC-1 | Carcinoma Non-Small Cell | NRF2 | D77V |

C. Splice Variant Analysis

Analysis of splice variants was performed using the SGSeq software package available from the Bioconductor project website (Gentleman et al. *Genome Biol.* 5:R80, 2004). Exons and splice junctions were predicted from BAM files for 7,384 TCGA samples at 54 genomic loci of known oncogenes using parameters alpha=2, psi=0, beta=0.2, gamma=0.2. Predicted features were merged across samples, and exons were processed into disjoint exon bins. Splice junctions and exon bins were assembled into a genome-wide splice graph. Splice events, which consist of two or more alternative splice variants, were identified from the graph. Splice variants were quantified in terms of FPKM and relative usage Ψ. Briefly, local estimates of relative usage at the start and end of the variant were obtained as the fraction of fragments that are compatible with the variant. Estimates at the event start and end were combined using a weighted mean, with weights proportional to the total number of fragments spanning the boundary. Relative usage estimates with denominator less than 20 were set to NA. To obtain a local estimate of absolute expression at the variant start and end, compatible counts n were converted to FPKMs as $n/(N \times L) \times 10^9$ where N is the total number of aligned fragments and L is the effective length (the number of allowed positions for a compatible fragment). Splice variants detected in TCGA samples were also quantified in 2,958 genotype-tissue expression project (GTEx) samples from normal human tissues (Consortium. *Science.* 348:648-660, 2015).

D. Identification of Cancer-Specific Splice Variants

Only internal splice variants (not involving alternative transcript starts or ends) were considered and the start and end of each splice variant were required to either overlap or extend exons that belong to annotated ref Gene transcripts downloaded from the UCSC Genome Browser website (Pruitt et al. *Nucleic Acids Res.* 33:D501-504, 2005; Rosenbloom et al. *Nucleic Acids Res.* 43:D670-681, 2015). Retained introns were excluded. 19 TCGA indications that included at least 100 cancer samples (6,359 cancer samples in total) were considered and splice variants with (i) FPKM>2 and relative usage LP>0.2 in at least one cancer sample and (ii) FPKM<1 in >99.9% of GTEx samples, and (iii) FPKM~0 in >97.5% of GTE x samples were selected. FPKM -based criteria were required to be satisfied at both the start and end of the splice variant. Variants satisfying the FPKM-based criteria for which LP could not be estimated were included after manual inspection.

E. Analysis of Targeted Paired-End Exome-seq Data

All samples within FoundationCORE were processed and sequenced similarly as previously described (Frampton et al. *Nat. Biotechnol.* 31, 1023-1031, 2014). NRF2 exon 2 and exon 2+3 deletions were screened across a Foundation-CORE dataset (n=58,707) using two distinct approaches.

First, rearrangement calls based on discordant read pairs and/or split reads were examined for direct evidence for loss of NRF2 exon 2 or exon 2+3. Although this approach provides direct evidence of the deletions of interest, deletions can only be discovered with this approach if the breakpoints are within a baited region because intronic regions of NRF2 are not captured. Thus, this approach identifies a limited subset of NRF2 exon 2 or exon 2+3 deletions in which the breakpoints occur near intron-exon boundaries or within exons.

The second approach utilizes copy number log ratio data from individual bait regions. Copy number log ratio values were determined with an in-house algorithm, educated to the specific tumor cellularity of each sample. A z-score was calculated comparing the log ratio for each exon in NRF2 to control polymorphism capture regions immediately adjacent to NRF2 (n=15; evenly spaced every ~1 MB from ~3 MB upstream and ~12 MB downstream of NRF2). Exon 2 deletions with and without concurrent exon 3 deletion were specifically examined. These are herein referred to as exons of interest (EOI). EOI deletions were called if (1) a z-score was <−2 for EOI and not for non-EOIs in NRF2 and (2) a log-ratio drop of 0.2 from non-EOIs in NRF2 was calculated. Mutual exclusivity between NRF2 exon 2 or exon 2+3 deletions and short variants in NRF2 or KEAP1 was examined specifically within lung squamous cell carcinoma (n=1, 218).

F. Cell Culture

KMS-27 (RPMI-1640), JHH-6 (Williams Media E), HuCCT1 (RPMI-1640), and HUH-1 (DMEM) cells were from JCRB, and 293 (EMEM) cells were from ATCC. Cells were cultured in the indicated media in the presence of 2 mM glutamine and 10% FBS.

G. Western Blotting

Cell lysates were prepared with RIPA Buffer (Sigma) supplemented with complete EDTA-free protease inhibitor (Roche) and phoSTOP (Roche), Phosphatase Inhibitor Cocktail 2 (Sigma) and Phosphatase Inhibitor Cocktail 3 (Sigma) phosphatase inhibitors. Lysates were run on Novex Tris-Glycine 4-12% gradient gels (ThermoFisher) and transferred onto iBlot nitrocellulose (Invitrogen). Blots were pre-incubated in 5% skim milk powder (Merck) in TBST (10 mM Tris pH8, 150 mM NaCl, 0.1% TWEEN-20), followed by 5% bovine serum albumin (Sigma) in TBST containing antibodies. Secondary antibodies used were ECL Anti-Rabbit HRP and ECL Anti-Mouse HRP (both from GE Heathcare). Blots were developed with a Chemiluminescence Substrate Kit (Protein Simple) and visualized with a FluorChem HD2 imager (Protein Simple). Antibodies used in this study are against KEAP1 (Cell Signaling G1010), NRF2 (Abcam ab62352), HSP90 (Cell Signaling 4877), HDAC2 (Cell Signaling 5113), β-actin (Sigma A2228), HA (Roche 11815016001), and FLAG (Sigma F2426). Lamda phosphatase was from NEB (P0753L), and phosphatase inhibitors were omitted from the lysis buffer in these experiments.

H. Cell Viability and DNA Fragmentation Analysis siRNAs were reverse transfected into cells with Dharmafect 2 reagent (ThermoFisher) and OptiMEM (Gibco). Four days post transfection, cells were measured for viability using CellTiter-Glo reagent (Promega) and luminescence was detected on an EnVision Multi-label Reader (Perkin Elmer). siRNAs were reverse transfected into cells with Dharmafect 2 reagent (ThermoFisher) and OptiMEM (Gibco). Four days post-tranfection, cells were measured for apoptosis using propidium iodide (P1) (LifeTechnologies) staining and flow cytometry following a published protocol (Riccardi and Nicoletti *Nat. Protoc.* 1:1458-1461, 2006). Staurosporin, 1 μM, (Enzo) was added to positive control cells 24 hours pre-staining. siRNAs targeting NRF2 exon 2 had the sequences: 5'-TGGAGTAAGTCGAGAAGTA-3' (SEQ ID NO: 29) and 5'-ACAACTAGATGAAGAGACA-3' (SEQ ID NO: 30). siRNAs targeting NRF2 exon 5 had the sequences: 5'-TGACAGAAGTTGACAATTA-3' (SEQ ID NO: 31) and 5'-GTAAGAAGCCAGATGTTAA-3' (SEQ ID NO: 32), and were used along with non-target siRNA as control siRNA. Stained cells were analyzed with a Becton Dickinson FACS Caliber instrument. siRNAs targeting KEAP1 were from Dhamacon (L012453-00).

DNA fragmentation was quantified by propidium iodide (P1) staining and measured by flow cytometry according to Riccardi et al. (*Nature Protocols,* 1:1458-1461 (2006)).

I. Taqman Analysis

Total cellular RNA was extracted with an RNeasy Kit (Qiagen). RNA was converted to cDNA using a High Capacity cDNA Reverse Transcription Kit (Applied Biosystems), and cDNAs were amplified with Taqman Gene Expression primer-probe sets (ThermoFisher) using Taqman Gene Expression Master Mix reagents (Applied Biosystems). Taqman amplification/detection was performed on a QuantStudio7 Flex Real-Time PCR System. Primer-probe sets used were Hs00232352_ml and Hs00975961_gl to detect NRF2 exons 2 and 5, respectively (ThermoFisher). NRF2 target gene Taqman primer-probe sets used were: SLC7A11 (Hs00921938_ml), SGRN (Hs00921938_ml), NR0B1 (Hs03043658_ml), GCLC (HsOOI55249_ml), and GPX2 (Hs01591589_ml), all from ThermoFisher.

J. 293 Transfections

Plasmid DNAs were transfected into cells using Lipofectamine 2000 (ThermoFisher) and OptiMEM (Gibco) as recommended by manufacturer protocol. Lysates were prepared 2-3 days post transfection. Expression plasmids used were pRK5.NRF2, pRK5.NRF2.delta.e2, pRK5.NRF2.delta.e2,3, pRK5.NRF2.FLAG and pRK5.KEAP1.HA.

K. Tumor Xenograft Models

Eleven to twelve week-old female C.B-17 SCID.beige mice (Charles River Laboratories) were subcutaneously inoculated in the right lateral flank with $10\times10^6$ A549 shRNA cells in 100 μl HBSS/MATRIGEL® (BD Biosciences) or with $10\times10^6$ H441 shRNA cells in 100 μl HBSS per mouse. When tumor volume reached approximately 150-250 $mm^3$, mice were randomized to receive drinking water containing 1 mg/ml doxycycline (in 5% sucrose) or no doxycycline (5% sucrose alone) ad libitum. The doxycycline was replaced 3 times a week and the sucrose replaced once a week. Tumor volumes were determined using digital calipers (Fred V. Fowler Company, Inc.) using the formula (L×W×W)/2 and plotted as mean tumor volume ($mm^3$)+/− SEM. Tumor growth inhibition (% TGI) was calculated as the percentage of the area under the fitted curve (AUC) for the respective dose group per day in relation to the vehicle, such that % TGI=100×1−(AUC treatment/day)/(AUC vehicle/day). In a separate study, mice with 150-250 $mm^3$ tumors were dosed with 1 mg/ml doxycycline for 5 days before the tumors were excised and analyzed by Western blotting for NRF2 levels.

L. A549 Xenografts Treated with ErbB3 Antibodies

Female nude mice (n=10) bearing subcutaneous A549 tumors (75-144 mm3) on Day 1 were treated with vehicle or 50 mg/kg YW57.88.5 (100 mg/kg loading dose) administered intravenously once each week for four weeks (qwk×4). Tumors were measured twice each week, and each animal was euthanized for endpoint at the earlier of its tumor reaching a volume of 1000 $mm^3$ or on the final day of the treatment regimen.

Example 2

Identification of NSCLC Cell Lines with Mutations in KEAP1 and NRF2

Figure 1B:
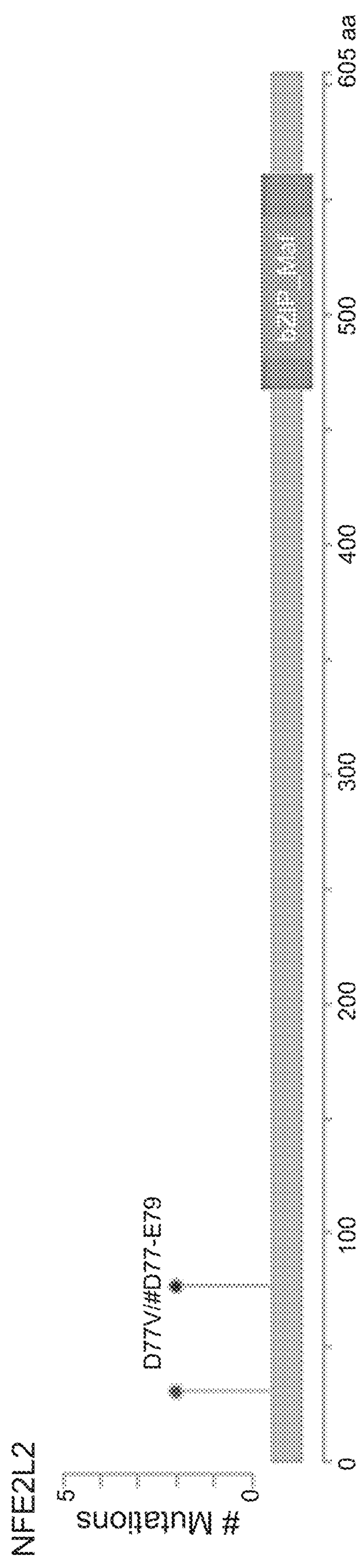
FIG. 1B is a protein sequence representation showing point mutations in the NFE2L2 (NRF2) gene.
Figure 1C:
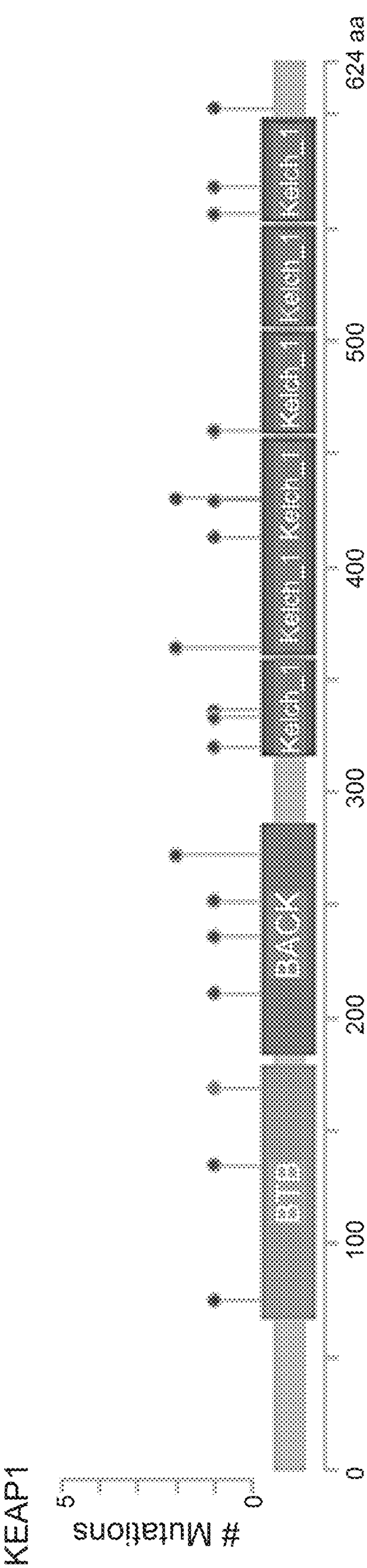
FIG. 1C is a protein sequence representation showing point mutations in the KEAP1 gene.
Figure 1D:
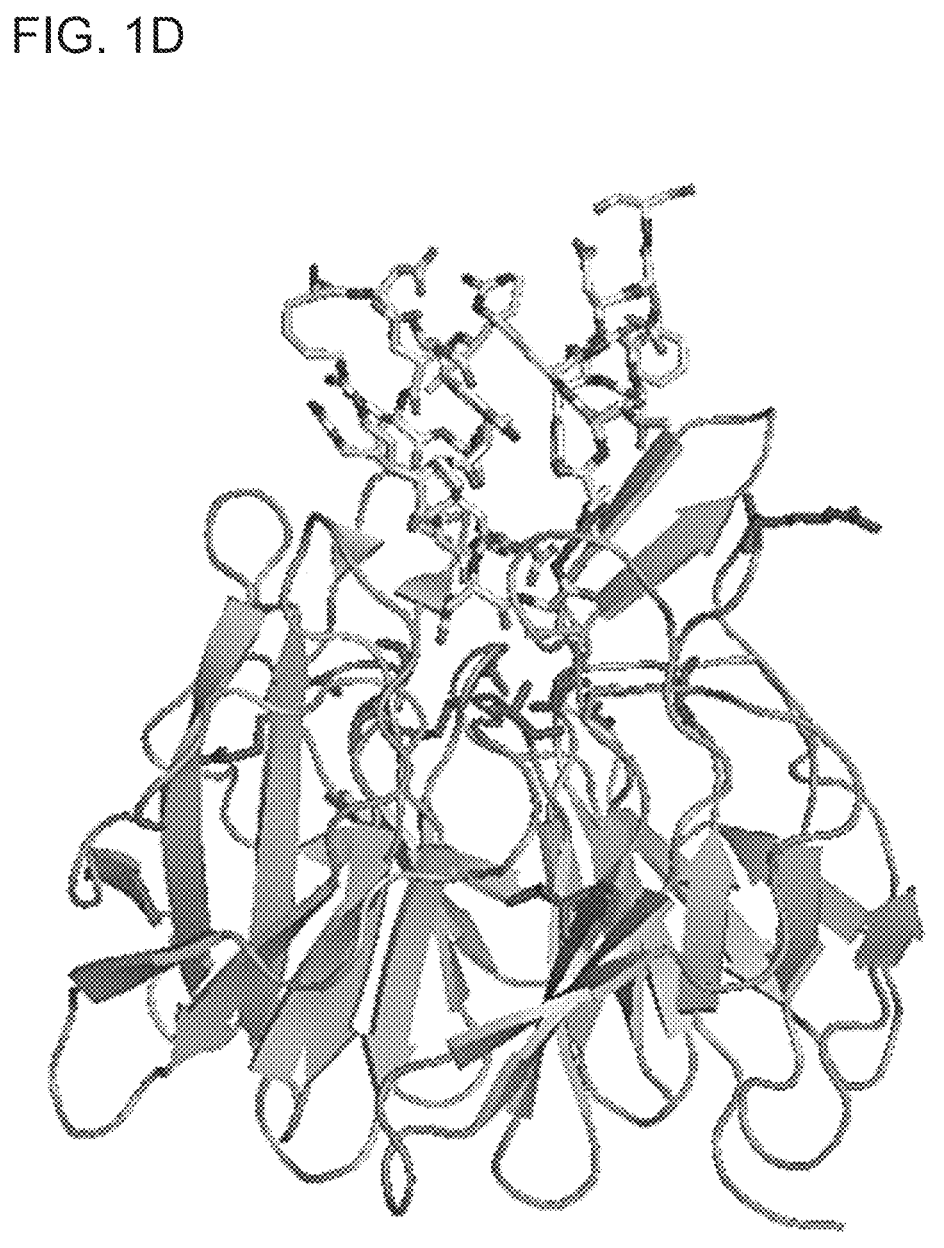
Figures 1, 26D:
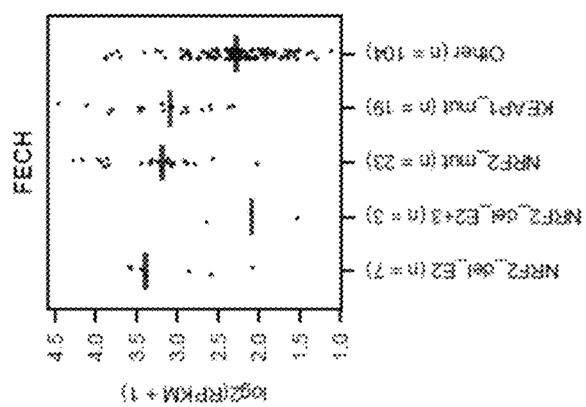
FIGS. 26A-1 to 26B-2 are a series of graphs showing the mRNA expression levels of indicated NRF2 target genes in TCGA squamous NSCLC tumors, plotted according to mutation status of KEAP1 and NRF2. Individual graphs show mRNA expression levels of NQO1 (FIG. 26A-1), SLC7A11 (FIG. 26B-1), KYNU (FIG. 26C-1), FECH (FIG. 26D-1), CABYR (FIG. 26E-1), GCLM (FIG. 26F-1), TXN (FIG. 26G-1), AKR1C4 (FIG. 26H-1), AKR1C3 (FIG. 26I-1), TXNRD1 (FIG. 26J-1), SRXN1 (FIG. 26K-1), GPX2 (FIG. 26L-1), AKR1C2 (FIG. 26M-1), OSGIN1 (FIG. 26N-1), TRIM16 (FIG. 26O-1), NR0B1 (FIG. 26P-1), GSR (FIG. 26Q-1), AKR1B10 (FIG. 26R-1), TRIM16L (FIG. 26S-1), PGD (FIG. 26T-1), ME1 (FIG. 26U-1), FTL (FIG. 26V-1), RSPO3 (FIG. 26W-1), CYP4F11 (FIG. 26X-1), UGDH (FIG. 26Y-1), TALDO1 (FIG. 26Z-1), ABCC2 (FIG. 26A-2), and AKR1B15 (FIG. 26B-2). Only samples for which both exome-seq and RNA-seq data were available were considered. One sample with mutations in both NRF2 and KEAP1 was excluded. In addition, samples with evidence for NRF2 copy number changes |log 2(CAN)|>0.5 were excluded.
Figures 1, 26C:
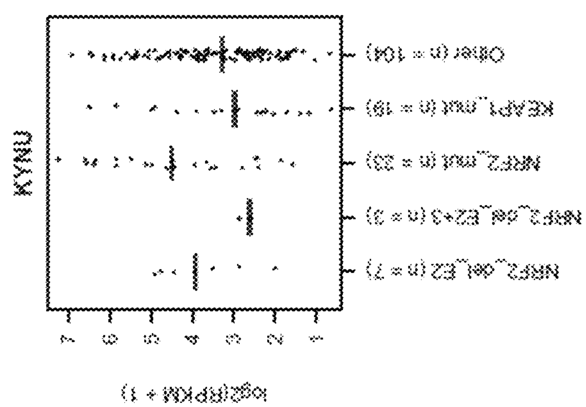
Figures 1, 26B:
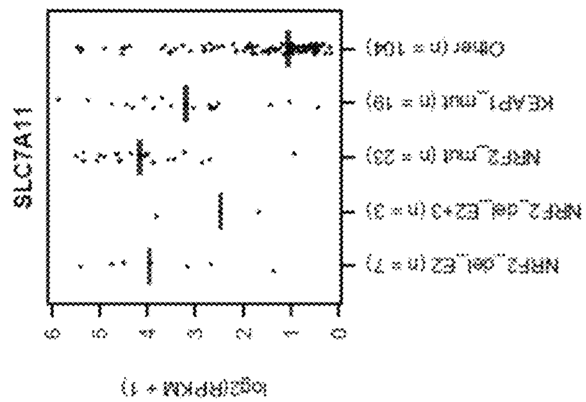
Figures 1, 26A:
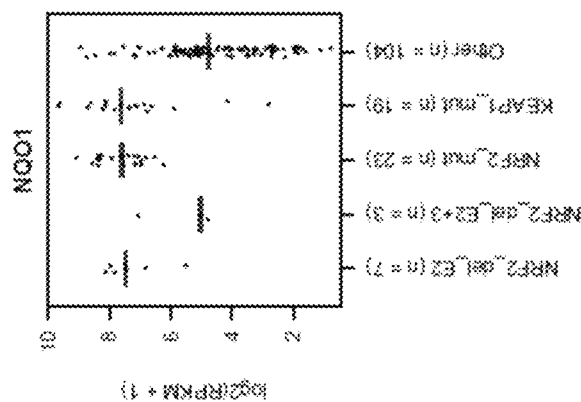
Figures 1, 26H:
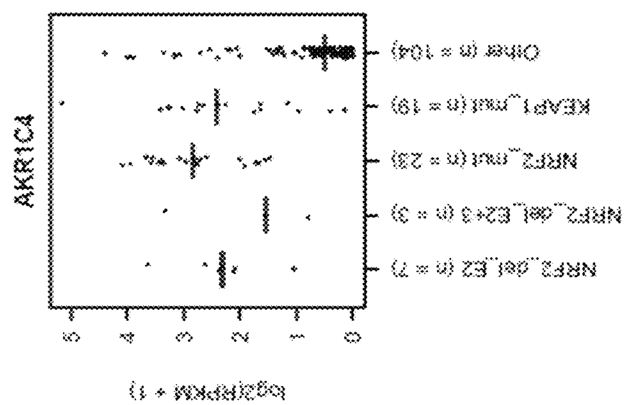
Figures 1, 26G:
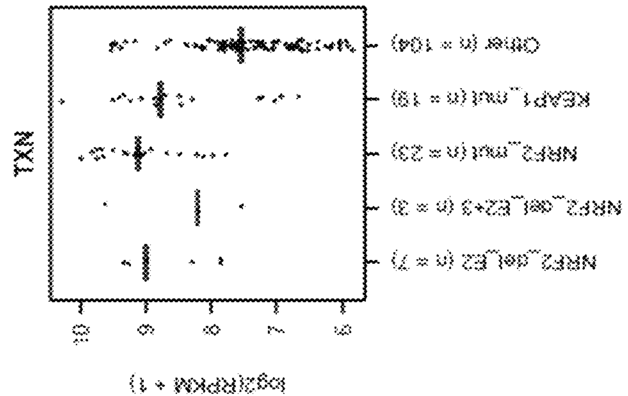
Figures 1, 26F:
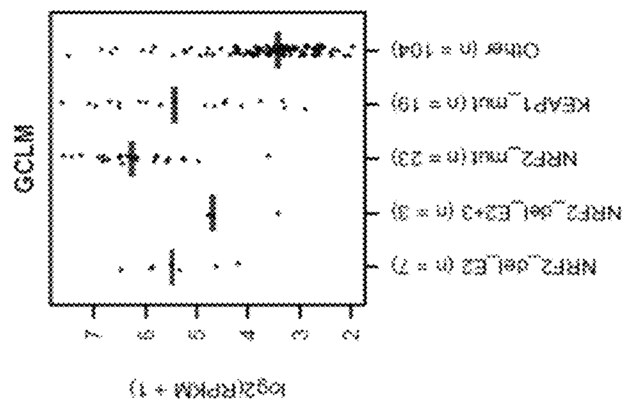
Figures 1, 26E:
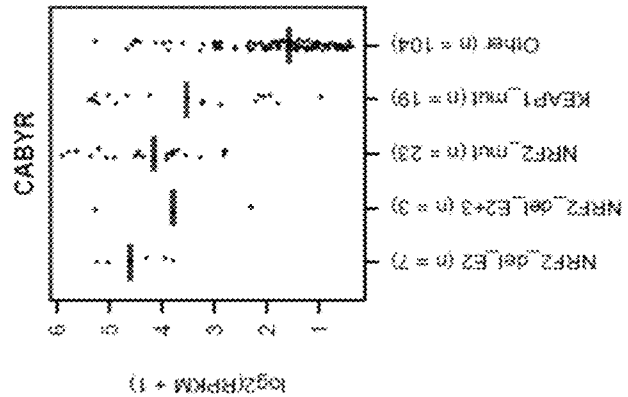
Figures 1, 26L:
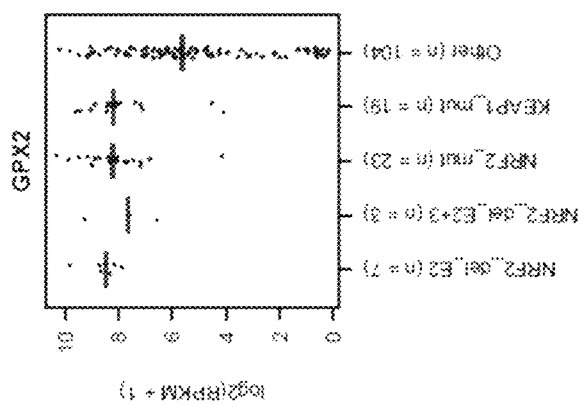
Figures 1, 26K:
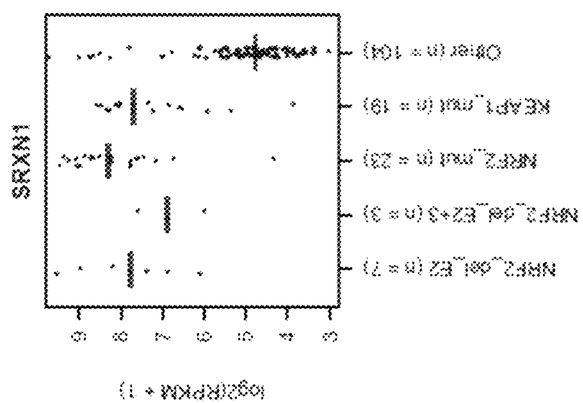
Figures 1, 26J:
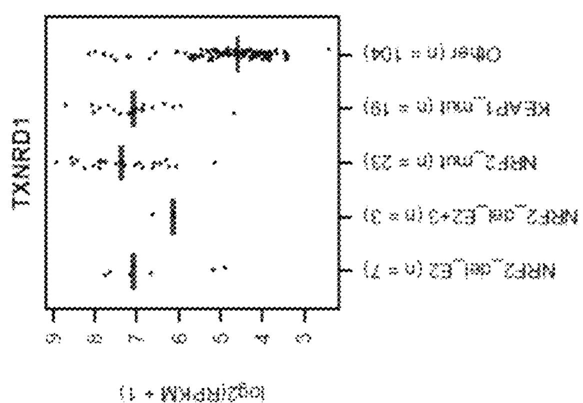
Figures 1, 26I:
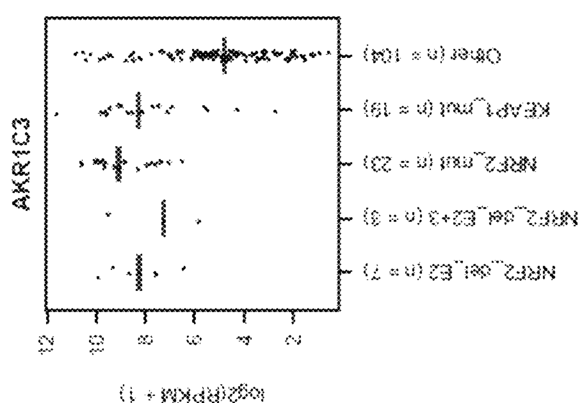
Figures 1, 26P:
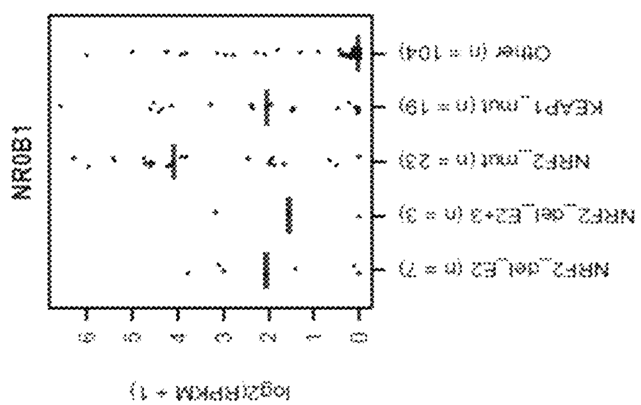
Figures 1, 26O:
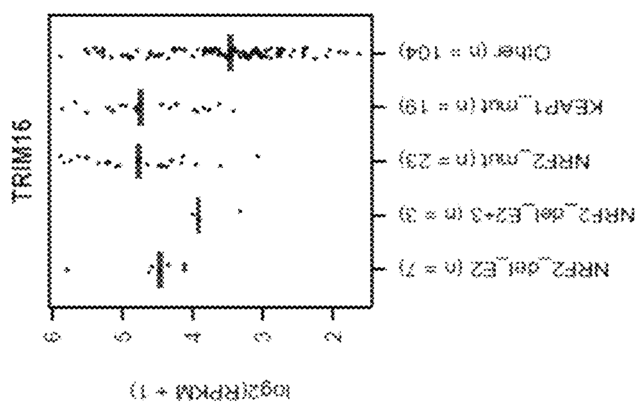
Figures 1, 26N:
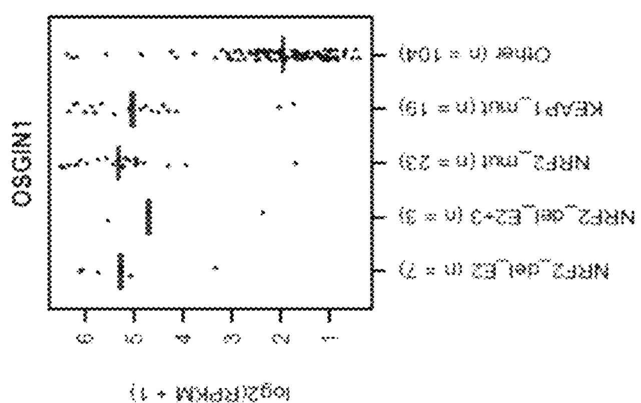
Figures 1, 26M:
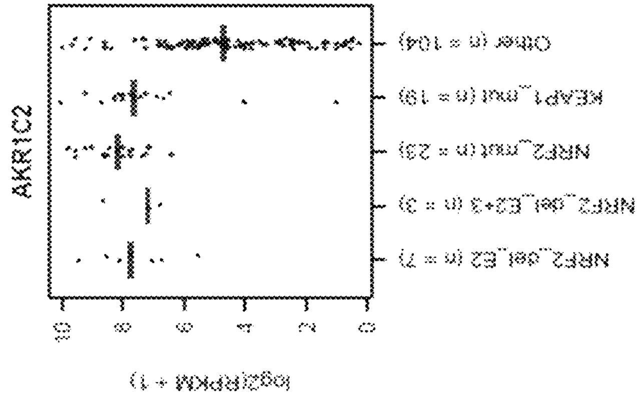
Figures 1, 26Q, 26R, 26S, 26T:
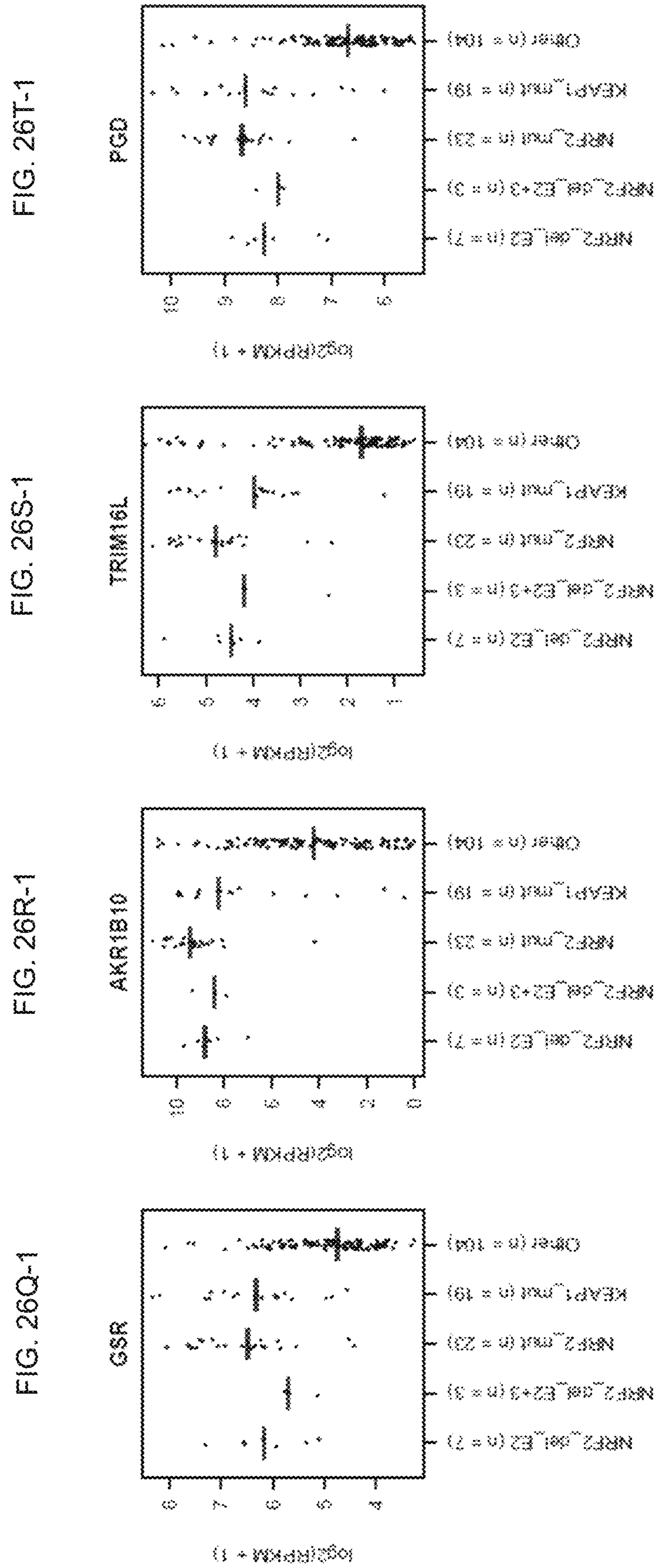
Figures 1, 26X:
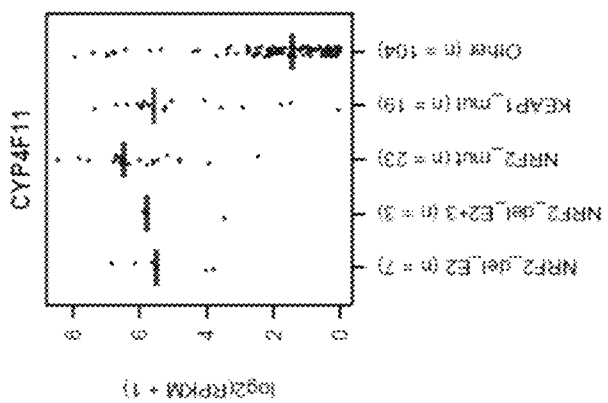
Figures 1, 26W:
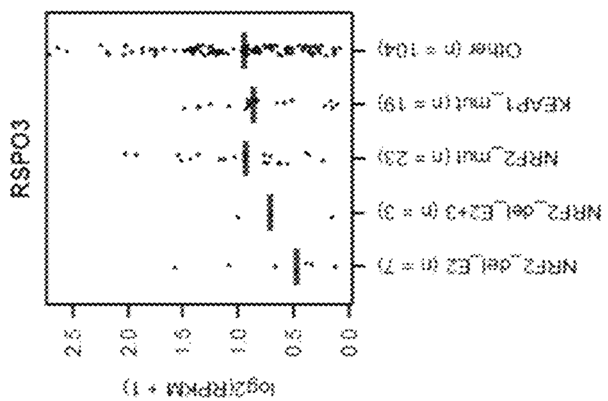
Figures 1, 26V:
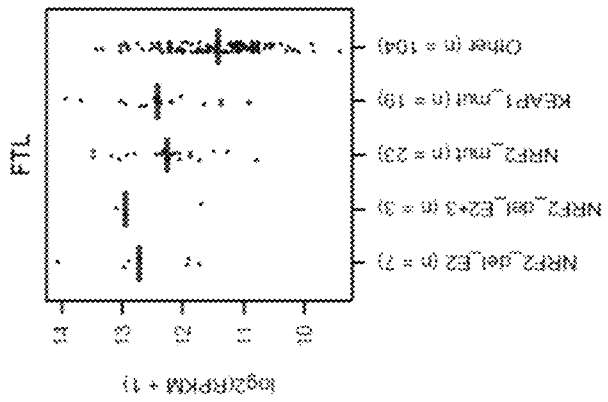
Figures 1, 26U:
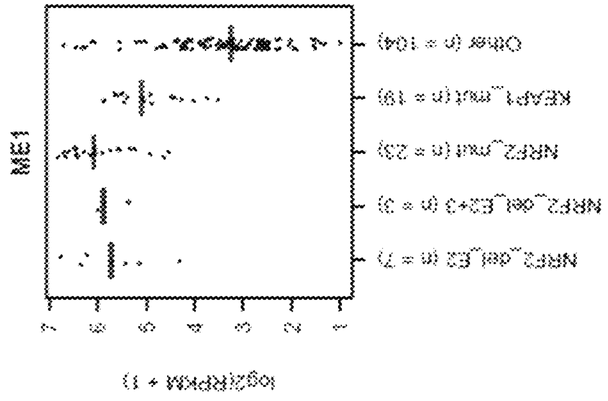
Figures 1, 2, 26A, 26B, 26Y, 26Z:
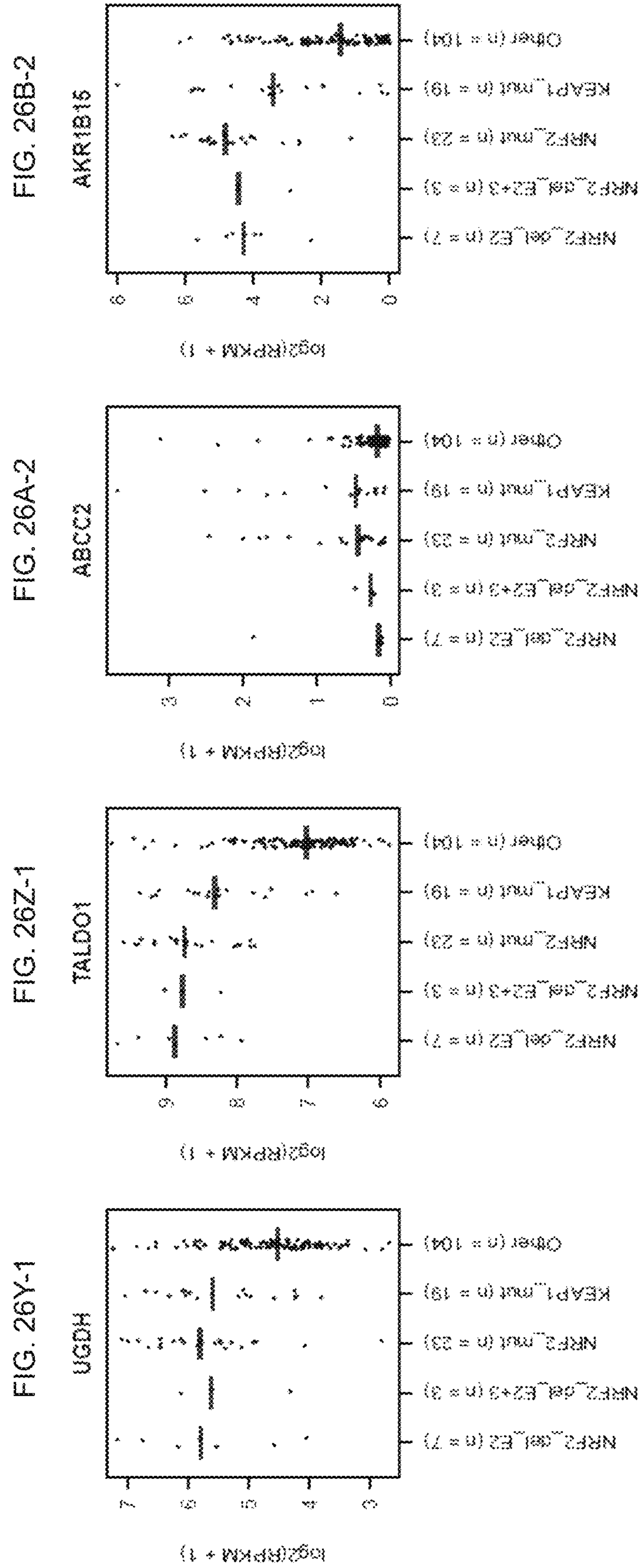

To identify mutations, copy number, and loss of heterozygosity (LOH) of KEAP1 and NRF2 in NSCLC, a panel of 113 NSCLC cell lines profiled by RNA-seq, exome-seq, or SNP arrays was documented (FIG. 1A). KEAP1 mutations were found in 29/113 cell lines (26%), and NRF2 mutations were detected in 4/113 cell lines (4%). Except for the NCI-H661 cell line, all KEAP1 mutated cell lines showed homozygous expression of the mutated allele, which was generally associated with copy neutral LOH. In contrast, the NRF2 mutations were heterozygous and not associated with LOH. A further two cell lines (HCC1534 and NCI-H1437) showed no detectable KEAP1 mRNA through bi-allelic loss of KEAP1 DNA. The NRF2 mutations were in the previously identified hotspots in the KEAP1 interface regions (FIG. 1B) (Shibata et al. *Proc. Natl. Acad. Sci. U.S.A.* 105:13568-13573, 2008), and comprised point mutations and an in-frame 3-amino-acid deletion. The mutations in KEAP1 were spread throughout the primary sequence (FIG. 1C), with few obvious hotspots. However, when mapped onto the KEAP1/NRF2 peptide crystal structure (Fukutomi et al. *Mol. Cell. Biol.* 34:832-846, 2014), the mutations cluster in the loops extending from the KEAP1 core beta propeller close to the interaction site with NRF2 (FIG. 1 D).

Example 3

Identification of a Mutant KEAP1 Gene Signature

Figures 2A, 2B:
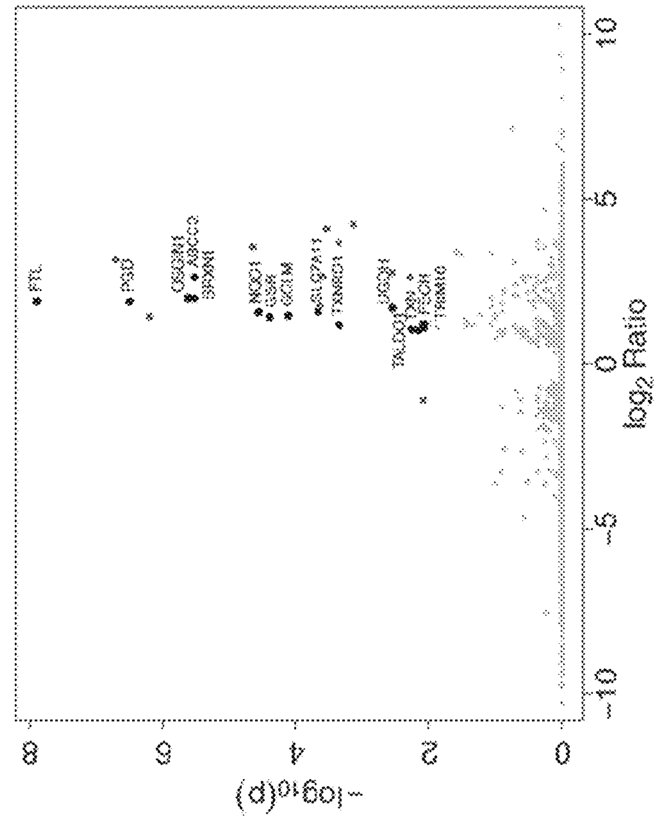
FIG. 2A is a volcano plot illustrating the ratios of average expression levels for all genes in mutant (n=25) versus wild-type (WT) (n=74) KEAP1 NSCLC cell lines and the associated adjusted p-values resulting from the differential expression analysis. Significantly differentially expressed genes (>2-fold, p<0.01) are indicated, and gene sets previously identified as NRF2 targets are identified as black dots.
FIG. 2B is a heatmap showing the results of unsupervised ward clustering showing the upregulation of the 27 genes associated with KEAP1 mutations in NSCLC cell lines.

To determine the transcriptional consequences of KEAP1 mutations in NSCLC cell lines, genes that were significantly differentially expressed ($p<0.01$, absolute mean fold-change>2) in the KEAP1 mutated cell lines compared to the wild-type KEAP1 cell lines were identified. Overall, 27 genes were significantly up-regulated in the KEAP1 mutant cell lines (FIGS. 2A-2B), 15 of which have previously been identified as NRF2 target genes from ChIP-seq or RNA-seq studies (Chorley et al. *Nucleic Acids Res.* 4:7416-7429, 2012; Hirotsu et al. *Nucleic Acids Res.* 40:10228-10239, 2012; Malhotra et al. *Nucleic Acids Res.* 38:5718-5734, 2010). Only one gene, HSPB1, was identified as significantly down-regulated using these cut-offs.

Figure 3B:
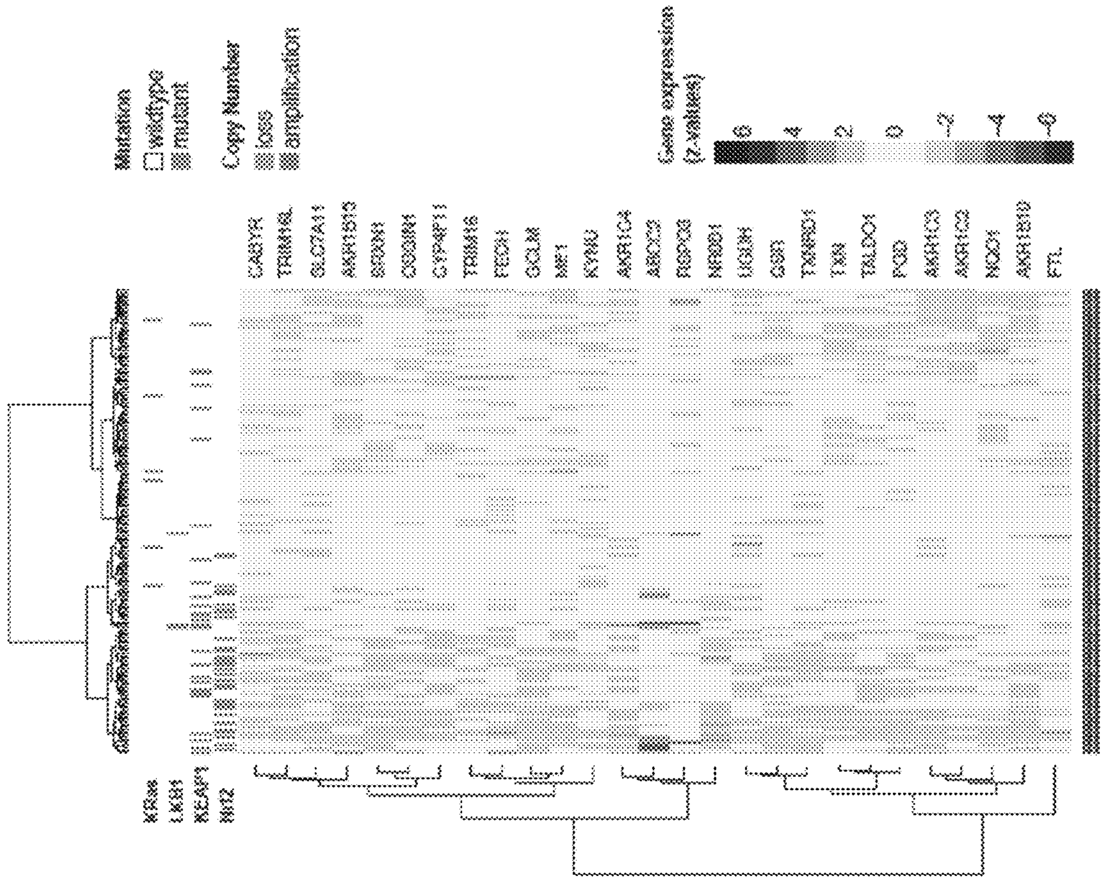
FIG. 3B is a heatmap showing the results of an unsupervised ward clustering showing that the NSCLC cell line-derived KEAP1 gene signature classifies 19 of 22 (86%) KEAP1 mutant and 27 of 27 (100%) NRF2 mutant lung squamous cell carcinomas from TCGA.
Figure 3A:
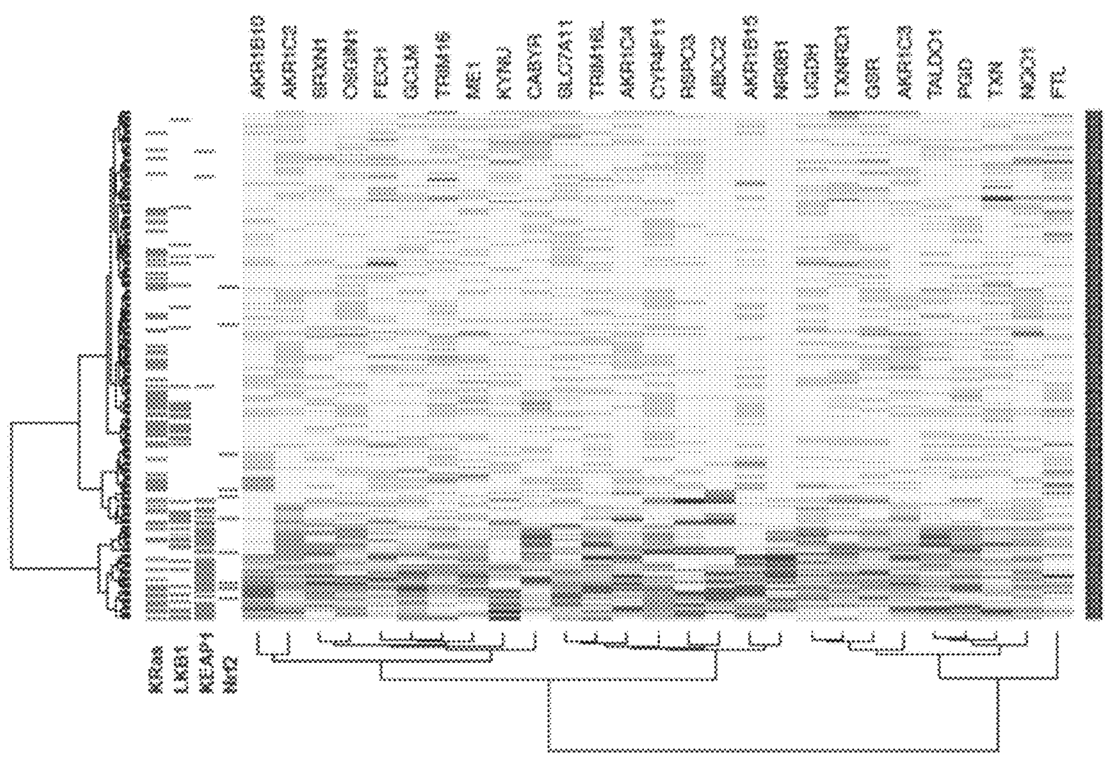
FIG. 3A is a heatmap showing the results of an unsupervised ward clustering showing that the NSCLC cell line-derived KEAP1 gene signature classified 32 of the 40 (80%) KEAP1 mutant lung adenocarcinomas from the cancer genome atlas (TCGA).
Figure 4:
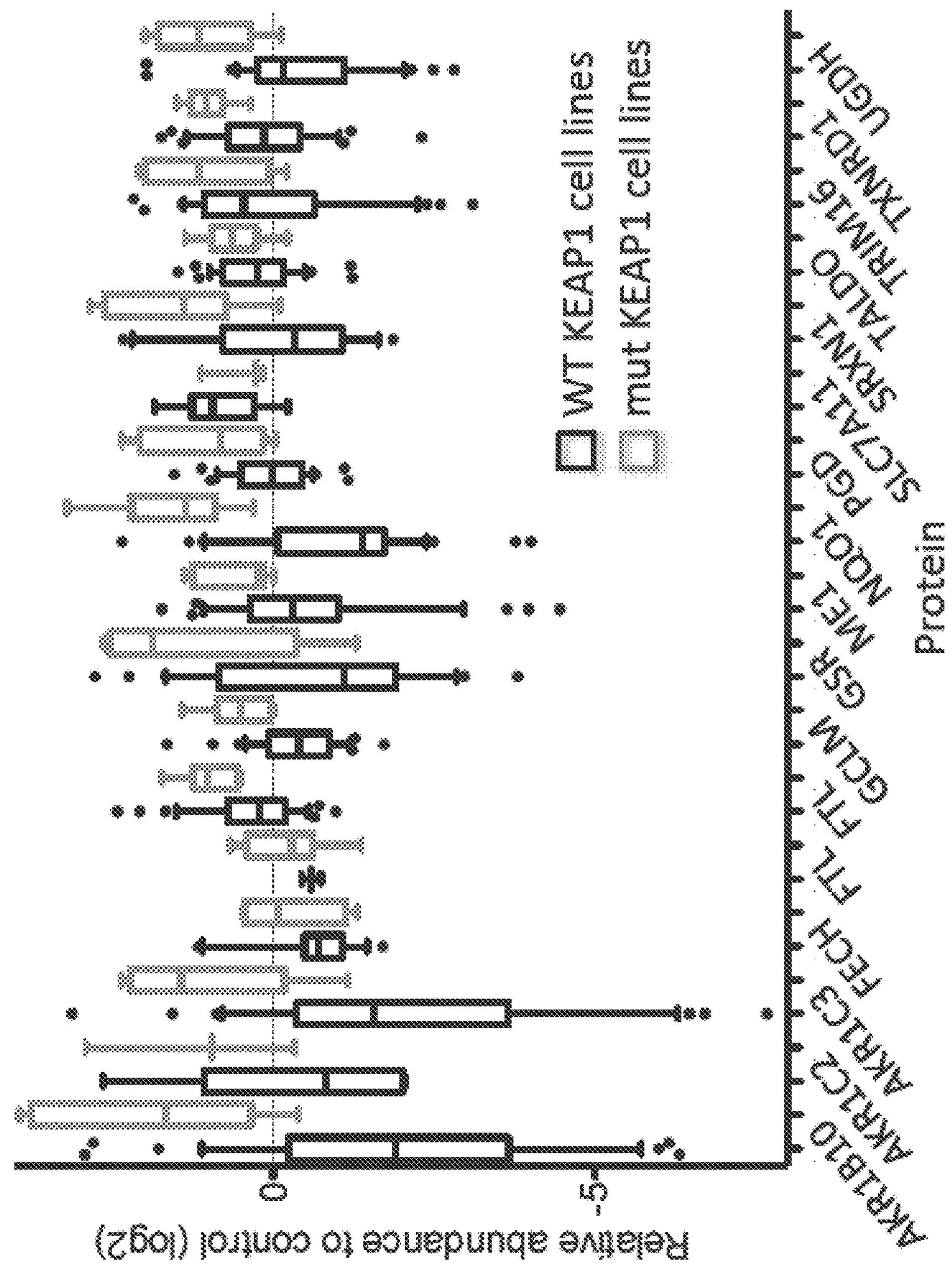
FIG. 4 is a graph showing the relative abundance of protein products of the KEAP1 gene signature in mutant (n=6) and WT (n=37) NSCLC cell lines.

Unsupervised clustering of 230 TCGA lung adenocarcinomas based on the expression of these 27 genes resulted in the division of two major groups (FIG. 3A). One group was mainly characterized by high expression of the 27 signature genes, and contained 43 tumors, out of which 32 (74%) were KEAP1 mutant. The other group, characterized by low expression, contained 187 tumors, out of which 179 were KEAP1 wild-type. Strikingly, using the same gene set to cluster lung squamous cell carcinomas, NRF2 as well as KEAP1 mutant tumors were distinguished from the NRF2/KEAP1 wild-type tumors (FIG. 3B), suggesting that NRF2 mediates most of the transcriptional consequences of KEAP1 loss/mutation. Interestingly, there were several squamous NSCLC tumors that showed high expression of the KEAP1 mutant genes without any known mutations in either KEAP1 or NRF2. Of the 27 genes up-regulated in the KEAP1 mutant cell lines, proteomic data was available for 17 in a smaller sub-set of cell lines (37 wild-type KEAP1, 6 mutant KEAP1). Consistent with the increased levels of mRNA of these genes in the mutant KEAP1 cell lines, the protein targets of all but one of these 17 genes (SLC7A11, which had low peptide coverage) also showed increased expression in the mutant KEAP1 cell lines relative to the wild-type cell lines (FIG. 4).

Example 4

Identification of Aberrant Splicing of NRF2 in Tumor Samples

Figure 5:
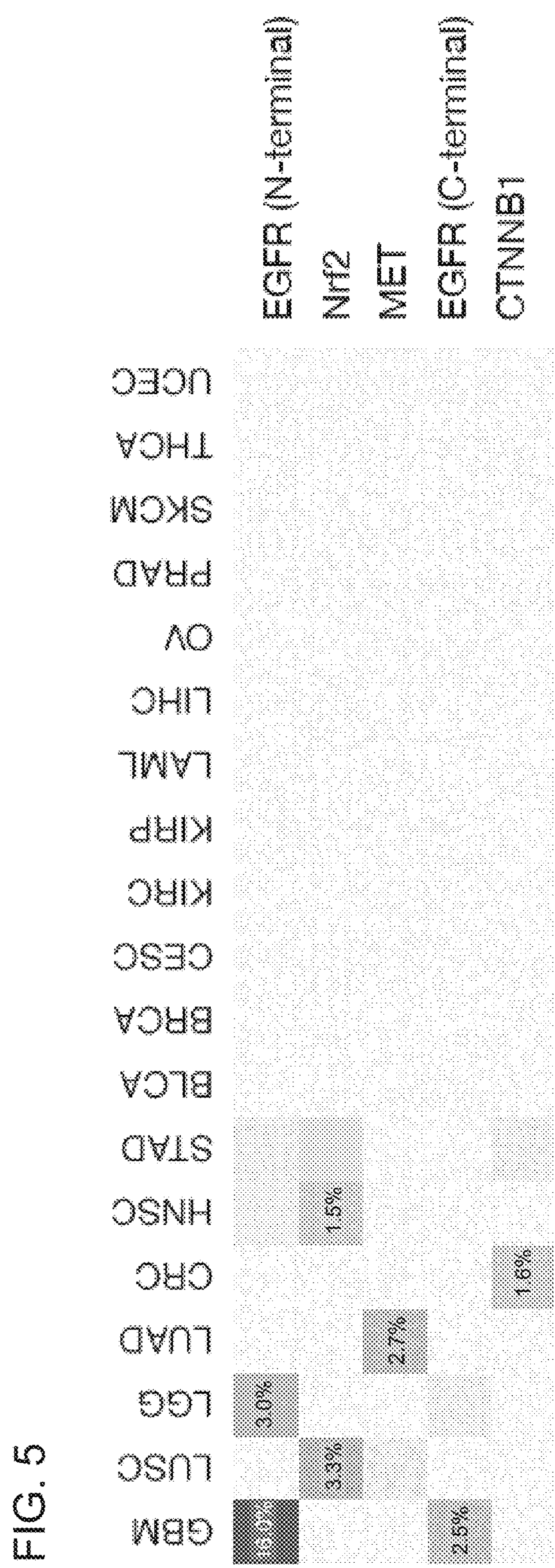
FIG. 5 is a heatmap indicating the frequency of recurrent splice alterations seen in 19 tumor indications.
Figure 6:
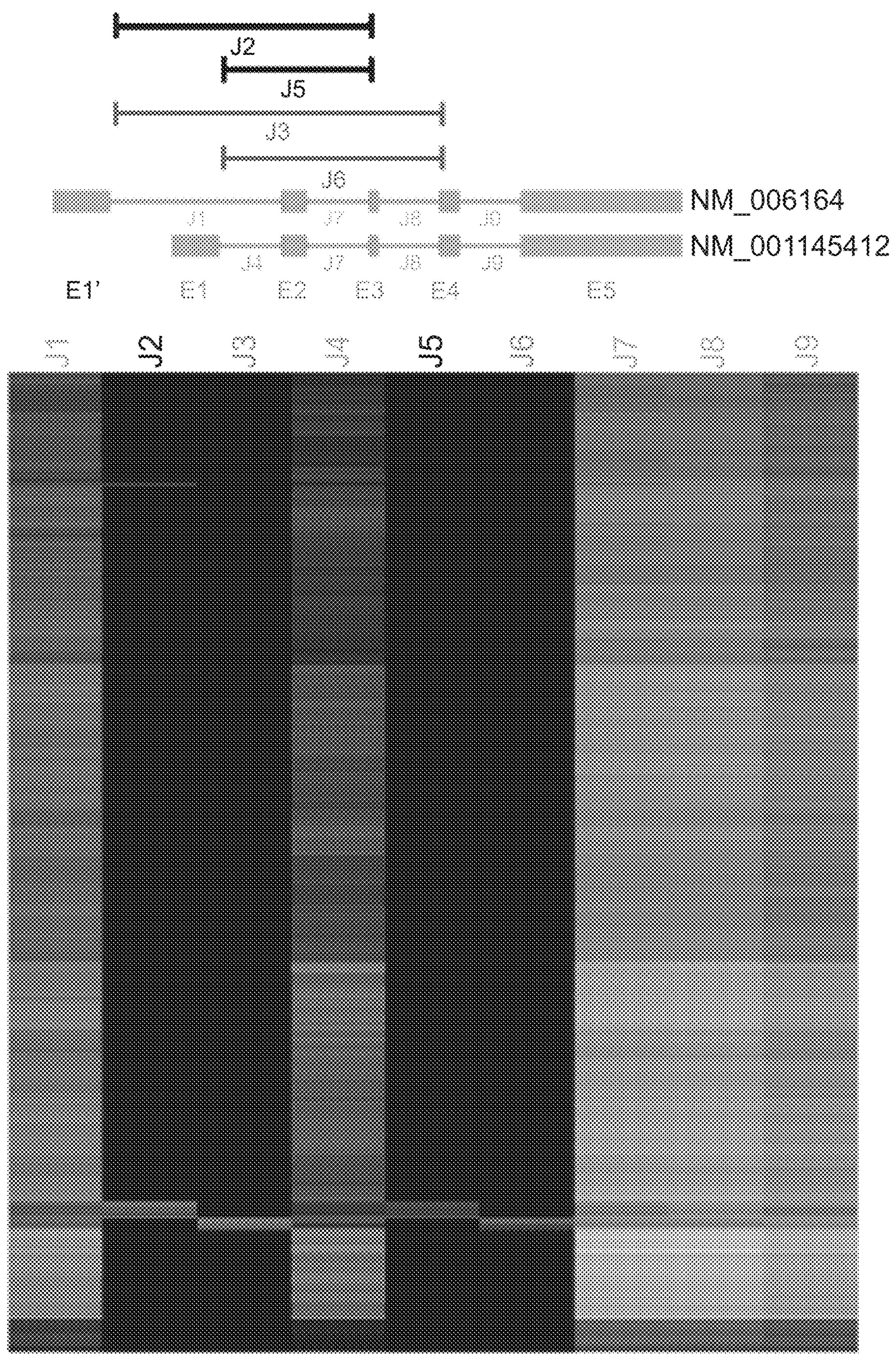
FIG. 6 shows the NRF2 exons and splice junctions predicted from RNA-seq data. Predicted features consistent with two annotated refGene transcripts are shown in gray. Identified exon-exon junctions corresponding to skip of exon 2 (J2, J5) or exon 2+3 (J3, J6) are shown in black and gray, respectively. A heatmap illustrates read evidence for exon-exon junctions (columns) across 482 TCGA lung squamous carcinoma (rows) on an FPKM scale after log 2(x+1) transformation.
Figure 7:
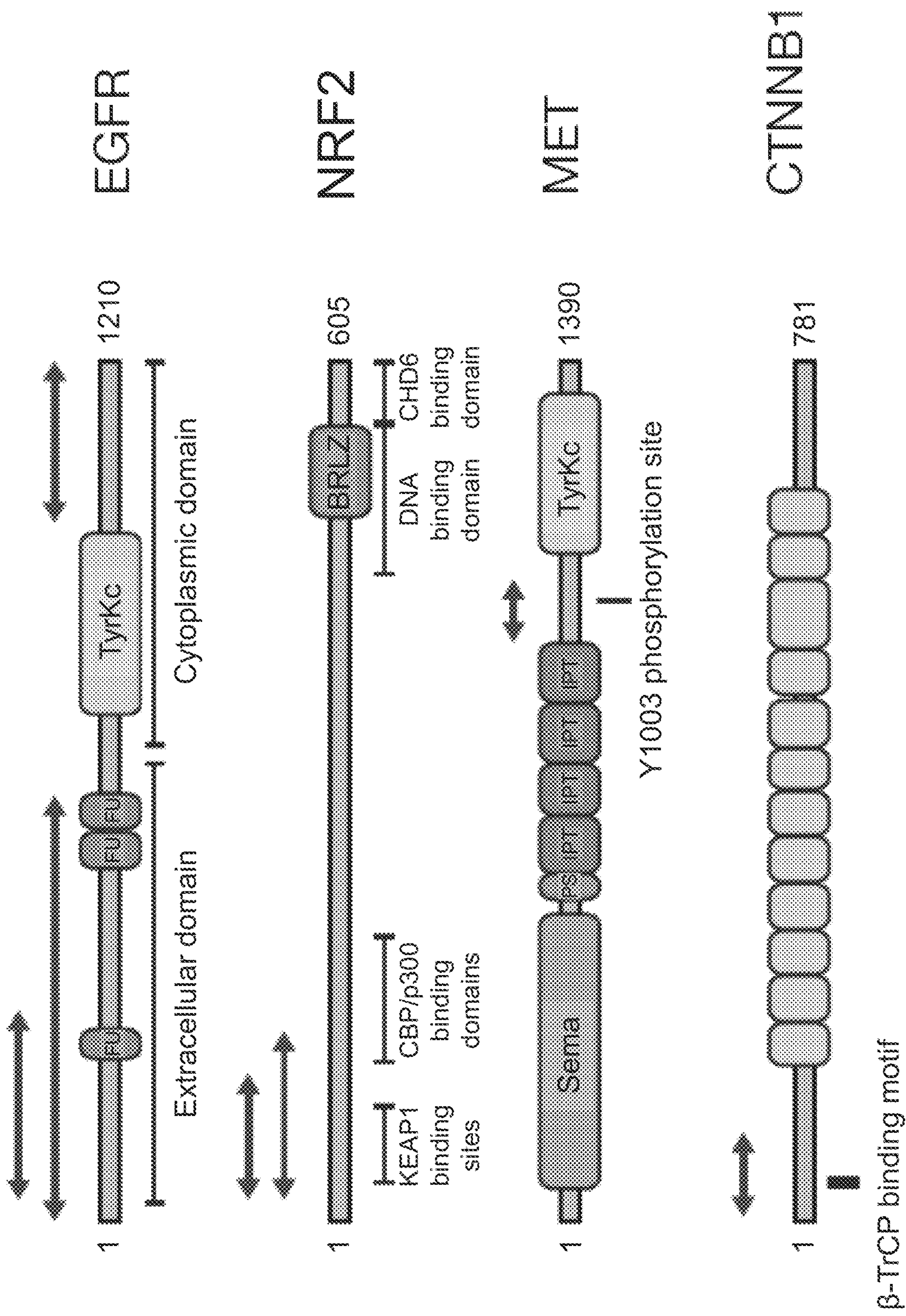
FIG. 7 is a schematic depicting the effect of splice alterations in EGFR, NRF2, MET, and CTNNB1 on protein structure. Arrows indicate in-frame deletions as the result of the splice alteration.

For the majority of tumors with high expression of the 27 candidate NRF2 target genes, elevated gene expression could be explained by mutations in KEAP1 or NRF2. However, there were some tumors that showed high expression of candidate NRF2 target genes in the absence of characterized mutations in either KEAP1 or NRF2. Cancer-associated transcript alterations are increasingly recognized as possible driver events. Therefore, it was hypothesized that NRF2 pathway activation in these tumors might be driven by splice alterations not recognized by whole-exome sequencing. 54 known oncogenes were analyzed to identify splice variants that are recurrently observed in cancer samples from the TCGA but are rarely detected in normal samples from the GTEx (see Example 1). 19 cancer types were selected, each including at least 100 cancer samples (6,359 samples in total). In the 54 considered oncogenes, nine recurrent candidate cancer-specific splice variants were identified 2 samples and >1% of samples for a given cancer type). Using the same detection criteria as in the cancer samples, none of these variants could be detected in normal controls (2,958 samples in total). Grouping together related variants with shared splice sites yielded five independent alterations in four oncogenes (FIG. 5). These alterations included several well-documented oncogenic splice variants, including EGFRvIII in brain cancers, MET exon 14 skipping in lung adenocarcinoma and CTNNB1 exon 3 deletions in colorectal cancers (Cho et al. *Cancer Res.* 71(24):7587-7596, 2011; Kong-Beltran et al. *Cancer Res.* 66(1):283-289, 2006; Iwao et al. *Cancer Res.* 58(5):1021-1026, 1998). Interestingly, previously uncharacterized splice variants in NRF2 were observed and occurred frequently in patients with squamous NSCLC (3.3%; 16/481) and at lower prevalence in patients with HNSC (1.5%; 6/403) (FIG. 5A). A more detailed analysis of NRF2 splice variants in lung squamous carcinoma revealed two splice variants co-occurring in the same patients, corresponding to a skip of NRF2 exon 2 in mRNAs transcribed from either one of two alternative promoters (2.1%; 10/481) (FIG. 6). Two additional splice variants co-occurred in a distinct set of patients (1.2%; 6/481), corresponding to a skip of both NRF2 exons 2 and 3 (exon 2+3) in mRNAs with either one of the two alternative transcript starts (FIG. 6). All patients expressing NRF2 splice variants lacking exon 2 or exon 2+3 also showed expression of normal NRF2 transcripts as evidenced by split reads supporting inclusion of exon 2. Both exons 2 and 3 are part of the NRF2 coding sequence, and skip of exon 2 or exon 2+3 are predicted to result in protein isoforms with either an N-terminal truncation or an in-frame deletion (FIG. 7). The high recurrence of NRF2 transcripts lacking exon 2 and preservation of coding potential suggest that these splice variants may present gain-of-function events conferring a selective advantage. This is supported by the finding that exon 2 encodes the Neh2 domain, which allows for interaction with KEAP1 (Itoh et al. *Genes Dev.* 13(1):76-86, 1999), which is mutated in 15% of squamous lung cancers.

Figure 8A:
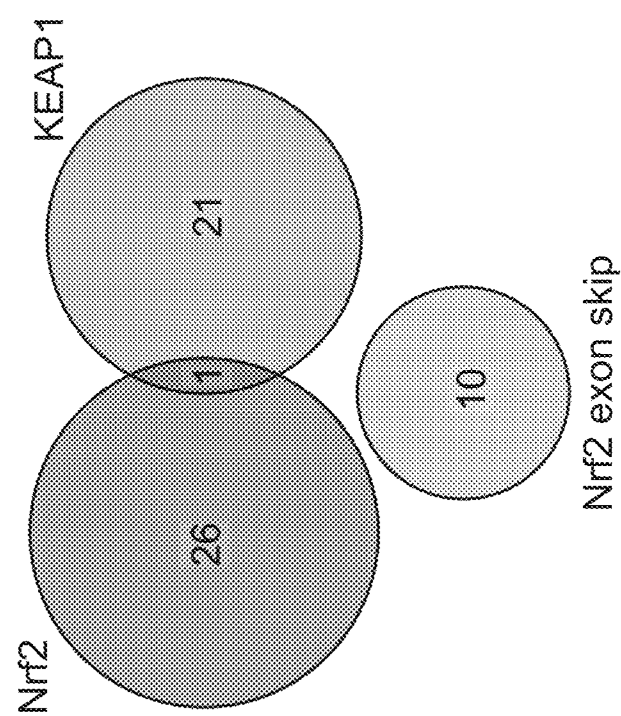
FIG. 8A is a Venn diagram illustrating the mutual exclusive occurrence of NRF2 splice alteration and mutation in KEAP1 or NRF2 in squamous NSCLC.
Figure 8B:
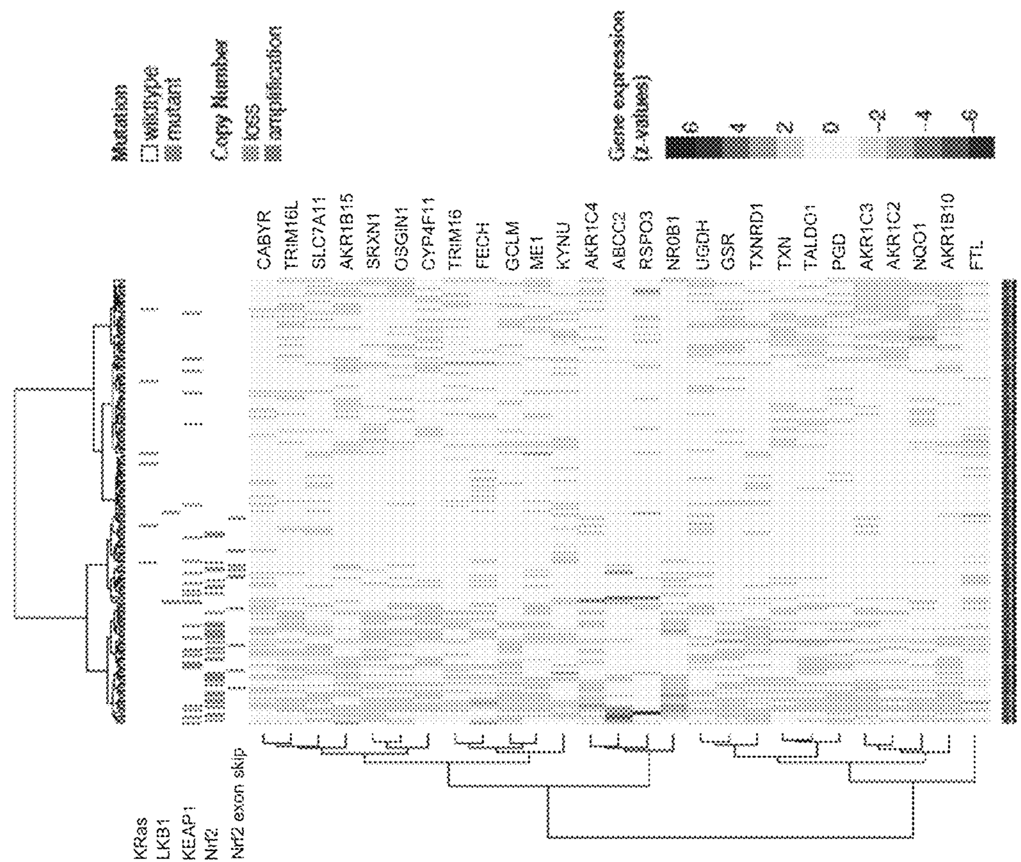
FIG. 8B is a heatmap showing clustering of squamous NSCLC based on 27 candidate NRF2 target genes. Mutation status and NRF2 splice alteration are indicated for each sample.
Figure 9B:
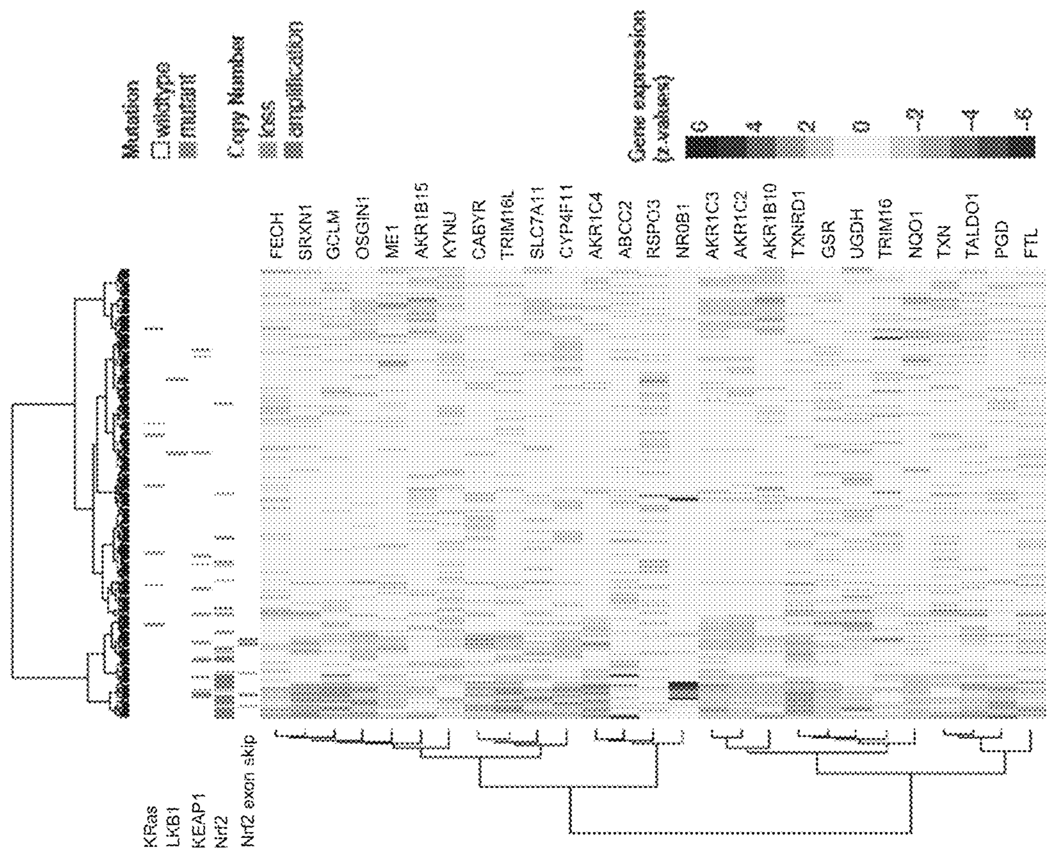
FIG. 9B is a heatmap showing clustering of head and neck cancers based on 27 candidate NRF2 target genes. Mutation status and NRF2 splice alteration are indicated for each sample.
Figure 9A:
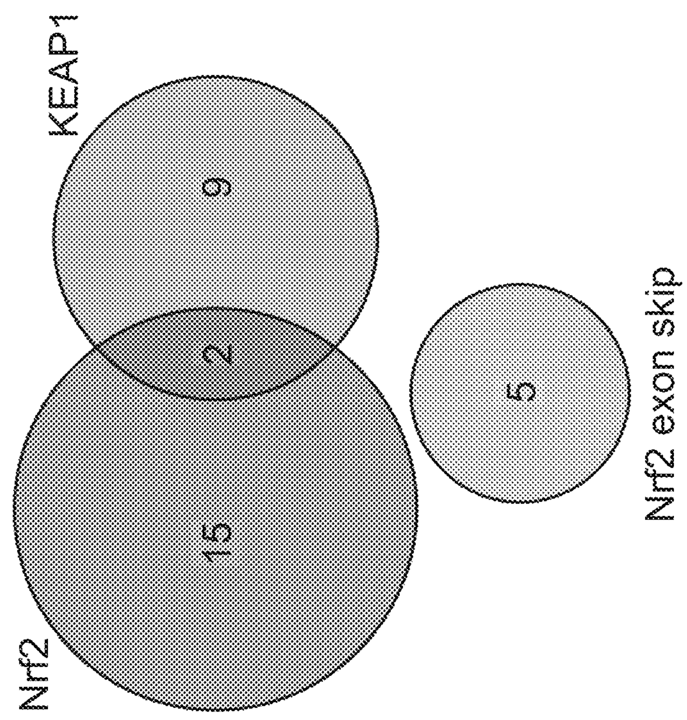
FIG. 9A is a Venn diagram illustrating the mutual exclusive occurrence of NRF2 splice alteration and mutation in KEAP1 or NRF2 in head and neck cancers.

To assess whether the observed NRF2 splice variants can account for NRF2 pathway activation in patients without mutations in KEAP1 or NRF2, co-occurrence of NRF2 splice variants and NRF2 pathway mutations were observed. In the TCGA collection, 178 of the squamous lung tumors were profiled by exome-seq. In this subset, 10 tumors (6%) displaying exon 2 or exon 2+3 deletion were mutually exclusive with 48 tumors (27%) showing mutations in either NRF2 or KEAP1 (FIG. 8A). Moreover, all exon-2 deleted tumors showed high expression of the 27 candidate NRF2 target genes (FIG. 8B). Similar observations were made for head and neck cancer, where NRF2 exon deletion in 5 tumors (2%) were mutually exclusive with mutations in NRF2 or KEAP1 in 26 tumors (9%) (FIGS. 9A-9B). These results suggest that deletion of exon 2 represents an alternative mechanism for activation of NRF2 in a subset of squamous NSCLC and head and neck tumors. Importantly, these results show that consideration of splice alterations, in addition to exome sequencing, increased the percentage of patients identified as having putative NRF2 pathway activation from 27% (48/178) to 33% (58/178) in lung squamous carcinoma and from 9% (26/275) to 11% (31/275) in head and neck squamous carcinoma.

Example 5

Validation of NRF2 Splicing Defects in Cell Lines

Figure 10:
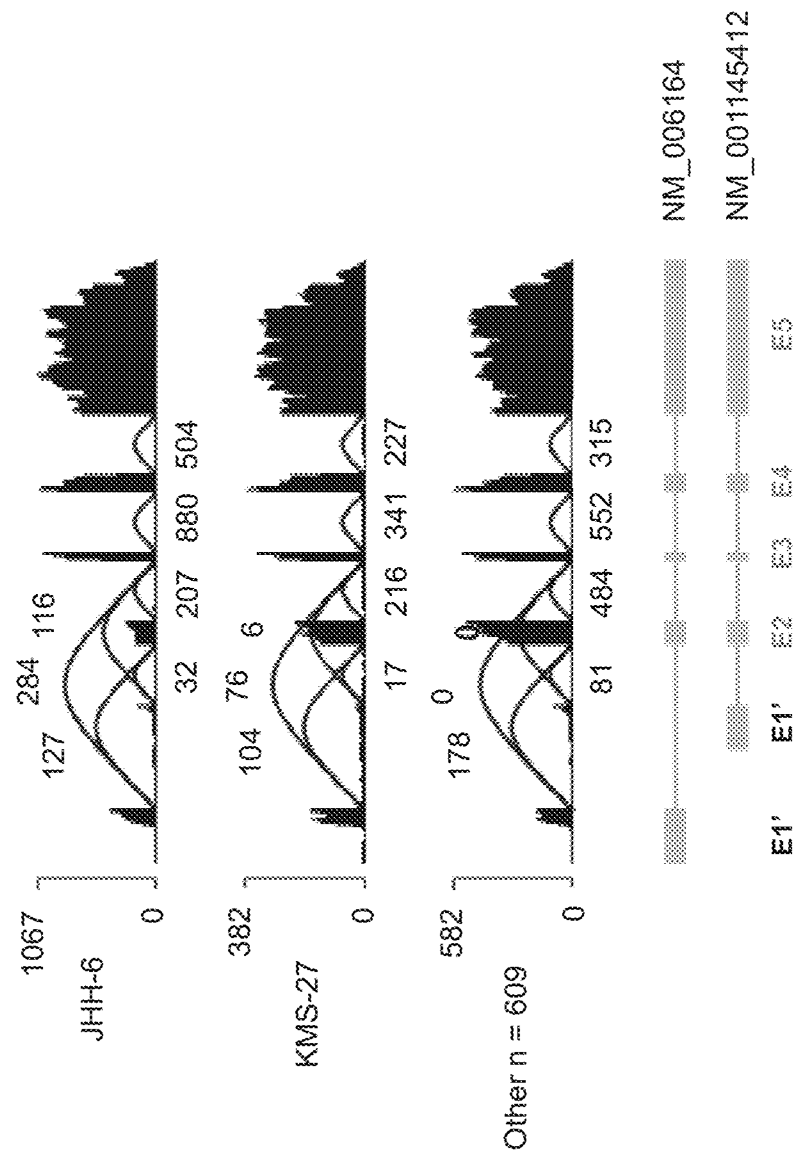
FIG. 10 is a graph showing the presence of junction reads skipping exon 2 in KMS-27 and JHH-6 cells, as quantified by RNA-seq.
Figures 11A, 11B:
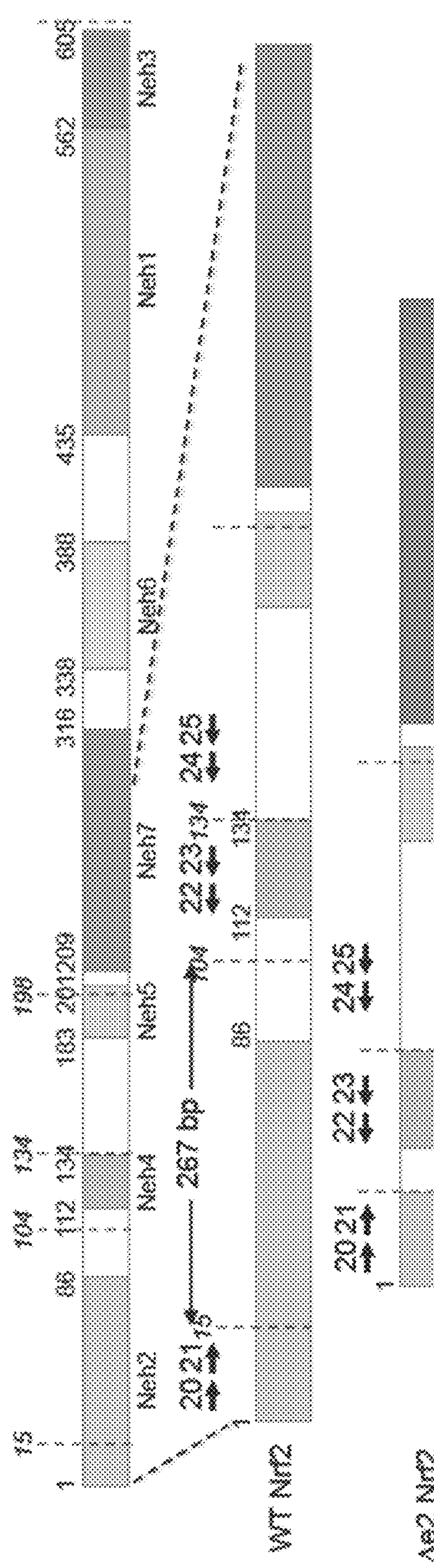
FIG. 11A is a schematic diagram showing the locations of exons within WT and exon 2-deleted NRF2 (Δe2 NRF2) mRNA, in relation to forward and reverse primers derived from exon 1 and exons 3/4, indicated by right-hand facing and left-hand facing arrows, respectively.
FIG. 11B is a series of agarose gel images showing RNA products amplified from total RNA of normal leucocytes, JHH-6 cells, and KMS-27 cells, by RT-PCR. Regions surrounding NRF2 exon 2 were amplified with the indicated primers. Fragments from wild-type NRF2, Δe2 NRF2, and primer dimers are indicated. Bands indicating the presence of Δe2 NRF2 RNA are visible in JHH-6 and KMS-27 cells.
Figures 12A, 12B, 12C:
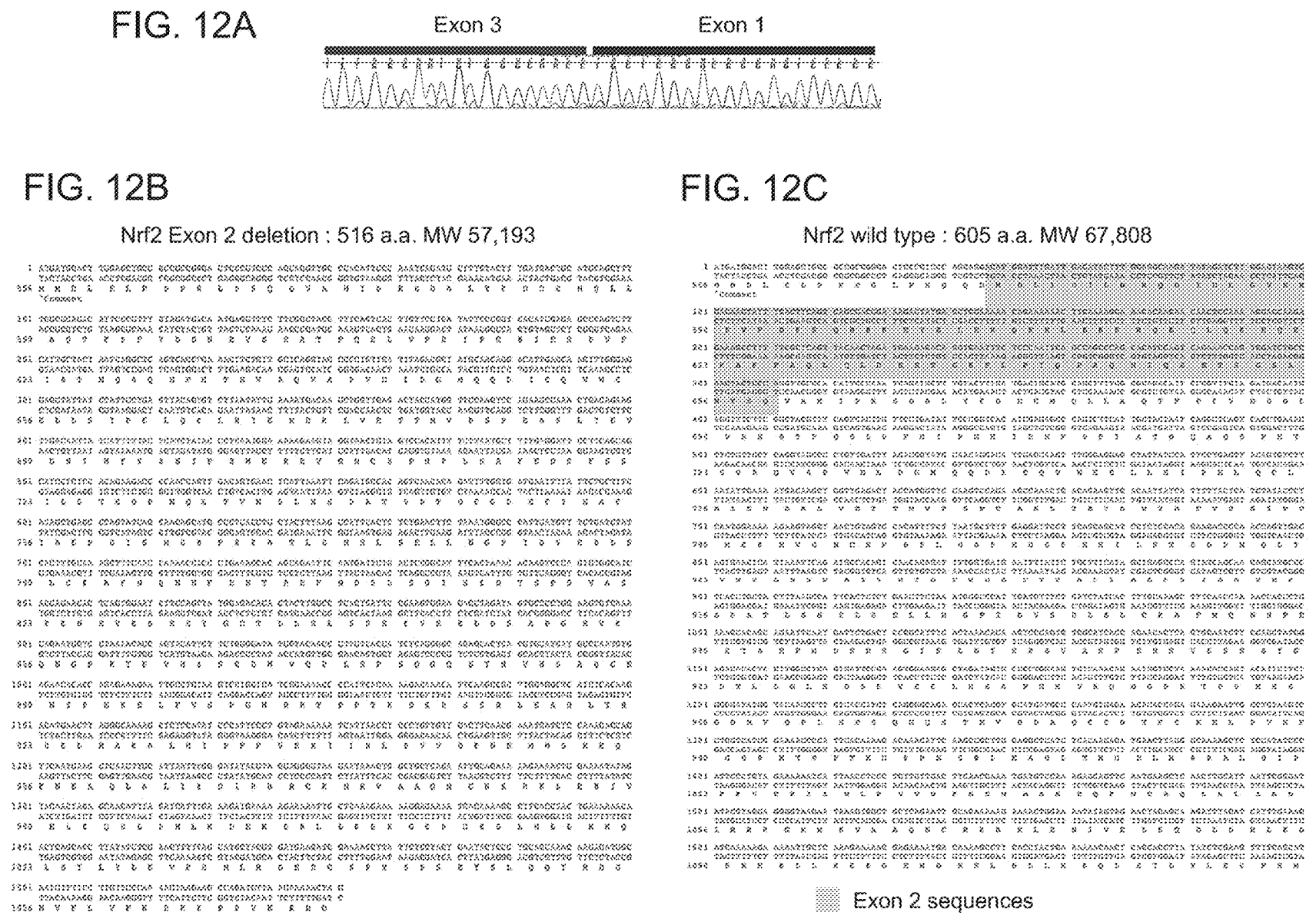

To identify cell line models for further study, read evidence for the identified splice variants in RNA-seq data was analyzed from a large panel of human cancer cell lines (described in Klijn et al. *Nat. Biotechnol.* 33(3):306-312, 2014). Out of 611 cell lines, one multiple myeloma cell line KMS-27 and one hepatocellular carcinoma cell line JHH-6 were identified, both showing evidence for heterozygous skip of NRF2 exon 2 by junction reads (FIG. 10). The NRF2 exon 2 skipping by RT-PCR in JHH-6 and KMS-27 mRNA was validated. Using a series of forward and reverse primers derived from exon 1 and exons 3/4 respectively (FIG. 11A), the exon 2 deletion (Δe2 NRF2) in mRNA isolated from JHH-6 and KMS-27 cells was confirmed (FIG. 11 B). Sequencing of the PCR products confirmed the expected deletion of exon 2 (FIGS. 12A-12C). Based on RNA-seq data no point mutations were detected in the coding sequence of NRF2 or KEAP1 in JHH-6 or KMS-27 (Klijn et al. *Nat. Biotechnol.* 33(3):306-312, 2014).

Figure 13:
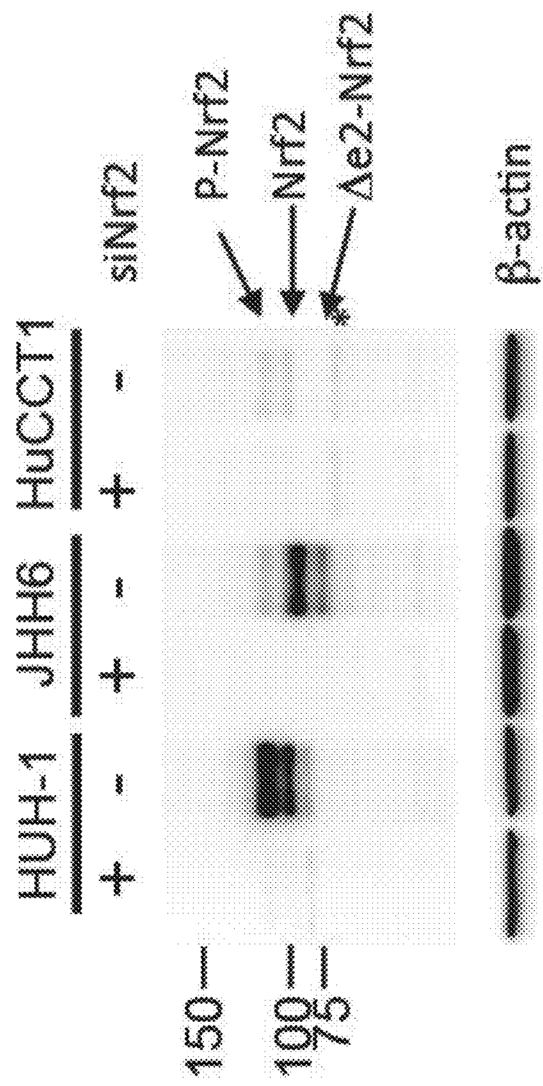
FIG. 13 shows the results of a Western blot experiment indicating the relative expression of phosphorylated NRF2, wild-type NRF2, and Δe2 NRF2 by HUH-1, JHH-6, and HuCCT1 cells. Protein lysates from the indicated cell lines were separated by SDS PAGE. * represents a likely non-specific band as it is not depleted by NRF2 siRNA transfection.
Figure 14A:
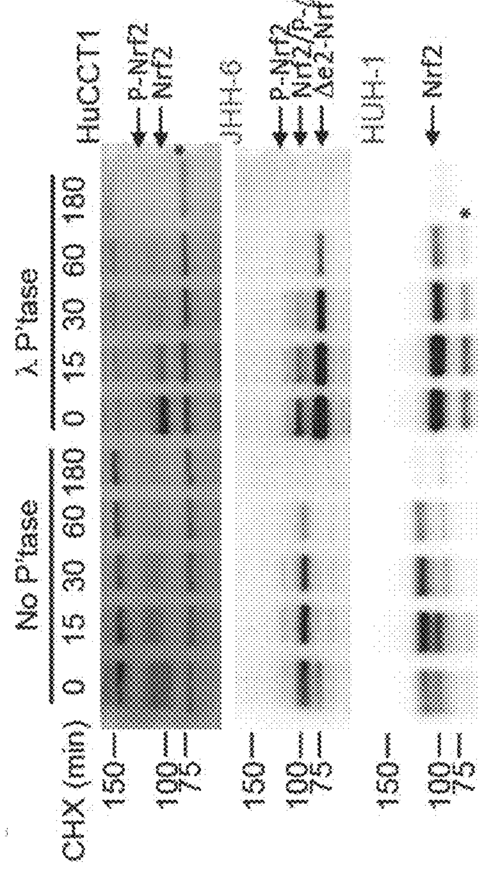
FIG. 14A shows the results of a Western blot experiment indicating the relative expression of phosphorylated NRF2, wild-type NRF2, and Δe2 NRF2 by HUH-1, JHH-6, and HuCCT1 cells in the presence and absence of lambda phosphatase (λP'tase). Cells were grown in 6-well dishes and treated with 100 μg/ml cyclohexamide (CHX) for the indicated times. The lysates were either incubated with buffer or 400 units lambda phosphatase for 30 min, before separation by SDS PAGE and Western blotting with NRF2 antibodies.
Figure 15:
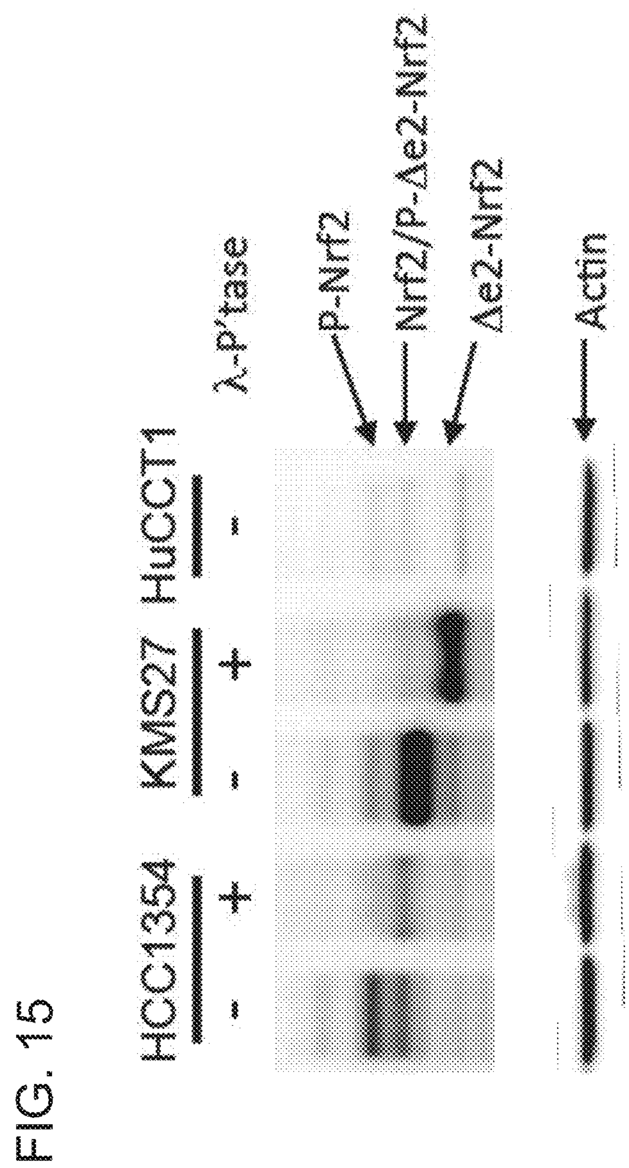
FIG. 15 shows the results of a Western blot experiment indicating the expression of Δe2 NRF2 by KMS-27 cells. 20 μg lysates from HCC-1354, KMS-27, and HuCCT1 cells were prepared, and for all except HuCCT1 treated with λ P'tase. Untreated and treated lysates were then subjected to SDS PAGE, and NRF2 and actin were detected.

As NRF2/KEAP1 alterations are fairly common in hepatocellular carcinoma (10%) but infrequent in multiple myeloma (0%), JHH-6 cells were further tested. Specifically, expression of the exon 2-deleted form of NRF2 protein was tested. Western blotting of whole-cell lysates from JHH-6 cells, as well as the KEAP1 mutant HUH-1 line, and HuCCT1 cells as a representative wild-type KEAP1 liver cancer cell line was performed. The levels of NRF2 in JHH-6 cells were comparable to those seen in HUH-1 cells, which were much higher than in the wild-type KEAP1 HuCCT1 cells (FIG. 13). Moreover, a smaller molecular weight species, consistent with a deletion of exon 2, was detectable in JHH-6 and was reduced upon NFE2L2 siRNA transfection, confirming that it indeed represents a form of NRF2. While the altered NRF2 isoform was visible, it was surprising that it was not more abundant, given the lack of KEAP1 interaction motifs. It was hypothesized that a phosphorylated form of exon 2-deleted NRF2 might co-migrate with the unphosphorylated form of wild-type NRF2 in the 4-12% gels used. Indeed, dephosphorylation of JHH-6 lysates showed that the exon 2-deleted form of NRF2 was significantly more abundant than the wild-type form (FIG. 14A, middle panel). Similarly, KMS-27 cells expressed the exon 2-deleted form of NRF2, which was the major species apparent upon dephosphorylation (FIG. 15).

Figure 14B:
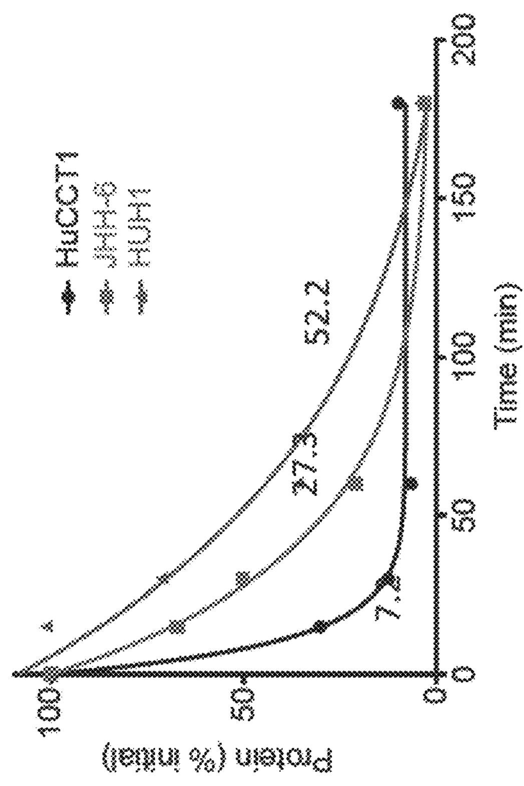
FIG. 14B is a graph showing the stability of NRF2 protein expressed by HuCCT1 cells (circles), JHH-6 cells (squares), and HUH1 cells (triangles) in the presence of CHX. Band intensities from the results shown in FIG. 14A were quantified and fitted to a one-phase decay curve to obtain protein half-life estimates, which are indicated next to each curve. Relative protein expression was taken as a percent of initial concentration of each cell line.
Figure 16:
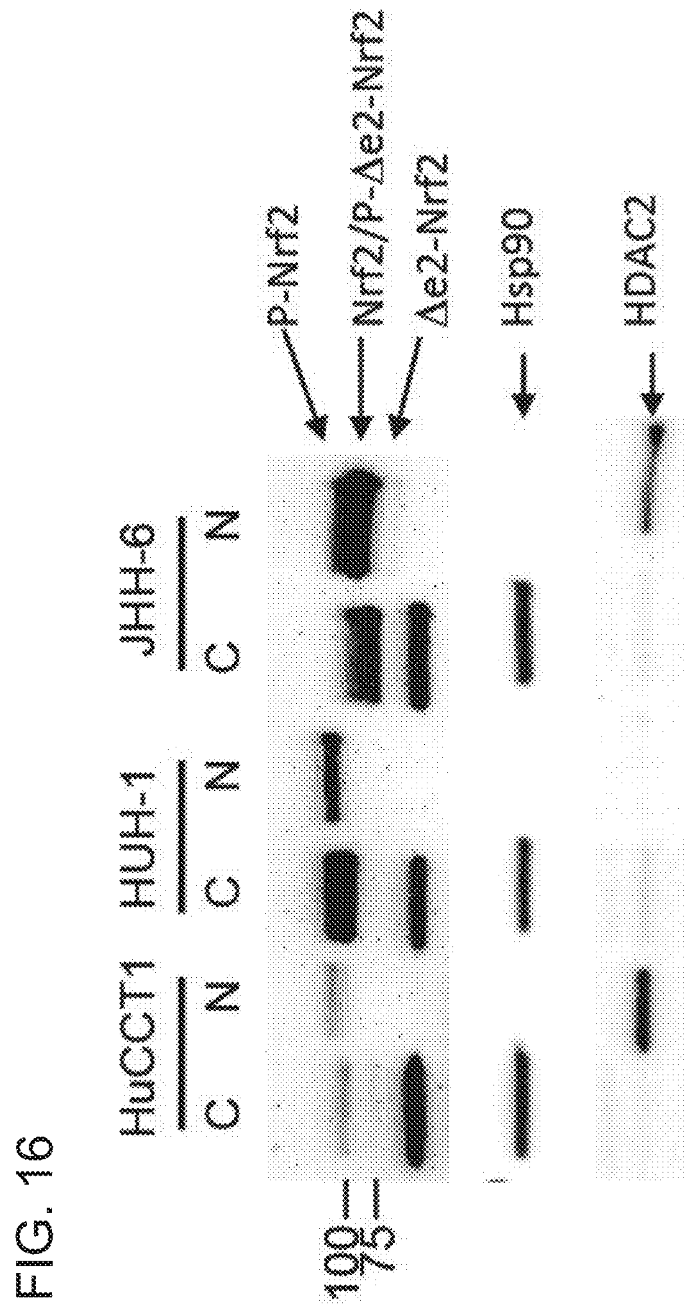
FIG. 16 shows the results of a Western blot experiment indicating nuclear localization of NRF2. HuCCT1, HUH-1, and JHH-6 cells were grown in 10 cm dishes and partitioned into nuclear and cytosol fractions. Fractions were separated by SDS PAGE and NRF2 was visualized. Nuclear and cytosolic purity was estimated using Hsp90 as a cytosolic marker and HDAC2 as a nuclear marker.

The stability of NRF2 in the three liver cancer cell lines was tested using cycloheximide to abolish total protein synthesis. Dephosphoryalted lysates were used to allow more accurate quantification of total NRF2. The experiments showed increased stability of Δe2 NRF2 in JHH-6 cells, comparable to NRF2 in HUH-1 cells, which were both more stable than NRF2 in HuCCT1 cells (FIGS. 14A-14B). The exon 2-deleted form of NRF2 in JHH-6 cells also showed prominent nuclear localization, also when compared to HUH-1 cells (FIG. 16).

Figure 14D:
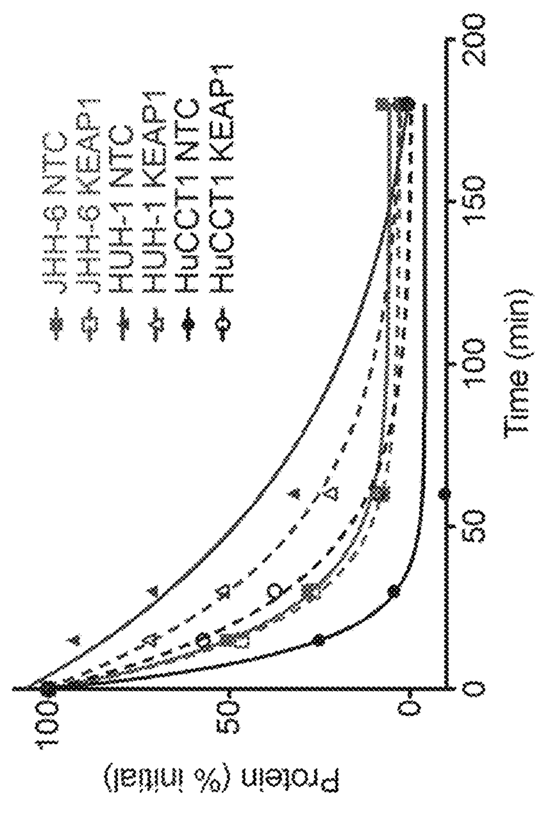
FIG. 14D is a graph showing the stability of NRF2 protein expressed by HuCCT1 cells (circles), JHH-6 cells (squares), and HUH1 cells (triangles) in the presence of CHX after tranfection with siNTC (solid lines) or siKEAP1 (dashed lines). Band intensities from the results shown in FIG. 14C were quantified and fitted to a one-phase decay curve to obtain protein half-life estimates, which are indicated next to each curve. Relative protein expression was taken as a percent of initial concentration of each cell line.
Figure 14C:
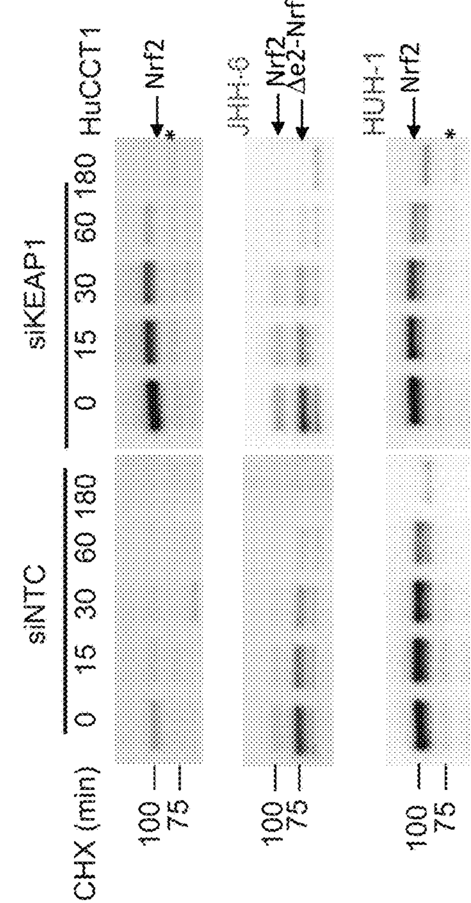
FIG. 14C shows the results of a Western blot experiment indicating the relative expression of NRF2 and Δe2 NRF2 by HUH-1, JHH-6, and HuCCT1 cells after tranfection with either siNTC (50 nM) or siKEAP1 (50 nM). Cells were grown in 6-well dishes and treated with 100 μg/ml cyclohexamide (CHX) for the indicated times. The lysates were incubated with 400 units lambda phosphatase for 30 minutes, before separation by SDS PAGE and Western blotting with NRF2 antibodies.

To determine whether the deletion of exon 2 in JHH-6 cells made NRF2 refractory to regulation by KEAP1, the stability of NRF2 in response to KEAP1 knockdown was tested. Knockdown of KEAP1 in HuCCT1 cells resulted in increased steady state levels of NRF2 due to increased stability (FIG. 14C). However, knockdown of KEAP1 in JHH-6 cells did not affect the levels or stability of exon 2-deleted NRF2. As expected, knockdown of KEAP1 did not increase the stability of wild-type NRF2 in the KEAP1 mutant HUH-1 cell line (FIG. 14D).

Example 6

Assessment of Exon 2 and/or Exon 2+3 Deletion on NRF2

Figure 17B:
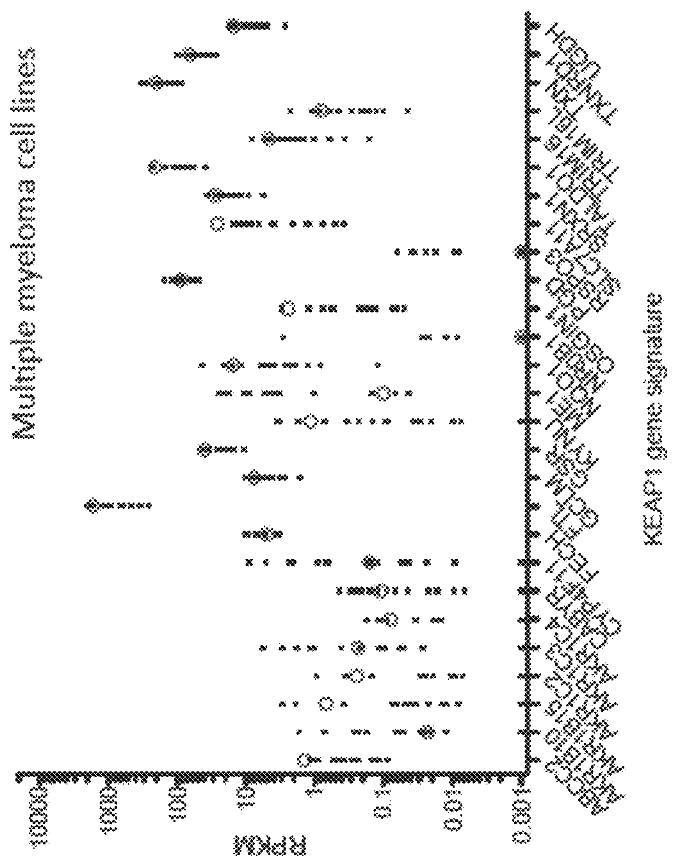
FIG. 17B is a graph showing the expression of the 27 signature NRF2 target genes of the KEAP1 gene signature (each displayed on the x-axis) in 18 multiple myeloma cell lines (represented by black squares and open gray circles) using RNA-seq data described in Klijn et al. (*Nat. Biotechnol.* 33(3):306-312, 2014). Open gray circles represent the KMS-27 cell line.
Figure 17A:
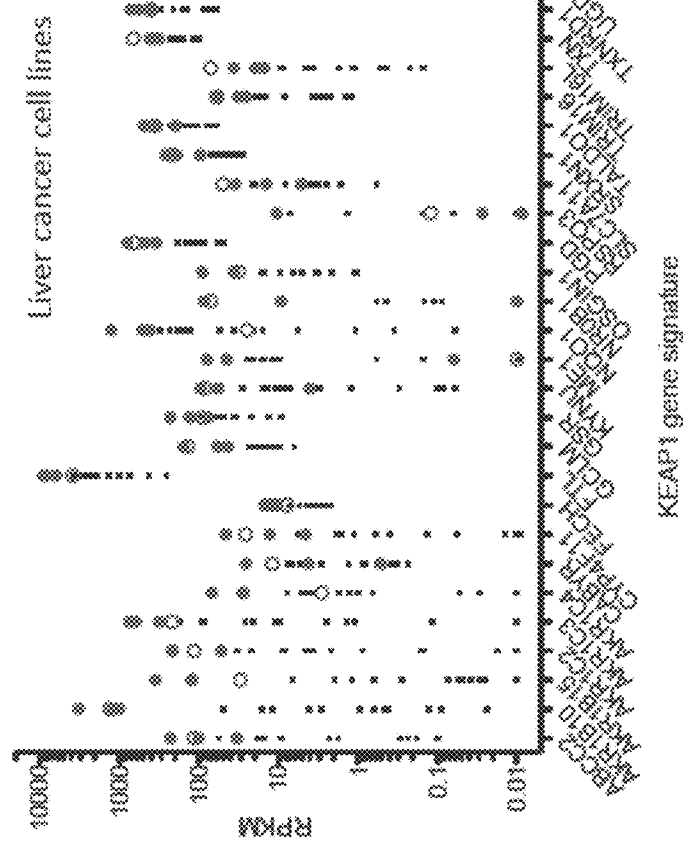
FIG. 17A is a graph showing the expression of the 27 signature NRF2 target genes of the KEAP1 gene signature (each displayed on the x-axis) in 16 hepatocellular carcinoma cell lines (represented by black squares, filled gray circles, and open gray circles) using RNA-seq data described in Klijn et al. (*Nat Biotechnol.* 33(3):306-312, 2014). Filled gray circles represent mutant KEAP1 liver cancer cell lines, and open gray circles represent the JHH-6 cell line.
Figure 18B:
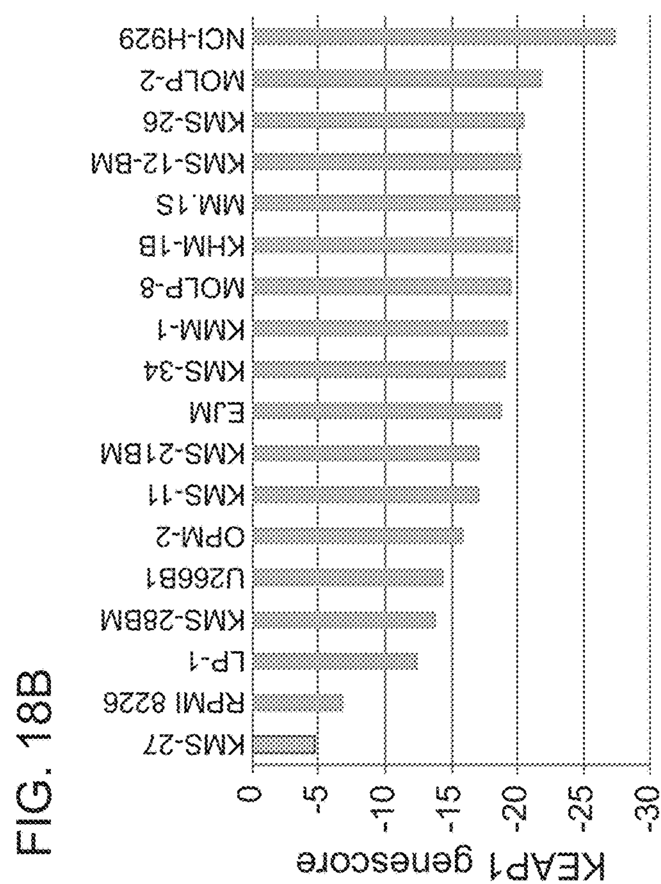
FIG. 18B is a bar graph showing the NRF2 target gene score (mean z-scores for the 27 NRF2 target genes determined over the full data set) in the 18 multiple myeloma cell lines. The outlined box indicates a NRF2 alteration.
Figure 18A:
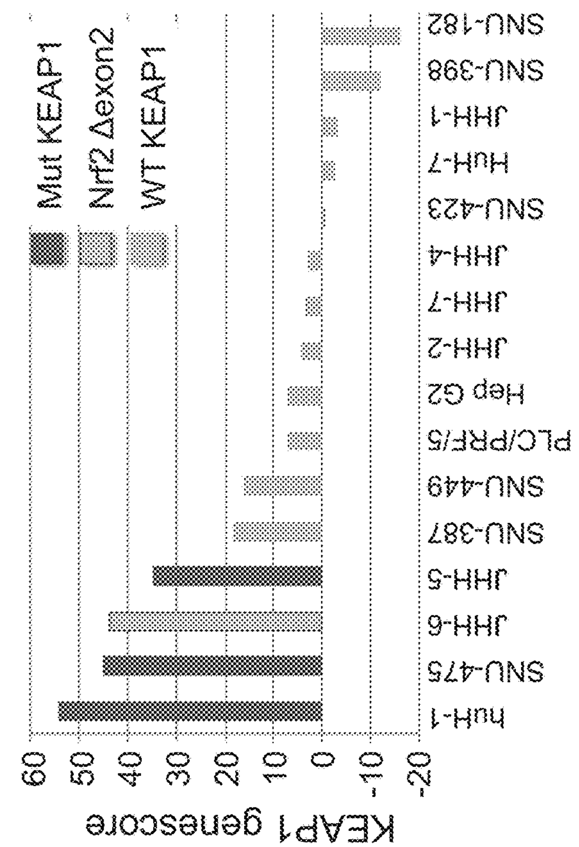
FIG. 18A is a bar graph showing the NRF2 target gene score (mean z-scores for the 27 NRF2 target genes determined over the full data set) in the 16 hepatocellular carcinoma cell lines. KEAP1 and NRF2 alterations are indicated as filled and outlined boxes, respectively.

Utilizing the NRF2/KEAP1 gene signature described in Example 3, it was determined that, of 16 hepatocellular carcinoma cell lines, JHH-6 cells show among the highest expression of NRF2 target genes from RNA-seq data, similar to those seen in mutant KEAP1 expressing lines (FIG. 17A). Similarly, out of 18 multiple myeloma cell lines examined, KMS-27 cells show among the highest expression of these genes (FIG. 17B). Expression of these genes can be summarized by a "NRF2 target gene score" calculated as the mean of z-scores for individual target genes across the 611 cell lines examined. This results in a single score per cell line that reflects the extent of overexpression of signature genes in the given line. The NRF2 target score confirms that JHH-6 cells show a similar score as liver cancer cell lines expressing KEAP1 mutations (FIG. 18A) and KMS-27 cells show the highest score among multiple myeloma cell lines (FIG. 18B), despite multiple myeloma showing a low overall NRF2 target gene score (indicated by the negative values).

Figure 19:
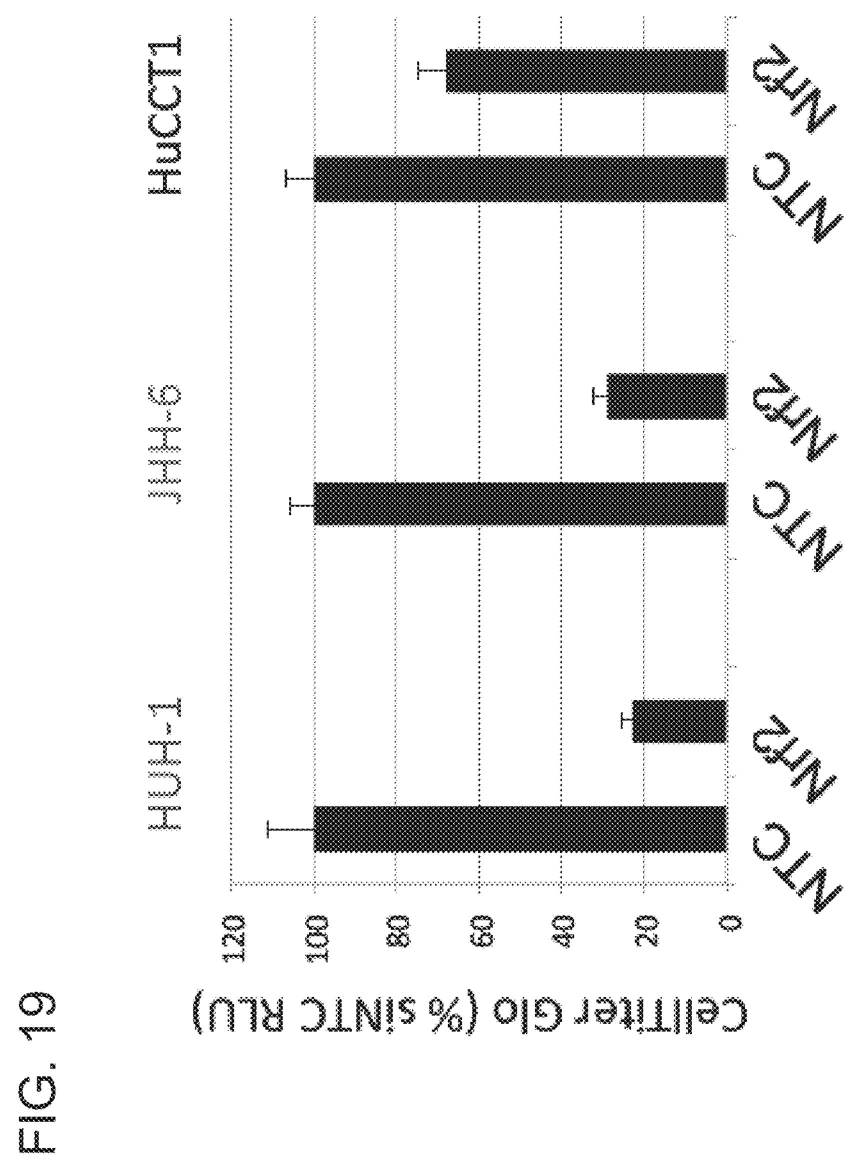
FIG. 19 is a bar graph showing the viability of HUH-1, JHH-6, and HuCCT1 cells in the presence or absence of siRNAs targeting NRF2. Cells were seeded into 96-well plates containing either a non-targeted siRNA control (NTC), or siRNA targeting NRF2 (NRF2). Viability was measured 4 days later using CellTiter-Glo. Viability is presented as a percentage of NTC luminescence.
Figure 21:
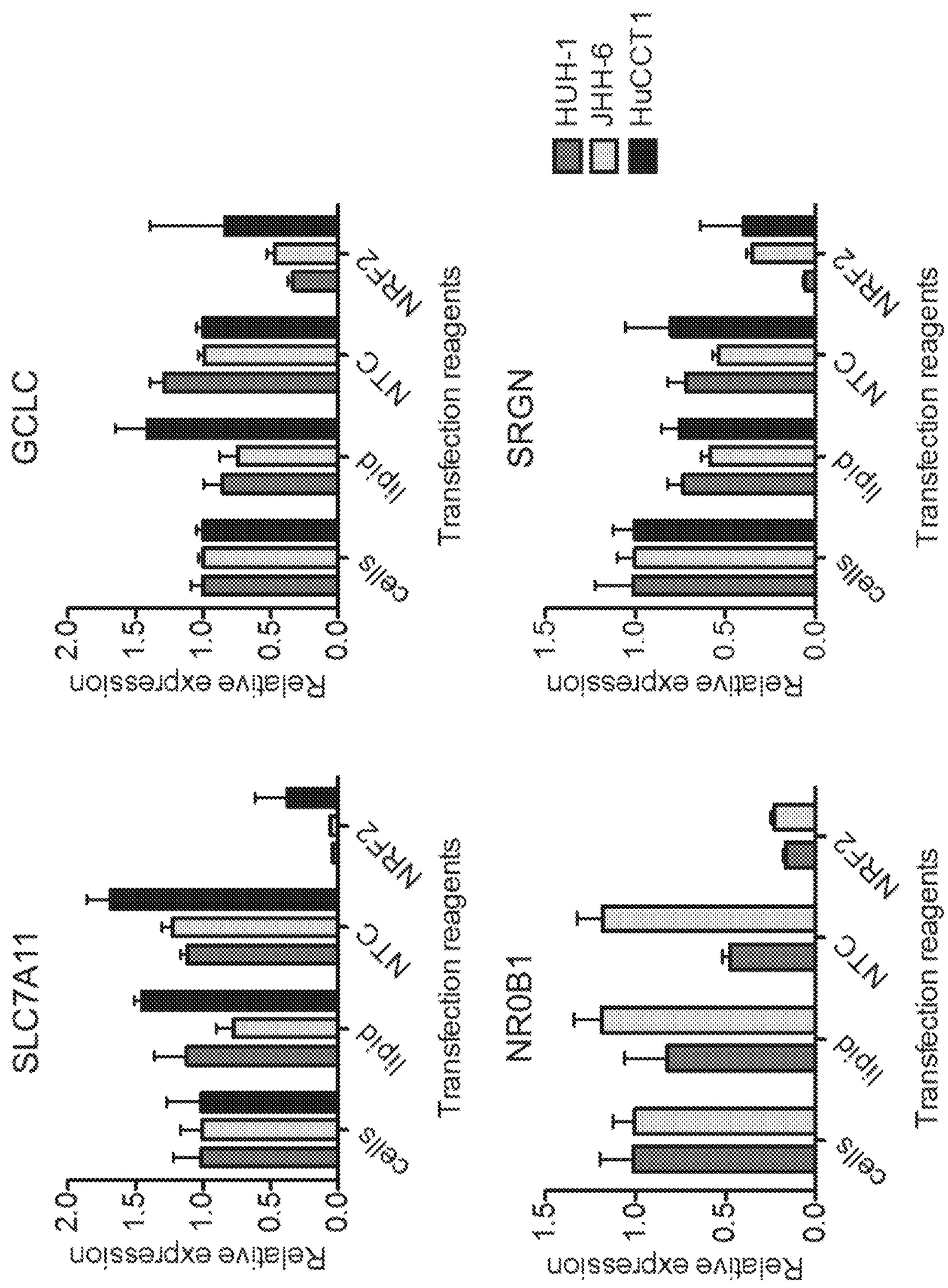
FIG. 21 is a series of bar graphs showing the effect of transfection reagents on four well-characterized NRF2 target genes, SLC7A11, GCLC, NR0B1, and SGRN, expressed by HUH-1 cells (dark gray shaded bars), JHH-6 cells (light gray shaded bars), and HuCCT1 cells (black shaded bars). Cells were grown in 6-well dishes and transfected with siRNA targeting NRF2exon 5 of NRF2, or non-targeted siRNA (NTC). Total RNA was isolated after 48 hours, and gene expression was measured using Taqman probes targeting the indicated NRF2 target genes.
Figure 22:
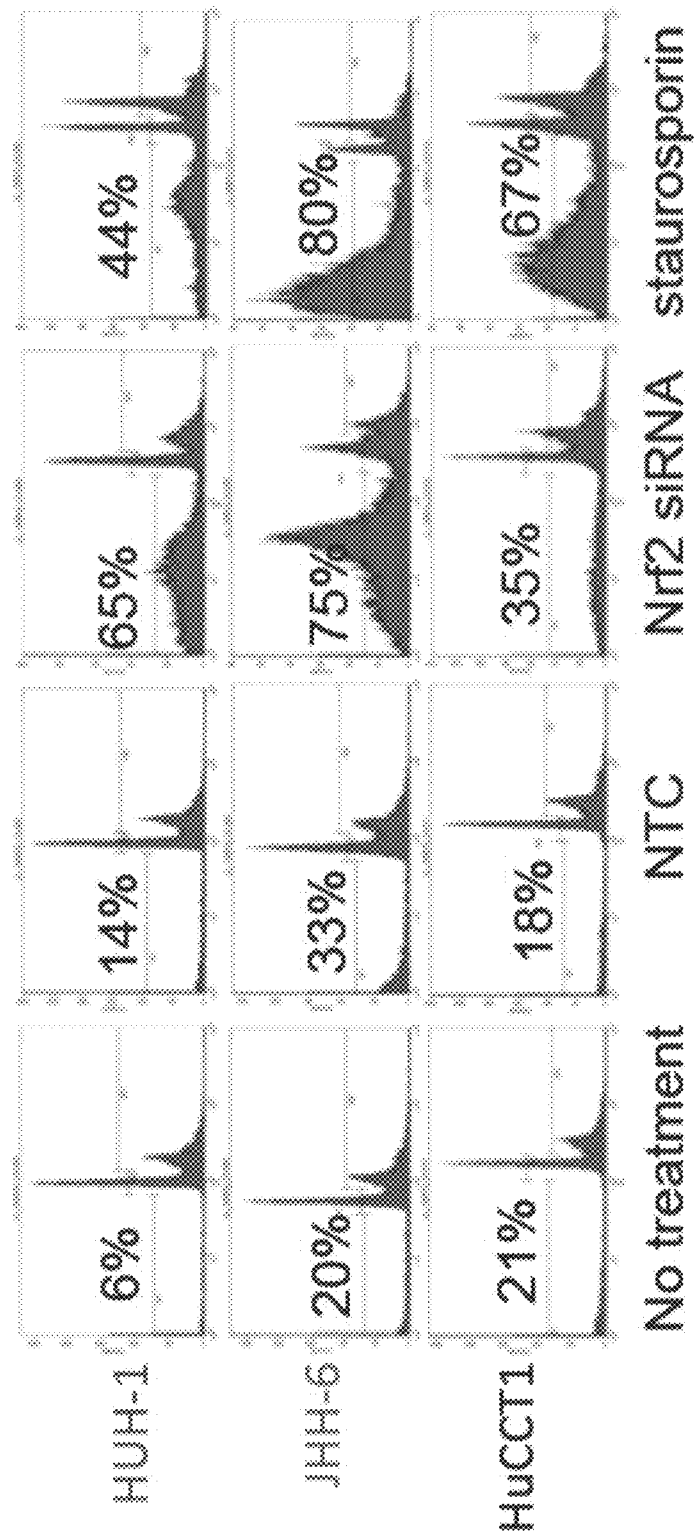
FIG. 22 is a series of representative FACS histograms showing the effect of NRF2 targeting siRNA on DNA fragmentation in HUH-1, JHH-6, and HuCCT1 cells. Cells were treated with staurosporin as a positive control.

Next, the dependence of JHH-6 cells expressing exon 2 deleted NRF2 on the expression of NRF2 protein was compared to wild-type NRF2 expressing HuCCT1 cell. Knockdown of NRF2 in JHH-6 cells caused a marked decrease in cell viability, similar to that seen in the mutant KEAP1 hepatocellular carcinoma cell line HUH-1. In contrast, NRF2 knockdown had a more modest effect on the viability of HuCCT1 cells (FIG. 19). This was not due to defective NRF2 knockdown in HuCCT1 cells, as NRF2 knockdown was equally efficient in all three cell lines (FIG. 20). Knockdown of NRF2 also resulted in decreased expression of four well-characterized NRF2 target genes, although this was slightly reduced in the wild-type KEAP1 HuCCT1 cell line (FIG. 21). Decreased viability was likely due, at least in part, to apoptosis as measured by an increase in fragmented DNA (FIG. 22).

Figure 23:
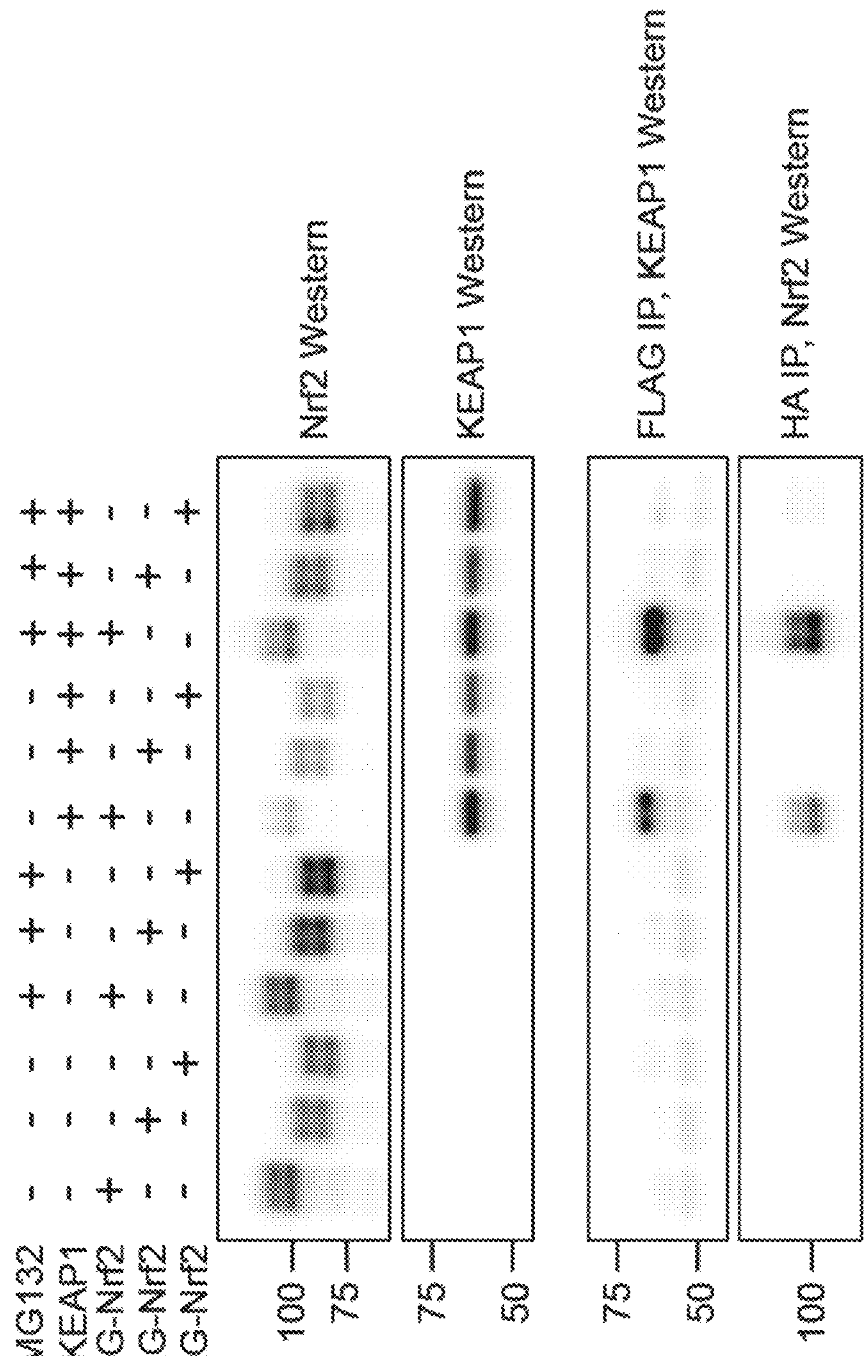
FIG. 23 is a set of immunoblots showing the effect of NRF2 exon 2 and exon 2+3 deletions on KEAP1 interaction. 293 cells were transfected with plasmids expressing FLAG-NRF2, Δe2 FLAG-NRF2, Δe2+3 FLAG-NRF2 or HA-KEAP1. 48 hours after transfection, cells were lysed, and either lysates (top gel) or anti-FLAG immunoprecipitations were analyzed by Western blotting using the indicated antibodies.
Figure 24A:
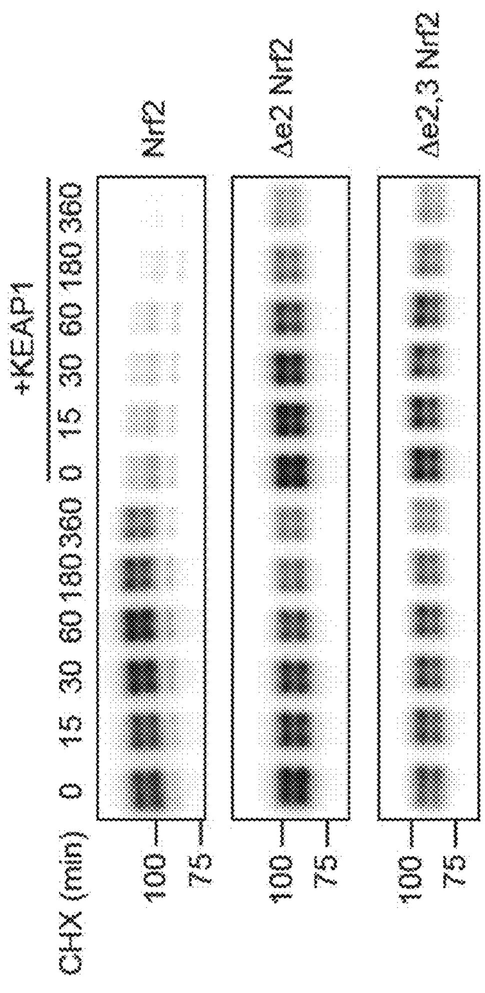
FIG. 24A is a set of immunoblots showing the effect of cyclohexamide on NRF2 stability. 293 cells were transfected with the same plasmids as described in FIG. 23 and treated with 100 μg/ml cycloheximide (CHX) for the indicated times. Cells were lysed and separated by SDS PAGE, and Western blotted using NRF2 and anti-actin antibodies.
Figure 24B:
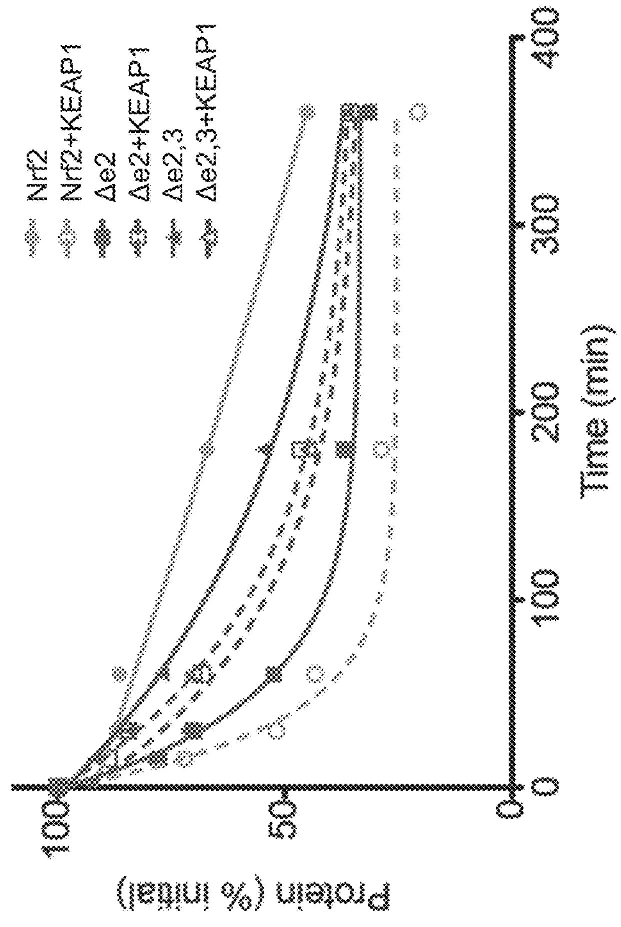
FIG. 24B is a graph showing the stability of truncated NRF2 following KEAP1 expression over time.
Figure 25:
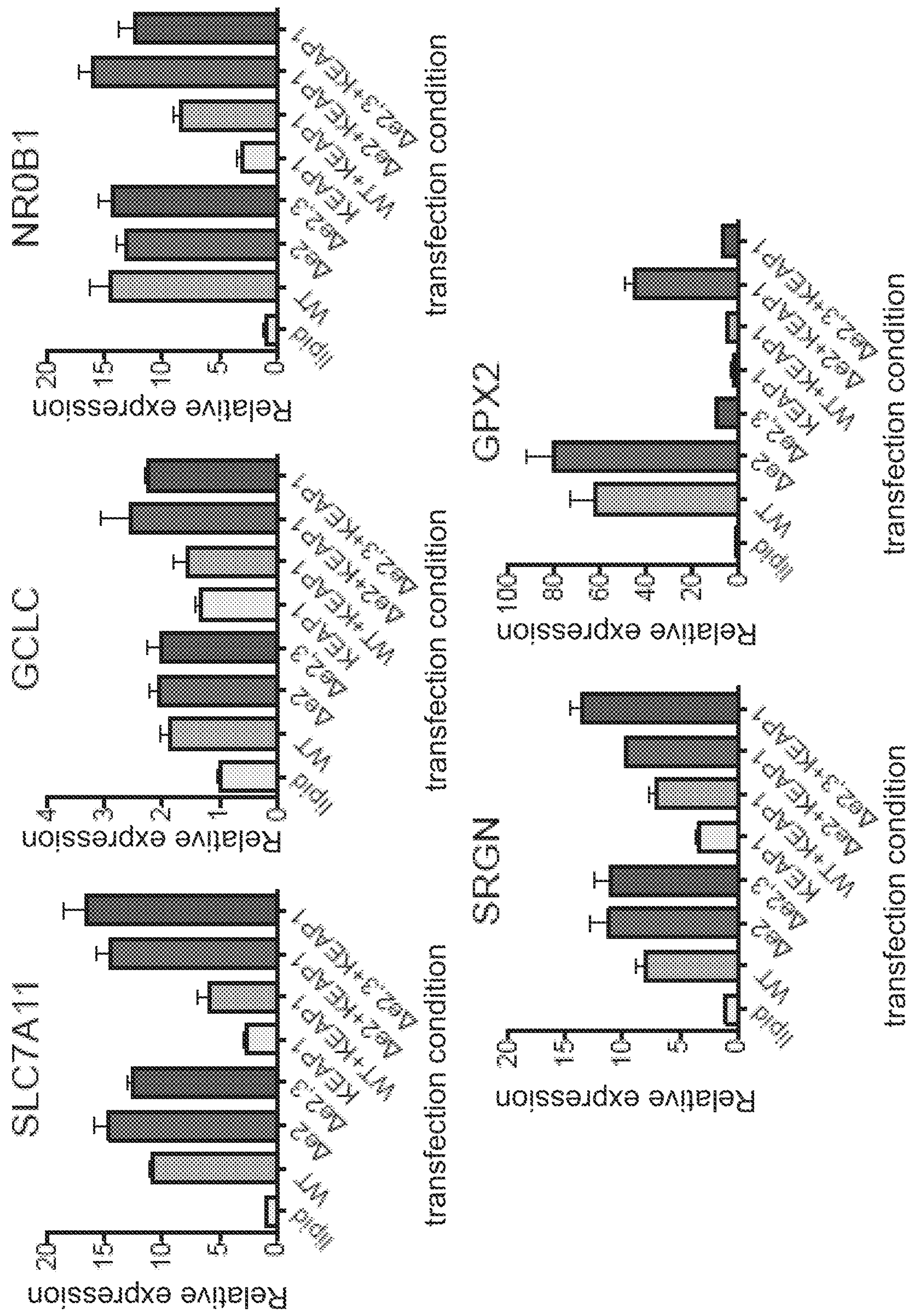
FIG. 25 is a series of bar graphs showing the expression of various NRF2 target genes under various transfection conditions. Cells were treated as in FIGS. 24A-24B but harvested for total RNA, which was used to analyze the expression of the indicated genes using Taqman RT-PCR.

To address how loss of NRF2 exon 2 affects the ability of NRF2 to be regulated by KEAP1, transient expression in 293 cells was used. KEAP1 decreased the expression of full-length NRF2, but had lesser effects on the expression of NRF2 lacking exon 2 or exons 2+3 (FIG. 23, upper panels). The inhibitory effect of KEAP1 on full-length NRF2 expression was mostly abolished by proteasome inhibitor MG132, as expected. Full-length NRF2 and KEAP1 interacted with each other, whereas deletion of exon 2 or exon 2+3 completely abolished the ability of KEAP1 to bind NRF2 (FIG. 23, lower panels). As a result, truncated NRF2 remained stable following KEAP1 expression, in contrast to wild-type NRF2 (FIGS. 24A-24B), although the truncated forms of NRF2 appeared to have slightly decreased intrinsic stability. However, altered NRF2 isoforms were transcriptionally active, as judged by their ability to increase NRF2 target gene expression (FIG. 25). Most genes were similarly increased by exon 2- or exon 2+3-deleted NRF2 compared to full-length NRF2 and were resistant to the effects of KEAP1 overexpression. Interestingly, exon 2+3-deleted NRF2 was defective for increasing GPX2 expression, suggesting that there might be subtle differences in the transcriptional activation of this form of NRF2. Consistent with this observation, 22 of the 27 target genes described in Example 3, in addition to GPX2, showed lower median expression in exon 2+3-deleted squamous lung tumors compared to exon 2-deleted tumors (FIG. 26).

Example 7

Mechanistic Analysis of NRF2 Exon 2 Splice Alteration

Figure 27B:
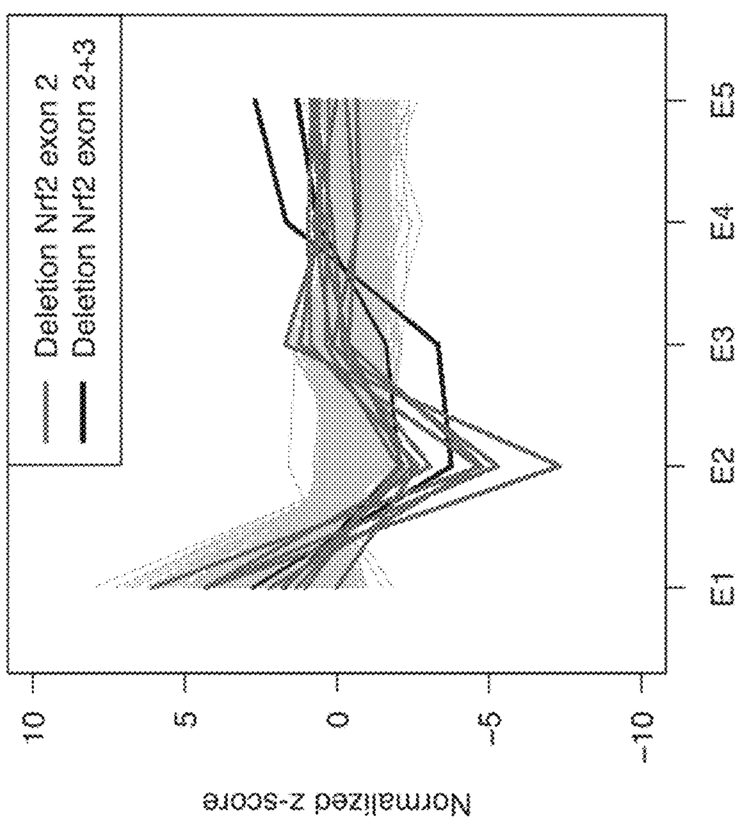
FIG. 27B is an exome-seq graph showing normalized z-scores for exon read coverage across 1,218 squamous NSCLC tumors. Eleven tumors showing decreased read count for exon 2 or exon 2+3 are compared to nearby control regions.
Figure 27A:
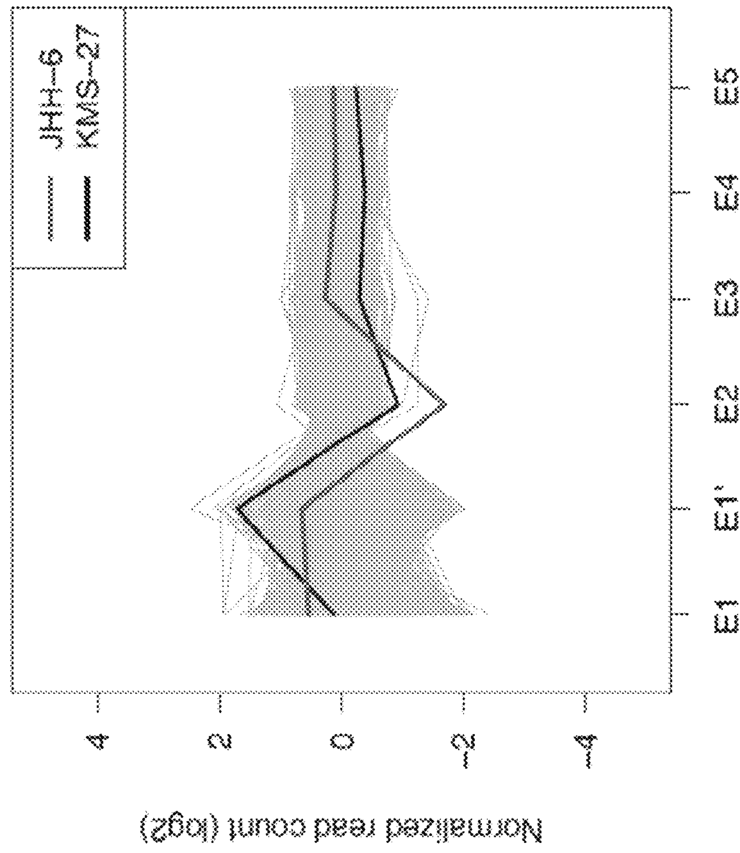
FIG. 27A is an exome-seq graph showing relative NRF2 exon abundance across 808 cancer cell lines, showing a decrease in reads mapping to exon 2.
Figure 28A:
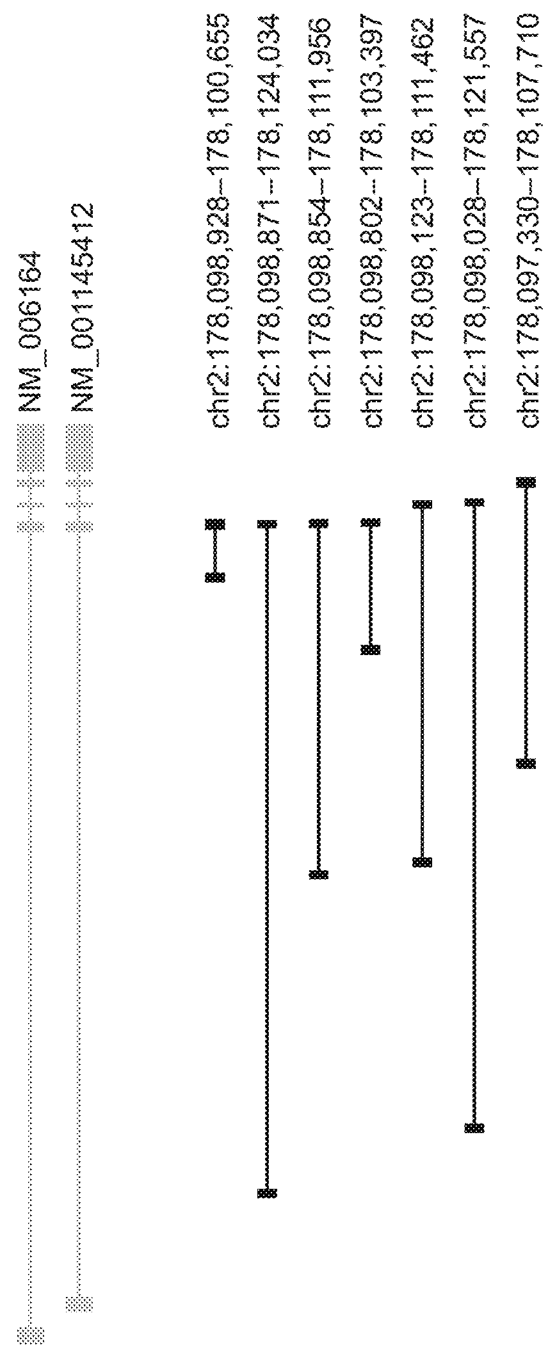
FIG. 28A is a schematic diagram showing the genomic location of discordant read pairs in seven tumors supporting genomic alterations affecting NRF2 exon 2 or exon 2+3.
Figure 28B:
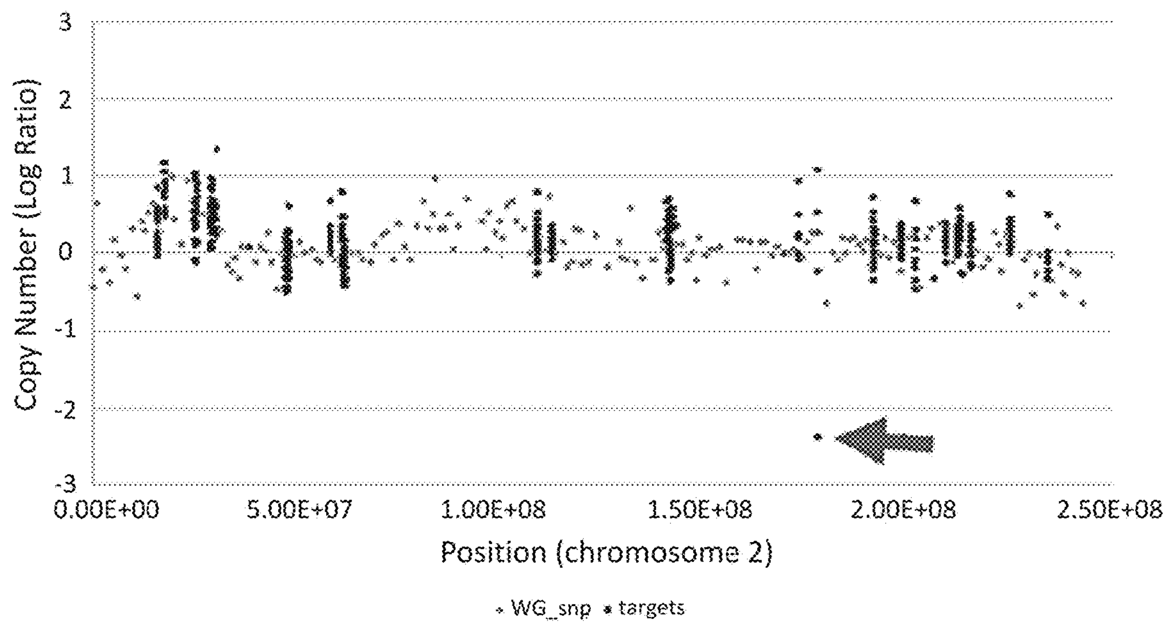
Figure 1:
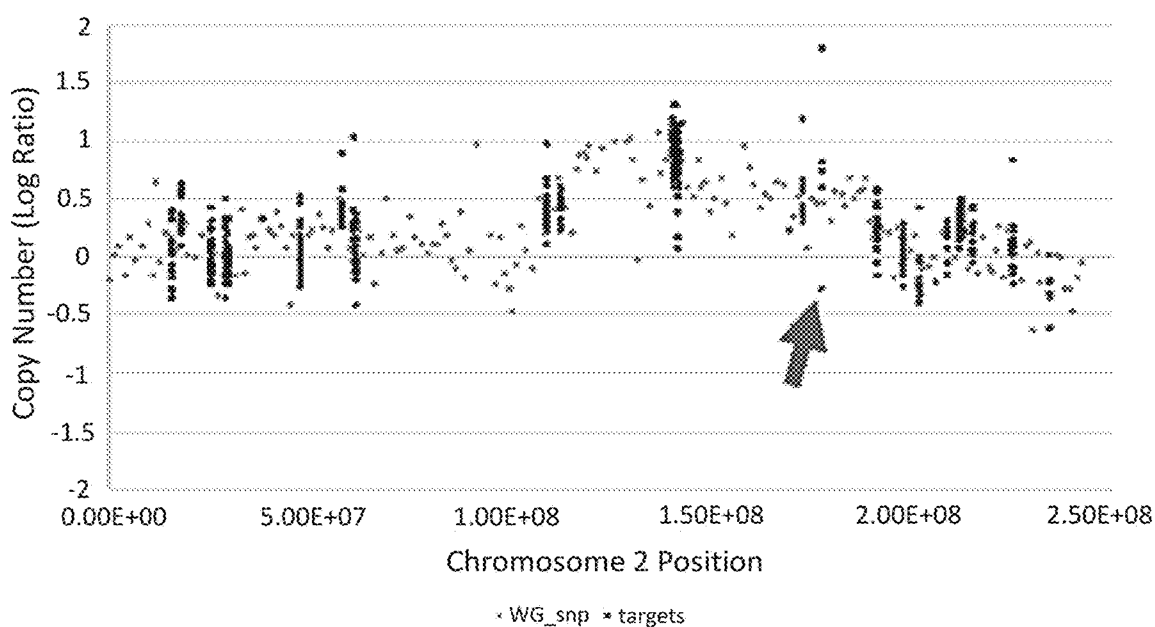
Figure 28B:
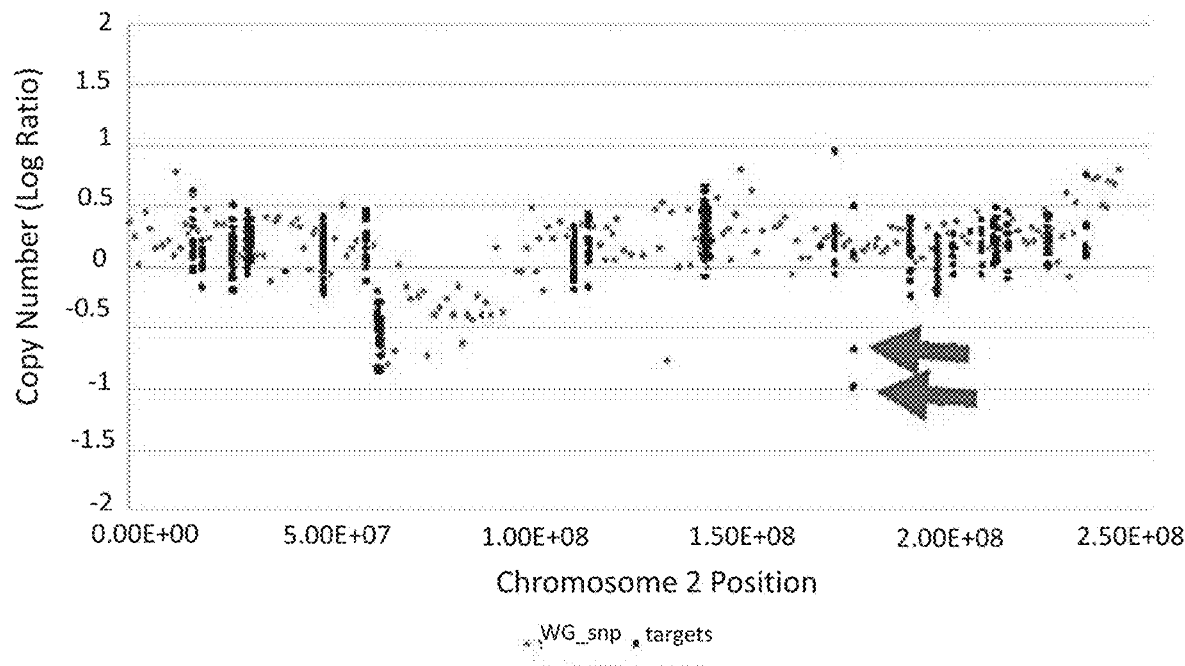
Figure 2:
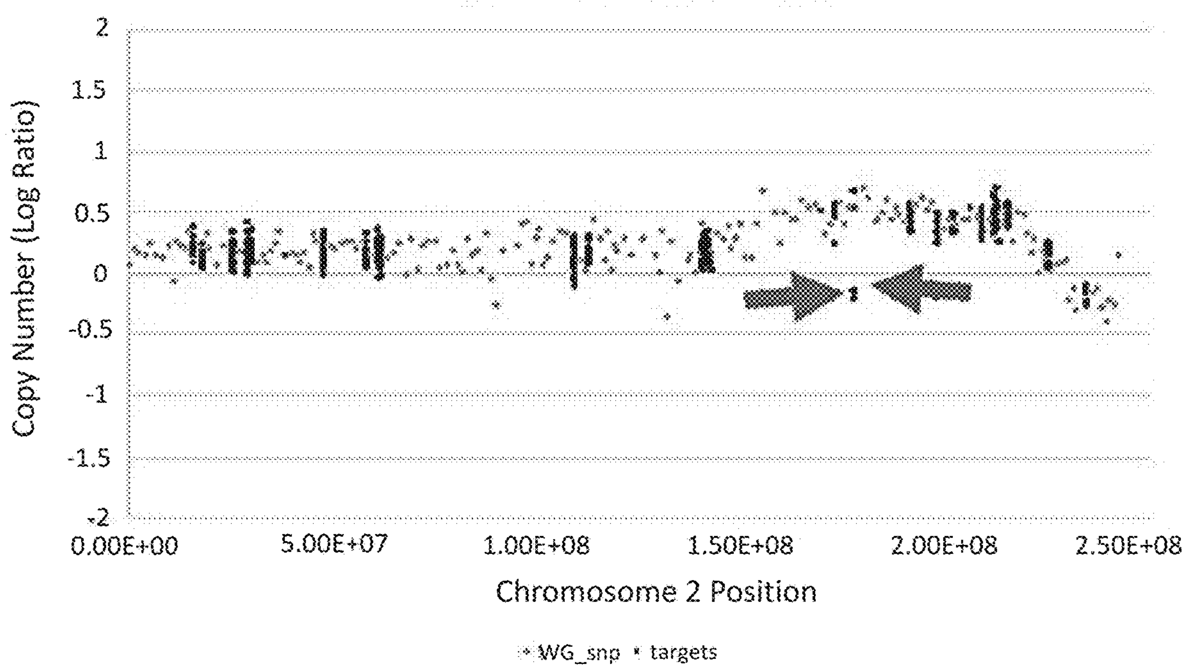
Figure 28C:
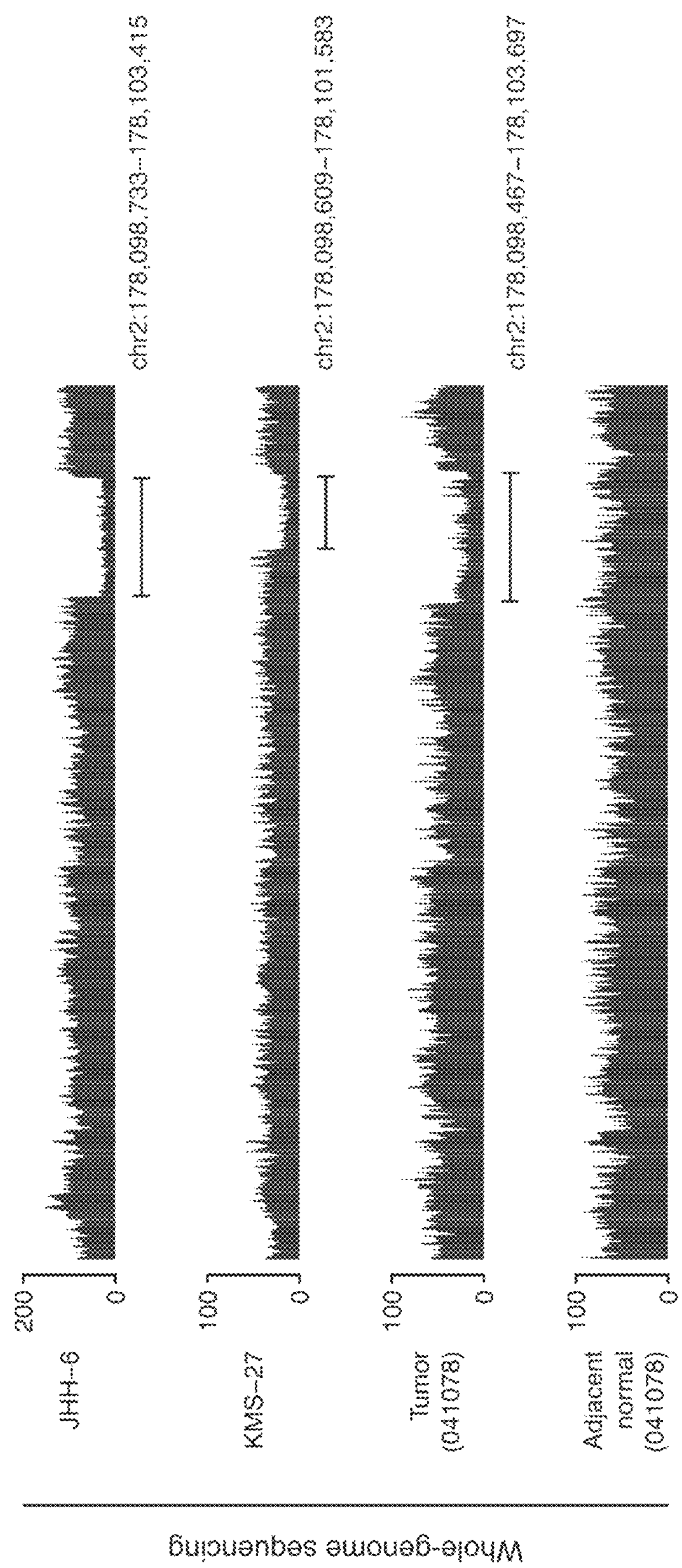
FIG. 28C is a series of whole-genome sequencing graphs showing the presence of microdeletions surrounding NRF2 exon 2 in JHH-6 cells, KMS-27 cells, as well as primary tumor and adjacent matched DNA. The sequences of reads spanning the deletions are shown NRF2NRF2.
Figure 29:
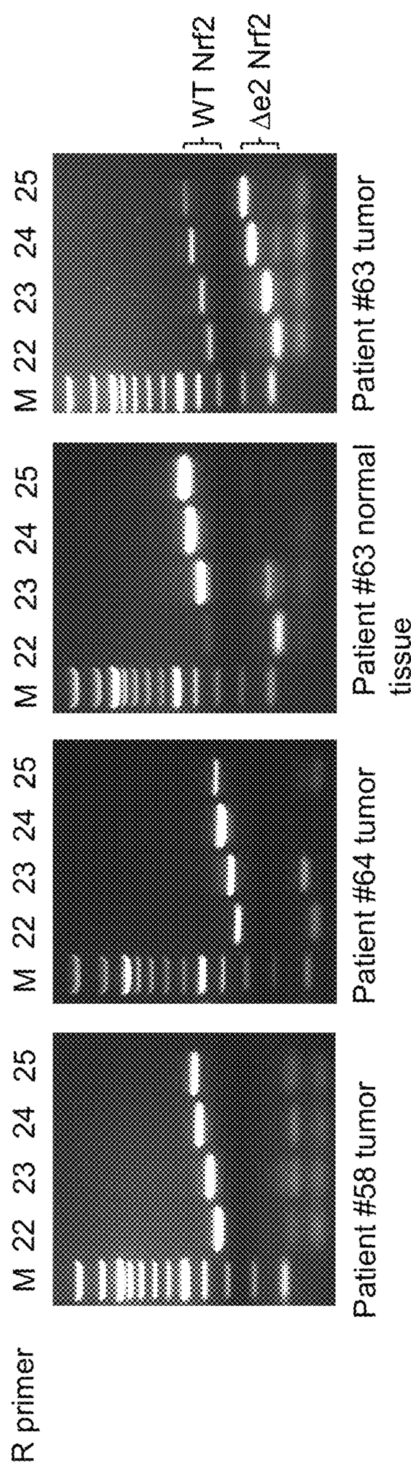
FIG. 29 is a series of agarose gel images showing RNA products amplified from total RNA of select patients with squamous NSCLC. Shown are amplification products from patient #58 tumor tissue, patient #64 tumor tissue, patient #63 normal tissue, and patient #63 tumor tissue by RT-PCR. Regions surrounding NRF2 exon 2 were amplified with the primers indicated in FIG. 11A. Fragments from wild-type NRF2 and Δe2 NRF2 are indicated. RT-PCR analysis identified patient #63 as having loss of NRF2 exon 2, which was strongly enriched in the tumor compared to the adjacent normal tissue.
Figure 30:
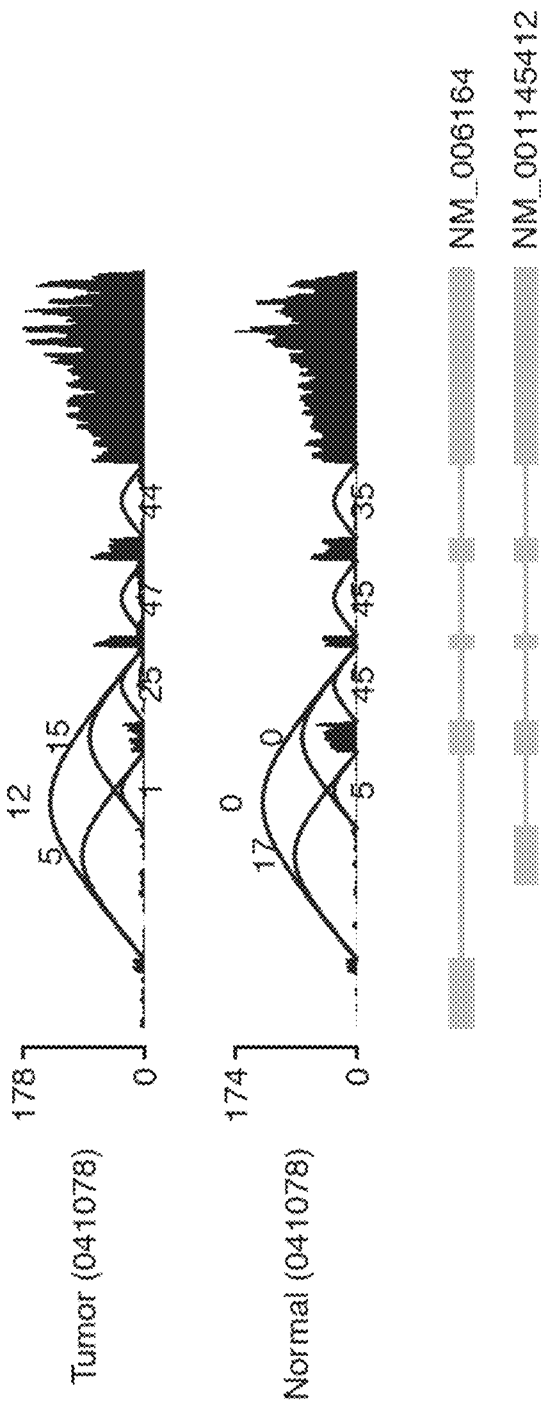
FIG. 30 is a graph showing the presence of junction reads skipping exon 2 in tumor and normal cells, as quantified by RNA-seq.
Figure 31:
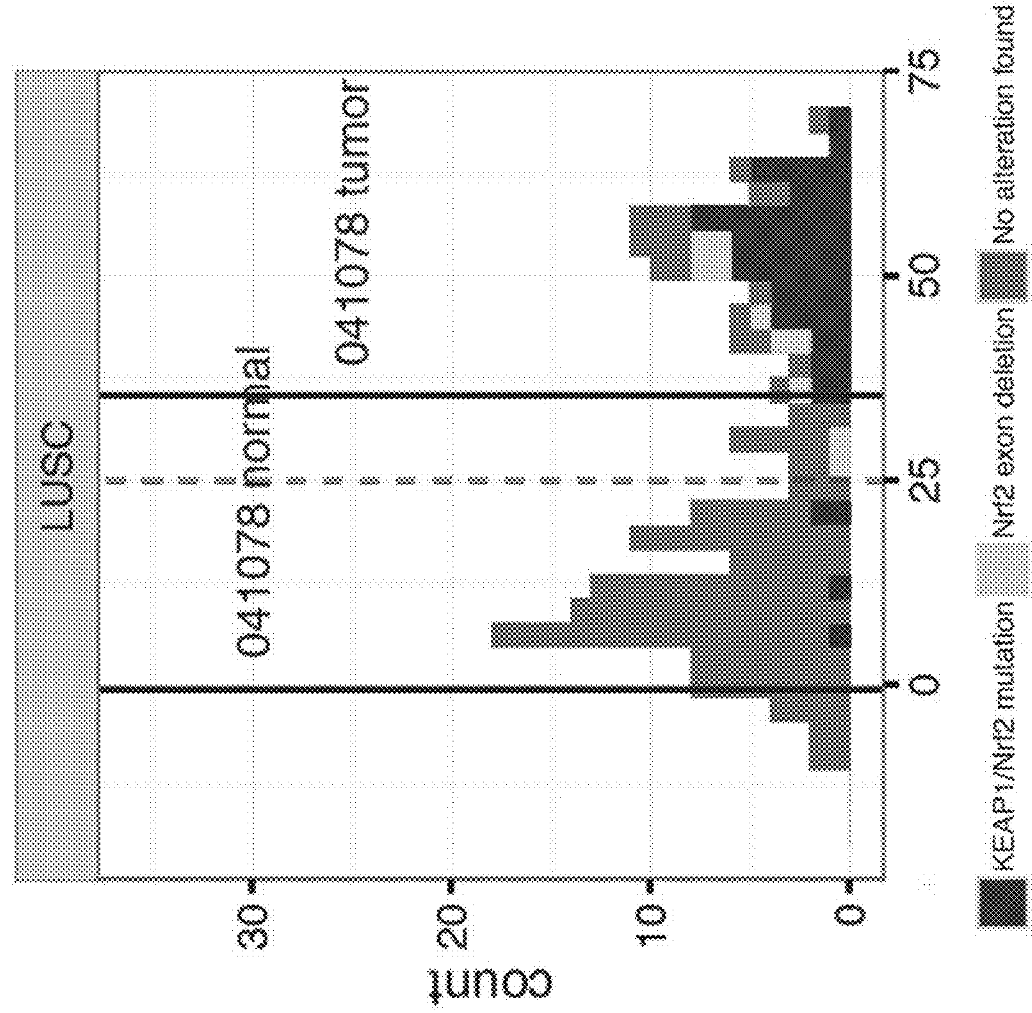
FIG. 31 is a histogram of the mutant KEAP1 gene signature score for TCGA samples from lung squamous carcinoma (LUSC). Dark gray histograms represent KEAP1/NRF2 mutant tumors, light gray histograms represent exon 2/3-deleted tumors, and medium gray histograms represent KEAP1/NRF2 wild-type tumors. The gene signature score for a given sample was determined by summation of gene expression z-scores over all genes in the gene signature.

Analysis of exome-seq data for KMS-27 and JHH-6 shows a decrease in reads mapping to exon 2, suggesting that the observed transcript variants could be the result of genomic alterations (FIG. 27A). Whole-genome sequencing (WGS) of JHH-6 and KMS-27 showed that these cell lines harbor microdeletions surrounding NRF2 exon 2, spanning 4,685 and 2,981 nucleotides, respectively (FIG. 27B). To investigate the causal mechanism in patients, targeted paired-end exome-seq data from a large cohort (n=1,218) of clinical squamous NSCLC tumors with high read coverage (>300×) were analyzed. In this data set, eleven tumors showed a decrease in copy number for exon 2 or exons 2+3 compared to nearby control regions (Materials and Methods; FIG. 27B). The focal nature of the deletions can be appreciated by investigating log-ratios from defined genomic regions targeted for sequencing (FIG. 28B). Seven tumors with discordant read pairs were consistent with structural variants encompassing several kilobases of DNA and affecting exon 2 or exon 2+3 (FIG. 28A). In total, sixteen patients showed evidence for genomic alterations affecting NRF2 exon 2 or exon 2+3, and the identified events were mutually exclusive with point mutations or indels in NRF2 and KEAP1, which are known to activate this pathway. An additional cohort of 45 squamous NSCLC tumors were analyzed, for which both RNA and DNA were available. RT-PCR analysis identified a single patient with loss of exon 2, which was strongly enriched in the tumor compared to adjacent normal tissue (FIG. 29). RNA-seq analysis confirmed that the transcript variant was expressed in the identified tumor, but was absent in adjacent normal tissue (FIG. 30). Expression of NRF2 target genes was also elevated to a similar extent as in TCGA tumors with known mutations in this pathway, whereas the adjacent normal tissue showed low expression of these genes (FIG. 31). Finally, whole-genome sequencing confirmed that the transcript variant was the result of a somatic genomic microdeletion of 5,233 nucleotides surrounding exon 2 (FIG. 28C). These data suggest that genomic microdeletions are a clinically relevant mechanism for NRF2 pathway activation.

Figure 32:
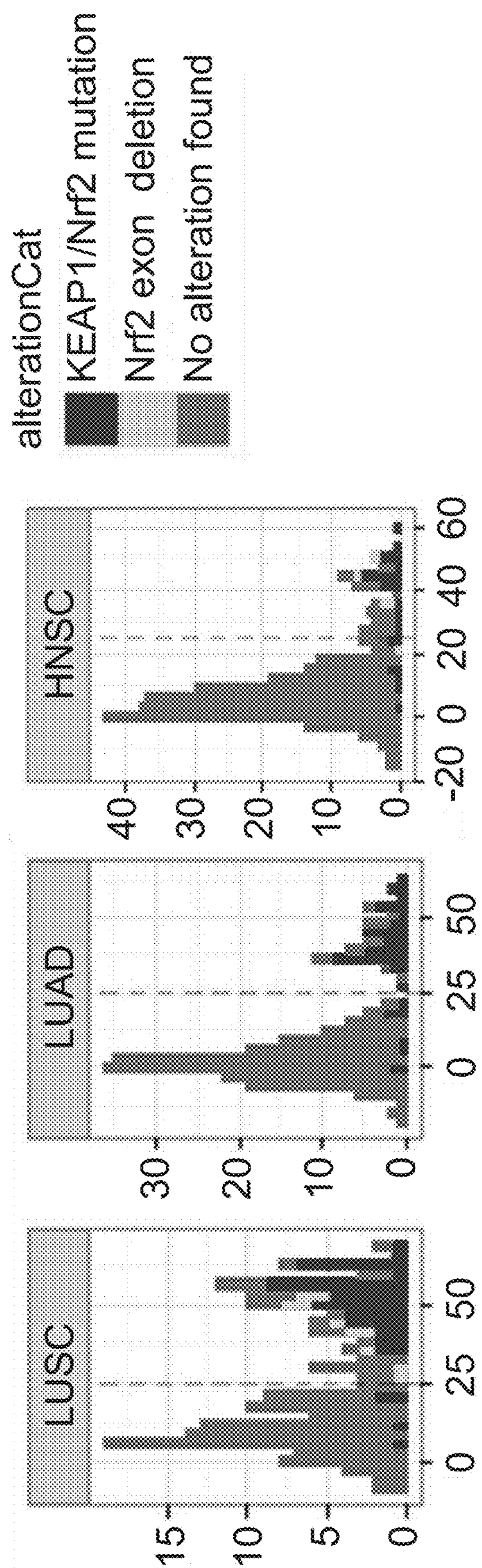
FIG. 32 is a series of histograms of the mutant KEAP1 gene signature score for TCGA samples from lung squamous carcinoma (LUSC), lung adenoma (LUAD), and head and neck squamous carcinoma (HNSC). Dark gray histograms represent KEAP1/NRF2 mutant tumors, light gray histograms represent exon 2/3-deleted tumors, and medium gray histograms represent KEAP1/NRF2 wild-type tumors. The gene signature score for a given sample was determined by summation of gene expression z-scores over all genes in the gene signature.
Figure 33:
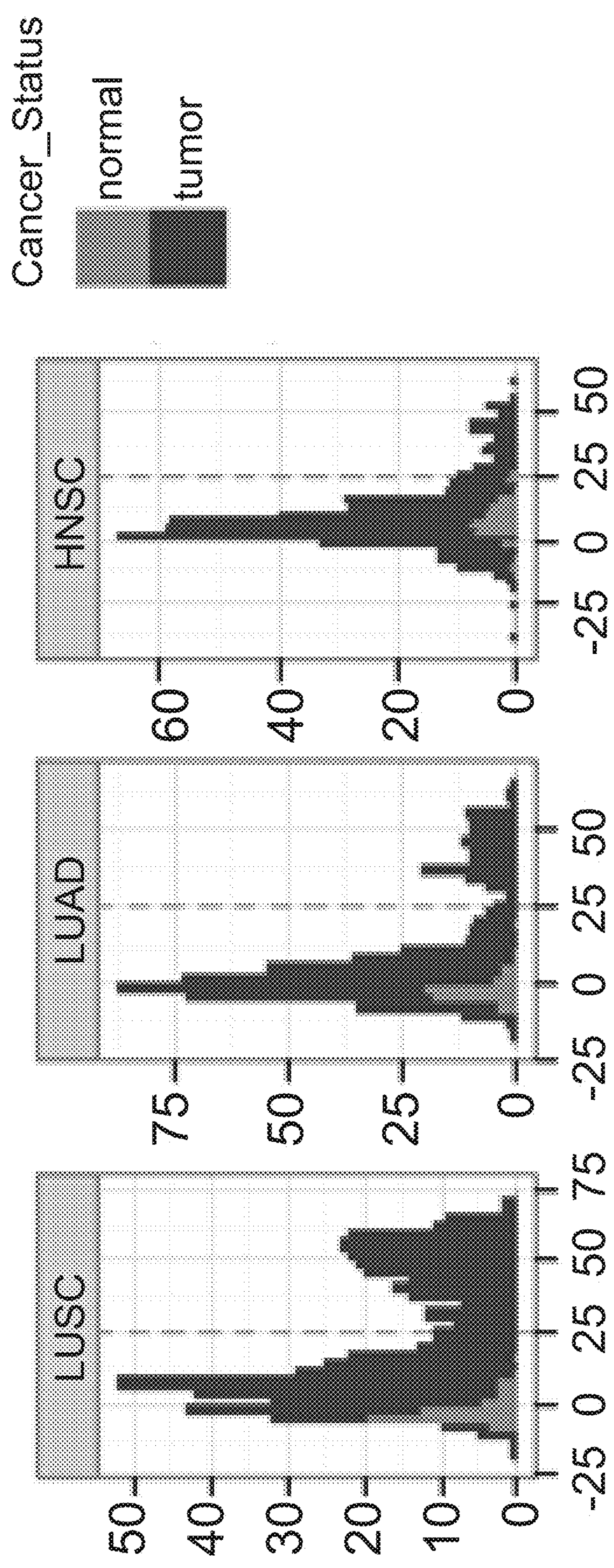
FIG. 33 is a series of histograms of the mutant KEAP1 gene signature score for TCGA samples from lung squamous carcinoma (LUSC), lung adenoma (LUAD), and head and neck squamous carcinoma (HNSC). Dark gray histograms represent tumor samples, and light gray histograms represent normal samples. The gene signature score for a given sample was determined by summation of gene expression z-scores over all genes in the gene signature.

These data suggest that the set of genes regulated by NRF2 is conserved across different tissues and conditions. This has practical value in the use of a single gene signature to identify tumors with NRF2 activation in both NSCLC and HNSC (FIG. 32). Interestingly, this NRF2/KEAP1 signature is only activated in tumors. Matched normal samples for lung and head and neck tumors showed only low NRF2 target gene activity (FIG. 33). This suggests that inhibition of the NRF2 pathway might have selective benefit in tumors showing pathway deregulation compared to normal tissues.

Intragenic genomic deletions that result in activation of proto-oncogenes have previously been reported for a number of genes, including EGFR and CTNNB1. Such variants are not routinely assayed, due in part to limitations of current genomic technologies. In particular, small aberrations affecting individual exons and involving small copy number changes are difficult to detect by exome-seq alone. Thus, intragenic deletions have remained relatively unexplored and new variants are still being discovered. Recent studies of small cell lung cancer and adult T cell leukemia/lymphoma identified recurrent microdeletions in TP73, IKZF2, and CARD11 using whole-genome sequencing (George et al. *Nature* 524, 47-53:2015; Kataoka et al. *Nat. Genet.* 47:1304-1315, 2015). In the present study, publicly available RNA-seq data generated as part of the TCGA project was used to identify recurrent transcript alterations in known oncogenes. Due to differences between patient cohorts, it is difficult to assess the general prevalence of NRF2 exon deletions. For example, when analyzing TCGA lung squamous cancers with available RNA-seq data (n=481), we identified 3% (16/481) of patients having a deletion of NRF2 exon 2 or exon 2+3. When analyzing the subset of patients with available exome-seq data (n=178), for which somatic mutation calling can be performed, the proportion of patients with NRF2 exon deletions was 6% (10/178). Accounting for NRF2 exon deletions increased the percentage of patients with putative NRF2 pathway activation from 27% (48/178) to 33% (58/178) in lung squamous carcinoma and from 9% (26/275) to 11% (31/275) in head and neck squamous carcinoma, compared to assessing mutations in NRF2 or KEAP1 by exome-seq alone (FIGS. 8A and 9A). Analysis of real-world clinical samples from patients that underwent genomic profiling suggested a prevalence of NRF2 exon deletions in 1-2% of lung squamous cell carcinoma. However, the latter analysis lacks sensitivity since optimized criteria for determining single-exon deletions in samples with variable tumor content have yet to be established and only unambiguous deletions were considered. Nevertheless, the results presented herein are consistent with the concept that modulation of this pathway is frequently altered in specific tumor indications, such as squamous NSCLC and head and neck carcinomas. Additional screening of known cancer genes through sequencing of complete gene loci, including introns, or by combining data from exome and RNA sequencing experiments may also be performed.

Analysis of the structure of the three deletions identified by WGS showed that breakpoints were distinct, but in each case genomic regions flanking the deletions showed 2-6 nucleotides with sequence homology (FIG. 34). The DNA sequences of the 3' end, 5' end, and junction read of JHH-6 cells are provided by SEQ ID NOs: 61-63, respectively. The DNA sequences of the 3' end, 5' end, and junction read of KMS-27 cells are provided by SEQ ID NOs: 64-66, respectively. The DNA sequences of the 3' end, 5' end, and junction read of primary tumor cells are provided by SEQ ID NOs: 67-69, respectively.

NRF2 often shows genomic amplification in addition to point mutations. Interestingly, while the intensity of the NRF2 deletion product in KMS-27 cells by RT-PCR analysis appeared similar to wild-type NRF2, it seemed to be more abundant in JHH-6 cells (FIG. 13). This was also reflected in WGS read counts, which suggested a higher abundance of the deleted form compared to the wild-type allele (FIG. 27B). These results are consistent with the observation that JHH-6 cells carry five copies of the NRF2 gene locus by SNP array, whereas KMS-27 cells carry two copies. Amplification of NRF2 is reasonably frequent in the TCGA samples analyzed, including squamous (4.5%) and adenomatous (2.6%) NSCLC, HNSC (12.2%), and liver cancers (3.6%), and represents a mechanism to increase NRF2 transcriptional output. In the case of JHH-6 cells, these data suggest that the deleted allele has been preferentially amplified, providing an additional mechanism to boost NRF2 signaling in this cell line. However, preferential amplification of the truncated/spliced allele was not observed in the primary tumors, suggesting that exon 2 or 2+3 deletion alone can provide sufficient NRF2 activity for clonal selection.

Deletion of exon 2 provides an elegant mechanism to increase NRF2 activity by removing the interaction site with KEAP1, while keeping the remainder of the gene functionally intact for DNA binding and transcriptional activation functions. Indeed, our biochemical analyses confirmed the almost complete loss of KEAP1 binding and resulting stabilization of NRF2 when exon 2 is deleted (FIGS. 23 and 24). When considering NRF2 point mutations found in tumors, mutations surrounding the ETGE high-affinity binding site result in complete loss of KEAP1 interaction, whereas mutations in the lower affinity DLG motif vary in their ability to disrupt the NRF2/KEAP1 complex (Fukutomi et al. *Mol Cell Biol.* 34(5):832-846, 2014; Shibata et al. *Proc. Natl. Acad. Sci. USA.* 105(36):13568-13573, 2008). However, even point mutations that do not disrupt the complex change the nature of the interaction such as to prevent KEAP1-mediated ubiquitination of NRF2 (Shibata et al. *Proc. Natl. Acad. Sci. USA.* 105(36):13568-13573, 2008). While the interaction with KEAP1 is similarly abolished in the case of deletion of both exon 2 and 3, exon 3 contains the Neh4 domain that has been previously implicated in transcriptional activation by NRF2 through binding to CREB (cAMP Responsive Element Binding protein) Binding Protein (CBP) (Katoh et al. *Genes Cells.* 6(10):857-868, 2001). Neh4 (contained in exon 3) and Neh5 (contained in exon 4) were shown to act synergistically in recruiting CBP. Consistent with this, a decreased ability of Δe2+3 NRF2 to induce some NRF2 target genes compared to Δe2 NRF2 or tumor-associated point mutations in NRF2 was observed (FIGS. 25 and 26).

Deletions found in human tumors that remove the interaction domain with E3 ligases have also been observed in other genes. For example, 7 out of 222 colorectal tumors showed small genomic deletions (234-677 bp) surrounding exon 3 of β-catenin (Iwao et al. *Cancer Res.* 58(5):1021-1026, 1998) that removes the interaction site for its E3 ligase β-TRCP (Hart et al. *Curr. Biol.* 9(4):207-210, 1999). Similarly, the majority of TMPRSS-ERG fusion proteins found in prostate cancer encode truncated versions of ERG that render them resistant to ubiquitination and degradation mediated by SPOP (An et al. *Mol. Cell.* 59(6):904-916, 2015).

In addition, mutations resulting in MET exon 14 skipping remove amino acid residue Y1003, which is required for Cbl recruitment and subsequent ubiquitination and down-regulation. Therefore, small intragenic deletions represent effective mechanisms for nascent oncogenes to escape normal degradation during tumor initiation and evolution.

Example 8

NRF2 Knockdown in Mutant KEAP1 Cells

This example provides a characterization of the effects of KEAP1 mutations on the requirement for NRF2 activity under different growth environments and shows that NRF2 activity is essential for growth in anchorage independent conditions.

Figure 35:
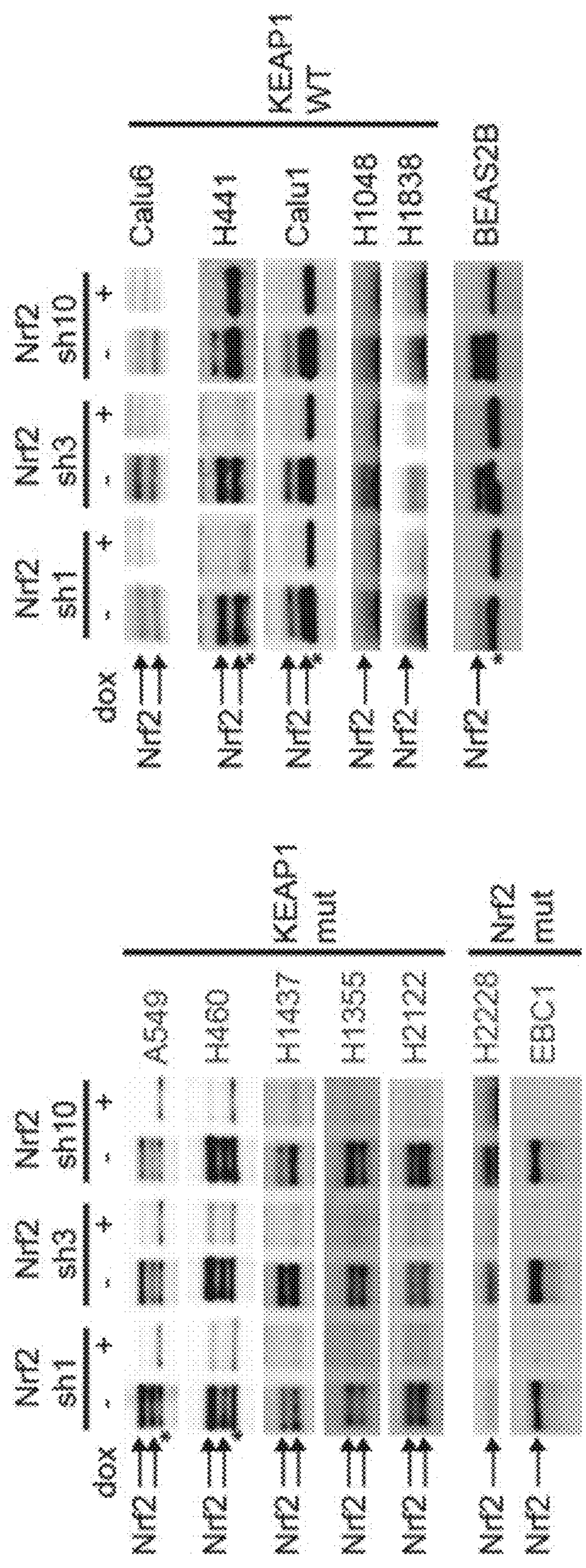
FIG. 35 is a series of Western blots showing the relative expression of NRF2. The indicated cell lines were infected with lentiviruses expressing independent non-target control (NTC) or three independent NRF2 shRNA sequences (sh1, sh2, and sh3) and were incubated for 48 hours with (+) or without (–) 500 ng/mL doxycycline (dox) following puromycin selection.
Figure 36:
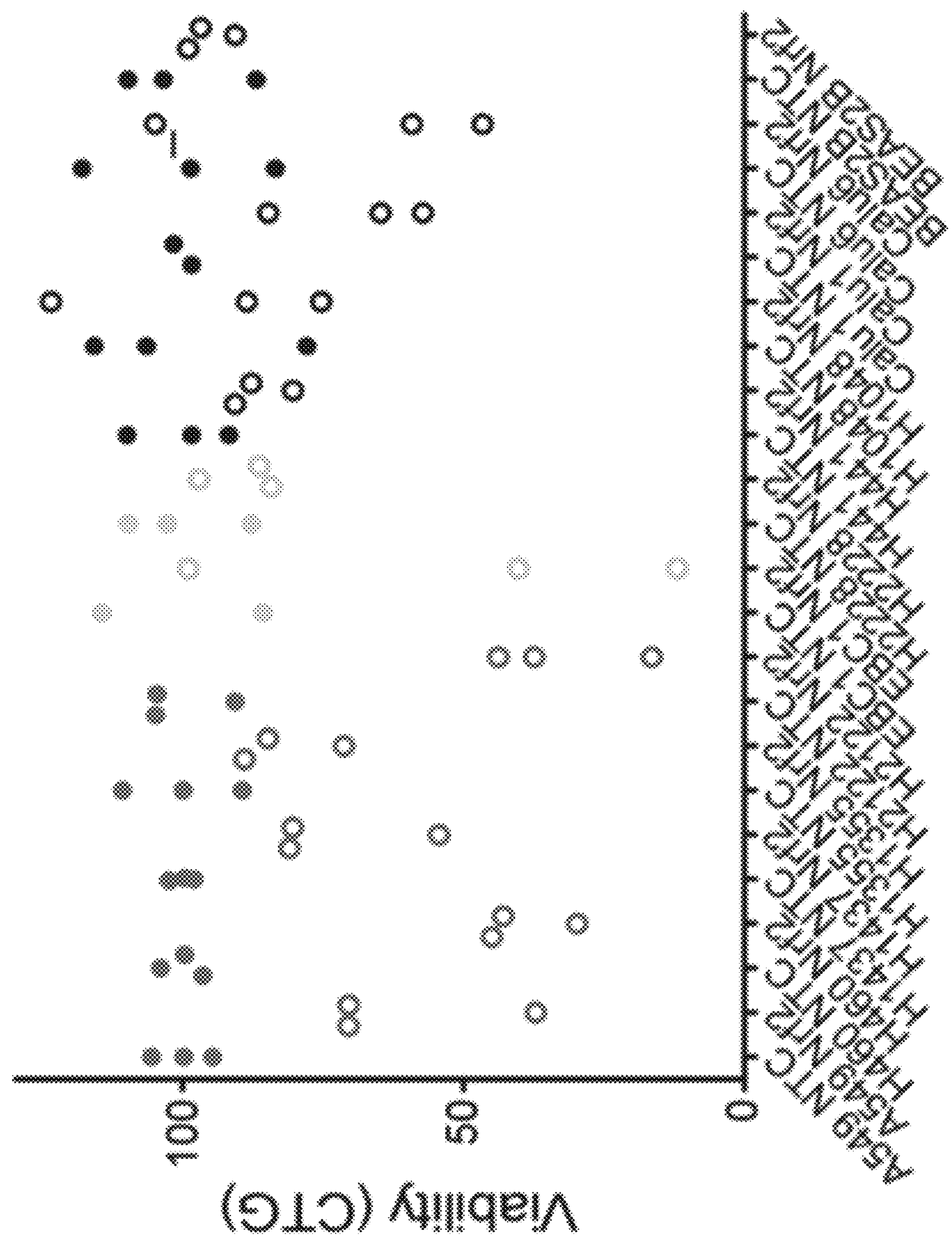
FIG. 36 is a graph showing the viability of the cell lines shown in FIG. 35 after incubation with or without dox for 7 days. Viability was measured using CellTiter-Glo (CTG) ATP detection. Each circle is the average of six technical replicates, and values were normalized to the average percent viability of three independent NTCs+dox.
Figure 38:
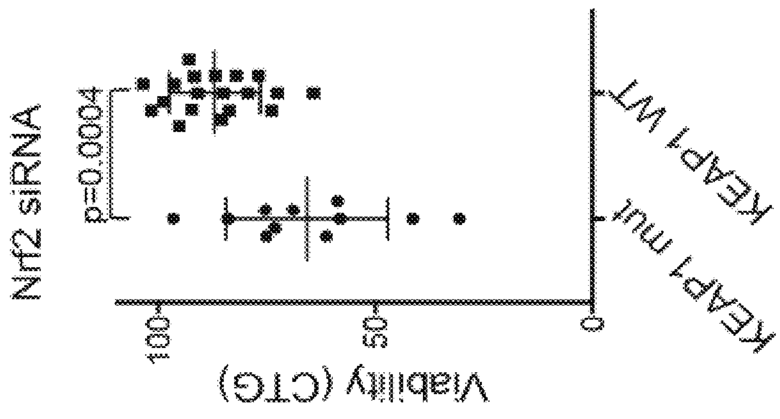
FIG. 38 is a graph showing the viability of 28 NSCLC cell lines following treatment with NRF2 siRNA relative to NTC treatment. Cells are grouped by KEAP1 genotype. Significance was calculated using Student's t test.
Figure 37:
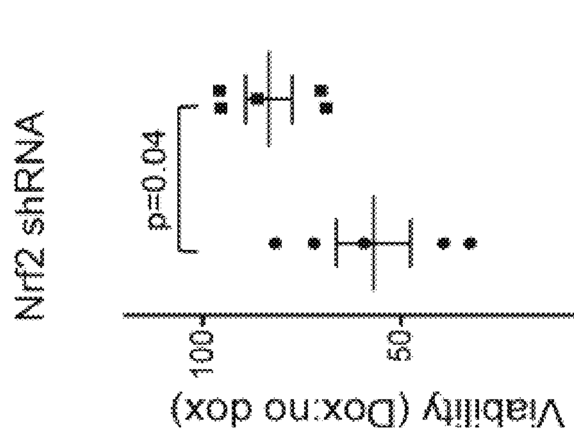
FIG. 37 is a graph showing the viability of cell lines treated with dox vs no dox. Cells were grown for four days and viability measured using CTG ATP measurement. Significance was calculated using Student's t test.

The consequences of NRF2 inhibition across wild-type and mutant KEAP1 and NRF2 cell lines were examined. Stable cell lines expressing three independent NRF2 shRNAs under the control of doxycycline, as well as three independent non-targeting controls (NTCs) were established. These NRF2 shRNAs were effective at reducing NRF2 protein levels in five KEAP1 mutant cell lines, two NRF2 mutant cell lines, and five wild-type NSCLC cell lines, as well as in immortalized but non-transformed lung epithelial BEAS2B cells (FIG. 35). Upon doxycycline addition, viability of most cell lines was decreased to varying extents, with the KEAP1 mutant cell lines generally exhibiting significantly greater decreases (FIGS. 36 and 37). Knockdown of NRF2 by siRNA in a larger panel of NSCLC cell lines confirmed a genotype-dependent effect on cell viability (FIG. 38).

Figure 39:
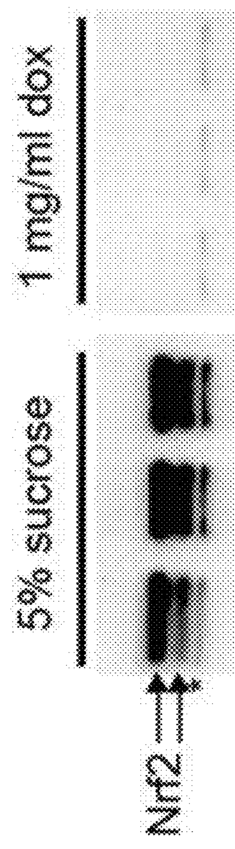
FIG. 39 is a Western blot experiment showing the expression of NRF2 in KEAP1 mutant tumors. Mice were implanted with A549 cells expressing NRF2 sh10. When tumors reached ~200 $mm^3$, 1 mg/ml doxycycline or 5% sucrose was added to the drinking water. After five days, tumor extracts were blotted for NRF2.
Figure 40:
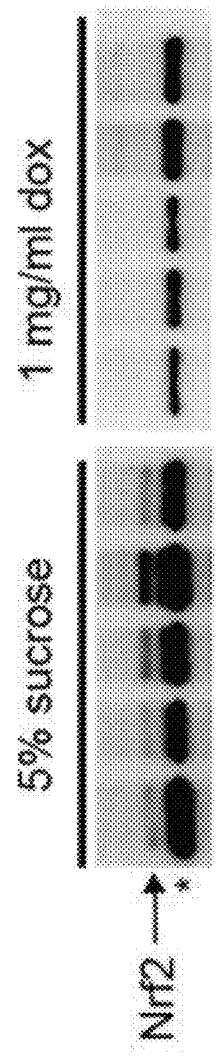
FIG. 40 is a Western blot experiment showing the expression of NRF2 in KEAP1 wild-type tumors. Mice were implanted with H441 cells expressing NRF2 sh10. When tumors reached ~200 $mm^3$, 1 mg/ml doxycycline or 5% sucrose was added to the drinking water. After five days, tumor extracts were blotted for NRF2.
Figure 41A:
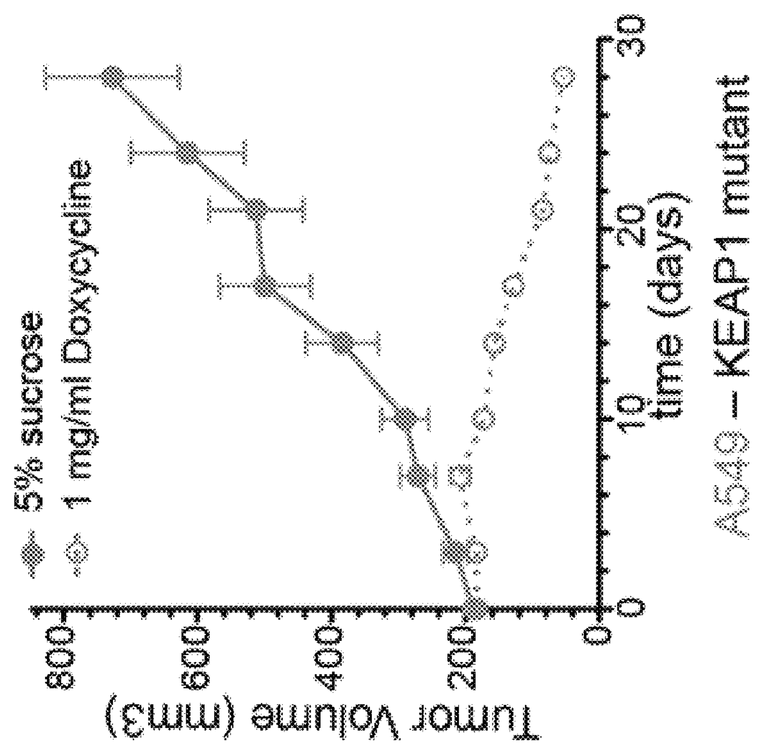
FIG. 41A is a graph showing the kinetics of tumor volume in mice implanted with KEAP1 mutant tumors. Mice were implanted with A549 cell lines expressing NRF2 sh10. When tumors reached ~200 $mm^3$, mice were randomized into groups of 10, and either 1 mg/ml doxycycline or 5% sucrose was added to the drinking water. Tumors were measured over a 28-day period. Error bars represent SEM (n=10).
Figure 41B:
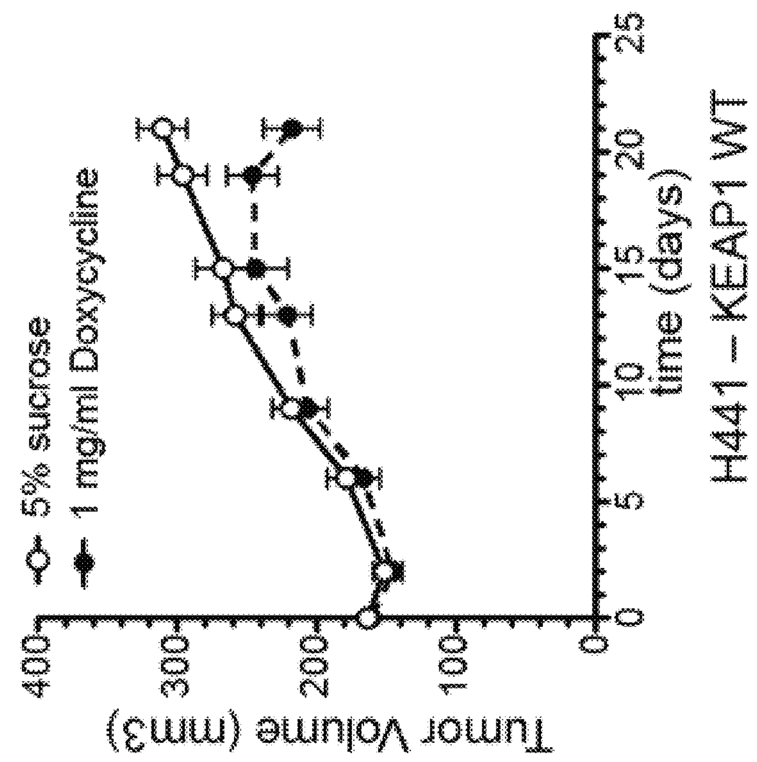
FIG. 41B is a graph showing the kinetics of tumor volume in mice implanted with KEAP1 wild-type tumors. Mice were implanted with H441 cell lines expressing NRF2 sh10. When tumors reached ~200 $mm^3$, mice were randomized into groups of 10, and either 1 mg/ml doxycycline or 5% sucrose was added to the drinking water. Tumors were measured over a 28-day period. Error bars represent SEM (n=10).

The consequence of NRF2 knockdown in tumor xenografts was characterized. The KEAP1 mutant A549 cell line and the KEAP1 wild-type H441 cell lines expressing dox-inducible NRF2 shRNAs were implanted into the flanks of female SCID mice. NRF2 was effectively knocked down in doxycycline treated mice in both tumors (FIGS. 39 and 40). NRF2 knockdown in the KEAP1 mutant A549 cell line had a dramatic effect on tumor growth, resulting in complete tumor regression in 5 out of 10 tumors (FIG. 41A). In contrast, the effect on KEAP1 wild-type H441 growth was more modest, resulting in a 37% reduction in tumor growth with all animals displaying maintained tumor burden (FIG. 41B).

Figure 42:
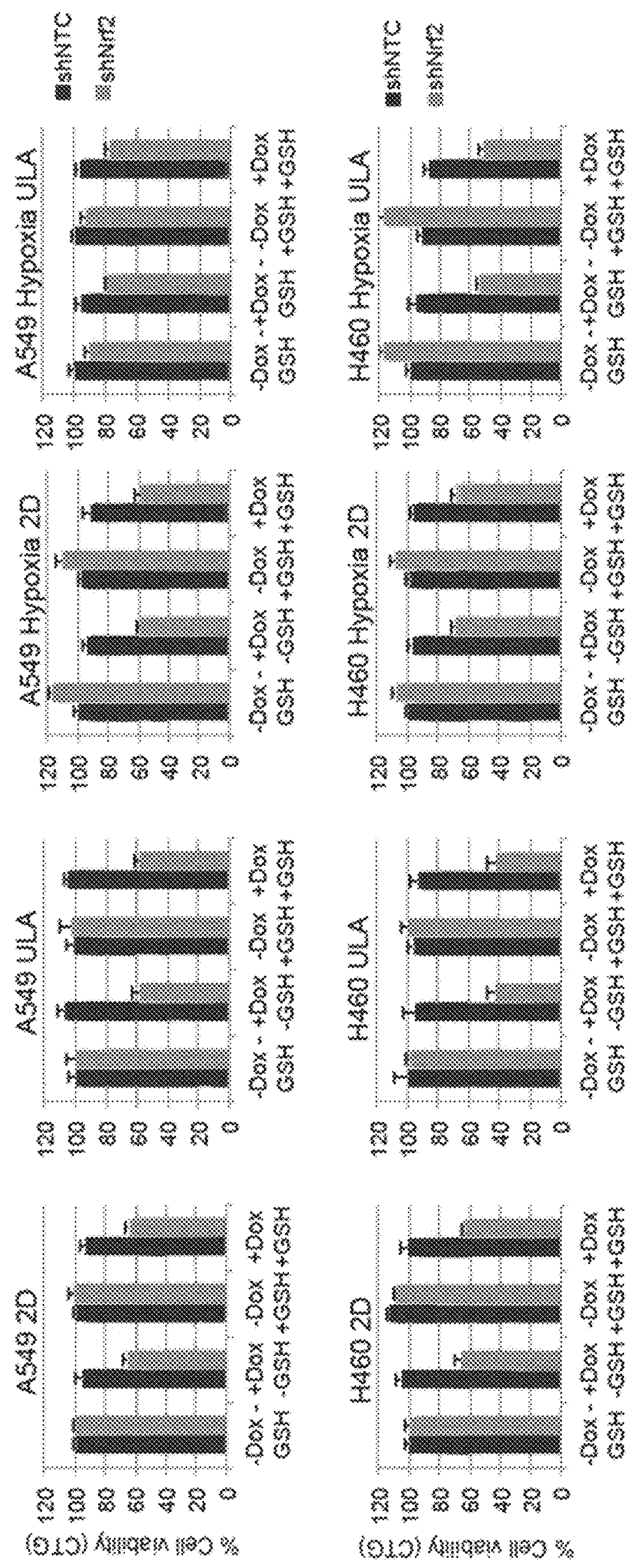
FIG. 42 is a series of bar graphs showing viability of A549 or H441 cells in various growth conditions. A549 and H460 cells expressing NTC or NRF2 sh10 shRNAs were plated into either 2D tissue culture treated plastic dishes or ultra-low attachment (ULA) coated tissue culture plates. They were then cultured for five days in either environmental oxygen concentrations or 0.5% oxygen (hypoxia). Cell viability was assessed by CTG ATP measurements.
Figure 43:
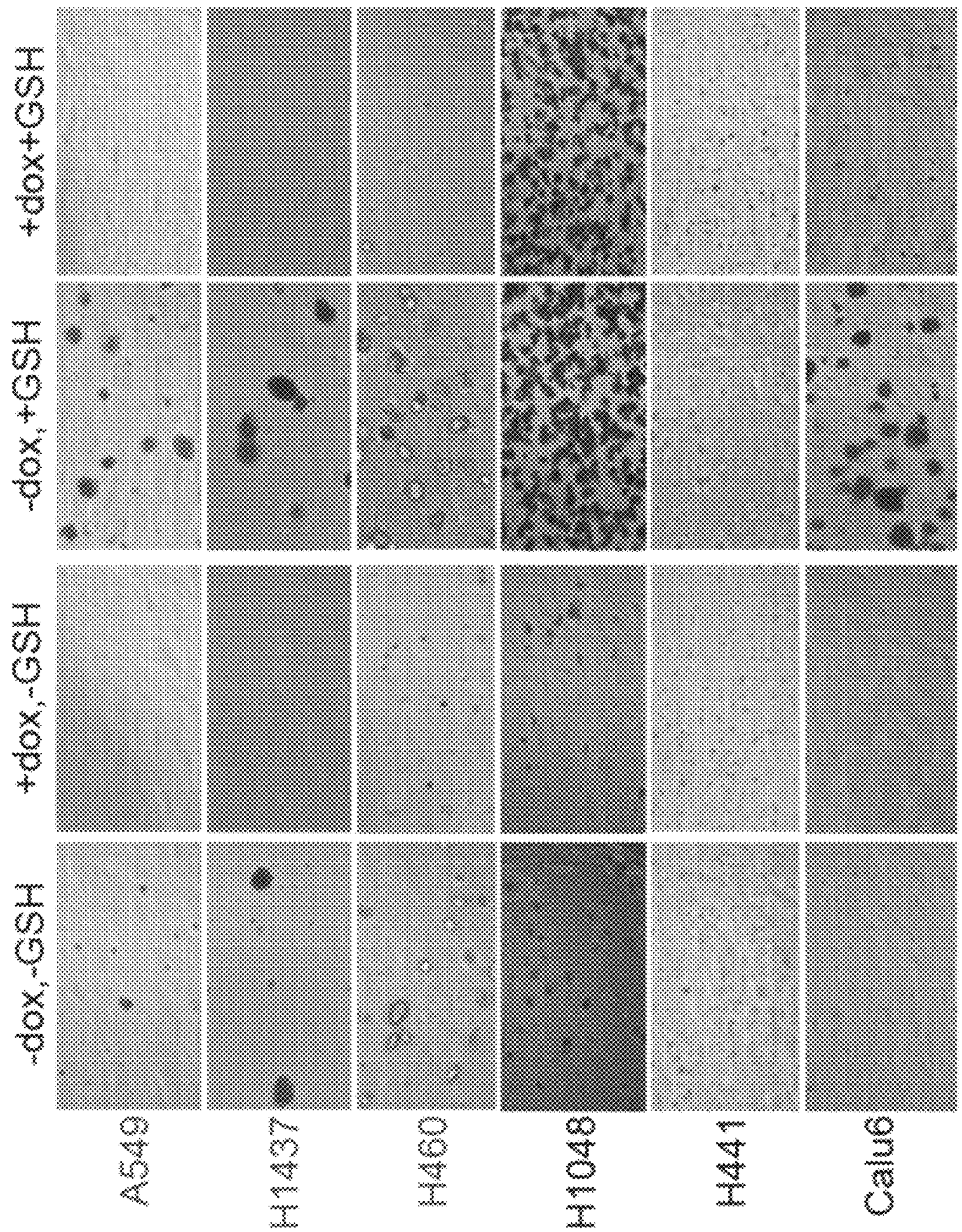
FIG. 43 is a series of photographs showing colony formation of KEAP1 mutant cell lines (A549, H1437, and H460) and KEAP1 wild-type cell lines (H1048, H441, and Calu6) in soft agar treated with vehicle, 500 ng/ml dox, or 1 mM reduced glutathione (GSH). Representative areas of the plate were photographed.
Figure 44:
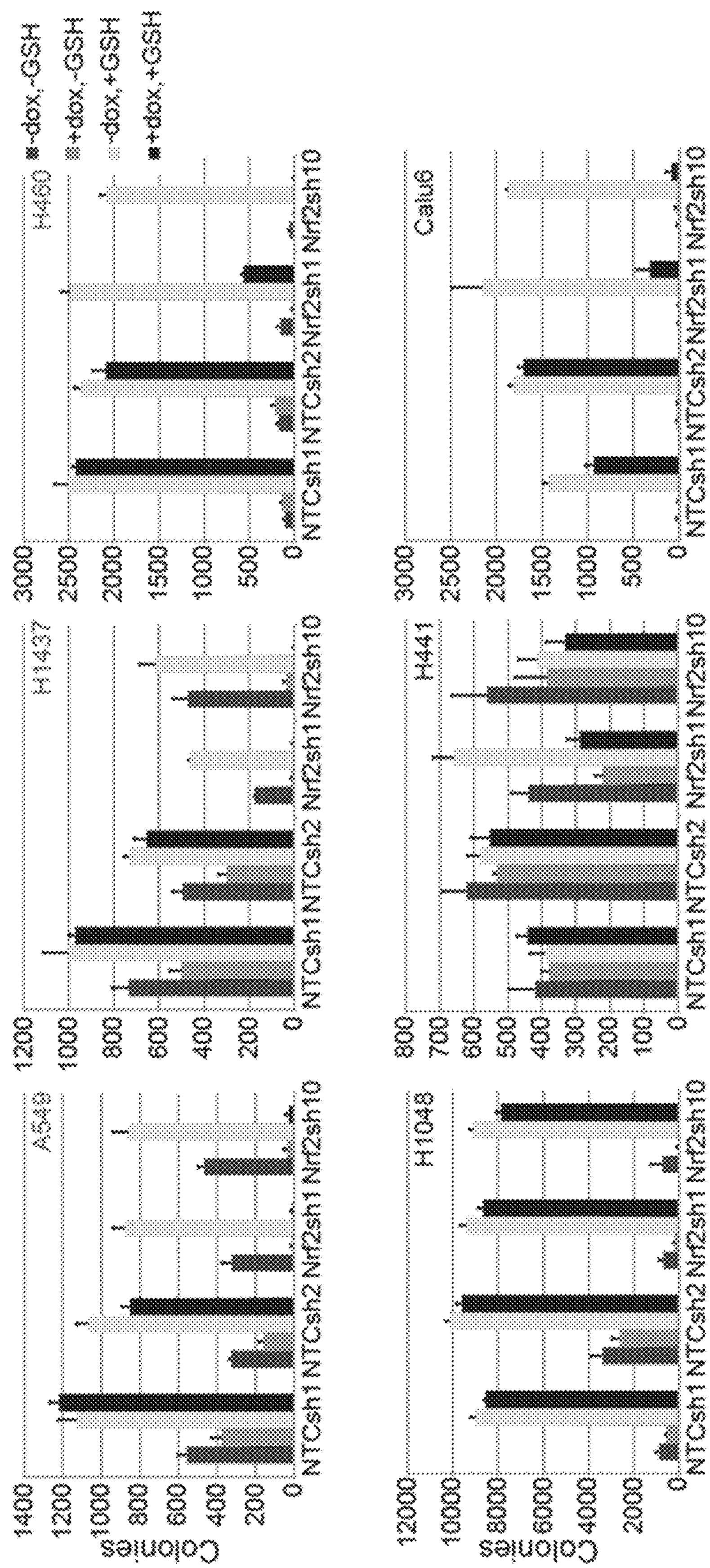
FIG. 44 is a series of bar graphs showing the quantified colony formation for each cell type and treatment group shown in FIG. 43. Error bars represent standard deviation from biological triplicate wells.
Figure 45:
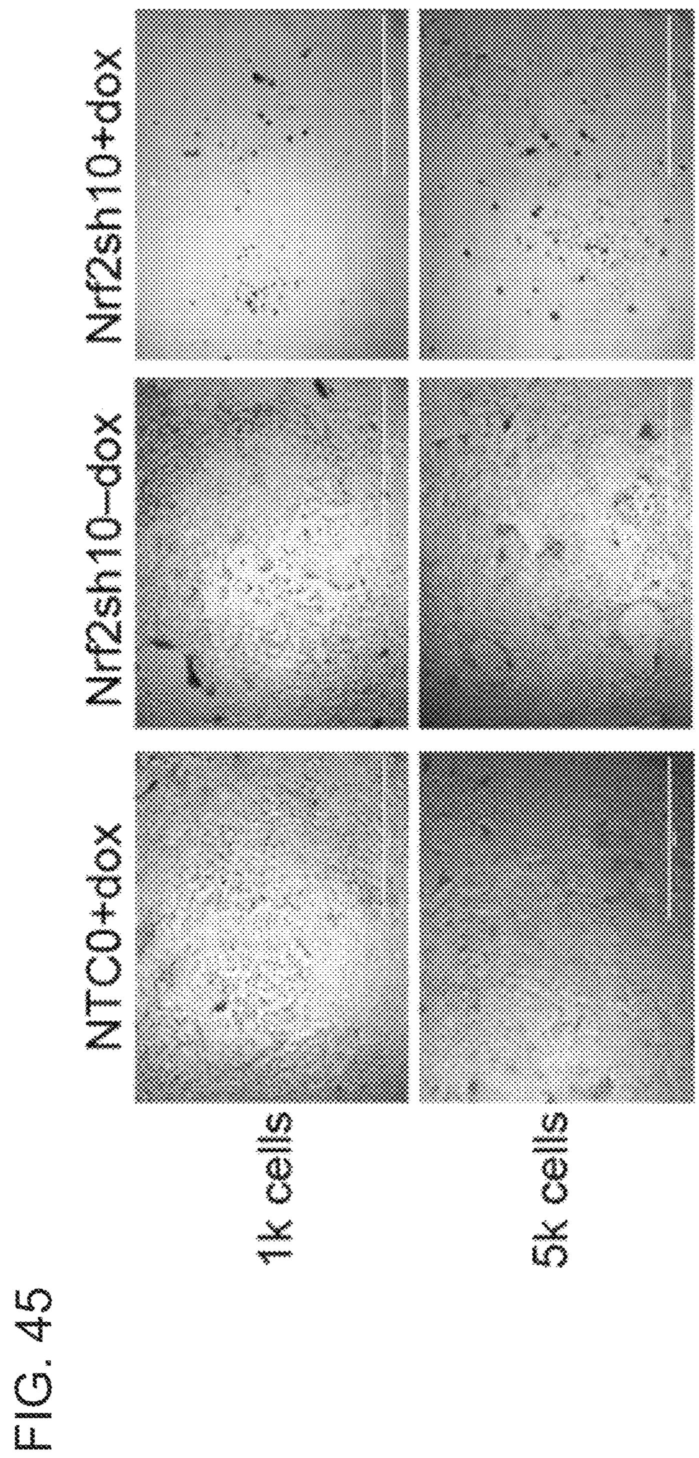
FIG. 45 is a series of photographs showing A549 colony formation on SCIVAX® micropatterned nanoculture dishes. Cells were photographed after about five days in culture in the presence or absence of 500 ng/ml dox.
Figure 46:
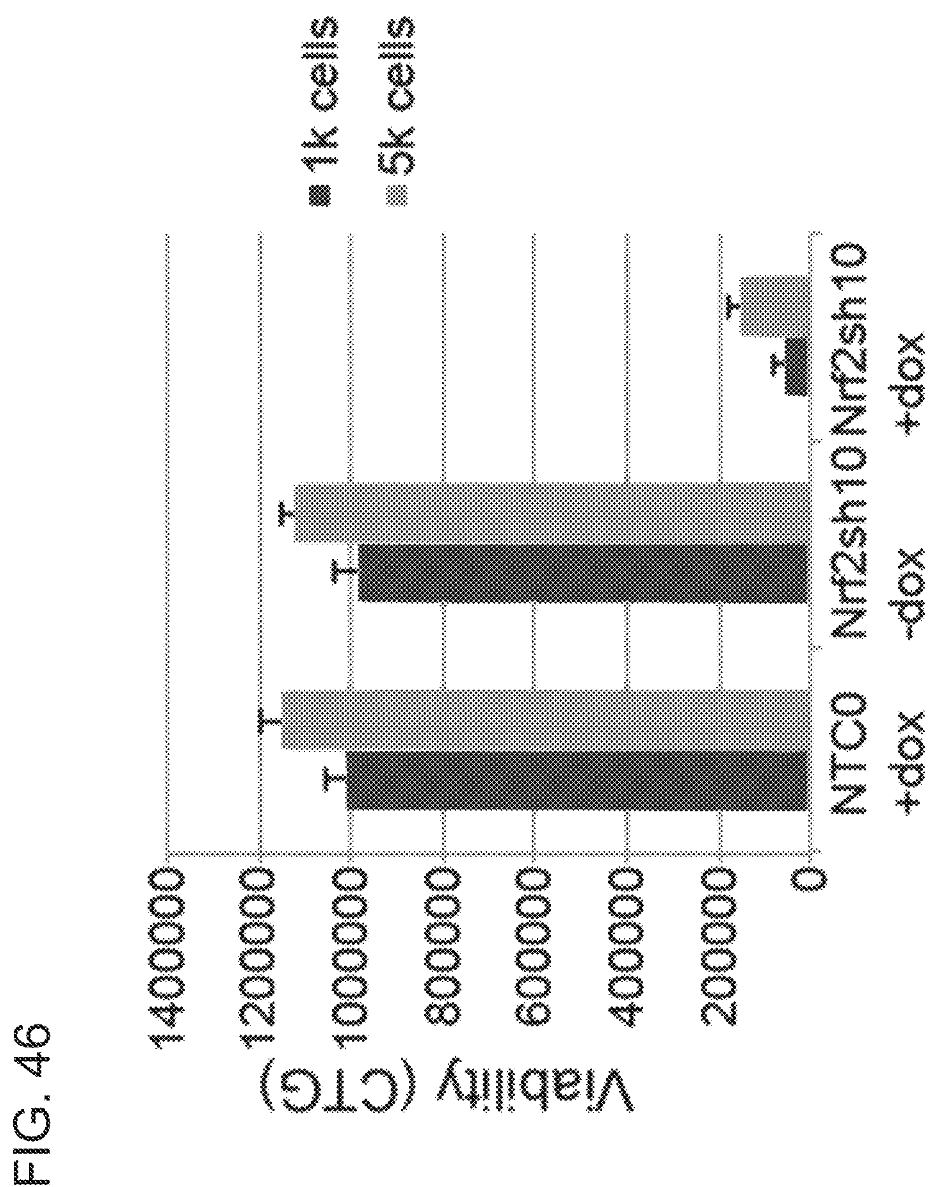
FIG. 46 is a bar graph showing viability of the cells from FIG. 45, quantified by CTG ATP measurements. The left column of each treatment group represents 1,000-cell cultures, and the right column represents 5,000-cell cultures.
Figure 47:
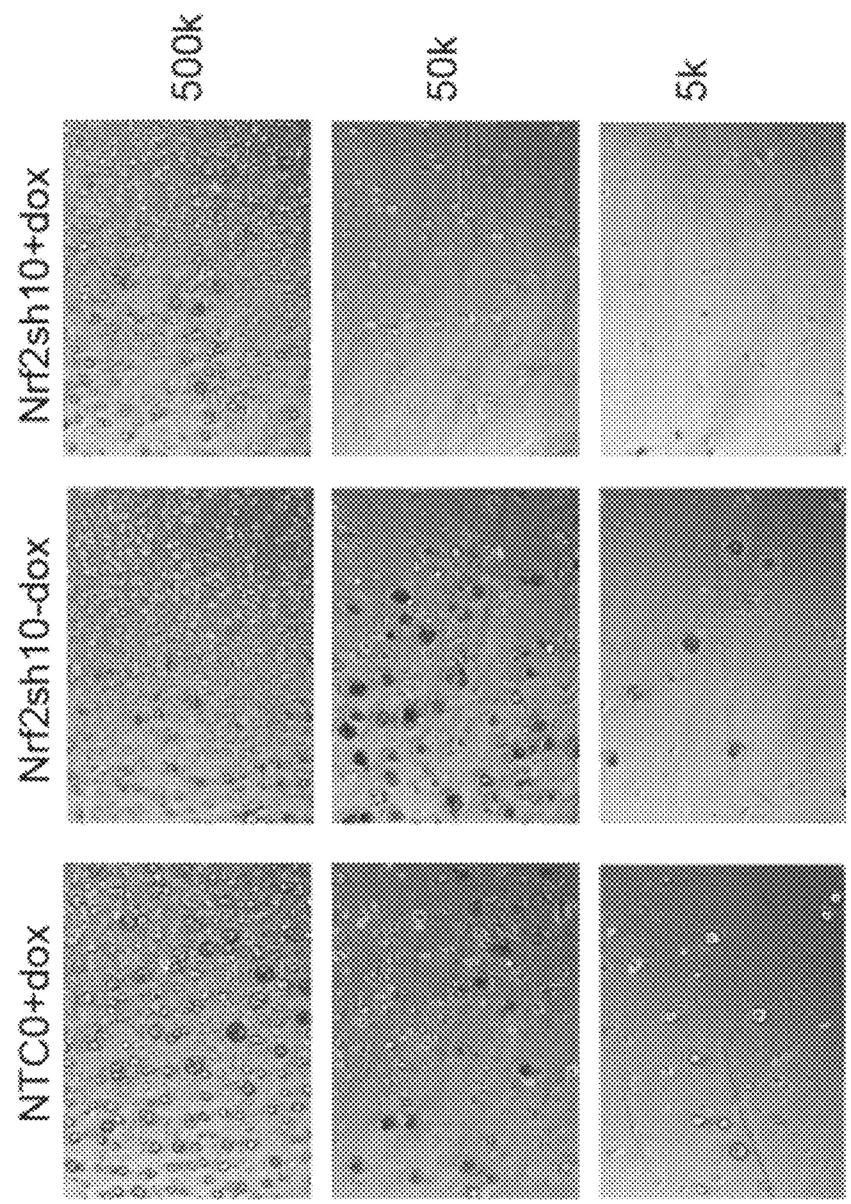
FIG. 47 is a series of photographs showing 5,000, 50,000, or 500,000 NTC or NRF2sh10 shRNA expressing A549 cells plated in methylcellulose-containing tissue culture dishes. Cells were photographed after ~10 days of culture in the presence or absence of 500 ng/ml doxycycline.
Figure 48:
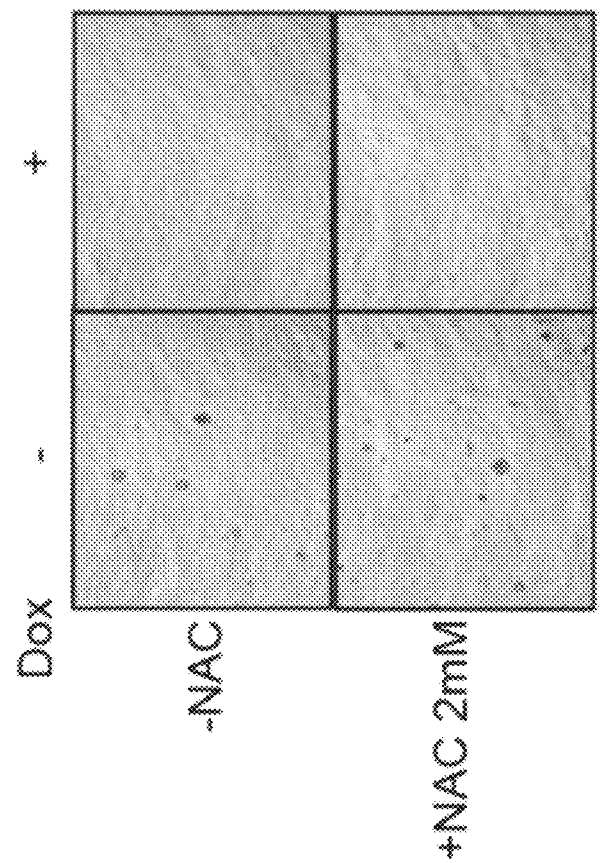
FIG. 48 is a series of photographs showing A549 cells expressing NRF2sh10 shRNA plated into regular tissue culture dishes (top) or soft agar (bottom). Cells were treated with either vehicle or 500 ng/ml doxycycline, in the presence or absence of 2 mM N-acetyl cysteine (NAC). Viability in 2D growth was measured after about five days by CTG ATP measurement, and photographs of cells in soft agar were taken after about ten days of growth.
Figure 49:
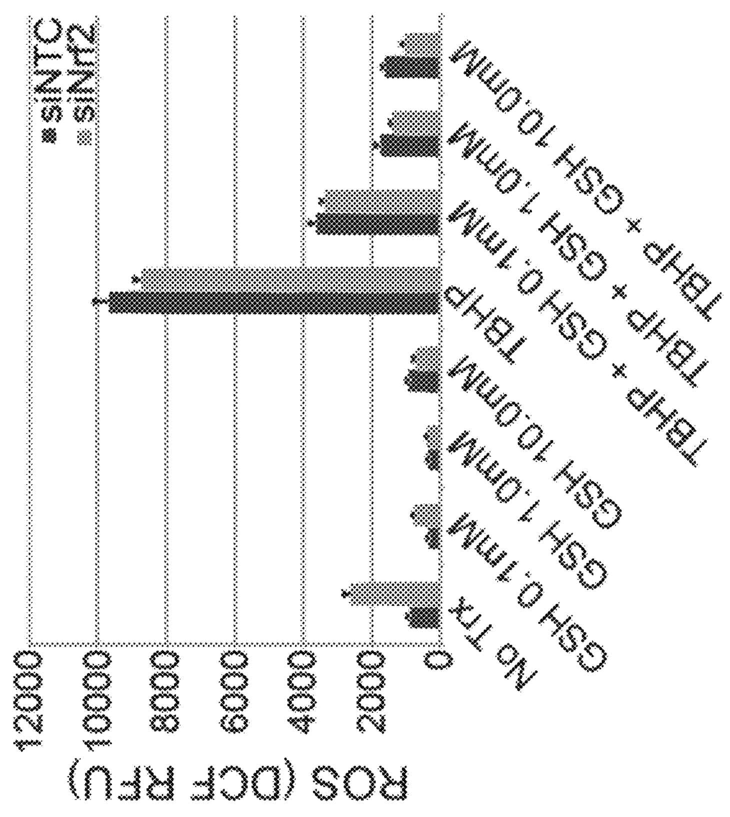
FIG. 49 is bar graph showing reactive oxygen species (ROS) levels under indicated conditions as measured using 2',7'-dichlorodihydrofluorescein diacetate (H2DCF). Error bars represent standard deviation from triplicate wells.

To understand the differential effects between NRF2 knockdown on tumor propagation in xenografts versus 2D growth on plastic, several additional cell culture environments were tested. NRF2 knockdown in cells grown in low adherence plates and/or low oxygen (0.5%) showed similar consequences to cells grown on plastic (FIG. 42). In contrast, the growth of KEAP1 mutant cell lines was severely compromised when cultured in soft agar (FIGS. 43 and 44), on micropatterned plastic films (FIGS. 45 and 46), or in methylcellulose (FIG. 47). Growth in soft agar was used to characterize the consequences of NRF2 knockdown in more detail. While knockdown of NRF2 completely abolished colony formation in three KEAP1 mutant cell lines, it had almost no effect in H1048 and H441, two wild-type KEAP1 NSCLC cell lines (FIGS. 43 and 44). The role of the glutathione pathway in the response to NRF2 knockdown was assessed, as this pathway has been shown to mediate survival properties facilitated by high NRF2 activity. While addition of reduced glutathione generally increased the ability of all tested cell lines to form colonies in soft agar, it was unable to rescue the consequences of NRF2 knockdown (FIGS. 43 and 44). Similar negative results were seen with N-acetyl cysteine (NAC; FIG. 48). Exogenous glutathione was able to enter cells and reduce reactive oxygen (ROS) levels, as measured by dichlorofluorescein staining (FIG. 49). Thus, the requirement for NRF2 activity is surprisingly independent of the glutathione synthesis pathway.

Figure 50:
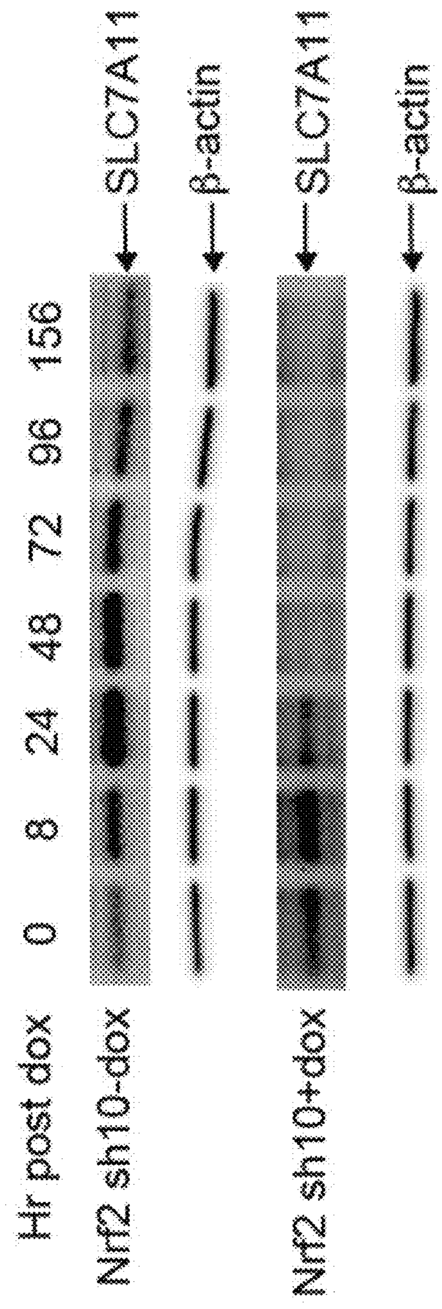
FIG. 50 is a Western blot experiment showing the effect on NRF2 knockdown on expression of SLC7A11. A549 cells expressing NRF2 sh10 were treated with vehicle or 500 ng/ml dox for the indicated time points and blotted using SLC7A11 and β-actin antibodies.
Figure 51:
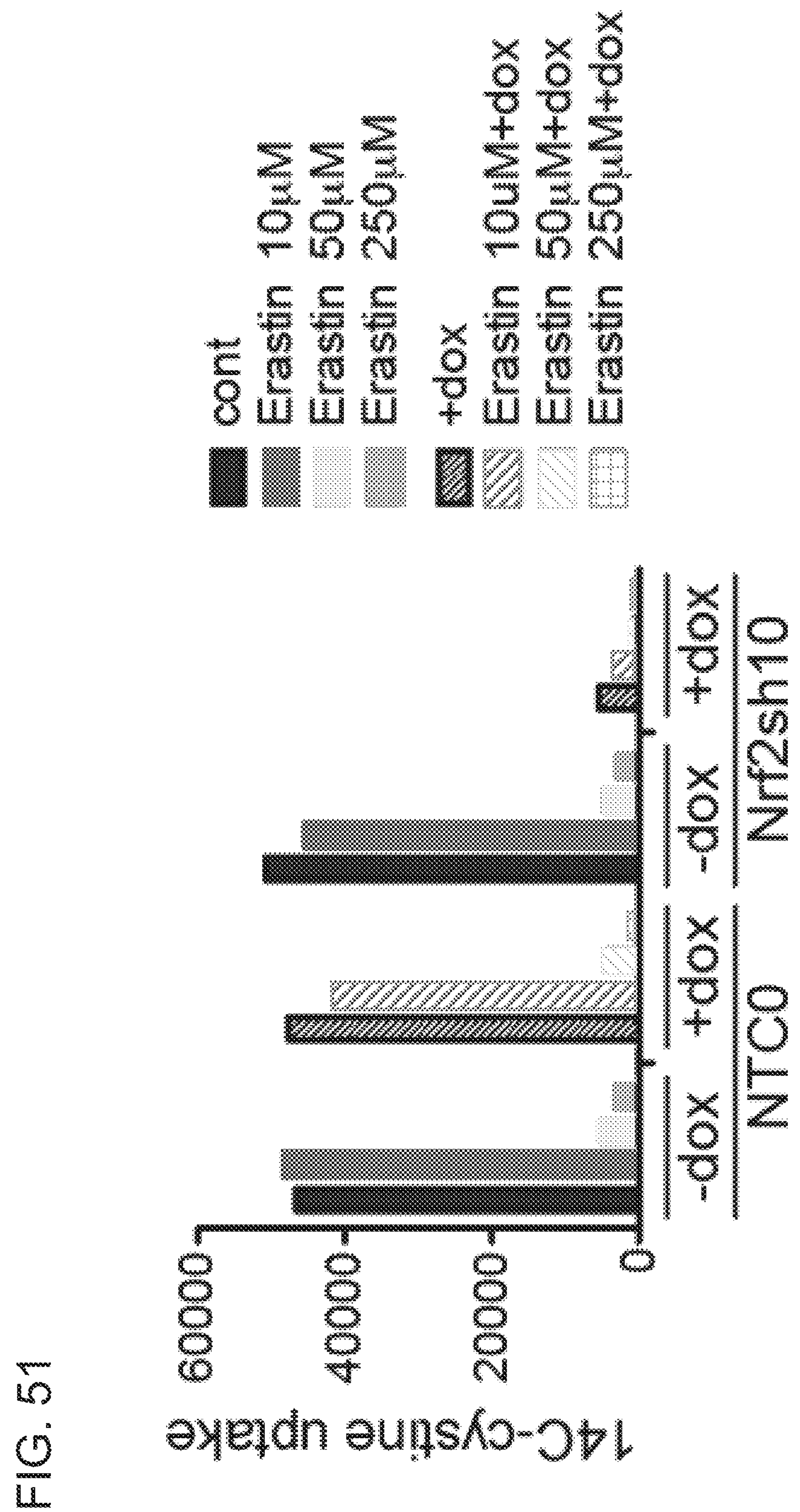
FIG. 51 is a bar graph showing cystine uptake by A549 cells expressing NTC1 or NRF2 sh10 over various concentrations of erastin. A549 cells expressing NTC1 or NRF2 sh10 were incubated with vehicle or dox for 48 hours, then incubated with 0.5 uCi $^{14}$C-Cystine for 20 minutes. Cells were lysed and intracellular cystine was measured by liquid scintillation counting.
Figure 52:
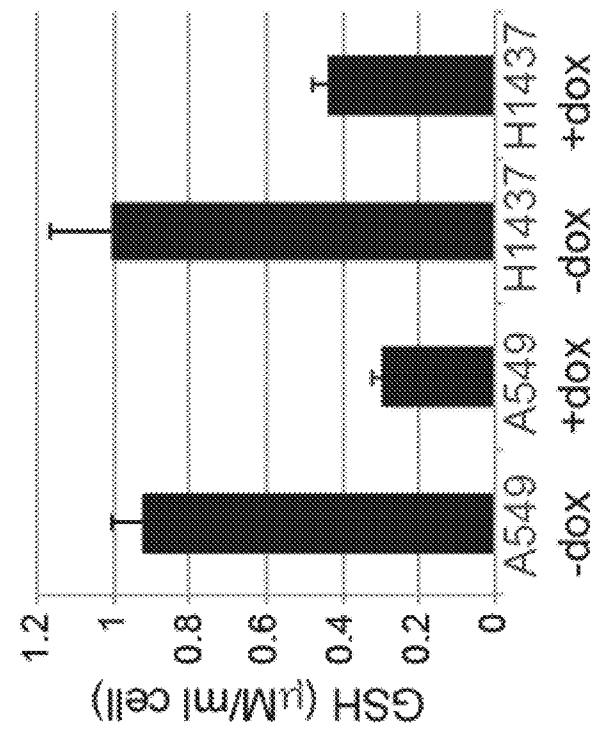
FIG. 52 is a bar graph showing glutathione (GSH) levels in A549 and H1437 cells in response to NRF2 knockdown.
Figure 53:
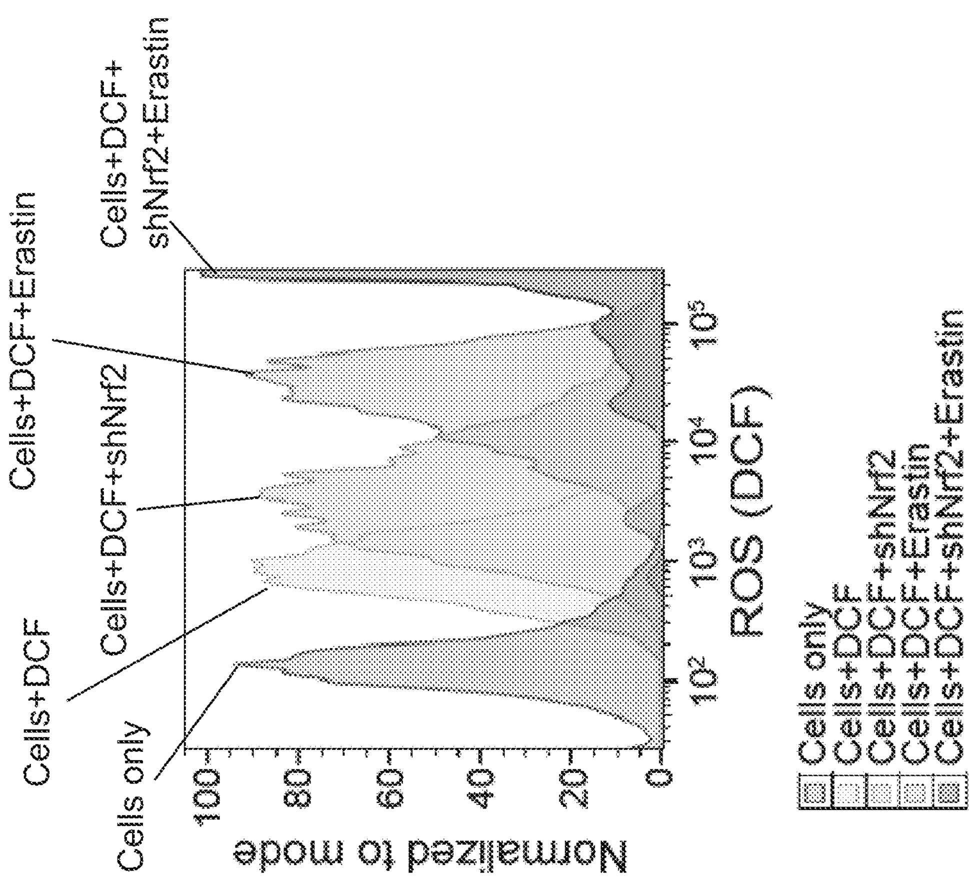
FIG. 53 is a histogram showing increasing ROS levels in response to shNRF2 and/or erastin, as measured by H2DCF.
Figure 54:
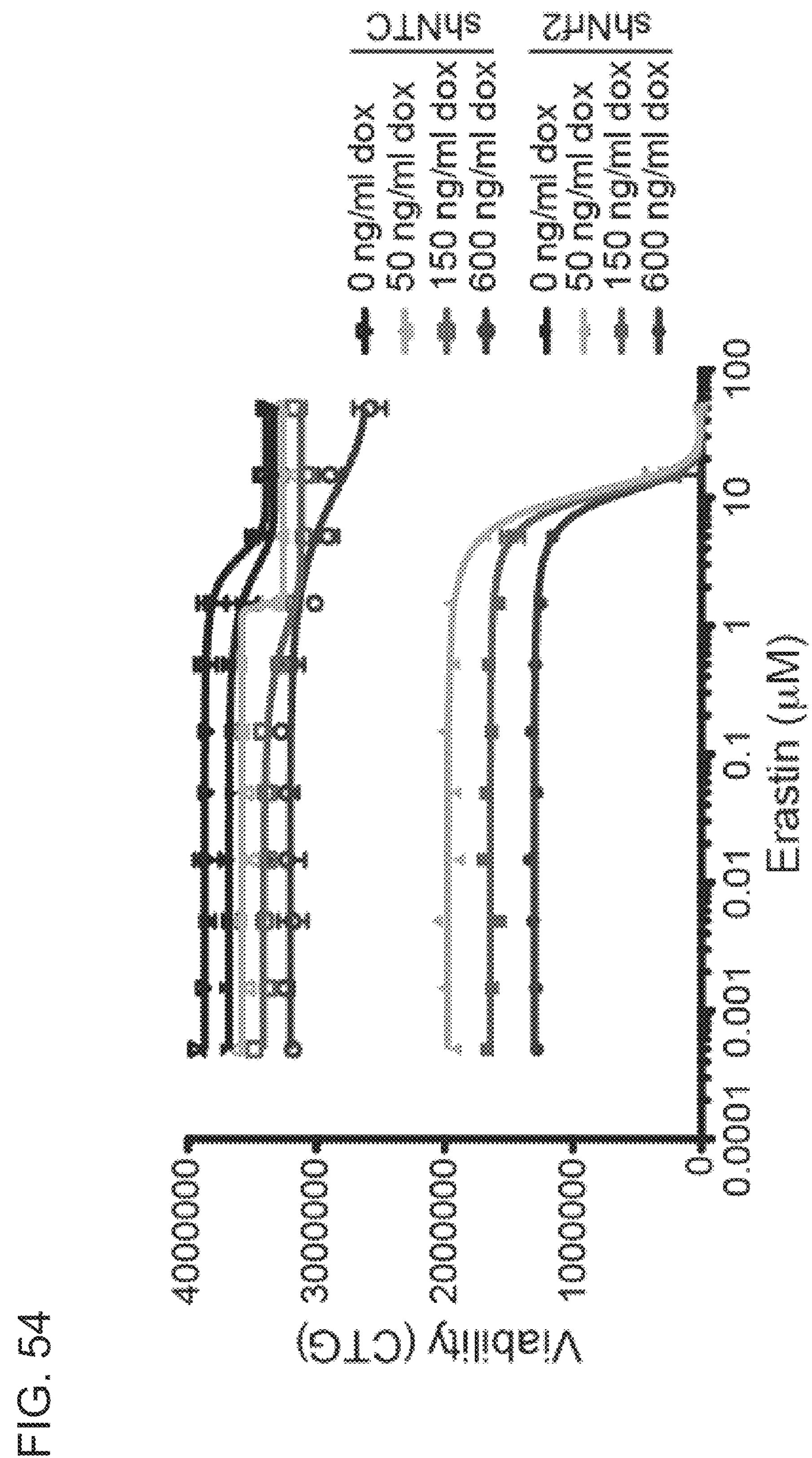
FIG. 54 is a graph showing viability of A549 cells expressing shNTC or shNFR2 over a dose response of erastin after about four days, as measured using CTG ATP measurements.
Figure 55B:
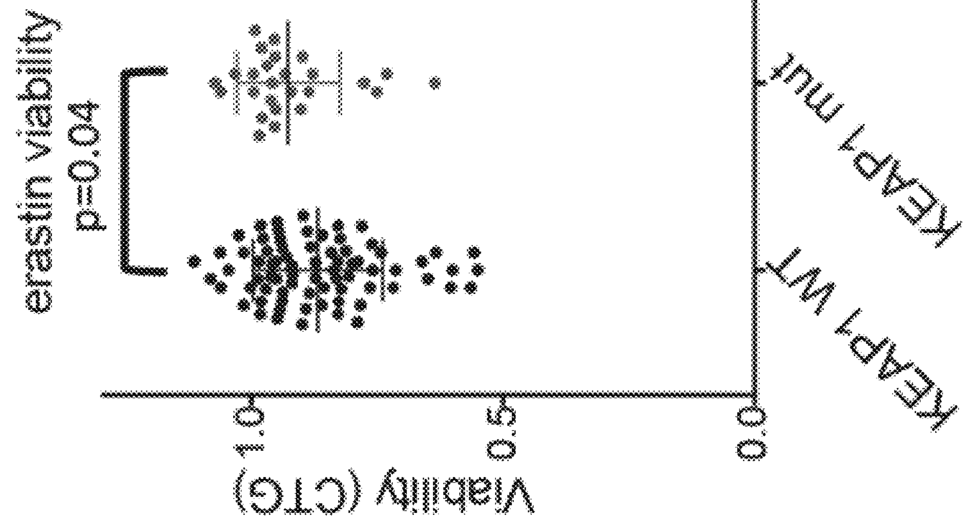
FIG. 55B is a graph showing the viability of KEAP1 wild-type cell lines versus KEAP1 mutant cell lines in response to erastin, as area under the curve of a dose response graph as shown in FIG. 54.
Figure 55A:
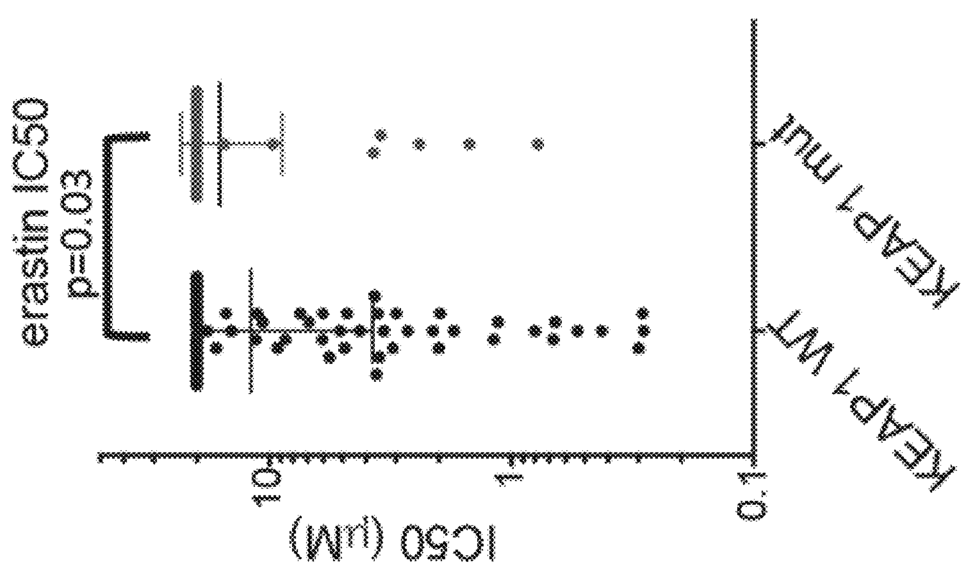
FIG. 55A is a graph showing the $IC_{50}$ of erastin on KEAP1 wild-type cell lines versus KEAP1 mutant cell lines, derived from a dose response graph as shown in FIG. 54.
Figure 56B:
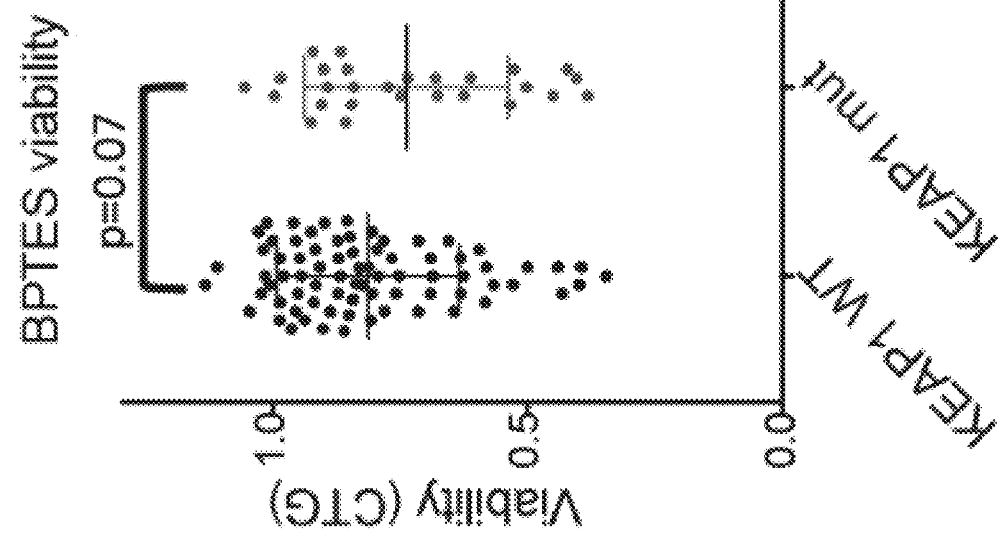
FIG. 56B is a graph showing the viability of KEAP1 wild-type cell lines versus KEAP1 mutant cell lines in response to the glutaminase inhibitor BPTES.
Figure 56A:
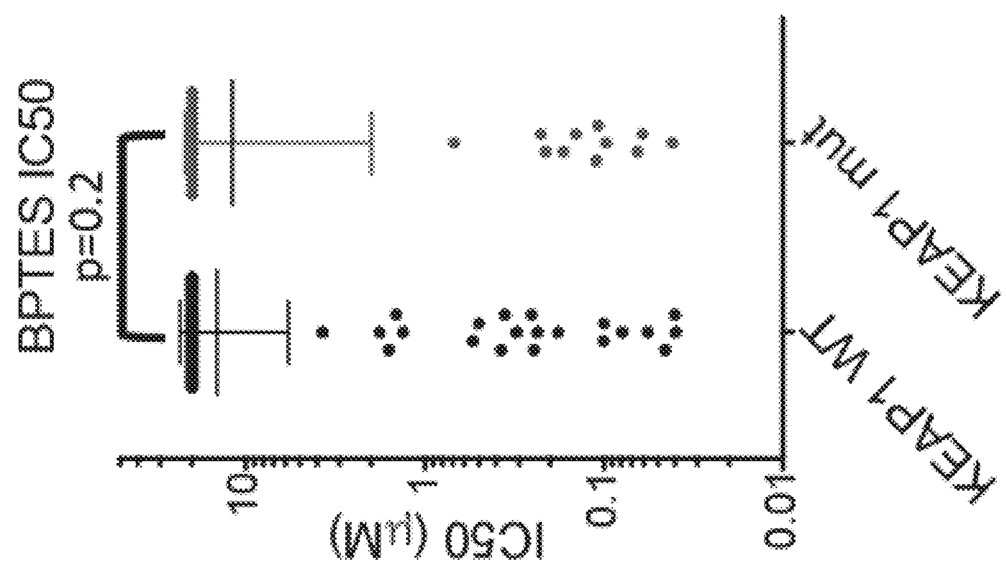
FIG. 56A is a graph showing the $IC_{50}$ of the glutaminase inhibitor BPTES on KEAP1 wild-type cell lines versus KEAP1 mutant cell lines.
Figure 57B:
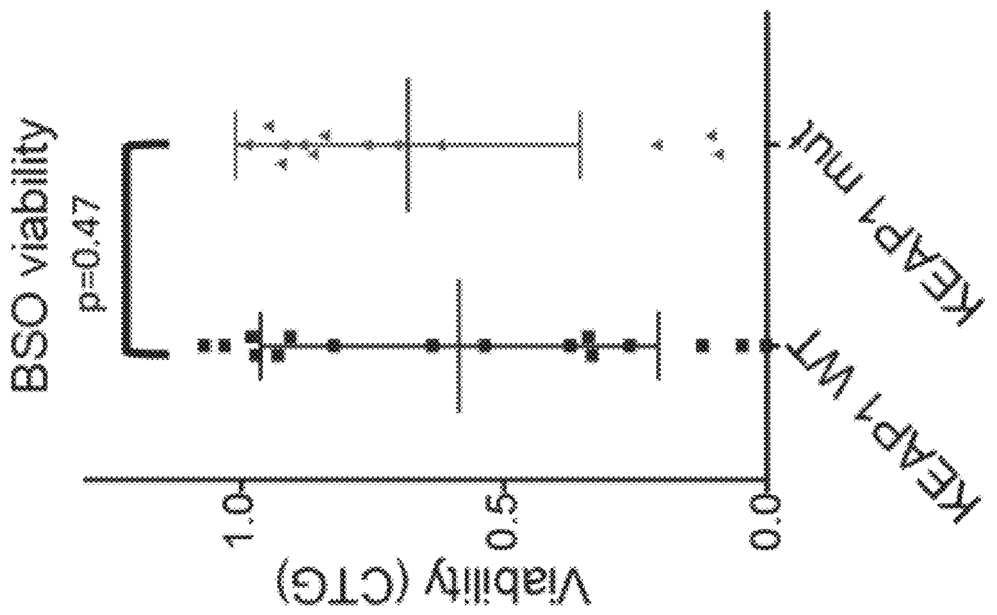
FIG. 57B is a graph showing the viability of KEAP1 wild-type cell lines versus KEAP1 mutant cell lines in response to BSO.
Figure 57A:
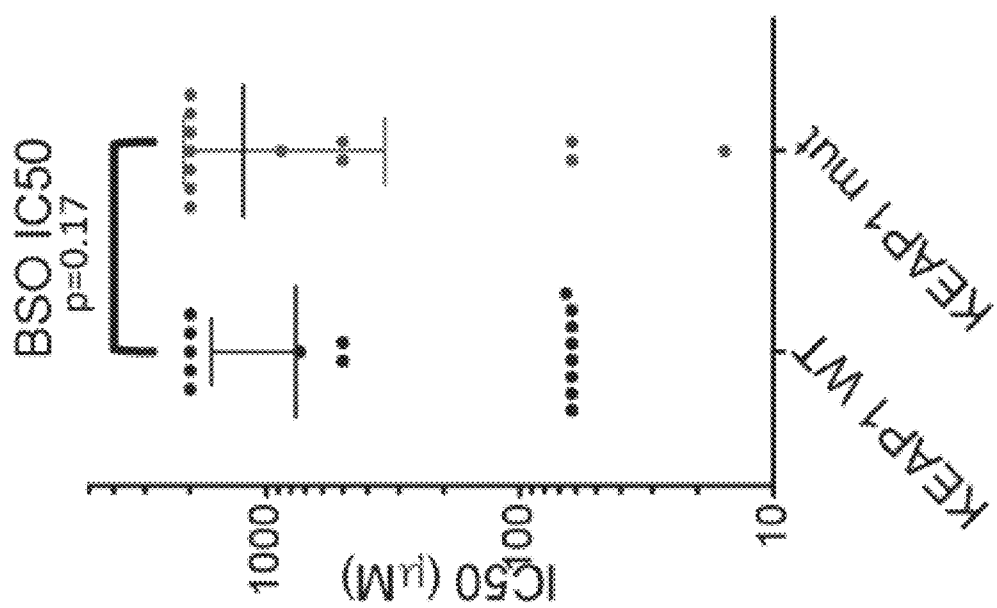
FIG. 57A is a graph showing the $IC_{50}$ of the glutathione synthase inhibitor buthionine sylphoximine (BSO) on KEAP1 wild-type cell lines versus KEAP1 mutant cell lines.

To further explore the effects of the glutathione pathway in NRF2 responses, the expression and activity of the xCT glutamate/cysteine antiporter, one of the rate limiting steps in glutathione synthesis, was monitored. SLC7A11 expression was reduced following NRF2 knockdown (FIG. 50), causing a decrease in cystine uptake (FIG. 51) associated with reduced glutathione (FIG. 52). NRF2 knockdown also caused a large increase in ROS levels (FIG. 53). To determine whether inhibition of SLC7A11 expression and cystine uptake contributed to decreased viability following NRF2 knockdown, xCT function was initiated using erastin, which inhibited cystine uptake (FIG. 51) and increased oxidative stress (FIG. 53). However, this was not sufficient to decrease the viability of the KEAP1 mutant cell line A549 (FIG. 54) or most other KEAP1 mutant cell lines (FIG. 55). The combination of erastin and NRF2 knockdown, however, did result in a dramatic decrease in viability (FIG. 54). Similarly, the glutathione synthase inhibitor buthionine sylphoximine (BSO) or the glutaminase inhibitor BPTES also did not display preferential toxicity for KEAP1 mutant cell lines (FIGS. 56 and 57). These results indicate that supplementation with glutathione was not sufficient to rescue lethality induced by NRF2 knockdown, nor was depletion of glutathione sufficient to kill KEAP1 mutant cell lines.

Figure 60:
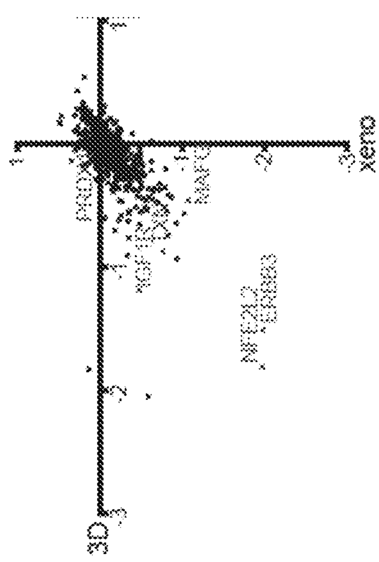
FIG. 60 is a scatterplot showing average gRNA expression per indicated gene in KEAP1 mutant NSCLC cells implanted in nude mice (xeno) versus grown for 15 days in a 3D methylcellulose culture. A549 cells were infected with lentivirus (0.3 MOI at 1000x coverage) expressing a gRNA library comprising 481 NRF2/KEAP1 target genes and 37 control genes. Puromycin-resistant cells were then grown in methyl cellulose or implanted into nude mice. After various time points, cells were collected and gRNAs identified by Next Gen sequencing.
Figure 59:
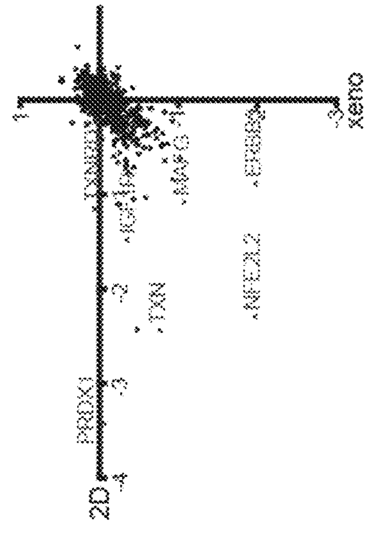
FIG. 59 is a scatterplot showing average gRNA expression per indicated gene in KEAP1 mutant NSCLC cells implanted in nude mice (xeno) versus grown for 15 days in a 2D plastic tissue culture dish. A549 cells were infected with lentivirus (0.3 MOI at 1000× coverage) expressing a gRNA library comprising 481 NRF2/KEAP1 target genes and 37 control genes. Puromycin-resistant cells were then plated into 2D plastic tissue culture dishes or implanted into nude mice. After various time points, cells were collected and gRNAs identified by Next Gen sequencing.
Figure 58:
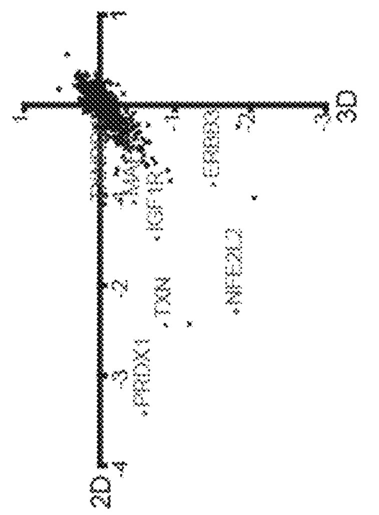
FIG. 58 is a scatterplot showing average gRNA expression per indicated gene in KEAP1 mutant NSCLC cells grown for 15 days in a 3D methylcellulose culture versus a 2D plastic tissue culture dish. A549 cells were infected with lentivirus (0.3 MOI at 1000× coverage) expressing a gRNA library comprising 481 NRF2/KEAP1 target genes and 37 control genes. Puromycin-resistant cells were then plated into 2D plastic tissue culture dishes or grown in methyl cellulose. After various time points, cells were collected and gRNAs identified by Next Gen sequencing.

In order to understand which pathways were activated as a consequence of NRF2 activation or KEAP1 loss, a CRISPR screen was performed using a library of genes that were decreased upon NRF2 knockdown in A549 cells and/or elevated in a panel of KEAP1 mutant NSCLC cell lines. As distinct consequences were observed following NRF2 knockdown in 2D, 3D, and xenograft growth conditions, the screen was performed under all three environments to determine whether discrete dependencies could be identified. At 15-day time point for all three conditions, all three screens performed similarly, with gRNAs representing only a small number of genes showing significant drop-out (FIGS. 58-60). NFE2L2 and its binding partner, MAFG, were among the most significant genes, showing that the screen performed as expected. The pentose phosphate pathway genes PGD, G6PD and TKT, known NRF2 target genes, also showed strong drop-out. Other strong hits in the screen were two growth factor receptor genes, IGF1R and ERBB3, and genes encoding three components of a redox signaling relay, PRDX1, TXN, and TXNRD1.

Figure 61:
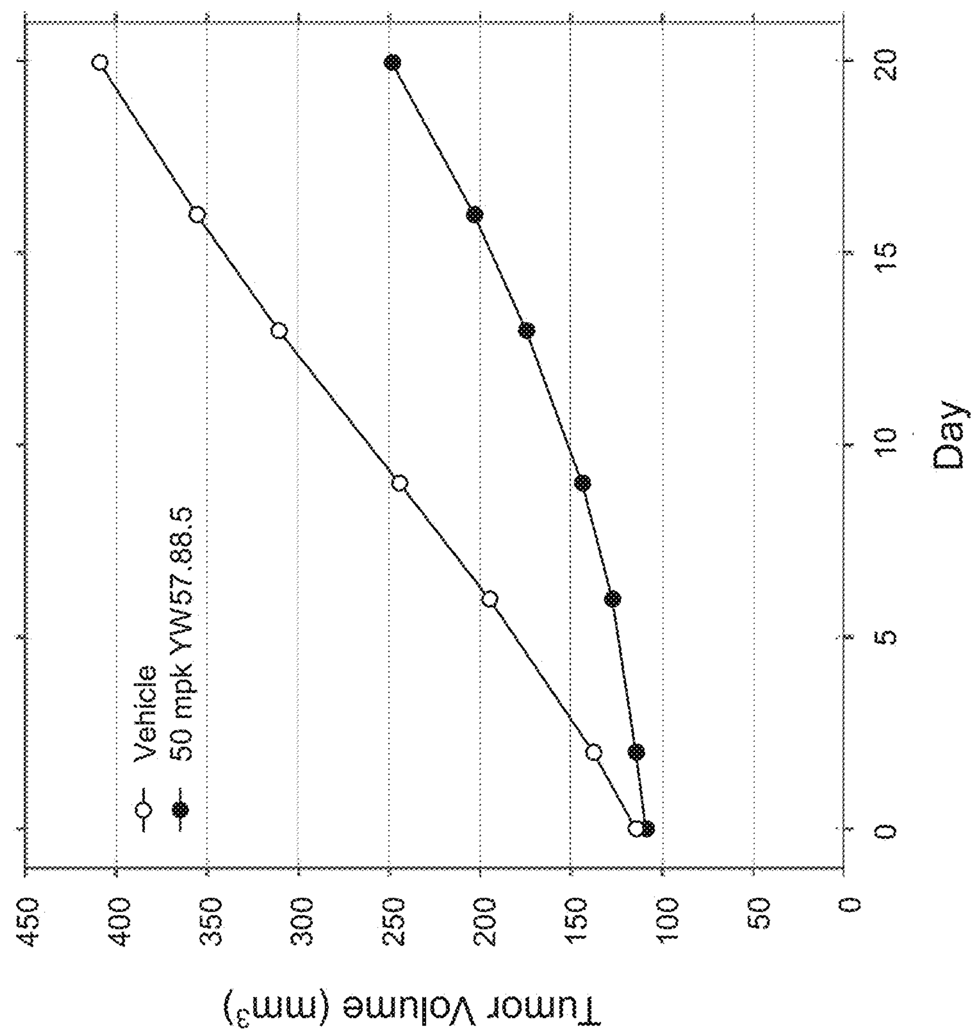
FIG. 61 is a graph showing kinetics of A549 xenograft tumor volume in response to treatment with the Erb2 antibody YW57.88.5.

Expression of ErbB3 was decreased following NRF2 knockdown in A549 cells (FIGS. 58-60). Treatment with YW57.88.5 in a tumor xenograft model indicated that ErbB3 was required for A549 proliferation (FIG. 61).

Figure 62:
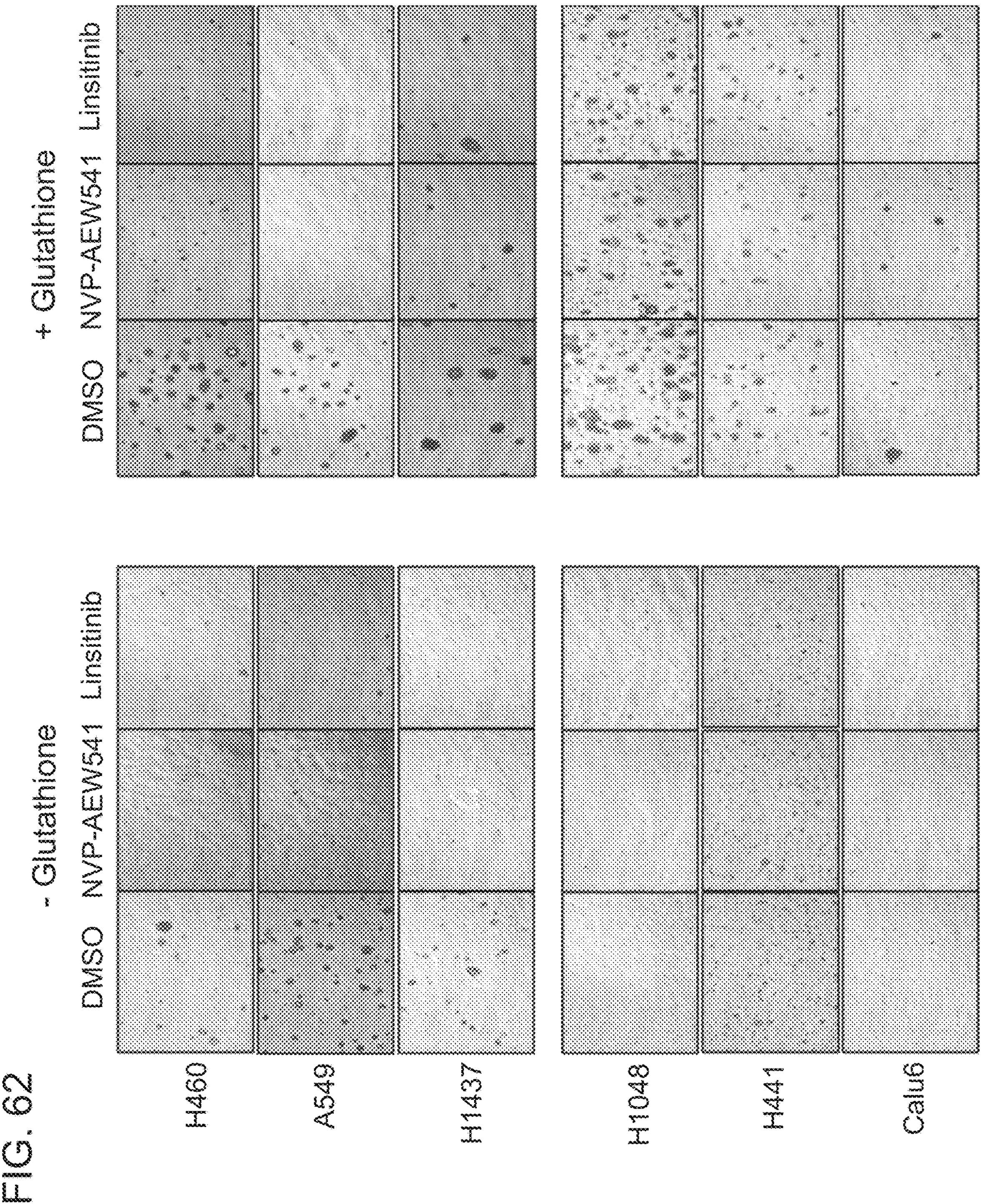
FIG. 62 is a series of photographs showing colony formation of KEAP1 mutant cell lines and KEAP1 wild-type cell lines grown in soft agar (anchorage independent conditions) in the presence of IGF1 R inhibitors linsitinib and NVP-AEW541, and in the presence or absence of glutathione.

Expression of IGF1 R was greater in KEAP1 mutant NSCLC cells relative to KEAP1 wild-type NSCLC cell lines. To test the effect of IGF1 R inhibition on KEAP1 mutant and KEAP1 wild-type cells, cell lines were treated with linsitinib, a potent and selective IGF1 R small molecule inhibitor. Linsitinib showed little effect on proliferation when tested in three wild-type and three mutant KEAP1 NSCLC cell lines. However, this compound was very potent at inhibiting colony growth of A549 cells in soft agar, having an $IC_{50}$ of about 20 nM. Moreover, when tested against a large panel of NSCLC cell lines, there appeared to be a selective growth inhibition in soft agar of this compound in KEAP1 mutant cell lines. A similar selective effect on KEAP1 mutant cell lines when grown under anchorage independent conditions was also seen with an independent IGF1 R inhibitor NVP-AEW541 (FIG. 62).

Thus, growth factors signaling through IGF1 R and ErbB3 are significant mediators of the growth of KEAP1 mutant cells.

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method of treating a subject having a cancer, the method comprising:

(a) determining the mRNA expression of NRF2 in a sample obtained from the subject, wherein the subject expresses NRF2 comprising an exon 2-deleted NRF2 splice variant, and wherein the presence of the exon 2-deleted NRF2 splice variant identifies the subject as likely to respond to a NRF2 pathway antagonist; and (b) administering to the subject a therapeutically effective amount of a NRF2 pathway antagonist.

2. The method of claim 1, wherein the NRF2 further comprises an exon 3-deleted NRF2 splice variant.

3. The method of claim 1, wherein the mRNA expression is determined by RNA-seq, PCR, RT-PCR, gene expression profiling, serial analysis of gene expression, or microarray analysis.

4. The method of claim 1, wherein the NRF2 pathway antagonist is a CREB antagonist, a CREB Binding Protein (CBP) antagonist, a Maf antagonist, an activating transcription factor 4 (ATF4) antagonist, a protein kinase C (PKC) antagonist, a Jun antagonist, a glucocorticoid receptor antagonist, a UbcM2 antagonist, a HACE1 antagonist, a c-Myc agonist, a SUMO agonist, a KEAP1 agonist, a CUL3 agonist, or a retinoic acid receptor a (RARα) agonist.

5. The method of claim 1, wherein the sample obtained from the subject is a tumor sample.

6. The method of claim 5, wherein the tumor sample is from a biopsy.

7. The method of claim 1, wherein the subject has a lung cancer or a head and neck cancer.

8. The method of claim 7, wherein the head and neck cancer is a squamous head and neck cancer.

9. The method of claim 7, wherein the lung cancer is a non-small cell lung cancer (NSCLC).

10. The method of claim 9, wherein the NSCLC is a squamous NSCLC.

11. A method of treating a subject having a cancer, the method comprising:

(a) determining a DNA sequence of NRF2 in a sample obtained from the subject, wherein the subject has a DNA sequence of NRF2 comprising a deletion of exon 2 that encodes an exon 2-deleted NRF2 splice variant, and wherein the presence of the deletion identifies the subject as likely to respond to a NRF2 pathway antagonist; and (b) administering to the subject a therapeutically effective amount of a NRF2 pathway antagonist.

12. The method of claim 11, wherein the subject has a DNA sequence of NRF2 further comprising a deletion of exon 3 that encodes an exon 3-deleted NRF2 splice variant.

13. The method of claim 11, wherein the DNA sequence is determined by PCR, exome-seq, microarray analysis, or whole genome sequencing.

14. The method of claim 11, wherein the NRF2 pathway antagonist is a CREB antagonist, a CREB Binding Protein (CBP) antagonist, a Maf antagonist, an activating transcription factor 4 (ATF4) antagonist, a protein kinase C (PKC) antagonist, a Jun antagonist, a glucocorticoid receptor antagonist, a UbcM2 antagonist, a HACE1 antagonist, a c-Myc agonist, a SUMO agonist, a KEAP1 agonist, a CUL3 agonist, or a retinoic acid receptor a (RARα) agonist.

15. The method of claim 11, wherein the sample obtained from the subject is a tumor sample.

16. The method of claim 15, wherein the tumor sample is from a biopsy.

17. The method of claim 11, wherein the subject has a lung cancer or a head and neck cancer.

18. The method of claim 17, wherein the head and neck cancer is a squamous head and neck cancer.

19. The method of claim 17, wherein the lung cancer is a non-small cell lung cancer (NSCLC).

20. The method of claim 19, wherein the NSCLC is a squamous NSCLC.

* * * * *

UNITED STATES PATENT AND TRADEMARK OFFICE

CERTIFICATE OF CORRECTION

PATENT NO. : 11,066,709 B2
APPLICATION NO. : 16/230223
DATED : July 20, 2021
INVENTOR(S) : Christiaan Nicolaas Klijn et al.

It is certified that error appears in the above-identified patent and that said Letters Patent is hereby corrected as shown below:

On the Title Page

In Column 2, Line 27, item (56) Application No. PCT/US2017/041398, replace “dated” with --mailed--;

In Column 2, Line 30, item (56) No. PCT/US2017/041398, replace “dated” with --mailed--;

In Column 2, Line 35, item (56) No. 17743124.4, replace “dated” with --mailed--.

In the Specification

Column 7, Line 30, replace “log 2” with --$\log_2$--.

Column 8, Line 17, replace “λP'tase” with --λ P'tase--.

Column 10, Line 20, replace “log 2” with --$\log_2$--.

Column 14, Line 1, replace “IGF1 R” with --IGF1R--.

Column 15, Line 57, replace “subjects or patients” with --subject’s or patient’s--.

Column 16, Line 61, replace “AKR1 B10” with --AKR1B10--;
Line 62, replace “AKR1 B10” with --AKR1B10--.

Column 17, Line 3, replace “AKR1 B10” with --AKR1B10--;
Line 5, replace “AKR1 B10” with --AKR1B10--;
Line 7, replace “AKR1 B15” with --AKR1B15--;
Line 8, replace “AKR1 B15” with --AKR1B15--;
Line 16, replace “AKR1 B15” with --AKR1B15--;
Line 18, replace “AKR1 B15” with --AKR1B15--.

Signed and Sealed this
Thirteenth Day of September, 2022

Katherine Kelly Vidal

Katherine Kelly Vidal
*Director of the United States Patent and Trademark Office*

Column 20, Lines 21-22, replace “form of ¶ RSPO3” with --form of RSPO3--.

Column 26, Line 9, replace “2-ethyl hydrazide” with --2-ethylhydrazide--.

Column 27, Line 10, replace “YW243.55.570” with --YW243.55.S70--;
Line 14, replace “MED14736” with --MEDI4736--;
Line 58, replace “VEGF165” with --$VEGF_{165}$--.

Column 29, Line 57, replace “48,000” with --~48,000--;
Line 65, replace “066686861” with --0666868B1--.

Column 37, Line 3, replace “YW243.55.570” with --YW243.55.S70--;
Line 4, replace “MED14736” with --MEDI4736--.

Column 39, Line 62, replace “(Fab’)2” with --$(Fab')_2$--.

Column 43, Line 2, replace “LP>0.2” with --$\psi>0.2$--;
Line 7, replace “which LP could” with --which $\psi$ could--.

Column 44, Line 12, replace “(P1)” with --(PI)--;
Line 27, replace “(P1)” with --(PI)--.

Column 45, Line 32, replace “H1437” with --HI437--.

Column 46, Line 43, replace “identified 2” with --identified (≥2--.

Column 47, Line 55, replace “FIG. 11 B” with --FIG. 11B--.

Column 54, Line 22, replace “IGF1 R” with --IGF1R--;
Line 24, replace “IGF1 R” with --IGF1R--;
Line 26, replace “IGF1 R” with --IGF1R--;
Line 37, replace “IGF1 R” with --IGF1R--;
Line 38, replace “IGF1 R” with --IGF1R--.